United States Patent
Abate-Daga et al.

(10) Patent No.: US 11,286,306 B2
(45) Date of Patent: Mar. 29, 2022

(54) TLR9-BINDING CHIMERIC ANTIGEN RECEPTORS

(71) Applicant: H. Lee Moffitt Cancer Center and Research Institute, Inc., Tampa, FL (US)

(72) Inventors: Daniel Abate-Daga, Tampa, FL (US); Alan F. List, Tampa, FL (US); Sheng Wei, Tampa, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 177 days.

(21) Appl. No.: 16/467,286

(22) PCT Filed: Dec. 8, 2017

(86) PCT No.: PCT/US2017/065249
§ 371 (c)(1),
(2) Date: Jun. 6, 2019

(87) PCT Pub. No.: WO2018/106993
PCT Pub. Date: Jun. 14, 2018

(65) Prior Publication Data
US 2019/0309086 A1 Oct. 10, 2019

Related U.S. Application Data

(60) Provisional application No. 62/432,325, filed on Dec. 9, 2016.

(51) Int. Cl.
*A61K 39/395* (2006.01)
*A61K 38/17* (2006.01)
*C07K 14/705* (2006.01)
*C07K 16/28* (2006.01)
*C07K 19/00* (2006.01)
*C12N 5/10* (2006.01)
*C12N 15/63* (2006.01)
*A61P 35/00* (2006.01)

(52) U.S. Cl.
CPC ........ *C07K 16/2896* (2013.01); *A61K 39/395* (2013.01); *A61P 35/00* (2018.01); *C07K 14/705* (2013.01); *C07K 14/70596* (2013.01); *C07K 16/28* (2013.01); *C12N 5/10* (2013.01); *C12N 15/63* (2013.01); *C07K 2317/56* (2013.01); *C07K 2317/565* (2013.01); *C07K 2317/569* (2013.01); *C07K 2317/622* (2013.01); *C07K 2319/03* (2013.01); *C07K 2319/33* (2013.01)

(58) Field of Classification Search
CPC .......... C07K 2317/622; C07K 2319/03; C07K 2319/33; C07K 2319/00; C07K 2319/74; C07K 2317/56; C07K 16/2866; C07K 16/2896; C07K 14/70596; C07K 2317/24; C07K 16/28; C07K 19/00; C07K 2317/565; C07K 2317/569; C07K 2317/53; A61K 2039/505; A61K 39/395; A61K 39/3955; A61K 38/177
See application file for complete search history.

(56) References Cited

U.S. PATENT DOCUMENTS

| | | | |
|---|---|---|---|
| 5,990,275 A | 11/1999 | Whitlow et al. | |
| 2005/0244410 A1* | 11/2005 | Bassiri | C07K 16/2896 424/144.1 |
| 2013/0243767 A1* | 9/2013 | Mudde | C07K 16/2896 424/134.1 |
| 2013/0323214 A1 | 12/2013 | Gottschalk et al. | |
| 2015/0329640 A1* | 11/2015 | Finer | C07K 16/2896 424/93.21 |
| 2016/0250258 A1 | 9/2016 | Delaney et al. | |
| 2016/0362472 A1* | 12/2016 | Bitter | A61K 39/001112 |
| 2017/0335009 A1* | 11/2017 | List | C07K 16/2896 |

FOREIGN PATENT DOCUMENTS

| | | | | |
|---|---|---|---|---|
| WO | WO-2006072620 A1 * | 7/2006 | | A61P 33/02 |
| WO | WO-2015158671 A1 * | 10/2015 | | C07K 16/2878 |
| WO | 2016070014 A1 | 5/2016 | | |
| WO | WO-2016149254 A1 * | 9/2016 | | C07K 16/2887 |

OTHER PUBLICATIONS

Eaton-Bassiri et al. Toll-like receptor 9 can be expressed at the cell surface of distinct populations of tonsils and human peripheral blood mononuclear cells. Infection Immunity 72(12): 7202-7211,2004.*
Fesnack et al. Engineered T cells: the promise and challenges of cancer immunotherapy. Nature 16: 566-581, 2016.*
Harris et al. Adoptive T cell therapies: a comparison of T cell receptors and chimeric antigen receptors. Trends Pharmacol Sci 37(3): 220-230, 2016.*
Jing et al. Up-regulation of toll-like receptor 9 in osteosarcoma. Anticancer Res 35: 5839-5844, 2015.*
Reimer et al. Molecular cloning and characterization of a novel anti-TLR9 intrabody. Cell Mol Biol Lett 18: 433-446, 2013.*
Srivastava et al. Engineering CAR-T cells: design concepts. Trends Immunol 36(8): 494-502, 2015.*

(Continued)

*Primary Examiner* — Bridget E Bunner
(74) *Attorney, Agent, or Firm* — Thomas|Horstemeyer LLP

(57) ABSTRACT

Disclosed herein are chimeric antigen receptor (CAR) polypeptides that can be used with adoptive cell transfer to target and kill cancer cells that express TLR9 on their surface. Also disclosed are immune effector cells, such as T cells or Natural Killer (NK) cells that are engineered to express these CARs. Therefore, also disclosed are methods of providing an anti-tumor immunity in a subject with a TLR9-expressing cancer that involves adoptive transfer of the disclosed immune effector cells engineered to express the disclosed CARs.

17 Claims, 11 Drawing Sheets
Specification includes a Sequence Listing.

(56) References Cited

OTHER PUBLICATIONS

Tanaka et al. Functional cell surface expression of toll-like receptor 9 promotes cell proliferation and survival in human hepatocellular carcinomas. Int J Oncol 37: 805-814, 2010.*
Urban-Wojciuk et al. The raise of TLRs in anti-cancer immunity and tumor rejection. Frontiers Immunol 10: 2388, 2019.*
International Search Report issued for application PCT/US2017/065249, dated Apr. 20, 2018.

* cited by examiner

GFP: mock-transduced T cells
UT: Untransduced
Conv: conventional $V_H$-$L_H$ CAR.

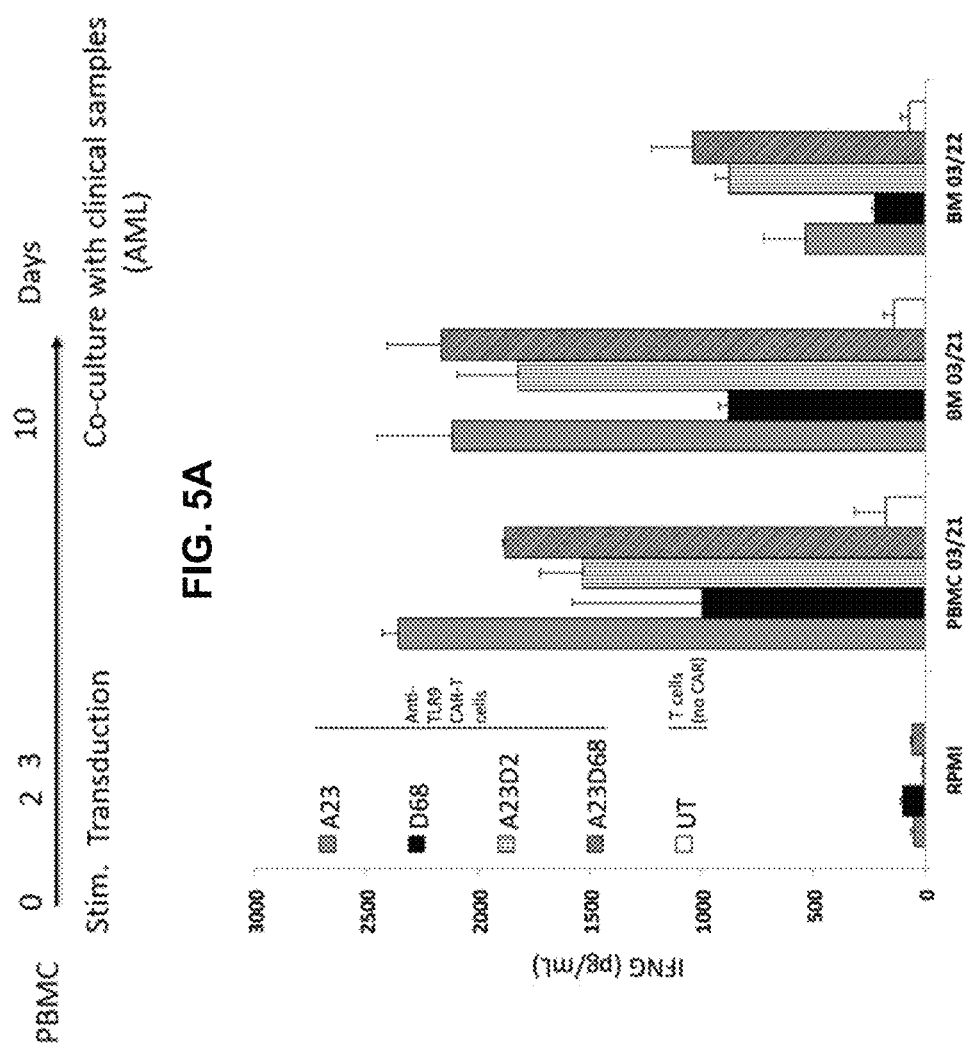

TLR9-BINDING CHIMERIC ANTIGEN RECEPTORS

CROSS-REFERENCE TO RELATED APPLICATIONS

This application claims benefit of U.S. Provisional Application No. 62/432,325, filed Dec. 9, 2016, which is hereby incorporated herein by reference in its entirety.

BACKGROUND

Myelodysplastic syndromes (MDS) are the most common bone marrow failure (BMF) syndrome, whose prevalence is increasing with the aging of the American population (Estey, E. J Clin Oncol 25:1908-15 (2007)). This hematopoietic stem cell malignancy shares features of cytological dysplasia accompanied by ineffective hematopoiesis and an increased risk for progression to acute myeloid leukemia (AML). Current management of MDS is largely focused on the control of symptoms, with hematopoietic stem cell transplant as the only curative option, indicated for patients who are 40-years-old or younger. Although three agents are approved for the treatment of MDS in the United States, lenalidomide (LEN) represents the only targeted therapeutic. Treatment with LEN yields sustained red blood cell transfusion independence accompanied by partial or complete cytogenetic remissions in the majority of patients harboring a chromosome 5q deletion (del5q) (List, A. et al. N Engl J Med 355:1456-1465 (2006); List, A. et al. N Engl J Med 352:549-557 (2005)). Although this represents a major advance for patients with del5q MDS, this cytogenetically defined subtype comprises only 8-12% of the overall population, therefore the vast majority of patients with non-del5q MDS do not benefit.

Cellular immunotherapies have come of age as an efficacious and safe therapeutic approach to treating human cancers (Dai, H., et al. J Natl Cancer Inst 108(2016); Brudno, J. N. et al. J Clin Oncol 34(10):1112-21 (2016); Feldman, S. A., et al. Semin Oncol 42:626-39 (2015); Lee, D. W. et al. Lancet 385:517-28 (2015); Kochenderfer, J. N. et al. Blood 122:4129-39 (2013)). In particular, adoptive transfer of CD19-targeted chimeric antigen receptor (CAR)-expressing autologous T cells resulted in remarkable remissions in patients that had failed all available standard therapies for leukemia. These unprecedented success stories suggest that other bone marrow proliferative diseases might be treated with this approach.

SUMMARY

Disclosed herein are chimeric antigen receptor (CAR) polypeptides that can be used with adoptive cell transfer to target and kill cancer cells that express TLR9 on their plasma membrane. The disclosed CAR polypeptides contain in an ectodomain an anti-TLR9 binding agent that can bind TLR9-expressing cancer cells, based on ectopic TLR9 expression on malignant MDS and AML clones, as well as in solid tumors such as hepatocellular carcinoma. Also disclosed is an immune effector cell genetically modified to express the disclosed CAR polypeptide.

The anti-TLR9 binding agent is in some embodiments an antibody fragment that specifically binds TLR9. For example, the antigen binding domain can be a Fab or a single-chain variable fragment (scFv) of an antibody that specifically binds TLR9. The anti-TLR9 binding agent is in some embodiments an aptamer that specifically binds TLR9. For example, the anti-TLR9 binding agent can be a peptide aptamer selected from a random sequence pool based on its ability to bind TLR9. The anti-TLR9 binding agent can also be a natural ligand of TLR9, or a variant and/or fragment thereof capable of binding TLR9.

As with other CARs, the disclosed polypeptides can also contain a transmembrane domain and an endodomain capable of activating an immune effector cell. For example, the endodomain can contain a signaling domain and one or more co-stimulatory signaling regions.

In some embodiments, the signaling domain is a CD3 zeta (CD3ζ) signaling domain. In some embodiments, the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules. In some embodiments, the co-stimulatory signaling region contains one or more mutations in the cytoplasmic domains of CD28 and/or 4-1BB that enhance signaling.

In some embodiments, the CAR polypeptide contains an incomplete endodomain. For example, the CAR polypeptide can contain only an intracellular signaling domain or a co-stimulatory domain, but not both. In these embodiments, the immune effector cell is not activated unless it and a second CAR polypeptide (or endogenous T-cell receptor) that contains the missing domain both bind their respective antigens. Therefore, in some embodiments, the CAR polypeptide contains a CD3 zeta (CD3ζ) signaling domain but does not contain a costimulatory signaling region (CSR). In other embodiments, the CAR polypeptide contains the cytoplasmic domain of CD28, 4-1BB, or a combination thereof, but does not contain a CD3 zeta (CD3ζ) signaling domain (SD).

Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell. In some embodiments, the cell exhibits an anti-tumor immunity when the antigen binding domain of the CAR binds to TLR9.

Also disclosed is a method of providing an anti-tumor immunity in a subject with cancer cells that express TLR9 on their plasma membrane that involves administering to the subject an effective amount of an immune effector cell genetically modified with a disclosed TLR9-specific CAR.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 shows that MDS HSPC Express TLR9 on the surface.

FIG. 3 shows the optimization of CAR design.

FIG. 4 shows anti-TLR9 CARs recognize SKM-1 cells in vitro.

FIG. 5 shows reactivity of CAR-T cells against Peripheral blood mononuclear cells (PBMC) and Bone Marrow aspirates (BM) from 2 different acute myelogenous leukemia (AML) patients. FIG. 5A is a schematic representation of experimental design where four second-generation CARs containing a CD28-derived costimulatory domain plus a CD3zeta T cell activation domain, but differing in their antigen-binding modules (A23, D68, A23-D2, A23-D68) were co-cultured with unfractionated BM or PBMC from AML patients, overnight. FIG. 5B is a bar graph showing interferon-gamma (IFNG) in co-culture supernatants, measured by ELISA. All four CARs tested induced IFNG secretion in response to AML cells, but not against culture medium (RPMI).

FIG. 8 shows inclusion of a 24 amino acid spacer region in the endodomain prevents tonic signaling through CAR-induced phosphorylation of the endogenous CD3ζ.

DETAILED DESCRIPTION

Figure 1:
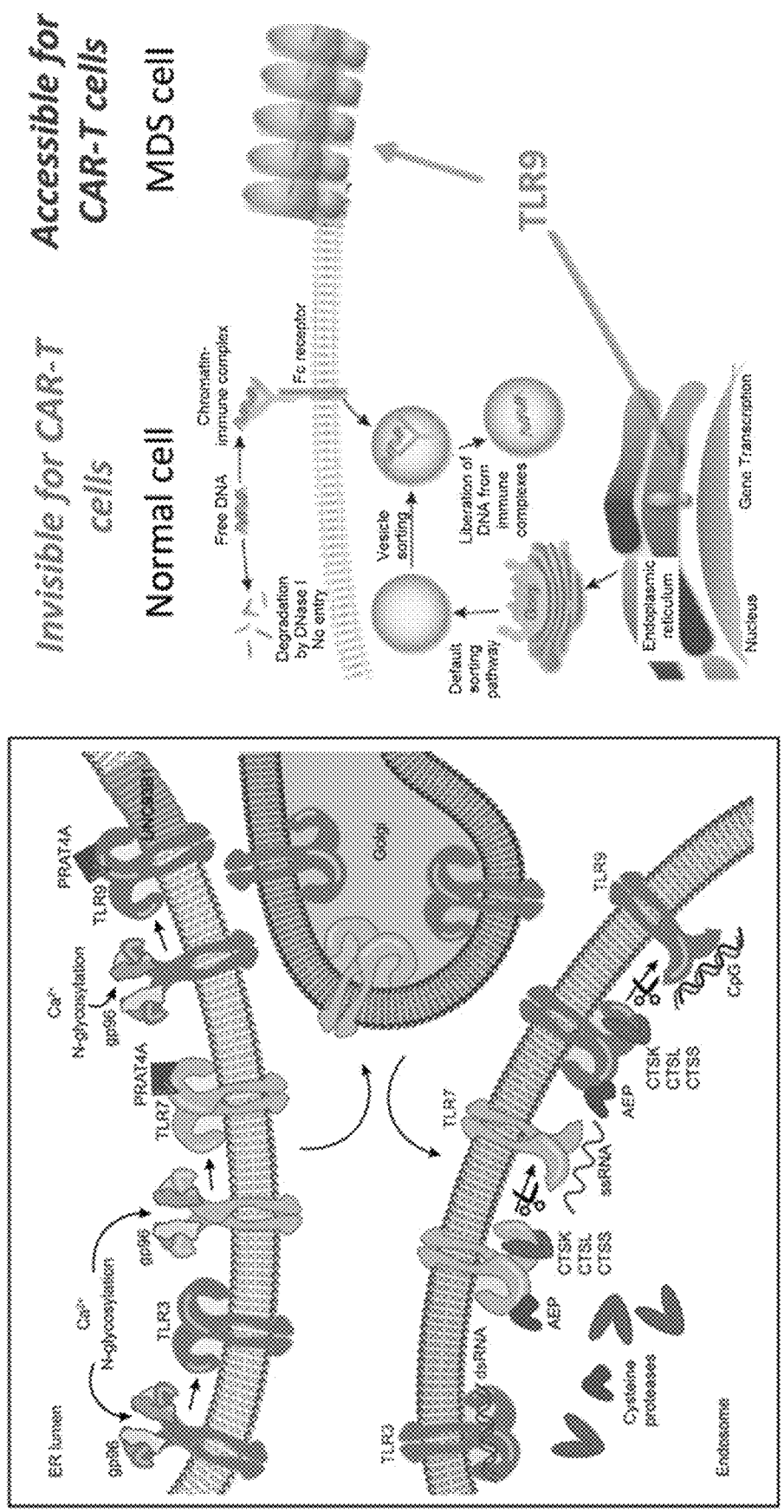
FIG. 1 illustrates TLR9 in normal and MDS cells. The left panel illustration how TLR9 is synthesized in the endoplasmic reticulum as a membrane-bound receptor, stabilized by chaperones UNC93B1 and PRAT4A. It then transits, via Golgi, to the endosomal compartment where it is processed by proteases of the cathepsin family and by AEP to yield the mature, functional form of TLR9. The right panel illustrates how in non-malignant cells, TLR9 is retained within the endosome, where it detects the presence of foreign nucleic acids and triggers a cascade of signaling leading to activation of innate immunity. In MDS cells, however, TLR9 localizes to the plasma membrane. Only plasma membrane-expressed TLR9 can be recognized and attacked by CAR-T cells. (Modified from Blasius, A. L. & Beutler, B. Immunity 32:305-315 (2010)).

Chimeric Antigen Receptor (CAR)-T cell immunotherapies have recently obtained FDA approval based on their outstanding clinical efficacy in the treatment B cell malignancies. While CAR-T cells have been developed against multiple hematological disorders, Myelodysplastic Syndrome (MDS) remains unexplored as a target, and a largely unmet clinical need. In the present application, disclosed herein are CAR-T cell products targeting TLR9. This approach is highly innovative due to the unique characteristics of TLR9: while tumor specificity is typically based on differential expression of a protein, between malignant and healthy tissues, TLR9 allows for selective targeting of malignant clones based on its differential subcellular localization. In healthy tissues, TLR9 remains in the lysosomal and endosomal vesicles, and is therefore "invisible" to CAR-T cells. However, in MDS cells, TLR9 is aberrantly localized to the plasma membrane, thus becoming accessible for recognition via CAR. Several CARs were generated that recognize TLR9-expressing SKM1 cells in vitro.

Disclosed herein are chimeric antigen receptors (CAR) that can specifically recognize TLR9 on cancers that ectopically express TLR9 on the plasma membrane. Also disclosed are immune effector cells, such as T cells or Natural Killer (NK) cells that are engineered to express these CARs. Therefore, also disclosed are methods for providing an anti-tumor immunity in a subject with TLR9-expressing cancers that involves adoptive transfer of the disclosed immune effector cells engineered to express the disclosed TLR9-specific CARs.

TLR9-Specific Chimeric Antigen Receptors (CAR)

CARs generally incorporate an antigen recognition domain, e.g. from the single-chain variable fragments (scFv) of a monoclonal antibody (mAb), with transmembrane signaling motifs involved in lymphocyte activation (Abate-Daga, D., et al. Molecular Therapy Oncolytics 3(2016); Sadelain M, et al. Nat Rev Cancer 2003 3:35-45). Disclosed herein is a TLR9-specific chimeric antigen receptor (CAR) that can be expressed in immune effector cells to enhance antitumor activity against tumor cells that ectopically express TLR9 on their surface.

The disclosed CAR is generally made up of three domains: an ectodomain, a transmembrane domain, and an endodomain. The ectodomain comprises the TLR9-binding region and is responsible for antigen recognition. It also contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an signaling domain (SD) and optionally a co-stimulatory signaling region (CSR).

A "signaling domain (SD)" generally contains immuno-receptor tyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a T-cell receptor) containing the missing domain also binds its respective antigen.

In some embodiments, the TLR9-binding region is an scFv antibody (anti-TLR9 antibody). For example, the anti-TLR9 scFv can comprise a variable heavy ($V_H$) domain having CDR1, CDR2 and CDR3 sequences and a variable light ($V_L$) domain having CDR1, CDR2 and CDR3 sequences, wherein the CDR1 sequence of the $V_H$ domain comprises the amino acid sequence TAGMQ (SEQ ID NO:1), wherein the CDR2 sequence of the $V_H$ domain comprises the amino acid sequence WINTHSGEPKYAEDFKG (SEQ ID NO:2), wherein the CDR3 sequence of the $V_H$ domain comprises the amino acid sequence GDSSGYGAWFAY (SEQ ID NO:3), wherein the CDR1 sequence of the $V_L$ domain comprises the amino acid sequence RSSTGAVTTSNYAN (SEQ ID NO:4), wherein the CDR2 sequence of the $V_L$ domain comprises the amino acid sequence DTNNRAP (SEQ ID NO:5), wherein the CDR3 sequence of the $V_L$ domain comprises the amino acid sequence ALWCSNHWV (SEQ ID NO:6), or any combination thereof.

In some embodiments, the anti-TLR9 scFv $V_H$ domain comprises the amino acid sequence (SEQ ID NO: 7)
QIQLVQSGPELKKPGETVKISCKASGYTFTTAGMQWYQKMPGKGFKWIGW

INTHSGEPKYAEDFKGRFAFSLETSASTAYLQISNLKNEDTATYFCARGD

SSGYGAWFAYWGQGTLVTVSAA.

In some embodiments, the anti-TLR9 scFv $V_H$ domain comprises the amino acid sequence (SEQ ID NO: 8)
QAVVTQESALTTSPGETVTLTCRSSTGAVTTSNYANVWQEKPDHLFTGLI

GDTNNRAPGVPARFSGSLIGDKAALTITGAQTEDEAIYFCALWCSNHWVF

GGGTKLTVL.

In some embodiments, the anti-TLR9 scFv $V_L$ domain comprises the amino acid sequence (SEQ ID NO: 9)
QAVVTQESALTTSPGETVTLTCRSSTGAVTTSNYANVWQEKPDHLFTGLI

GDTNNRAPGVPARFSGSLIGDKAALTITGAQTEDEAIYFCALWCSNHWVF

GGGTKLTVL.

In some embodiments, the anti-TLR9 scFv $V_L$ domain comprises the amino acid sequence (SEQ ID NO: 10)
QAVVTQESALTTSPGETVTLTCRSSTGAVTTSNYANVWQEKPDHLFTGLI

GDTNNRAPGVPARFSGSLIGDKAALTITGAQTEDEAIYFCALWCSNHWVF

GGGTKLTVL.

In some embodiments, the anti-TLR9 scFv antibody comprises a linker between the $V_H$ domain and the $V_L$ domain. In some cases, the linker can have the amino acid sequence GSTSGSGKPGSGEGSTKG (218 linker, SEQ ID NO:11), or a conservative variant thereof. In some cases, the linker can have the amino acid sequence GGGGSGGGGSGGGGS (G4S linker, SEQ ID NO:12), or a conservative variant thereof. In some cases, the linker comprises 2, 3, or 4 G4S linkers.

In some embodiments, the anti-TLR9 scFv antibody comprises a signal peptide. For example, the signal peptide can have the amino acid sequence MVLLVTSLLLCELPHPAFLLIP (SEQ ID NO:13), or a conservative variant thereof.

Therefore, in some embodiments, the CAR comprises a signal peptide, anti-TLR9 scFv antibody, and linkers having the amino acid sequence (SEQ ID NO: 14)
MVLLVTSLLLCELPHPAFLLIPQIQLVQSGPELKKPGETVKISCKASGYT

FTTAGMQWYQKMPGKGFKWIGWINTHSGEPKYAEDFKGRFAFSLETSAST

AYLQISNLKNEDTATYFCARGDSSGYGAWFAYWGQGTLVTVSAAGSTSGS

GKPGSGEGSTKGQAVVTQESALTTSPGETVTLTCRSSTGAVTTSNYANWV

QEKPDHLFTGLIGDTNNRAPGVPARFSGSLIGDKAALTITGAQTEDEAIY

FCALWCSNHWVFGGGTKLTVL.

Therefore, in some embodiments, the CAR comprises a signal peptide, anti-TLR9 scFv antibody, and linkers having the amino acid sequence (SEQ ID NO: 15)
MVLLVTSLLLCELPHPAFLLIPQAVVTQESALTTSPGETVTLTCRSSTGA

VTTSNYANWVQEKPDHLFTGLIGDTNNRAPGVPARFSGSLIGDKAALTIT

GAQTEDEAIYFCALWCSNHWVFGGGTKLTVLGSTSGSGKPGSGEGSTKGQ

AVVTQESALTTSPGETVTLTCRSSTGAVTTSNYANWVQEKPDHLFTGLIG

DTNNRAPGVPARFSGSLIGDKAALTITGAQTEDEAIYFCALWCSNHWVFG

GGTKLTVL.

Therefore, in some embodiments, the CAR comprises a signal peptide, anti-TLR9 scFv antibody, and linkers having the amino acid sequence (SEQ ID NO: 16)
MVLLVTSLLLCELPHPAFLLIPQIQLVQSGPELKKPGETVKISCKASGYT

FTTAGMQWYQKMPGKGFKWIGWINTHSGEPKYAEDFKGRFAFSLETSAST

AYLQISNLKNEDTATYFCARGDSSGYGAWFAYWGQGTLVTVSAAGGGGSG

GGGSGGGGSQAVVTQESALTTSPGETVTLTCRSSTGAVTTSNYANWVQEK

PDHLFTGLIGDTNNRAPGVPARFSGSLIGDKAALTITGAQTEDEAIYFCA

LWCSNHWVFGGGTKLTVL.

Therefore, in some embodiments, the CAR comprises a signal peptide, anti-TLR9 scFv antibody, and linkers having the amino acid sequence (SEQ ID NO: 17)
MVLLVTSLLLCELPHPAFLLIPQAVVTQESALTTSPGETVTLTCRSSTGA

VTTSNYANWVQEKPDHLFTGLIGDTNNRAPGVPARFSGSLIGDKAALTIT

GAQTEDEAIYFCALWCSNHWVFGGGTKLTVLGGGGSGGGGSGGGGSQAVV

TQESALTTSPGETVTLTCRSSTGAVTTSNYANWVQEKPDHLFTGLIGDTN

NRAPGVPARFSGSLIGDKAALTITGAQTEDEAIYFCALWCSNHWVFGGGT

KLTVL.

In some embodiments, the TLR9-binding region comprises a peptide fragment of an immunoglobulin comprising a structural loop region (e.g., CH1, CH2, or CH3) having at least one modification allowing the peptide to bind TLR9. For example, anti-TLR9 peptides produced by modifying a structural loop region of an immunoglobulin are described in WO 2006/072620, which is incorporated by reference for the teaching of these antibodies.

In some embodiments, the anti-TLR9 peptide can have the amino acid sequence (clone A23, SEQ ID NO: 18)
PREPQVYTLPPSRDELGIAQVSLTCLVKGFYPSDIAVEWESNGQPENNYK

TTPPVLDSDGSFFLYSKLTVLGRRWTLGNVFSCSVMHEALHNHYTQKSLS

LSPGK.

In some embodiments, the anti-TLR9 peptide can have the amino acid sequence (clone D2, SEQ ID NO: 19)
PREPQVYTLPPSRDELLPCQVSLTCLVKGFYPSDIAVEWESNGQPENNYK

TTPPVLDSDGSFFYSKLTVFCPRWLGGNVFSCSVMHEALHNHYTQKSLSL

SPGK.

In some embodiments, the anti-TLR9 peptide can have the amino acid sequence (clone D68, SEQ ID NO: 20)
PREPQVYTLPPSRDELTKNQVSLTCLVKGFYPSDIAVEWESNGQPENNYK

TTPPVLDSDGSFFLYSKLTVPCMRWWGGNVFSCSVMHEALHNHYTQKSLS

LSPGK.

Also disclosed are CARs comprising combinations of two or more TLR9-binding peptides, e.g., in tandem. This includes two or more of the same TLR9-binding peptide, or two or more distinct TLR9-binding peptides. These two or more anti-TLR9 peptides can be separated by a linker, such as a G4S linker. Example combinations include A23-A23, A23-D2, A23-D68, D68-D68, D68-A23, D68-D2, D2-D2, D2-A23, and D2-D68.

For example, in some embodiments, the TLR9-binding region comprises a combination of two anti-TLR9 peptides separated by a linker, having the amino acid sequence (A23-D2, SEQ ID NO: 21)
PREPQVYTLPPSRDELGIAQVSLTCLVKGFYPSDIAVEWESNGQPENNYK

TTPPVLDSDGSFFLYSKLTVLGRRWTLGNVFSCSVMHEALHNHYTQKSLS

LSPGKGGGGSGGGGSGGGGSPREPQVYTLPPSRDELLPCQVSLTCLVKGF

YPSDIAVEWESNGQPENNYKTTPPVLDSDGSFFLYSKLTVFCPRWLGGNV

FSCSVMHEALHNHYTQKSLSLSPGK.

In some embodiments, the TLR9-binding region comprises a combination of two anti-TLR9 peptides separated by a linker, having the amino acid sequence (A23-D68, SEQ ID NO: 22)
PREPQVYTLPPSRDELGIAQVSLTCLVKGFYPSDIAVEWESNGQPENNYK

TTPPVLDSDGSFFLYSKLTVLGRRWTLGNVFSCSVMHEALHNHYTQKSLS

LSPGKGGGGSGGGGSGGGGSPREPQVYTLPPSRDELTKNQVSLTCLVKGF

YPSDIAVEWESNGQPENNYKTTPPVLDSDGSFFLYSKLTVPCMRWWGGNV

FSCSVMHEALHNHYTQKSLSLSPGK.

Therefore, in some embodiments, the CAR comprises a signal peptide and TLR9-binding region having the amino acid sequence (SP-A23-D2, SEQ ID NO: 23)
MVLLVTSLLLCELPHPAFLLIPPREPQVYTLPPSRDELGIAQVSLTCLVK

GFYPSDIAVEWESNGQPENNYKTTPPVLDSDGSFFLYSKLTVLGRRWTLG

NVFSCSVMHEALHNHYTQKSLSLSPGKGGGGSGGGGSGGGGSPREPQVYT

LPPSRDELLPCQVSLTCLVKGFYPSDIAVEWESNGQPENNYKTTPPVLDS

DGSFFLYSKLTVFCPRWLGGNVFSCSVMHEALHNHYTQKSLSLSPGK.

Therefore, in some embodiments, the CAR comprises a signal peptide and TLR9-binding region having the amino acid sequence (SP-A23-D68, SEQ ID NO: 24)
MVLLVTSLLLCELPHPAFLLIPPREPQVYTLPPSRDELGIAQVSLTCLVK
GFYPSDIAVEWESNGQPENNYKTTPPVLDSDGSFFLYSKLTVLGRRWTLG
NVFSCSVMHEALHNHYTQKSLSLSPGKGGGGSGGGGSGGGGSPREPQVYT
LPPSRDELTKNQVSLTCLVKGFYPSDIAVEWESNGQPENNYKTTPPVLDS
DGSFFLYSKLTVPCMRWWGGNVFSCSVMHEALHNHYTQKSLSLSPGK.

The CAR can further comprise a linker (e.g., 218 linker or G4S linker) to link TLR9-binding region to a hinge domain. Therefore, in some embodiments, the CAR comprises a signal peptide, TLR9-binding region, and linker having the amino acid sequence (SP-A23-D2-218, SEQ ID NO: 25)
MVLLVTSLLLCELPHPAFLLIPPREPQVYTLPPSRDELGIAQVSLTCLVK
GFYPSDIAVEWESNGQPENNYKTTPPVLDSDGSFFLYSKLTVLGRRWTLG
NVFSCSVMHEALHNHYTQKSLSLSPGKGGGGSGGGGSGGGGSPREPQVYT
LPPSRDELLPCQVSLTCLVKGFYPSDIAVEWESNGQPENNYKTTPPVLDS
DGSFFLYSKLTVFCPRWLGGNVFSCSVMHEALHNHYTQKSLSLSPGKGST
SGSGKPGSGEGSTKG.

The CAR can further comprise a linker (e.g., 218 linker or G4S linker) to link TLR9-binding region to a hinge domain. Therefore, in some embodiments, the CAR comprises a signal peptide, TLR9-binding region, and linker having the amino acid sequence (SP-A23-D68-218, SEQ ID NO: 26)
MVLLVTSLLLCELPHPAFLLIPPREPQVYTLPPSRDELGIAQVSLTCLVK
GFYPSDIAVEWESNGQPENNYKTTPPVLDSDGSFFLYSKLTVLGRRWTLG
NVFSCSVMHEALHNHYTQKSLSLSPGKGGGGSGGGGSGGGGSPREPQVYT
LPPSRDELTKNQVSLTCLVKGFYPSDIAVEWESNGQPENNYKTTPPVLDS
DGSFFLYSKLTVPCMRWWGGNVFSCSVMHEALHNHYTQKSLSLSPGKGST
SGSGKPGSGEGSTKG.

In some embodiments, the CAR comprises a hinge and transmembrane domain derived from CD8. For example, the hinge and transmembrane domain can comprise the amino acid sequence (8t, SEQ ID NO: 27)
FVPVFLPAKPTTTPAPRPPTPAPTIASQPLSLRPEACRPAAGGAVHTRGL
DFACDIYIWAPLAGTCGVLLLSLVITLYCNHRNR.

In some embodiments, the endodomain comprises a CD28 costimulatory domain. For example, the CD28 costimulatory domain can comprise the amino acid sequence (SEQ ID NO: 28)
RSKRSRLLHSDYMNMTPRRPGPTRKHYQPYAPPRDFAAYRS.

In some embodiments, the endodomain comprises a 4-1BB costimulatory molecule. For example, the 4-1BB costimulatory domain can comprise the amino acid sequence (SEQ ID NO: 29)
RFSVVKRGRKKLLYIFKQPFMRPVQTTQEEDGCSCRFPEEEEGGCEL.

In some embodiments, the endodomain comprises a CD3ζ domain. For example, the CD3ζ domain can comprise the amino acid sequence (SEQ ID NO: 30)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.

In some embodiments, the transmembrane domain is linked to the signal domain or costimulatory domain with a spacer from 1 to 80 amino acids in length, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 61, 62, 64, 65, 66, 67, 68, 69, 70, 71, 72, 73, 74, 75, 76, 77. 78, 79, or 80 amino acids in length. In some embodiments, this spacer comprises an LCK-binding site derived from the C-terminus of CD8alpha (Kim et al, Science. 301(5640):1725-8 (2003)). LCK is an immediate downstream signaling effector of the T-cell activation pathway. For example, the LCK-binding site can comprise the amino acid sequence RRVCK-CPRPWKSGDKPSLSARYV (LCK, SEQ ID NO:31). In some embodiments, the spacer comprises additional amino acids before and/or after the LCK-binding site.

In some embodiments, the spacer comprises amino acid sequences different from the LCK binding site, whose function is to increase the length of the CAR endodomain. These amino acid sequences may or may not include binding sites for other intracellular proteins. In some embodiments, the spacer can be located immediately after the transmembrane domain, or elsewhere in the endodomain.

Therefore, in some embodiments, the CAR comprises a hinge, transmembrane domain, and spacer having the amino acid sequence (8t(LCK), SEQ ID NO: 32)
FVPVFLPAKPTTTPAPRPPTPAPTIASQPLSLRPEACRPAAGGAVHTRGL
DFACDIYIWAPLAGTCGVLLLSLVITLYCNHRNRRRVCKCPRPVVKSGDK
PSLSARYV.

In some embodiments, the CAR comprises a costimulatory domain containing modules derived from CD27, CD7, BTNL3, or CD28.

In some embodiments, the CAR comprises a hinge, transmembrane, and/or costimulatory domains derived from CD28 (28Z). In some embodiments, the CAR comprises a hinge, transmembrane, and/or costimulatory domains derived from CD27 (27Z). In some embodiments, the CAR comprises a hinge, transmembrane, and/or costimulatory domains derived from CD7 (7Z). In some embodiments, the CAR comprises a hinge, transmembrane, and/or costimulatory domains derived from BTNL3 (BTNC3Z). In some embodiments the CAR comprises a 4-1BB signaling domain (BBZ).

Example CAR constructs therefore include A23-28Z, D68-28Z, A23-D68-28Z, A23-D2-28Z, D68-8t-BBZ, A23-D2-8t-BBZ, A23-D2-8t(LCK)-BBZ, D68-8t(LCK)-BBZ, A23-D68-8t(LCK)-BBZ, A23-D2-8t(LCK)-BBZ, A23-8t-27Z, D68-8t-27Z, A23-D68-8t-27Z, A23-D2-8t-27Z, A23-

8t-7Z, D68-8t-7Z, A23-D58-8t-7Z, A23-D2-8t-7Z, A23-8t-BTNL3Z, D68-8t-BTNL3Z, A23-D68-8t-BTNL3Z, A23-D2-8t-BTNL3Z, A23-8t-28Z, D68-8t-28Z, A23-D68-8t-28Z, and A23-D2-8t-28Z.

In some embodiments, the disclosed CAR is defined by the formula:

SP-TLR9-HG-TM-CSR-SD; or

SP-TLR9-HG-TM-SD-CSR;

wherein "SP" represents an optional signal peptide,
wherein "TLR9" represents a TLR9-binding region,
wherein "HG" represents an optional hinge domain,
wherein "TM" represents a transmembrane domain,
wherein "CSR" represents one or more co-stimulatory signaling regions,
wherein "SD" represents an signaling domain, and
wherein "-" represents a peptide bond, linker, or spacer.

In some case, the spacer linking the TLR9-binding domain to the hinge domain comprises the amino acid sequence SEQ ID NO:11 or SEQ ID NO:12.

In some case, the spacer linking the transmembrane domain to the SD or CSR comprises an LCK-binding region of CD8alpha. For example, the LCK-binding site can have the amino acid sequence SEQ ID NO:31.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CART cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv or antibody fragment. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the endodomain comprises a 4-1BB costimulatory molecule linked to CD3zeta or its derivative containing an extra LCK binding site. LCK is an immediate downstream signaling effector of the T-cell activation pathway.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-TLR9 scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1, 2, and 3 below provide some example combinations of TLR9-binding region, co-stimulatory signaling regions, and intracellular signaling domain that can occur in the disclosed CARs. Tables 4 to 6 provide examples of combinations without either a signaling domain or a co-stimulatory signal region, i.e. so the CAR provides suboptimal activation upon binding to TLR9 and requires a second CAR containing the missing domain to bind its respective antigen in order for the cell to be activated.

TABLE 1

First Generation CARs

| Binding Region | Signal Domain |
|---|---|
| TLR9 | CD8 |
| TLR9 | CD3ζ |
| TLR9 | CD3δ |
| TLR9 | CD3γ |
| TLR9 | CD3ε |
| TLR9 | FcγRI-γ |
| TLR9 | FcγRIII-γ |
| TLR9 | FcεRIβ |
| TLR9 | FcεRIγ |
| TLR9 | DAP10 |
| TLR9 | DAP12 |
| TLR9 | CD32 |
| TLR9 | CD79a |
| TLR9 | CD79b |

TABLE 2

Second Generation CARs

| Binding Region | Co-stimulatory Signal | Signal Domain | ScFv | Co-stimulatory Signal | Signal Domain |
|---|---|---|---|---|---|
| TLR9 | CD28 | CD8 | TLR9 | CD80 | FcεRIβ |
| TLR9 | CD28 | CD3ζ | TLR9 | CD80 | FcεRIγ |
| TLR9 | CD28 | CD3δ | TLR9 | CD80 | DAP10 |
| TLR9 | CD28 | CD3γ | TLR9 | CD80 | DAP12 |
| TLR9 | CD28 | CD3ε | TLR9 | CD80 | CD32 |
| TLR9 | CD28 | FcγRI-γ | TLR9 | CD80 | CD79a |

TABLE 2-continued

Second Generation CARs

| Binding Region | Co-stimulatory Signal | Signal Domain | ScFv | Co-stimulatory Signal | Signal Domain |
|---|---|---|---|---|---|
| TLR9 | CD28 | FcγRIII-γ | TLR9 | CD80 | CD79b |
| TLR9 | CD28 | FcεRIβ | TLR9 | CD86 | CD8 |
| TLR9 | CD28 | FcεRIγ | TLR9 | CD86 | CD3ζ |
| TLR9 | CD28 | DAP10 | TLR9 | CD86 | CD3δ |
| TLR9 | CD28 | DAP12 | TLR9 | CD86 | CD3γ |
| TLR9 | CD28 | CD32 | TLR9 | CD86 | CD3ε |
| TLR9 | CD28 | CD79a | TLR9 | CD86 | FcγRI-γ |
| TLR9 | CD28 | CD79b | TLR9 | CD86 | FcγRIII-γ |
| TLR9 | CD8 | CD8 | TLR9 | CD86 | FcεRIβ |
| TLR9 | CD8 | CD3ζ | TLR9 | CD86 | FcεRIγ |
| TLR9 | CD8 | CD3δ | TLR9 | CD86 | DAP10 |
| TLR9 | CD8 | CD3γ | TLR9 | CD86 | DAP12 |
| TLR9 | CD8 | CD3ε | TLR9 | CD86 | CD32 |
| TLR9 | CD8 | FcγRI-γ | TLR9 | CD86 | CD79a |
| TLR9 | CD8 | FcγRIII-γ | TLR9 | CD86 | CD79b |
| TLR9 | CD8 | FcεRIβ | TLR9 | OX40 | CD8 |
| TLR9 | CD8 | FcεRIγ | TLR9 | OX40 | CD3ζ |
| TLR9 | CD8 | DAP10 | TLR9 | OX40 | CD3δ |
| TLR9 | CD8 | DAP12 | TLR9 | OX40 | CD3γ |
| TLR9 | CD8 | CD32 | TLR9 | OX40 | CD3ε |
| TLR9 | CD8 | CD79a | TLR9 | OX40 | FcγRI-γ |
| TLR9 | CD8 | CD79b | TLR9 | OX40 | FcγRIII-γ |
| TLR9 | CD4 | CD8 | TLR9 | OX40 | FcεRIβ |
| TLR9 | CD4 | CD3ζ | TLR9 | OX40 | FcεRIγ |
| TLR9 | CD4 | CD3δ | TLR9 | OX40 | DAP10 |
| TLR9 | CD4 | CD3γ | TLR9 | OX40 | DAP12 |
| TLR9 | CD4 | CD3ε | TLR9 | OX40 | CD32 |
| TLR9 | CD4 | FcγRI-γ | TLR9 | OX40 | CD79a |
| TLR9 | CD4 | FcγRIII-γ | TLR9 | OX40 | CD79b |
| TLR9 | CD4 | FcεRIβ | TLR9 | DAP10 | CD8 |
| TLR9 | CD4 | FcεRIγ | TLR9 | DAP10 | CD3ζ |
| TLR9 | CD4 | DAP10 | TLR9 | DAP10 | CD3δ |
| TLR9 | CD4 | DAP12 | TLR9 | DAP10 | CD3γ |
| TLR9 | CD4 | CD32 | TLR9 | DAP10 | CD3ε |
| TLR9 | CD4 | CD79a | TLR9 | DAP10 | FcγRI-γ |
| TLR9 | CD4 | CD79b | TLR9 | DAP10 | FcγRIII-γ |
| TLR9 | b2c | CD8 | TLR9 | DAP10 | FcεRIβ |
| TLR9 | b2c | CD3ζ | TLR9 | DAP10 | FcεRIγ |
| TLR9 | b2c | CD3δ | TLR9 | DAP10 | DAP10 |
| TLR9 | b2c | CD3γ | TLR9 | DAP10 | DAP12 |
| TLR9 | b2c | CD3ε | TLR9 | DAP10 | CD32 |
| TLR9 | b2c | FcγRI-γ | TLR9 | DAP10 | CD79a |
| TLR9 | b2c | FcγRIII-γ | TLR9 | DAP10 | CD79b |
| TLR9 | b2c | FcεRIβ | TLR9 | DAP12 | CD8 |
| TLR9 | b2c | FcεRIγ | TLR9 | DAP12 | CD3ζ |
| TLR9 | b2c | DAP10 | TLR9 | DAP12 | CD3δ |
| TLR9 | b2c | DAP12 | TLR9 | DAP12 | CD3γ |
| TLR9 | b2c | CD32 | TLR9 | DAP12 | CD3ε |
| TLR9 | b2c | CD79a | TLR9 | DAP12 | FcγRI-γ |
| TLR9 | b2c | CD79b | TLR9 | DAP12 | FcγRIII-γ |
| TLR9 | CD137/41BB | CD8 | TLR9 | DAP12 | FcεRIβ |
| TLR9 | CD137/41BB | CD3ζ | TLR9 | DAP12 | FcεRIγ |
| TLR9 | CD137/41BB | CD3δ | TLR9 | DAP12 | DAP10 |
| TLR9 | CD137/41BB | CD3γ | TLR9 | DAP12 | DAP12 |
| TLR9 | CD137/41BB | CD3ε | TLR9 | DAP12 | CD32 |
| TLR9 | CD137/41BB | FcγRI-γ | TLR9 | DAP12 | CD79a |
| TLR9 | CD137/41BB | FcγRIII-γ | TLR9 | DAP12 | CD79b |
| TLR9 | CD137/41BB | FcεRIβ | TLR9 | MyD88 | CD8 |
| TLR9 | CD137/41BB | FcεRIγ | TLR9 | MyD88 | CD3ζ |
| TLR9 | CD137/41BB | DAP10 | TLR9 | MyD88 | CD3δ |
| TLR9 | CD137/41BB | DAP12 | TLR9 | MyD88 | CD3γ |
| TLR9 | CD137/41BB | CD32 | TLR9 | MyD88 | CD3ε |
| TLR9 | CD137/41BB | CD79a | TLR9 | MyD88 | FcγRI-γ |
| TLR9 | CD137/41BB | CD79b | TLR9 | MyD88 | FcγRIII-γ |
| TLR9 | ICOS | CD8 | TLR9 | MyD88 | FcεRIβ |
| TLR9 | ICOS | CD3ζ | TLR9 | MyD88 | FcεRIγ |
| TLR9 | ICOS | CD3δ | TLR9 | MyD88 | DAP10 |
| TLR9 | ICOS | CD3γ | TLR9 | MyD88 | DAP12 |
| TLR9 | ICOS | CD3ε | TLR9 | MyD88 | CD32 |
| TLR9 | ICOS | FcγRI-γ | TLR9 | MyD88 | CD79a |
| TLR9 | ICOS | FcγRIII-γ | TLR9 | MyD88 | CD79b |
| TLR9 | ICOS | FcεRIβ | TLR9 | CD7 | CD8 |
| TLR9 | ICOS | FcεRIγ | TLR9 | CD7 | CD3ζ |
| TLR9 | ICOS | DAP10 | TLR9 | CD7 | CD3δ |
| TLR9 | ICOS | DAP12 | TLR9 | CD7 | CD3γ |
| TLR9 | ICOS | CD32 | TLR9 | CD7 | CD3ε |
| TLR9 | ICOS | CD79a | TLR9 | CD7 | FcγRI-γ |
| TLR9 | ICOS | CD79b | TLR9 | CD7 | FcγRIII-γ |
| TLR9 | CD27 | CD8 | TLR9 | CD7 | FcεRIβ |
| TLR9 | CD27 | CD3ζ | TLR9 | CD7 | FcεRIγ |
| TLR9 | CD27 | CD3δ | TLR9 | CD7 | DAP10 |
| TLR9 | CD27 | CD3γ | TLR9 | CD7 | DAP12 |
| TLR9 | CD27 | CD3ε | TLR9 | CD7 | CD32 |
| TLR9 | CD27 | FcγRI-γ | TLR9 | CD7 | CD79a |
| TLR9 | CD27 | FcγRIII-γ | TLR9 | CD7 | CD79b |
| TLR9 | CD27 | FcεRIβ | TLR9 | BTNL3 | CD8 |
| TLR9 | CD27 | FcεRIγ | TLR9 | BTNL3 | CD3ζ |
| TLR9 | CD27 | DAP10 | TLR9 | BTNL3 | CD3δ |
| TLR9 | CD27 | DAP12 | TLR9 | BTNL3 | CD3γ |
| TLR9 | CD27 | CD32 | TLR9 | BTNL3 | CD3ε |
| TLR9 | CD27 | CD79a | TLR9 | BTNL3 | FcγRI-γ |
| TLR9 | CD27 | CD79b | TLR9 | BTNL3 | FcγRIII-γ |
| TLR9 | CD28δ | CD8 | TLR9 | BTNL3 | FcεRIβ |
| TLR9 | CD28δ | CD3ζ | TLR9 | BTNL3 | FcεRIγ |
| TLR9 | CD28δ | CD3δ | TLR9 | BTNL3 | DAP10 |
| TLR9 | CD28δ | CD3γ | TLR9 | BTNL3 | DAP12 |
| TLR9 | CD28δ | CD3ε | TLR9 | BTNL3 | CD32 |
| TLR9 | CD28δ | FcγRI-γ | TLR9 | BTNL3 | CD79a |
| TLR9 | CD28δ | FcγRIII-γ | TLR9 | BTNL3 | CD79b |
| TLR9 | CD28δ | FcεRIβ | TLR9 | NKG2D | CD8 |
| TLR9 | CD28δ | FcεRIγ | TLR9 | NKG2D | CD3ζ |
| TLR9 | CD28δ | DAP10 | TLR9 | NKG2D | CD3δ |
| TLR9 | CD28δ | DAP12 | TLR9 | NKG2D | CD3γ |
| TLR9 | CD28δ | CD32 | TLR9 | NKG2D | CD3ε |
| TLR9 | CD28δ | CD79a | TLR9 | NKG2D | FcγRI-γ |
| TLR9 | CD28δ | CD79b | TLR9 | NKG2D | FcγRIII-γ |
| TLR9 | CD80 | CD8 | TLR9 | NKG2D | FcεRIβ |
| TLR9 | CD80 | CD3ζ | TLR9 | NKG2D | FcεRIγ |
| TLR9 | CD80 | CD3δ | TLR9 | NKG2D | DAP10 |
| TLR9 | CD80 | CD3γ | TLR9 | NKG2D | DAP12 |
| TLR9 | CD80 | CD3ε | TLR9 | NKG2D | CD32 |
| TLR9 | CD80 | FcγRI-γ | TLR9 | NKG2D | CD79a |
| TLR9 | CD80 | FcγRIII-γ | TLR9 | NKG2D | CD79b |

TABLE 3

Third Generation CARs

| Binding Region | Co-stimulatory Signal | Co-stimulatory Signal | Signal Domain |
|---|---|---|---|
| TLR9 | CD28 | CD28 | CD8 |
| TLR9 | CD28 | CD28 | CD3ζ |
| TLR9 | CD28 | CD28 | CD3δ |
| TLR9 | CD28 | CD28 | CD3γ |
| TLR9 | CD28 | CD28 | CD3ε |
| TLR9 | CD28 | CD28 | FcγRI-γ |
| TLR9 | CD28 | CD28 | FcγRIII-γ |
| TLR9 | CD28 | CD28 | FcεRIβ |
| TLR9 | CD28 | CD28 | FcεRIγ |
| TLR9 | CD28 | CD28 | DAP10 |
| TLR9 | CD28 | CD28 | DAP12 |
| TLR9 | CD28 | CD28 | CD32 |
| TLR9 | CD28 | CD28 | CD79a |
| TLR9 | CD28 | CD28 | CD79b |
| TLR9 | CD28 | CD8 | CD8 |
| TLR9 | CD28 | CD8 | CD3ζ |
| TLR9 | CD28 | CD8 | CD3δ |
| TLR9 | CD28 | CD8 | CD3γ |
| TLR9 | CD28 | CD8 | CD3ε |
| TLR9 | CD28 | CD8 | FcγRI-γ |
| TLR9 | CD28 | CD8 | FcγRIII-γ |
| TLR9 | CD28 | CD8 | FcεRIβ |
| TLR9 | CD28 | CD8 | FcεRIγ |

TABLE 3-continued

Third Generation CARs

| Binding Region | Co-stimulatory Signal | Co-stimulatory Signal | Signal Domain |
|---|---|---|---|
| TLR9 | CD28 | CD8 | DAP10 |
| TLR9 | CD28 | CD8 | DAP12 |
| TLR9 | CD28 | CD8 | CD32 |
| TLR9 | CD28 | CD8 | CD79a |
| TLR9 | CD28 | CD8 | CD79b |
| TLR9 | CD28 | CD4 | CD8 |
| TLR9 | CD28 | CD4 | CD3ζ |
| TLR9 | CD28 | CD4 | CD3δ |
| TLR9 | CD28 | CD4 | CD3γ |
| TLR9 | CD28 | CD4 | CD3ε |
| TLR9 | CD28 | CD4 | FcγRI-γ |
| TLR9 | CD28 | CD4 | FcγRIII-γ |
| TLR9 | CD28 | CD4 | FcεRIβ |
| TLR9 | CD28 | CD4 | FcεRIγ |
| TLR9 | CD28 | CD4 | DAP10 |
| TLR9 | CD28 | CD4 | DAP12 |
| TLR9 | CD28 | CD4 | CD32 |
| TLR9 | CD28 | CD4 | CD79a |
| TLR9 | CD28 | CD4 | CD79b |
| TLR9 | CD28 | b2c | CD8 |
| TLR9 | CD28 | b2c | CD3ζ |
| TLR9 | CD28 | b2c | CD3δ |
| TLR9 | CD28 | b2c | CD3γ |
| TLR9 | CD28 | b2c | CD3ε |
| TLR9 | CD28 | b2c | FcγRI-γ |
| TLR9 | CD28 | b2c | FcγRIII-γ |
| TLR9 | CD28 | b2c | FcεRIβ |
| TLR9 | CD28 | b2c | FcεRIγ |
| TLR9 | CD28 | b2c | DAP10 |
| TLR9 | CD28 | b2c | DAP12 |
| TLR9 | CD28 | b2c | CD32 |
| TLR9 | CD28 | b2c | CD79a |
| TLR9 | CD28 | b2c | CD79b |
| TLR9 | CD28 | CD137/41BB | CD8 |
| TLR9 | CD28 | CD137/41BB | CD3ζ |
| TLR9 | CD28 | CD137/41BB | CD3δ |
| TLR9 | CD28 | CD137/41BB | CD3γ |
| TLR9 | CD28 | CD137/41BB | CD3ε |
| TLR9 | CD28 | CD137/41BB | FcγRI-γ |
| TLR9 | CD28 | CD137/41BB | FcγRIII-γ |
| TLR9 | CD28 | CD137/41BB | FcεRIβ |
| TLR9 | CD28 | CD137/41BB | FcεRIγ |
| TLR9 | CD28 | CD137/41BB | DAP10 |
| TLR9 | CD28 | CD137/41BB | DAP12 |
| TLR9 | CD28 | CD137/41BB | CD32 |
| TLR9 | CD28 | CD137/41BB | CD79a |
| TLR9 | CD28 | CD137/41BB | CD79b |
| TLR9 | CD28 | ICOS | CD8 |
| TLR9 | CD28 | ICOS | CD3ζ |
| TLR9 | CD28 | ICOS | CD3δ |
| TLR9 | CD28 | ICOS | CD3γ |
| TLR9 | CD28 | ICOS | CD3ε |
| TLR9 | CD28 | ICOS | FcγRI-γ |
| TLR9 | CD28 | ICOS | FcγRIII-γ |
| TLR9 | CD28 | ICOS | FcεRIβ |
| TLR9 | CD28 | ICOS | FcεRIγ |
| TLR9 | CD28 | ICOS | DAP10 |
| TLR9 | CD28 | ICOS | DAP12 |
| TLR9 | CD28 | ICOS | CD32 |
| TLR9 | CD28 | ICOS | CD79a |
| TLR9 | CD28 | ICOS | CD79b |
| TLR9 | CD28 | CD27 | CD8 |
| TLR9 | CD28 | CD27 | CD3ζ |
| TLR9 | CD28 | CD27 | CD3δ |
| TLR9 | CD28 | CD27 | CD3γ |
| TLR9 | CD28 | CD27 | CD3ε |
| TLR9 | CD28 | CD27 | FcγRI-γ |
| TLR9 | CD28 | CD27 | FcγRIII-γ |
| TLR9 | CD28 | CD27 | FcεRIβ |
| TLR9 | CD28 | CD27 | FcεRIγ |
| TLR9 | CD28 | CD27 | DAP10 |
| TLR9 | CD28 | CD27 | DAP12 |
| TLR9 | CD28 | CD27 | CD32 |
| TLR9 | CD28 | CD27 | CD79a |
| TLR9 | CD28 | CD27 | CD79b |
| TLR9 | CD28 | CD28δ | CD8 |
| TLR9 | CD28 | CD28δ | CD3ζ |
| TLR9 | CD28 | CD28δ | CD3δ |
| TLR9 | CD28 | CD28δ | CD3γ |
| TLR9 | CD28 | CD28δ | CD3ε |
| TLR9 | CD28 | CD28δ | FcγRI-γ |
| TLR9 | CD28 | CD28δ | FcγRIII-γ |
| TLR9 | CD28 | CD28δ | FcεRIβ |
| TLR9 | CD28 | CD28δ | FcεRIγ |
| TLR9 | CD28 | CD28δ | DAP10 |
| TLR9 | CD28 | CD28δ | DAP12 |
| TLR9 | CD28 | CD28δ | CD32 |
| TLR9 | CD28 | CD28δ | CD79a |
| TLR9 | CD28 | CD28δ | CD79b |
| TLR9 | CD28 | CD80 | CD8 |
| TLR9 | CD28 | CD80 | CD3ζ |
| TLR9 | CD28 | CD80 | CD3δ |
| TLR9 | CD28 | CD80 | CD3γ |
| TLR9 | CD28 | CD80 | CD3ε |
| TLR9 | CD28 | CD80 | FcγRI-γ |
| TLR9 | CD28 | CD80 | FcγRIII-γ |
| TLR9 | CD28 | CD80 | FcεRIβ |
| TLR9 | CD28 | CD80 | FcεRIγ |
| TLR9 | CD28 | CD80 | DAP10 |
| TLR9 | CD28 | CD80 | DAP12 |
| TLR9 | CD28 | CD80 | CD32 |
| TLR9 | CD28 | CD80 | CD79a |
| TLR9 | CD28 | CD80 | CD79b |
| TLR9 | CD28 | CD86 | CD8 |
| TLR9 | CD28 | CD86 | CD3ζ |
| TLR9 | CD28 | CD86 | CD3δ |
| TLR9 | CD28 | CD86 | CD3γ |
| TLR9 | CD28 | CD86 | CD3ε |
| TLR9 | CD28 | CD86 | FcγRI-γ |
| TLR9 | CD28 | CD86 | FcγRIII-γ |
| TLR9 | CD28 | CD86 | FcεRIβ |
| TLR9 | CD28 | CD86 | FcεRIγ |
| TLR9 | CD28 | CD86 | DAP10 |
| TLR9 | CD28 | CD86 | DAP12 |
| TLR9 | CD28 | CD86 | CD32 |
| TLR9 | CD28 | CD86 | CD79a |
| TLR9 | CD28 | CD86 | CD79b |
| TLR9 | CD28 | OX40 | CD8 |
| TLR9 | CD28 | OX40 | CD3ζ |
| TLR9 | CD28 | OX40 | CD3δ |
| TLR9 | CD28 | OX40 | CD3γ |
| TLR9 | CD28 | OX40 | CD3ε |
| TLR9 | CD28 | OX40 | FcγRI-γ |
| TLR9 | CD28 | OX40 | FcγRIII-γ |
| TLR9 | CD28 | OX40 | FcεRIβ |
| TLR9 | CD28 | OX40 | FcεRIγ |
| TLR9 | CD28 | OX40 | DAP10 |
| TLR9 | CD28 | OX40 | DAP12 |
| TLR9 | CD28 | OX40 | CD32 |
| TLR9 | CD28 | OX40 | CD79a |
| TLR9 | CD28 | OX40 | CD79b |
| TLR9 | CD28 | DAP10 | CD8 |
| TLR9 | CD28 | DAP10 | CD3ζ |
| TLR9 | CD28 | DAP10 | CD3δ |
| TLR9 | CD28 | DAP10 | CD3γ |
| TLR9 | CD28 | DAP10 | CD3ε |
| TLR9 | CD28 | DAP10 | FcγRI-γ |
| TLR9 | CD28 | DAP10 | FcγRIII-γ |
| TLR9 | CD28 | DAP10 | FcεRIβ |
| TLR9 | CD28 | DAP10 | FcεRIγ |
| TLR9 | CD28 | DAP10 | DAP10 |
| TLR9 | CD28 | DAP10 | DAP12 |
| TLR9 | CD28 | DAP10 | CD32 |
| TLR9 | CD28 | DAP10 | CD79a |
| TLR9 | CD28 | DAP10 | CD79b |
| TLR9 | CD28 | DAP12 | CD8 |
| TLR9 | CD28 | DAP12 | CD3ζ |
| TLR9 | CD28 | DAP12 | CD3δ |

TABLE 3-continued

Third Generation CARs

| Binding Region | Co-stimulatory Signal | Co-stimulatory Signal | Signal Domain |
|---|---|---|---|
| TLR9 | CD28 | DAP12 | CD3γ |
| TLR9 | CD28 | DAP12 | CD3ε |
| TLR9 | CD28 | DAP12 | FcγRI-γ |
| TLR9 | CD28 | DAP12 | FcγRIII-γ |
| TLR9 | CD28 | DAP12 | FcεRIβ |
| TLR9 | CD28 | DAP12 | FcεRIγ |
| TLR9 | CD28 | DAP12 | DAP10 |
| TLR9 | CD28 | DAP12 | DAP12 |
| TLR9 | CD28 | DAP12 | CD32 |
| TLR9 | CD28 | DAP12 | CD79a |
| TLR9 | CD28 | DAP12 | CD79b |
| TLR9 | CD28 | MyD88 | CD8 |
| TLR9 | CD28 | MyD88 | CD3ζ |
| TLR9 | CD28 | MyD88 | CD3δ |
| TLR9 | CD28 | MyD88 | CD3γ |
| TLR9 | CD28 | MyD88 | CD3ε |
| TLR9 | CD28 | MyD88 | FcγRI-γ |
| TLR9 | CD28 | MyD88 | FcγRIII-γ |
| TLR9 | CD28 | MyD88 | FcεRIβ |
| TLR9 | CD28 | MyD88 | FcεRIγ |
| TLR9 | CD28 | MyD88 | DAP10 |
| TLR9 | CD28 | MyD88 | DAP12 |
| TLR9 | CD28 | MyD88 | CD32 |
| TLR9 | CD28 | MyD88 | CD79a |
| TLR9 | CD28 | MyD88 | CD79b |
| TLR9 | CD28 | CD7 | CD8 |
| TLR9 | CD28 | CD7 | CD3ζ |
| TLR9 | CD28 | CD7 | CD3δ |
| TLR9 | CD28 | CD7 | CD3γ |
| TLR9 | CD28 | CD7 | CD3ε |
| TLR9 | CD28 | CD7 | FcγRI-γ |
| TLR9 | CD28 | CD7 | FcγRIII-γ |
| TLR9 | CD28 | CD7 | FcεRIβ |
| TLR9 | CD28 | CD7 | FcεRIγ |
| TLR9 | CD28 | CD7 | DAP10 |
| TLR9 | CD28 | CD7 | DAP12 |
| TLR9 | CD28 | CD7 | CD32 |
| TLR9 | CD28 | CD7 | CD79a |
| TLR9 | CD28 | CD7 | CD79b |
| TLR9 | CD28 | BTNL3 | CD8 |
| TLR9 | CD28 | BTNL3 | CD3ζ |
| TLR9 | CD28 | BTNL3 | CD3δ |
| TLR9 | CD28 | BTNL3 | CD3γ |
| TLR9 | CD28 | BTNL3 | CD3ε |
| TLR9 | CD28 | BTNL3 | FcγRI-γ |
| TLR9 | CD28 | BTNL3 | FcγRIII-γ |
| TLR9 | CD28 | BTNL3 | FcεRIβ |
| TLR9 | CD28 | BTNL3 | FcεRIγ |
| TLR9 | CD28 | BTNL3 | DAP10 |
| TLR9 | CD28 | BTNL3 | DAP12 |
| TLR9 | CD28 | BTNL3 | CD32 |
| TLR9 | CD28 | BTNL3 | CD79a |
| TLR9 | CD28 | BTNL3 | CD79b |
| TLR9 | CD28 | NKG2D | CD8 |
| TLR9 | CD28 | NKG2D | CD3ζ |
| TLR9 | CD28 | NKG2D | CD3δ |
| TLR9 | CD28 | NKG2D | CD3γ |
| TLR9 | CD28 | NKG2D | CD3ε |
| TLR9 | CD28 | NKG2D | FcγRI-γ |
| TLR9 | CD28 | NKG2D | FcγRIII-γ |
| TLR9 | CD28 | NKG2D | FcεRIβ |
| TLR9 | CD28 | NKG2D | FcεRIγ |
| TLR9 | CD28 | NKG2D | DAP10 |
| TLR9 | CD28 | NKG2D | DAP12 |
| TLR9 | CD28 | NKG2D | CD32 |
| TLR9 | CD28 | NKG2D | CD79a |
| TLR9 | CD28 | NKG2D | CD79b |
| TLR9 | CD8 | CD28 | CD8 |
| TLR9 | CD8 | CD28 | CD3ζ |
| TLR9 | CD8 | CD28 | CD3δ |
| TLR9 | CD8 | CD28 | CD3γ |
| TLR9 | CD8 | CD28 | CD3ε |
| TLR9 | CD8 | CD28 | FcγRI-γ |
| TLR9 | CD8 | CD28 | FcγRIII-γ |
| TLR9 | CD8 | CD28 | FcεRIβ |
| TLR9 | CD8 | CD28 | FcεRIγ |
| TLR9 | CD8 | CD28 | DAP10 |
| TLR9 | CD8 | CD28 | DAP12 |
| TLR9 | CD8 | CD28 | CD32 |
| TLR9 | CD8 | CD28 | CD79a |
| TLR9 | CD8 | CD28 | CD79b |
| TLR9 | CD8 | CD8 | CD8 |
| TLR9 | CD8 | CD8 | CD3ζ |
| TLR9 | CD8 | CD8 | CD3δ |
| TLR9 | CD8 | CD8 | CD3γ |
| TLR9 | CD8 | CD8 | CD3ε |
| TLR9 | CD8 | CD8 | FcγRI-γ |
| TLR9 | CD8 | CD8 | FcγRIII-γ |
| TLR9 | CD8 | CD8 | FcεRIβ |
| TLR9 | CD8 | CD8 | FcεRIγ |
| TLR9 | CD8 | CD8 | DAP10 |
| TLR9 | CD8 | CD8 | DAP12 |
| TLR9 | CD8 | CD8 | CD32 |
| TLR9 | CD8 | CD8 | CD79a |
| TLR9 | CD8 | CD8 | CD79b |
| TLR9 | CD8 | CD4 | CD8 |
| TLR9 | CD8 | CD4 | CD3ζ |
| TLR9 | CD8 | CD4 | CD3δ |
| TLR9 | CD8 | CD4 | CD3γ |
| TLR9 | CD8 | CD4 | CD3ε |
| TLR9 | CD8 | CD4 | FcγRI-γ |
| TLR9 | CD8 | CD4 | FcγRIII-γ |
| TLR9 | CD8 | CD4 | FcεRIβ |
| TLR9 | CD8 | CD4 | FcεRIγ |
| TLR9 | CD8 | CD4 | DAP10 |
| TLR9 | CD8 | CD4 | DAP12 |
| TLR9 | CD8 | CD4 | CD32 |
| TLR9 | CD8 | CD4 | CD79a |
| TLR9 | CD8 | CD4 | CD79b |
| TLR9 | CD8 | b2c | CD8 |
| TLR9 | CD8 | b2c | CD3ζ |
| TLR9 | CD8 | b2c | CD3δ |
| TLR9 | CD8 | b2c | CD3γ |
| TLR9 | CD8 | b2c | CD3ε |
| TLR9 | CD8 | b2c | FcγRI-γ |
| TLR9 | CD8 | b2c | FcγRIII-γ |
| TLR9 | CD8 | b2c | FcεRIβ |
| TLR9 | CD8 | b2c | FcεRIγ |
| TLR9 | CD8 | b2c | DAP10 |
| TLR9 | CD8 | b2c | DAP12 |
| TLR9 | CD8 | b2c | CD32 |
| TLR9 | CD8 | b2c | CD79a |
| TLR9 | CD8 | b2c | CD79b |
| TLR9 | CD8 | CD137/41BB | CD8 |
| TLR9 | CD8 | CD137/41BB | CD3ζ |
| TLR9 | CD8 | CD137/41BB | CD3δ |
| TLR9 | CD8 | CD137/41BB | CD3γ |
| TLR9 | CD8 | CD137/41BB | CD3ε |
| TLR9 | CD8 | CD137/41BB | FcγRI-γ |
| TLR9 | CD8 | CD137/41BB | FcγRIII-γ |
| TLR9 | CD8 | CD137/41BB | FcεRIβ |
| TLR9 | CD8 | CD137/41BB | FcεRIγ |
| TLR9 | CD8 | CD137/41BB | DAP10 |
| TLR9 | CD8 | CD137/41BB | DAP12 |
| TLR9 | CD8 | CD137/41BB | CD32 |
| TLR9 | CD8 | CD137/41BB | CD79a |
| TLR9 | CD8 | CD137/41BB | CD79b |
| TLR9 | CD8 | ICOS | CD8 |
| TLR9 | CD8 | ICOS | CD3ζ |
| TLR9 | CD8 | ICOS | CD3δ |
| TLR9 | CD8 | ICOS | CD3γ |
| TLR9 | CD8 | ICOS | CD3ε |
| TLR9 | CD8 | ICOS | FcγRI-γ |
| TLR9 | CD8 | ICOS | FcγRIII-γ |
| TLR9 | CD8 | ICOS | FcεRIβ |
| TLR9 | CD8 | ICOS | FcεRIγ |
| TLR9 | CD8 | ICOS | DAP10 |
| TLR9 | CD8 | ICOS | DAP12 |

TABLE 3-continued

Third Generation CARs

| Binding Region | Co-stimulatory Signal | Co-stimulatory Signal | Signal Domain |
|---|---|---|---|
| TLR9 | CD8 | ICOS | CD32 |
| TLR9 | CD8 | ICOS | CD79a |
| TLR9 | CD8 | ICOS | CD79b |
| TLR9 | CD8 | CD27 | CD8 |
| TLR9 | CD8 | CD27 | CD3ζ |
| TLR9 | CD8 | CD27 | CD3δ |
| TLR9 | CD8 | CD27 | CD3γ |
| TLR9 | CD8 | CD27 | CD3ε |
| TLR9 | CD8 | CD27 | FcγRI-γ |
| TLR9 | CD8 | CD27 | FcγRIII-γ |
| TLR9 | CD8 | CD27 | FcεRIβ |
| TLR9 | CD8 | CD27 | FcεRIγ |
| TLR9 | CD8 | CD27 | DAP10 |
| TLR9 | CD8 | CD27 | DAP12 |
| TLR9 | CD8 | CD27 | CD32 |
| TLR9 | CD8 | CD27 | CD79a |
| TLR9 | CD8 | CD27 | CD79b |
| TLR9 | CD8 | CD28δ | CD8 |
| TLR9 | CD8 | CD28δ | CD3ζ |
| TLR9 | CD8 | CD28δ | CD3δ |
| TLR9 | CD8 | CD28δ | CD3γ |
| TLR9 | CD8 | CD28δ | CD3ε |
| TLR9 | CD8 | CD28δ | FcγRI-γ |
| TLR9 | CD8 | CD28δ | FcγRIII-γ |
| TLR9 | CD8 | CD28δ | FcεRIβ |
| TLR9 | CD8 | CD28δ | FcεRIγ |
| TLR9 | CD8 | CD28δ | DAP10 |
| TLR9 | CD8 | CD28δ | DAP12 |
| TLR9 | CD8 | CD28δ | CD32 |
| TLR9 | CD8 | CD28δ | CD79a |
| TLR9 | CD8 | CD28δ | CD79b |
| TLR9 | CD8 | CD80 | CD8 |
| TLR9 | CD8 | CD80 | CD3ζ |
| TLR9 | CD8 | CD80 | CD3δ |
| TLR9 | CD8 | CD80 | CD3γ |
| TLR9 | CD8 | CD80 | CD3ε |
| TLR9 | CD8 | CD80 | FcγRI-γ |
| TLR9 | CD8 | CD80 | FcγRIII-γ |
| TLR9 | CD8 | CD80 | FcεRIβ |
| TLR9 | CD8 | CD80 | FcεRIγ |
| TLR9 | CD8 | CD80 | DAP10 |
| TLR9 | CD8 | CD80 | DAP12 |
| TLR9 | CD8 | CD80 | CD32 |
| TLR9 | CD8 | CD80 | CD79a |
| TLR9 | CD8 | CD80 | CD79b |
| TLR9 | CD8 | CD86 | CD8 |
| TLR9 | CD8 | CD86 | CD3ζ |
| TLR9 | CD8 | CD86 | CD3δ |
| TLR9 | CD8 | CD86 | CD3γ |
| TLR9 | CD8 | CD86 | CD3ε |
| TLR9 | CD8 | CD86 | FcγRI-γ |
| TLR9 | CD8 | CD86 | FcγRIII-γ |
| TLR9 | CD8 | CD86 | FcεRIβ |
| TLR9 | CD8 | CD86 | FcεRIγ |
| TLR9 | CD8 | CD86 | DAP10 |
| TLR9 | CD8 | CD86 | DAP12 |
| TLR9 | CD8 | CD86 | CD32 |
| TLR9 | CD8 | CD86 | CD79a |
| TLR9 | CD8 | CD86 | CD79b |
| TLR9 | CD8 | OX40 | CD8 |
| TLR9 | CD8 | OX40 | CD3ζ |
| TLR9 | CD8 | OX40 | CD3δ |
| TLR9 | CD8 | OX40 | CD3γ |
| TLR9 | CD8 | OX40 | CD3ε |
| TLR9 | CD8 | OX40 | FcγRI-γ |
| TLR9 | CD8 | OX40 | FcγRIII-γ |
| TLR9 | CD8 | OX40 | FcεRIβ |
| TLR9 | CD8 | OX40 | FcεRIγ |
| TLR9 | CD8 | OX40 | DAP10 |
| TLR9 | CD8 | OX40 | DAP12 |
| TLR9 | CD8 | OX40 | CD32 |
| TLR9 | CD8 | OX40 | CD79a |
| TLR9 | CD8 | OX40 | CD79b |
| TLR9 | CD8 | DAP10 | CD8 |
| TLR9 | CD8 | DAP10 | CD3ζ |
| TLR9 | CD8 | DAP10 | CD3δ |
| TLR9 | CD8 | DAP10 | CD3γ |
| TLR9 | CD8 | DAP10 | CD3ε |
| TLR9 | CD8 | DAP10 | FcγRI-γ |
| TLR9 | CD8 | DAP10 | FcγRIII-γ |
| TLR9 | CD8 | DAP10 | FcεRIβ |
| TLR9 | CD8 | DAP10 | FcεRIγ |
| TLR9 | CD8 | DAP10 | DAP10 |
| TLR9 | CD8 | DAP10 | DAP12 |
| TLR9 | CD8 | DAP10 | CD32 |
| TLR9 | CD8 | DAP10 | CD79a |
| TLR9 | CD8 | DAP10 | CD79b |
| TLR9 | CD8 | DAP12 | CD8 |
| TLR9 | CD8 | DAP12 | CD3ζ |
| TLR9 | CD8 | DAP12 | CD3δ |
| TLR9 | CD8 | DAP12 | CD3γ |
| TLR9 | CD8 | DAP12 | CD3ε |
| TLR9 | CD8 | DAP12 | FcγRI-γ |
| TLR9 | CD8 | DAP12 | FcγRIII-γ |
| TLR9 | CD8 | DAP12 | FcεRIβ |
| TLR9 | CD8 | DAP12 | FcεRIγ |
| TLR9 | CD8 | DAP12 | DAP10 |
| TLR9 | CD8 | DAP12 | DAP12 |
| TLR9 | CD8 | DAP12 | CD32 |
| TLR9 | CD8 | DAP12 | CD79a |
| TLR9 | CD8 | DAP12 | CD79b |
| TLR9 | CD8 | MyD88 | CD8 |
| TLR9 | CD8 | MyD88 | CD3ζ |
| TLR9 | CD8 | MyD88 | CD3δ |
| TLR9 | CD8 | MyD88 | CD3γ |
| TLR9 | CD8 | MyD88 | CD3ε |
| TLR9 | CD8 | MyD88 | FcγRI-γ |
| TLR9 | CD8 | MyD88 | FcγRIII-γ |
| TLR9 | CD8 | MyD88 | FcεRIβ |
| TLR9 | CD8 | MyD88 | FcεRIγ |
| TLR9 | CD8 | MyD88 | DAP10 |
| TLR9 | CD8 | MyD88 | DAP12 |
| TLR9 | CD8 | MyD88 | CD32 |
| TLR9 | CD8 | MyD88 | CD79a |
| TLR9 | CD8 | MyD88 | CD79b |
| TLR9 | CD8 | CD7 | CD8 |
| TLR9 | CD8 | CD7 | CD3ζ |
| TLR9 | CD8 | CD7 | CD3δ |
| TLR9 | CD8 | CD7 | CD3γ |
| TLR9 | CD8 | CD7 | CD3ε |
| TLR9 | CD8 | CD7 | FcγRI-γ |
| TLR9 | CD8 | CD7 | FcγRIII-γ |
| TLR9 | CD8 | CD7 | FcεRIβ |
| TLR9 | CD8 | CD7 | FcεRIγ |
| TLR9 | CD8 | CD7 | DAP10 |
| TLR9 | CD8 | CD7 | DAP12 |
| TLR9 | CD8 | CD7 | CD32 |
| TLR9 | CD8 | CD7 | CD79a |
| TLR9 | CD8 | CD7 | CD79b |
| TLR9 | CD8 | BTNL3 | CD8 |
| TLR9 | CD8 | BTNL3 | CD3ζ |
| TLR9 | CD8 | BTNL3 | CD3δ |
| TLR9 | CD8 | BTNL3 | CD3γ |
| TLR9 | CD8 | BTNL3 | CD3ε |
| TLR9 | CD8 | BTNL3 | FcγRI-γ |
| TLR9 | CD8 | BTNL3 | FcγRIII-γ |
| TLR9 | CD8 | BTNL3 | FcεRIβ |
| TLR9 | CD8 | BTNL3 | FcεRIγ |
| TLR9 | CD8 | BTNL3 | DAP10 |
| TLR9 | CD8 | BTNL3 | DAP12 |
| TLR9 | CD8 | BTNL3 | CD32 |
| TLR9 | CD8 | BTNL3 | CD79a |
| TLR9 | CD8 | BTNL3 | CD79b |
| TLR9 | CD8 | NKG2D | CD8 |
| TLR9 | CD8 | NKG2D | CD3ζ |
| TLR9 | CD8 | NKG2D | CD3δ |
| TLR9 | CD8 | NKG2D | CD3γ |
| TLR9 | CD8 | NKG2D | CD3ε |

TABLE 3-continued

Third Generation CARs

| Binding Region | Co-stimulatory Signal | Co-stimulatory Signal | Signal Domain |
|---|---|---|---|
| TLR9 | CD8 | NKG2D | FcγRI-γ |
| TLR9 | CD8 | NKG2D | FcγRIII-γ |
| TLR9 | CD8 | NKG2D | FcεRIβ |
| TLR9 | CD8 | NKG2D | FcεRIγ |
| TLR9 | CD8 | NKG2D | DAP10 |
| TLR9 | CD8 | NKG2D | DAP12 |
| TLR9 | CD8 | NKG2D | CD32 |
| TLR9 | CD8 | NKG2D | CD79a |
| TLR9 | CD8 | NKG2D | CD79b |
| TLR9 | CD4 | CD28 | CD8 |
| TLR9 | CD4 | CD28 | CD3ζ |
| TLR9 | CD4 | CD28 | CD3δ |
| TLR9 | CD4 | CD28 | CD3γ |
| TLR9 | CD4 | CD28 | CD3ε |
| TLR9 | CD4 | CD28 | FcγRI-γ |
| TLR9 | CD4 | CD28 | FcγRIII-γ |
| TLR9 | CD4 | CD28 | FcεRIβ |
| TLR9 | CD4 | CD28 | FcεRIγ |
| TLR9 | CD4 | CD28 | DAP10 |
| TLR9 | CD4 | CD28 | DAP12 |
| TLR9 | CD4 | CD28 | CD32 |
| TLR9 | CD4 | CD28 | CD79a |
| TLR9 | CD4 | CD28 | CD79b |
| TLR9 | CD4 | CD8 | CD8 |
| TLR9 | CD4 | CD8 | CD3ζ |
| TLR9 | CD4 | CD8 | CD3δ |
| TLR9 | CD4 | CD8 | CD3γ |
| TLR9 | CD4 | CD8 | CD3ε |
| TLR9 | CD4 | CD8 | FcγRI-γ |
| TLR9 | CD4 | CD8 | FcγRIII-γ |
| TLR9 | CD4 | CD8 | FcεRIβ |
| TLR9 | CD4 | CD8 | FcεRIγ |
| TLR9 | CD4 | CD8 | DAP10 |
| TLR9 | CD4 | CD8 | DAP12 |
| TLR9 | CD4 | CD8 | CD32 |
| TLR9 | CD4 | CD8 | CD79a |
| TLR9 | CD4 | CD8 | CD79b |
| TLR9 | CD4 | CD4 | CD8 |
| TLR9 | CD4 | CD4 | CD3ζ |
| TLR9 | CD4 | CD4 | CD3δ |
| TLR9 | CD4 | CD4 | CD3γ |
| TLR9 | CD4 | CD4 | CD3ε |
| TLR9 | CD4 | CD4 | FcγRI-γ |
| TLR9 | CD4 | CD4 | FcγRIII-γ |
| TLR9 | CD4 | CD4 | FcεRIβ |
| TLR9 | CD4 | CD4 | FcεRIγ |
| TLR9 | CD4 | CD4 | DAP10 |
| TLR9 | CD4 | CD4 | DAP12 |
| TLR9 | CD4 | CD4 | CD32 |
| TLR9 | CD4 | CD4 | CD79a |
| TLR9 | CD4 | CD4 | CD79b |
| TLR9 | CD4 | b2c | CD8 |
| TLR9 | CD4 | b2c | CD3ζ |
| TLR9 | CD4 | b2c | CD3δ |
| TLR9 | CD4 | b2c | CD3γ |
| TLR9 | CD4 | b2c | CD3ε |
| TLR9 | CD4 | b2c | FcγRI-γ |
| TLR9 | CD4 | b2c | FcγRIII-γ |
| TLR9 | CD4 | b2c | FcεRIβ |
| TLR9 | CD4 | b2c | FcεRIγ |
| TLR9 | CD4 | b2c | DAP10 |
| TLR9 | CD4 | b2c | DAP12 |
| TLR9 | CD4 | b2c | CD32 |
| TLR9 | CD4 | b2c | CD79a |
| TLR9 | CD4 | b2c | CD79b |
| TLR9 | CD4 | CD137/41BB | CD8 |
| TLR9 | CD4 | CD137/41BB | CD3ζ |
| TLR9 | CD4 | CD137/41BB | CD3δ |
| TLR9 | CD4 | CD137/41BB | CD3γ |
| TLR9 | CD4 | CD137/41BB | CD3ε |
| TLR9 | CD4 | CD137/41BB | FcγRI-γ |
| TLR9 | CD4 | CD137/41BB | FcγRIII-γ |
| TLR9 | CD4 | CD137/41BB | FcεRIβ |
| TLR9 | CD4 | CD137/41BB | FcεRIγ |
| TLR9 | CD4 | CD137/41BB | DAP10 |
| TLR9 | CD4 | CD137/41BB | DAP12 |
| TLR9 | CD4 | CD137/41BB | CD32 |
| TLR9 | CD4 | CD137/41BB | CD79a |
| TLR9 | CD4 | CD137/41BB | CD79b |
| TLR9 | CD4 | ICOS | CD8 |
| TLR9 | CD4 | ICOS | CD3ζ |
| TLR9 | CD4 | ICOS | CD3δ |
| TLR9 | CD4 | ICOS | CD3γ |
| TLR9 | CD4 | ICOS | CD3ε |
| TLR9 | CD4 | ICOS | FcγRI-γ |
| TLR9 | CD4 | ICOS | FcγRIII-γ |
| TLR9 | CD4 | ICOS | FcεRIβ |
| TLR9 | CD4 | ICOS | FcεRIγ |
| TLR9 | CD4 | ICOS | DAP10 |
| TLR9 | CD4 | ICOS | DAP12 |
| TLR9 | CD4 | ICOS | CD32 |
| TLR9 | CD4 | ICOS | CD79a |
| TLR9 | CD4 | ICOS | CD79b |
| TLR9 | CD4 | CD27 | CD8 |
| TLR9 | CD4 | CD27 | CD3ζ |
| TLR9 | CD4 | CD27 | CD3δ |
| TLR9 | CD4 | CD27 | CD3γ |
| TLR9 | CD4 | CD27 | CD3ε |
| TLR9 | CD4 | CD27 | FcγRI-γ |
| TLR9 | CD4 | CD27 | FcγRIII-γ |
| TLR9 | CD4 | CD27 | FcεRIβ |
| TLR9 | CD4 | CD27 | FcεRIγ |
| TLR9 | CD4 | CD27 | DAP10 |
| TLR9 | CD4 | CD27 | DAP12 |
| TLR9 | CD4 | CD27 | CD32 |
| TLR9 | CD4 | CD27 | CD79a |
| TLR9 | CD4 | CD27 | CD79b |
| TLR9 | CD4 | CD28δ | CD8 |
| TLR9 | CD4 | CD28δ | CD3ζ |
| TLR9 | CD4 | CD28δ | CD3δ |
| TLR9 | CD4 | CD28δ | CD3γ |
| TLR9 | CD4 | CD28δ | CD3ε |
| TLR9 | CD4 | CD28δ | FcγRI-γ |
| TLR9 | CD4 | CD28δ | FcγRIII-γ |
| TLR9 | CD4 | CD28δ | FcεRIβ |
| TLR9 | CD4 | CD28δ | FcεRIγ |
| TLR9 | CD4 | CD28δ | DAP10 |
| TLR9 | CD4 | CD28δ | DAP12 |
| TLR9 | CD4 | CD28δ | CD32 |
| TLR9 | CD4 | CD28δ | CD79a |
| TLR9 | CD4 | CD28δ | CD79b |
| TLR9 | CD4 | CD80 | CD8 |
| TLR9 | CD4 | CD80 | CD3ζ |
| TLR9 | CD4 | CD80 | CD3δ |
| TLR9 | CD4 | CD80 | CD3γ |
| TLR9 | CD4 | CD80 | CD3ε |
| TLR9 | CD4 | CD80 | FcγRI-γ |
| TLR9 | CD4 | CD80 | FcγRIII-γ |
| TLR9 | CD4 | CD80 | FcεRIβ |
| TLR9 | CD4 | CD80 | FcεRIγ |
| TLR9 | CD4 | CD80 | DAP10 |
| TLR9 | CD4 | CD80 | DAP12 |
| TLR9 | CD4 | CD80 | CD32 |
| TLR9 | CD4 | CD80 | CD79a |
| TLR9 | CD4 | CD80 | CD79b |
| TLR9 | CD4 | CD86 | CD8 |
| TLR9 | CD4 | CD86 | CD3ζ |
| TLR9 | CD4 | CD86 | CD3δ |
| TLR9 | CD4 | CD86 | CD3γ |
| TLR9 | CD4 | CD86 | CD3ε |
| TLR9 | CD4 | CD86 | FcγRI-γ |
| TLR9 | CD4 | CD86 | FcγRIII-γ |
| TLR9 | CD4 | CD86 | FcεRIβ |
| TLR9 | CD4 | CD86 | FcεRIγ |
| TLR9 | CD4 | CD86 | DAP10 |
| TLR9 | CD4 | CD86 | DAP12 |
| TLR9 | CD4 | CD86 | CD32 |
| TLR9 | CD4 | CD86 | CD79a |

TABLE 3-continued

Third Generation CARs

| Binding Region | Co-stimulatory Signal | Co-stimulatory Signal | Signal Domain |
|---|---|---|---|
| TLR9 | CD4 | CD86 | CD79b |
| TLR9 | CD4 | OX40 | CD8 |
| TLR9 | CD4 | OX40 | CD3ζ |
| TLR9 | CD4 | OX40 | CD3δ |
| TLR9 | CD4 | OX40 | CD3γ |
| TLR9 | CD4 | OX40 | CD3ε |
| TLR9 | CD4 | OX40 | FcγRI-γ |
| TLR9 | CD4 | OX40 | FcγRIII-γ |
| TLR9 | CD4 | OX40 | FcεRIβ |
| TLR9 | CD4 | OX40 | FcεRIγ |
| TLR9 | CD4 | OX40 | DAP10 |
| TLR9 | CD4 | OX40 | DAP12 |
| TLR9 | CD4 | OX40 | CD32 |
| TLR9 | CD4 | OX40 | CD79a |
| TLR9 | CD4 | OX40 | CD79b |
| TLR9 | CD4 | DAP10 | CD8 |
| TLR9 | CD4 | DAP10 | CD3ζ |
| TLR9 | CD4 | DAP10 | CD3δ |
| TLR9 | CD4 | DAP10 | CD3γ |
| TLR9 | CD4 | DAP10 | CD3ε |
| TLR9 | CD4 | DAP10 | FcγRI-γ |
| TLR9 | CD4 | DAP10 | FcγRIII-γ |
| TLR9 | CD4 | DAP10 | FcεRIβ |
| TLR9 | CD4 | DAP10 | FcεRIγ |
| TLR9 | CD4 | DAP10 | DAP10 |
| TLR9 | CD4 | DAP10 | DAP12 |
| TLR9 | CD4 | DAP10 | CD32 |
| TLR9 | CD4 | DAP10 | CD79a |
| TLR9 | CD4 | DAP10 | CD79b |
| TLR9 | CD4 | DAP12 | CD8 |
| TLR9 | CD4 | DAP12 | CD3ζ |
| TLR9 | CD4 | DAP12 | CD3δ |
| TLR9 | CD4 | DAP12 | CD3γ |
| TLR9 | CD4 | DAP12 | CD3ε |
| TLR9 | CD4 | DAP12 | FcγRI-γ |
| TLR9 | CD4 | DAP12 | FcγRIII-γ |
| TLR9 | CD4 | DAP12 | FcεRIβ |
| TLR9 | CD4 | DAP12 | FcεRIγ |
| TLR9 | CD4 | DAP12 | DAP10 |
| TLR9 | CD4 | DAP12 | DAP12 |
| TLR9 | CD4 | DAP12 | CD32 |
| TLR9 | CD4 | DAP12 | CD79a |
| TLR9 | CD4 | DAP12 | CD79b |
| TLR9 | CD4 | MyD88 | CD8 |
| TLR9 | CD4 | MyD88 | CD3ζ |
| TLR9 | CD4 | MyD88 | CD3δ |
| TLR9 | CD4 | MyD88 | CD3γ |
| TLR9 | CD4 | MyD88 | CD3ε |
| TLR9 | CD4 | MyD88 | FcγRI-γ |
| TLR9 | CD4 | MyD88 | FcγRIII-γ |
| TLR9 | CD4 | MyD88 | FcεRIβ |
| TLR9 | CD4 | MyD88 | FcεRIγ |
| TLR9 | CD4 | MyD88 | DAP10 |
| TLR9 | CD4 | MyD88 | DAP12 |
| TLR9 | CD4 | MyD88 | CD32 |
| TLR9 | CD4 | MyD88 | CD79a |
| TLR9 | CD4 | MyD88 | CD79b |
| TLR9 | CD4 | CD7 | CD8 |
| TLR9 | CD4 | CD7 | CD3ζ |
| TLR9 | CD4 | CD7 | CD3δ |
| TLR9 | CD4 | CD7 | CD3γ |
| TLR9 | CD4 | CD7 | CD3ε |
| TLR9 | CD4 | CD7 | FcγRI-γ |
| TLR9 | CD4 | CD7 | FcγRIII-γ |
| TLR9 | CD4 | CD7 | FcεRIβ |
| TLR9 | CD4 | CD7 | FcεRIγ |
| TLR9 | CD4 | CD7 | DAP10 |
| TLR9 | CD4 | CD7 | DAP12 |
| TLR9 | CD4 | CD7 | CD32 |
| TLR9 | CD4 | CD7 | CD79a |
| TLR9 | CD4 | CD7 | CD79b |
| TLR9 | CD4 | BTNL3 | CD8 |
| TLR9 | CD4 | BTNL3 | CD3ζ |
| TLR9 | CD4 | BTNL3 | CD3δ |
| TLR9 | CD4 | BTNL3 | CD3γ |
| TLR9 | CD4 | BTNL3 | CD3ε |
| TLR9 | CD4 | BTNL3 | FcγRI-γ |
| TLR9 | CD4 | BTNL3 | FcγRIII-γ |
| TLR9 | CD4 | BTNL3 | FcεRIβ |
| TLR9 | CD4 | BTNL3 | FcεRIγ |
| TLR9 | CD4 | BTNL3 | DAP10 |
| TLR9 | CD4 | BTNL3 | DAP12 |
| TLR9 | CD4 | BTNL3 | CD32 |
| TLR9 | CD4 | BTNL3 | CD79a |
| TLR9 | CD4 | BTNL3 | CD79b |
| TLR9 | CD4 | NKG2D | CD8 |
| TLR9 | CD4 | NKG2D | CD3ζ |
| TLR9 | CD4 | NKG2D | CD3δ |
| TLR9 | CD4 | NKG2D | CD3γ |
| TLR9 | CD4 | NKG2D | CD3ε |
| TLR9 | CD4 | NKG2D | FcγRI-γ |
| TLR9 | CD4 | NKG2D | FcγRIII-γ |
| TLR9 | CD4 | NKG2D | FcεRIβ |
| TLR9 | CD4 | NKG2D | FcεRIγ |
| TLR9 | CD4 | NKG2D | DAP10 |
| TLR9 | CD4 | NKG2D | DAP12 |
| TLR9 | CD4 | NKG2D | CD32 |
| TLR9 | CD4 | NKG2D | CD79a |
| TLR9 | CD4 | NKG2D | CD79b |
| TLR9 | b2c | CD28 | CD8 |
| TLR9 | b2c | CD28 | CD3ζ |
| TLR9 | b2c | CD28 | CD3δ |
| TLR9 | b2c | CD28 | CD3γ |
| TLR9 | b2c | CD28 | CD3ε |
| TLR9 | b2c | CD28 | FcγRI-γ |
| TLR9 | b2c | CD28 | FcγRIII-γ |
| TLR9 | b2c | CD28 | FcεRIβ |
| TLR9 | b2c | CD28 | FcεRIγ |
| TLR9 | b2c | CD28 | DAP10 |
| TLR9 | b2c | CD28 | DAP12 |
| TLR9 | b2c | CD28 | CD32 |
| TLR9 | b2c | CD28 | CD79a |
| TLR9 | b2c | CD28 | CD79b |
| TLR9 | b2c | CD8 | CD8 |
| TLR9 | b2c | CD8 | CD3ζ |
| TLR9 | b2c | CD8 | CD3δ |
| TLR9 | b2c | CD8 | CD3γ |
| TLR9 | b2c | CD8 | CD3ε |
| TLR9 | b2c | CD8 | FcγRI-γ |
| TLR9 | b2c | CD8 | FcγRIII-γ |
| TLR9 | b2c | CD8 | FcεRIβ |
| TLR9 | b2c | CD8 | FcεRIγ |
| TLR9 | b2c | CD8 | DAP10 |
| TLR9 | b2c | CD8 | DAP12 |
| TLR9 | b2c | CD8 | CD32 |
| TLR9 | b2c | CD8 | CD79a |
| TLR9 | b2c | CD8 | CD79b |
| TLR9 | b2c | CD4 | CD8 |
| TLR9 | b2c | CD4 | CD3ζ |
| TLR9 | b2c | CD4 | CD3δ |
| TLR9 | b2c | CD4 | CD3γ |
| TLR9 | b2c | CD4 | CD3ε |
| TLR9 | b2c | CD4 | FcγRI-γ |
| TLR9 | b2c | CD4 | FcγRIII-γ |
| TLR9 | b2c | CD4 | FcεRIβ |
| TLR9 | b2c | CD4 | FcεRIγ |
| TLR9 | b2c | CD4 | DAP10 |
| TLR9 | b2c | CD4 | DAP12 |
| TLR9 | b2c | CD4 | CD32 |
| TLR9 | b2c | CD4 | CD79a |
| TLR9 | b2c | CD4 | CD79b |
| TLR9 | b2c | b2c | CD8 |
| TLR9 | b2c | b2c | CD3ζ |
| TLR9 | b2c | b2c | CD3δ |
| TLR9 | b2c | b2c | CD3γ |
| TLR9 | b2c | b2c | CD3ε |
| TLR9 | b2c | b2c | FcγRI-γ |
| TLR9 | b2c | b2c | FcγRIII-γ |

TABLE 3-continued

Third Generation CARs

| Binding Region | Co-stimulatory Signal | Co-stimulatory Signal | Signal Domain |
|---|---|---|---|
| TLR9 | b2c | b2c | FcεRIβ |
| TLR9 | b2c | b2c | FcεRIγ |
| TLR9 | b2c | b2c | DAP10 |
| TLR9 | b2c | b2c | DAP12 |
| TLR9 | b2c | b2c | CD32 |
| TLR9 | b2c | b2c | CD79a |
| TLR9 | b2c | b2c | CD79b |
| TLR9 | b2c | CD137/41BB | CD8 |
| TLR9 | b2c | CD137/41BB | CD3ζ |
| TLR9 | b2c | CD137/41BB | CD3δ |
| TLR9 | b2c | CD137/41BB | CD3γ |
| TLR9 | b2c | CD137/41BB | CD3ε |
| TLR9 | b2c | CD137/41BB | FcγRI-γ |
| TLR9 | b2c | CD137/41BB | FcγRIII-γ |
| TLR9 | b2c | CD137/41BB | FcεRIβ |
| TLR9 | b2c | CD137/41BB | FcεRIγ |
| TLR9 | b2c | CD137/41BB | DAP10 |
| TLR9 | b2c | CD137/41BB | DAP12 |
| TLR9 | b2c | CD137/41BB | CD32 |
| TLR9 | b2c | CD137/41BB | CD79a |
| TLR9 | b2c | CD137/41BB | CD79b |
| TLR9 | b2c | ICOS | CD8 |
| TLR9 | b2c | ICOS | CD3ζ |
| TLR9 | b2c | ICOS | CD3δ |
| TLR9 | b2c | ICOS | CD3γ |
| TLR9 | b2c | ICOS | CD3ε |
| TLR9 | b2c | ICOS | FcγRI-γ |
| TLR9 | b2c | ICOS | FcγRIII-γ |
| TLR9 | b2c | ICOS | FcεRIβ |
| TLR9 | b2c | ICOS | FcεRIγ |
| TLR9 | b2c | ICOS | DAP10 |
| TLR9 | b2c | ICOS | DAP12 |
| TLR9 | b2c | ICOS | CD32 |
| TLR9 | b2c | ICOS | CD79a |
| TLR9 | b2c | ICOS | CD79b |
| TLR9 | b2c | CD27 | CD8 |
| TLR9 | b2c | CD27 | CD3ζ |
| TLR9 | b2c | CD27 | CD3δ |
| TLR9 | b2c | CD27 | CD3γ |
| TLR9 | b2c | CD27 | CD3ε |
| TLR9 | b2c | CD27 | FcγRI-γ |
| TLR9 | b2c | CD27 | FcγRIII-γ |
| TLR9 | b2c | CD27 | FcεRIβ |
| TLR9 | b2c | CD27 | FcεRIγ |
| TLR9 | b2c | CD27 | DAP10 |
| TLR9 | b2c | CD27 | DAP12 |
| TLR9 | b2c | CD27 | CD32 |
| TLR9 | b2c | CD27 | CD79a |
| TLR9 | b2c | CD27 | CD79b |
| TLR9 | b2c | CD28δ | CD8 |
| TLR9 | b2c | CD28δ | CD3ζ |
| TLR9 | b2c | CD28δ | CD3δ |
| TLR9 | b2c | CD28δ | CD3γ |
| TLR9 | b2c | CD28δ | CD3ε |
| TLR9 | b2c | CD28δ | FcγRI-γ |
| TLR9 | b2c | CD28δ | FcγRIII-γ |
| TLR9 | b2c | CD28δ | FcεRIβ |
| TLR9 | b2c | CD28δ | FcεRIγ |
| TLR9 | b2c | CD28δ | DAP10 |
| TLR9 | b2c | CD28δ | DAP12 |
| TLR9 | b2c | CD28δ | CD32 |
| TLR9 | b2c | CD28δ | CD79a |
| TLR9 | b2c | CD28δ | CD79b |
| TLR9 | b2c | CD80 | CD8 |
| TLR9 | b2c | CD80 | CD3ζ |
| TLR9 | b2c | CD80 | CD3δ |
| TLR9 | b2c | CD80 | CD3γ |
| TLR9 | b2c | CD80 | CD3ε |
| TLR9 | b2c | CD80 | FcγRI-γ |
| TLR9 | b2c | CD80 | FcγRIII-γ |
| TLR9 | b2c | CD80 | FcεRIβ |
| TLR9 | b2c | CD80 | FcεRIγ |
| TLR9 | b2c | CD80 | DAP10 |
| TLR9 | b2c | CD80 | DAP12 |
| TLR9 | b2c | CD80 | CD32 |
| TLR9 | b2c | CD80 | CD79a |
| TLR9 | b2c | CD80 | CD79b |
| TLR9 | b2c | CD86 | CD8 |
| TLR9 | b2c | CD86 | CD3ζ |
| TLR9 | b2c | CD86 | CD3δ |
| TLR9 | b2c | CD86 | CD3γ |
| TLR9 | b2c | CD86 | CD3ε |
| TLR9 | b2c | CD86 | FcγRI-γ |
| TLR9 | b2c | CD86 | FcγRIII-γ |
| TLR9 | b2c | CD86 | FcεRIβ |
| TLR9 | b2c | CD86 | FcεRIγ |
| TLR9 | b2c | CD86 | DAP10 |
| TLR9 | b2c | CD86 | DAP12 |
| TLR9 | b2c | CD86 | CD32 |
| TLR9 | b2c | CD86 | CD79a |
| TLR9 | b2c | CD86 | CD79b |
| TLR9 | b2c | OX40 | CD8 |
| TLR9 | b2c | OX40 | CD3ζ |
| TLR9 | b2c | OX40 | CD3δ |
| TLR9 | b2c | OX40 | CD3γ |
| TLR9 | b2c | OX40 | CD3ε |
| TLR9 | b2c | OX40 | FcγRI-γ |
| TLR9 | b2c | OX40 | FcγRIII-γ |
| TLR9 | b2c | OX40 | FcεRIβ |
| TLR9 | b2c | OX40 | FcεRIγ |
| TLR9 | b2c | OX40 | DAP10 |
| TLR9 | b2c | OX40 | DAP12 |
| TLR9 | b2c | OX40 | CD32 |
| TLR9 | b2c | OX40 | CD79a |
| TLR9 | b2c | OX40 | CD79b |
| TLR9 | b2c | DAP10 | CD8 |
| TLR9 | b2c | DAP10 | CD3ζ |
| TLR9 | b2c | DAP10 | CD3δ |
| TLR9 | b2c | DAP10 | CD3γ |
| TLR9 | b2c | DAP10 | CD3ε |
| TLR9 | b2c | DAP10 | FcγRI-γ |
| TLR9 | b2c | DAP10 | FcγRIII-γ |
| TLR9 | b2c | DAP10 | FcεRIβ |
| TLR9 | b2c | DAP10 | FcεRIγ |
| TLR9 | b2c | DAP10 | DAP10 |
| TLR9 | b2c | DAP10 | DAP12 |
| TLR9 | b2c | DAP10 | CD32 |
| TLR9 | b2c | DAP10 | CD79a |
| TLR9 | b2c | DAP10 | CD79b |
| TLR9 | b2c | DAP12 | CD8 |
| TLR9 | b2c | DAP12 | CD3ζ |
| TLR9 | b2c | DAP12 | CD3δ |
| TLR9 | b2c | DAP12 | CD3γ |
| TLR9 | b2c | DAP12 | CD3ε |
| TLR9 | b2c | DAP12 | FcγRI-γ |
| TLR9 | b2c | DAP12 | FcγRIII-γ |
| TLR9 | b2c | DAP12 | FcεRIβ |
| TLR9 | b2c | DAP12 | FcεRIγ |
| TLR9 | b2c | DAP12 | DAP10 |
| TLR9 | b2c | DAP12 | DAP12 |
| TLR9 | b2c | DAP12 | CD32 |
| TLR9 | b2c | DAP12 | CD79a |
| TLR9 | b2c | DAP12 | CD79b |
| TLR9 | b2c | MyD88 | CD8 |
| TLR9 | b2c | MyD88 | CD3ζ |
| TLR9 | b2c | MyD88 | CD3δ |
| TLR9 | b2c | MyD88 | CD3γ |
| TLR9 | b2c | MyD88 | CD3ε |
| TLR9 | b2c | MyD88 | FcγRI-γ |
| TLR9 | b2c | MyD88 | FcγRIII-γ |
| TLR9 | b2c | MyD88 | FcεRIβ |
| TLR9 | b2c | MyD88 | FcεRIγ |
| TLR9 | b2c | MyD88 | DAP10 |
| TLR9 | b2c | MyD88 | DAP12 |
| TLR9 | b2c | MyD88 | CD32 |
| TLR9 | b2c | MyD88 | CD79a |
| TLR9 | b2c | MyD88 | CD79b |
| TLR9 | b2c | CD7 | CD8 |

TABLE 3-continued

Third Generation CARs

| Binding Region | Co-stimulatory Signal | Co-stimulatory Signal | Signal Domain |
|---|---|---|---|
| TLR9 | b2c | CD7 | CD3ζ |
| TLR9 | b2c | CD7 | CD3δ |
| TLR9 | b2c | CD7 | CD3γ |
| TLR9 | b2c | CD7 | CD3ε |
| TLR9 | b2c | CD7 | FcγRI-γ |
| TLR9 | b2c | CD7 | FcγRIII-γ |
| TLR9 | b2c | CD7 | FcεRIβ |
| TLR9 | b2c | CD7 | FcεRIγ |
| TLR9 | b2c | CD7 | DAP10 |
| TLR9 | b2c | CD7 | DAP12 |
| TLR9 | b2c | CD7 | CD32 |
| TLR9 | b2c | CD7 | CD79a |
| TLR9 | b2c | CD7 | CD79b |
| TLR9 | b2c | BTNL3 | CD8 |
| TLR9 | b2c | BTNL3 | CD3ζ |
| TLR9 | b2c | BTNL3 | CD3δ |
| TLR9 | b2c | BTNL3 | CD3γ |
| TLR9 | b2c | BTNL3 | CD3ε |
| TLR9 | b2c | BTNL3 | FcγRI-γ |
| TLR9 | b2c | BTNL3 | FcγRIII-γ |
| TLR9 | b2c | BTNL3 | FcεRIβ |
| TLR9 | b2c | BTNL3 | FcεRIγ |
| TLR9 | b2c | BTNL3 | DAP10 |
| TLR9 | b2c | BTNL3 | DAP12 |
| TLR9 | b2c | BTNL3 | CD32 |
| TLR9 | b2c | BTNL3 | CD79a |
| TLR9 | b2c | BTNL3 | CD79b |
| TLR9 | b2c | NKG2D | CD8 |
| TLR9 | b2c | NKG2D | CD3ζ |
| TLR9 | b2c | NKG2D | CD3δ |
| TLR9 | b2c | NKG2D | CD3γ |
| TLR9 | b2c | NKG2D | CD3ε |
| TLR9 | b2c | NKG2D | FcγRI-γ |
| TLR9 | b2c | NKG2D | FcγRIII-γ |
| TLR9 | b2c | NKG2D | FcεRIβ |
| TLR9 | b2c | NKG2D | FcεRIγ |
| TLR9 | b2c | NKG2D | DAP10 |
| TLR9 | b2c | NKG2D | DAP12 |
| TLR9 | b2c | NKG2D | CD32 |
| TLR9 | b2c | NKG2D | CD79a |
| TLR9 | b2c | NKG2D | CD79b |
| TLR9 | CD137/41BB | CD28 | CD8 |
| TLR9 | CD137/41BB | CD28 | CD3ζ |
| TLR9 | CD137/41BB | CD28 | CD3δ |
| TLR9 | CD137/41BB | CD28 | CD3γ |
| TLR9 | CD137/41BB | CD28 | CD3ε |
| TLR9 | CD137/41BB | CD28 | FcγRI-γ |
| TLR9 | CD137/41BB | CD28 | FcγRIII-γ |
| TLR9 | CD137/41BB | CD28 | FcεRIβ |
| TLR9 | CD137/41BB | CD28 | FcεRIγ |
| TLR9 | CD137/41BB | CD28 | DAP10 |
| TLR9 | CD137/41BB | CD28 | DAP12 |
| TLR9 | CD137/41BB | CD28 | CD32 |
| TLR9 | CD137/41BB | CD28 | CD79a |
| TLR9 | CD137/41BB | CD28 | CD79b |
| TLR9 | CD137/41BB | CD8 | CD8 |
| TLR9 | CD137/41BB | CD8 | CD3ζ |
| TLR9 | CD137/41BB | CD8 | CD3δ |
| TLR9 | CD137/41BB | CD8 | CD3γ |
| TLR9 | CD137/41BB | CD8 | CD3ε |
| TLR9 | CD137/41BB | CD8 | FcγRI-γ |
| TLR9 | CD137/41BB | CD8 | FcγRIII-γ |
| TLR9 | CD137/41BB | CD8 | FcεRIβ |
| TLR9 | CD137/41BB | CD8 | FcεRIγ |
| TLR9 | CD137/41BB | CD8 | DAP10 |
| TLR9 | CD137/41BB | CD8 | DAP12 |
| TLR9 | CD137/41BB | CD8 | CD32 |
| TLR9 | CD137/41BB | CD8 | CD79a |
| TLR9 | CD137/41BB | CD8 | CD79b |
| TLR9 | CD137/41BB | CD4 | CD8 |
| TLR9 | CD137/41BB | CD4 | CD3ζ |
| TLR9 | CD137/41BB | CD4 | CD3δ |
| TLR9 | CD137/41BB | CD4 | CD3γ |
| TLR9 | CD137/41BB | CD4 | CD3ε |
| TLR9 | CD137/41BB | CD4 | FcγRI-γ |
| TLR9 | CD137/41BB | CD4 | FcγRIII-γ |
| TLR9 | CD137/41BB | CD4 | FcεRIβ |
| TLR9 | CD137/41BB | CD4 | FcεRIγ |
| TLR9 | CD137/41BB | CD4 | DAP10 |
| TLR9 | CD137/41BB | CD4 | DAP12 |
| TLR9 | CD137/41BB | CD4 | CD32 |
| TLR9 | CD137/41BB | CD4 | CD79a |
| TLR9 | CD137/41BB | CD4 | CD79b |
| TLR9 | CD137/41BB | b2c | CD8 |
| TLR9 | CD137/41BB | b2c | CD3ζ |
| TLR9 | CD137/41BB | b2c | CD3δ |
| TLR9 | CD137/41BB | b2c | CD3γ |
| TLR9 | CD137/41BB | b2c | CD3ε |
| TLR9 | CD137/41BB | b2c | FcγRI-γ |
| TLR9 | CD137/41BB | b2c | FcγRIII-γ |
| TLR9 | CD137/41BB | b2c | FcεRIβ |
| TLR9 | CD137/41BB | b2c | FcεRIγ |
| TLR9 | CD137/41BB | b2c | DAP10 |
| TLR9 | CD137/41BB | b2c | DAP12 |
| TLR9 | CD137/41BB | b2c | CD32 |
| TLR9 | CD137/41BB | b2c | CD79a |
| TLR9 | CD137/41BB | b2c | CD79b |
| TLR9 | CD137/41BB | CD137/41BB | CD8 |
| TLR9 | CD137/41BB | CD137/41BB | CD3ζ |
| TLR9 | CD137/41BB | CD137/41BB | CD3δ |
| TLR9 | CD137/41BB | CD137/41BB | CD3γ |
| TLR9 | CD137/41BB | CD137/41BB | CD3ε |
| TLR9 | CD137/41BB | CD137/41BB | FcγRI-γ |
| TLR9 | CD137/41BB | CD137/41BB | FcγRIII-γ |
| TLR9 | CD137/41BB | CD137/41BB | FcεRIβ |
| TLR9 | CD137/41BB | CD137/41BB | FcεRIγ |
| TLR9 | CD137/41BB | CD137/41BB | DAP10 |
| TLR9 | CD137/41BB | CD137/41BB | DAP12 |
| TLR9 | CD137/41BB | CD137/41BB | CD32 |
| TLR9 | CD137/41BB | CD137/41BB | CD79a |
| TLR9 | CD137/41BB | CD137/41BB | CD79b |
| TLR9 | CD137/41BB | ICOS | CD8 |
| TLR9 | CD137/41BB | ICOS | CD3ζ |
| TLR9 | CD137/41BB | ICOS | CD3δ |
| TLR9 | CD137/41BB | ICOS | CD3γ |
| TLR9 | CD137/41BB | ICOS | CD3ε |
| TLR9 | CD137/41BB | ICOS | FcγRI-γ |
| TLR9 | CD137/41BB | ICOS | FcγRIII-γ |
| TLR9 | CD137/41BB | ICOS | FcεRIβ |
| TLR9 | CD137/41BB | ICOS | FcεRIγ |
| TLR9 | CD137/41BB | ICOS | DAP10 |
| TLR9 | CD137/41BB | ICOS | DAP12 |
| TLR9 | CD137/41BB | ICOS | CD32 |
| TLR9 | CD137/41BB | ICOS | CD79a |
| TLR9 | CD137/41BB | ICOS | CD79b |
| TLR9 | CD137/41BB | CD27 | CD8 |
| TLR9 | CD137/41BB | CD27 | CD3ζ |
| TLR9 | CD137/41BB | CD27 | CD3δ |
| TLR9 | CD137/41BB | CD27 | CD3γ |
| TLR9 | CD137/41BB | CD27 | CD3ε |
| TLR9 | CD137/41BB | CD27 | FcγRI-γ |
| TLR9 | CD137/41BB | CD27 | FcγRIII-γ |
| TLR9 | CD137/41BB | CD27 | FcεRIβ |
| TLR9 | CD137/41BB | CD27 | FcεRIγ |
| TLR9 | CD137/41BB | CD27 | DAP10 |
| TLR9 | CD137/41BB | CD27 | DAP12 |
| TLR9 | CD137/41BB | CD27 | CD32 |
| TLR9 | CD137/41BB | CD27 | CD79a |
| TLR9 | CD137/41BB | CD27 | CD79b |
| TLR9 | CD137/41BB | CD28δ | CD8 |
| TLR9 | CD137/41BB | CD28δ | CD3ζ |
| TLR9 | CD137/41BB | CD28δ | CD3δ |
| TLR9 | CD137/41BB | CD28δ | CD3γ |
| TLR9 | CD137/41BB | CD28δ | CD3ε |
| TLR9 | CD137/41BB | CD28δ | FcγRI-γ |
| TLR9 | CD137/41BB | CD28δ | FcγRIII-γ |
| TLR9 | CD137/41BB | CD28δ | FcεRIβ |
| TLR9 | CD137/41BB | CD28δ | FcεRIγ |

TABLE 3-continued

Third Generation CARs

| Binding Region | Co-stimulatory Signal | Co-stimulatory Signal | Signal Domain |
|---|---|---|---|
| TLR9 | CD137/41BB | CD28δ | DAP10 |
| TLR9 | CD137/41BB | CD28δ | DAP12 |
| TLR9 | CD137/41BB | CD28δ | CD32 |
| TLR9 | CD137/41BB | CD28δ | CD79a |
| TLR9 | CD137/41BB | CD28δ | CD79b |
| TLR9 | CD137/41BB | CD80 | CD8 |
| TLR9 | CD137/41BB | CD80 | CD3ζ |
| TLR9 | CD137/41BB | CD80 | CD3δ |
| TLR9 | CD137/41BB | CD80 | CD3γ |
| TLR9 | CD137/41BB | CD80 | CD3ε |
| TLR9 | CD137/41BB | CD80 | FcγRI-γ |
| TLR9 | CD137/41BB | CD80 | FcγRIII-γ |
| TLR9 | CD137/41BB | CD80 | FcεRIβ |
| TLR9 | CD137/41BB | CD80 | FcεRIγ |
| TLR9 | CD137/41BB | CD80 | DAP10 |
| TLR9 | CD137/41BB | CD80 | DAP12 |
| TLR9 | CD137/41BB | CD80 | CD32 |
| TLR9 | CD137/41BB | CD80 | CD79a |
| TLR9 | CD137/41BB | CD80 | CD79b |
| TLR9 | CD137/41BB | CD86 | CD8 |
| TLR9 | CD137/41BB | CD86 | CD3ζ |
| TLR9 | CD137/41BB | CD86 | CD3δ |
| TLR9 | CD137/41BB | CD86 | CD3γ |
| TLR9 | CD137/41BB | CD86 | CD3ε |
| TLR9 | CD137/41BB | CD86 | FcγRI-γ |
| TLR9 | CD137/41BB | CD86 | FcγRIII-γ |
| TLR9 | CD137/41BB | CD86 | FcεRIβ |
| TLR9 | CD137/41BB | CD86 | FcεRIγ |
| TLR9 | CD137/41BB | CD86 | DAP10 |
| TLR9 | CD137/41BB | CD86 | DAP12 |
| TLR9 | CD137/41BB | CD86 | CD32 |
| TLR9 | CD137/41BB | CD86 | CD79a |
| TLR9 | CD137/41BB | CD86 | CD79b |
| TLR9 | CD137/41BB | OX40 | CD8 |
| TLR9 | CD137/41BB | OX40 | CD3ζ |
| TLR9 | CD137/41BB | OX40 | CD3δ |
| TLR9 | CD137/41BB | OX40 | CD3γ |
| TLR9 | CD137/41BB | OX40 | CD3ε |
| TLR9 | CD137/41BB | OX40 | FcγRI-γ |
| TLR9 | CD137/41BB | OX40 | FcγRIII-γ |
| TLR9 | CD137/41BB | OX40 | FcεRIβ |
| TLR9 | CD137/41BB | OX40 | FcεRIγ |
| TLR9 | CD137/41BB | OX40 | DAP10 |
| TLR9 | CD137/41BB | OX40 | DAP12 |
| TLR9 | CD137/41BB | OX40 | CD32 |
| TLR9 | CD137/41BB | OX40 | CD79a |
| TLR9 | CD137/41BB | OX40 | CD79b |
| TLR9 | CD137/41BB | DAP10 | CD8 |
| TLR9 | CD137/41BB | DAP10 | CD3ζ |
| TLR9 | CD137/41BB | DAP10 | CD3δ |
| TLR9 | CD137/41BB | DAP10 | CD3γ |
| TLR9 | CD137/41BB | DAP10 | CD3ε |
| TLR9 | CD137/41BB | DAP10 | FcγRI-γ |
| TLR9 | CD137/41BB | DAP10 | FcγRIII-γ |
| TLR9 | CD137/41BB | DAP10 | FcεRIβ |
| TLR9 | CD137/41BB | DAP10 | FcεRIγ |
| TLR9 | CD137/41BB | DAP10 | DAP10 |
| TLR9 | CD137/41BB | DAP10 | DAP12 |
| TLR9 | CD137/41BB | DAP10 | CD32 |
| TLR9 | CD137/41BB | DAP10 | CD79a |
| TLR9 | CD137/41BB | DAP10 | CD79b |
| TLR9 | CD137/41BB | DAP12 | CD8 |
| TLR9 | CD137/41BB | DAP12 | CD3ζ |
| TLR9 | CD137/41BB | DAP12 | CD3δ |
| TLR9 | CD137/41BB | DAP12 | CD3γ |
| TLR9 | CD137/41BB | DAP12 | CD3ε |
| TLR9 | CD137/41BB | DAP12 | FcγRI-γ |
| TLR9 | CD137/41BB | DAP12 | FcγRIII-γ |
| TLR9 | CD137/41BB | DAP12 | FcεRIβ |
| TLR9 | CD137/41BB | DAP12 | FcεRIγ |
| TLR9 | CD137/41BB | DAP12 | DAP10 |
| TLR9 | CD137/41BB | DAP12 | DAP12 |
| TLR9 | CD137/41BB | DAP12 | CD32 |
| TLR9 | CD137/41BB | DAP12 | CD79a |
| TLR9 | CD137/41BB | DAP12 | CD79b |
| TLR9 | CD137/41BB | MyD88 | CD8 |
| TLR9 | CD137/41BB | MyD88 | CD3ζ |
| TLR9 | CD137/41BB | MyD88 | CD3δ |
| TLR9 | CD137/41BB | MyD88 | CD3γ |
| TLR9 | CD137/41BB | MyD88 | CD3ε |
| TLR9 | CD137/41BB | MyD88 | FcγRI-γ |
| TLR9 | CD137/41BB | MyD88 | FcγRIII-γ |
| TLR9 | CD137/41BB | MyD88 | FcεRIβ |
| TLR9 | CD137/41BB | MyD88 | FcεRIγ |
| TLR9 | CD137/41BB | MyD88 | DAP10 |
| TLR9 | CD137/41BB | MyD88 | DAP12 |
| TLR9 | CD137/41BB | MyD88 | CD32 |
| TLR9 | CD137/41BB | MyD88 | CD79a |
| TLR9 | CD137/41BB | MyD88 | CD79b |
| TLR9 | CD137/41BB | CD7 | CD8 |
| TLR9 | CD137/41BB | CD7 | CD3ζ |
| TLR9 | CD137/41BB | CD7 | CD3δ |
| TLR9 | CD137/41BB | CD7 | CD3γ |
| TLR9 | CD137/41BB | CD7 | CD3ε |
| TLR9 | CD137/41BB | CD7 | FcγRI-γ |
| TLR9 | CD137/41BB | CD7 | FcγRIII-γ |
| TLR9 | CD137/41BB | CD7 | FcεRIβ |
| TLR9 | CD137/41BB | CD7 | FcεRIγ |
| TLR9 | CD137/41BB | CD7 | DAP10 |
| TLR9 | CD137/41BB | CD7 | DAP12 |
| TLR9 | CD137/41BB | CD7 | CD32 |
| TLR9 | CD137/41BB | CD7 | CD79a |
| TLR9 | CD137/41BB | CD7 | CD79b |
| TLR9 | CD137/41BB | BTNL3 | CD8 |
| TLR9 | CD137/41BB | BTNL3 | CD3ζ |
| TLR9 | CD137/41BB | BTNL3 | CD3δ |
| TLR9 | CD137/41BB | BTNL3 | CD3γ |
| TLR9 | CD137/41BB | BTNL3 | CD3ε |
| TLR9 | CD137/41BB | BTNL3 | FcγRI-γ |
| TLR9 | CD137/41BB | BTNL3 | FcγRIII-γ |
| TLR9 | CD137/41BB | BTNL3 | FcεRIβ |
| TLR9 | CD137/41BB | BTNL3 | FcεRIγ |
| TLR9 | CD137/41BB | BTNL3 | DAP10 |
| TLR9 | CD137/41BB | BTNL3 | DAP12 |
| TLR9 | CD137/41BB | BTNL3 | CD32 |
| TLR9 | CD137/41BB | BTNL3 | CD79a |
| TLR9 | CD137/41BB | BTNL3 | CD79b |
| TLR9 | CD137/41BB | NKG2D | CD8 |
| TLR9 | CD137/41BB | NKG2D | CD3ζ |
| TLR9 | CD137/41BB | NKG2D | CD3δ |
| TLR9 | CD137/41BB | NKG2D | CD3γ |
| TLR9 | CD137/41BB | NKG2D | CD3ε |
| TLR9 | CD137/41BB | NKG2D | FcγRI-γ |
| TLR9 | CD137/41BB | NKG2D | FcγRIII-γ |
| TLR9 | CD137/41BB | NKG2D | FcεRIβ |
| TLR9 | CD137/41BB | NKG2D | FcεRIγ |
| TLR9 | CD137/41BB | NKG2D | DAP10 |
| TLR9 | CD137/41BB | NKG2D | DAP12 |
| TLR9 | CD137/41BB | NKG2D | CD32 |
| TLR9 | CD137/41BB | NKG2D | CD79a |
| TLR9 | CD137/41BB | NKG2D | CD79b |
| TLR9 | ICOS | CD28 | CD8 |
| TLR9 | ICOS | CD28 | CD3ζ |
| TLR9 | ICOS | CD28 | CD3δ |
| TLR9 | ICOS | CD28 | CD3γ |
| TLR9 | ICOS | CD28 | CD3ε |
| TLR9 | ICOS | CD28 | FcγRI-γ |
| TLR9 | ICOS | CD28 | FcγRIII-γ |
| TLR9 | ICOS | CD28 | FcεRIβ |
| TLR9 | ICOS | CD28 | FcεRIγ |
| TLR9 | ICOS | CD28 | DAP10 |
| TLR9 | ICOS | CD28 | DAP12 |
| TLR9 | ICOS | CD28 | CD32 |
| TLR9 | ICOS | CD28 | CD79a |
| TLR9 | ICOS | CD28 | CD79b |
| TLR9 | ICOS | CD8 | CD8 |
| TLR9 | ICOS | CD8 | CD3ζ |
| TLR9 | ICOS | CD8 | CD3δ |

TABLE 3-continued

Third Generation CARs

| Binding Region | Co-stimulatory Signal | Co-stimulatory Signal | Signal Domain |
|---|---|---|---|
| TLR9 | ICOS | CD8 | CD3γ |
| TLR9 | ICOS | CD8 | CD3ε |
| TLR9 | ICOS | CD8 | FcγRI-γ |
| TLR9 | ICOS | CD8 | FcγRIII-γ |
| TLR9 | ICOS | CD8 | FcεRIβ |
| TLR9 | ICOS | CD8 | FcεRIγ |
| TLR9 | ICOS | CD8 | DAP10 |
| TLR9 | ICOS | CD8 | DAP12 |
| TLR9 | ICOS | CD8 | CD32 |
| TLR9 | ICOS | CD8 | CD79a |
| TLR9 | ICOS | CD8 | CD79b |
| TLR9 | ICOS | CD4 | CD8 |
| TLR9 | ICOS | CD4 | CD3ζ |
| TLR9 | ICOS | CD4 | CD3δ |
| TLR9 | ICOS | CD4 | CD3γ |
| TLR9 | ICOS | CD4 | CD3ε |
| TLR9 | ICOS | CD4 | FcγRI-γ |
| TLR9 | ICOS | CD4 | FcγRIII-γ |
| TLR9 | ICOS | CD4 | FcεRIβ |
| TLR9 | ICOS | CD4 | FcεRIγ |
| TLR9 | ICOS | CD4 | DAP10 |
| TLR9 | ICOS | CD4 | DAP12 |
| TLR9 | ICOS | CD4 | CD32 |
| TLR9 | ICOS | CD4 | CD79a |
| TLR9 | ICOS | CD4 | CD79b |
| TLR9 | ICOS | b2c | CD8 |
| TLR9 | ICOS | b2c | CD3ζ |
| TLR9 | ICOS | b2c | CD3δ |
| TLR9 | ICOS | b2c | CD3γ |
| TLR9 | ICOS | b2c | CD3ε |
| TLR9 | ICOS | b2c | FcγRI-γ |
| TLR9 | ICOS | b2c | FcγRIII-γ |
| TLR9 | ICOS | b2c | FcεRIβ |
| TLR9 | ICOS | b2c | FcεRIγ |
| TLR9 | ICOS | b2c | DAP10 |
| TLR9 | ICOS | b2c | DAP12 |
| TLR9 | ICOS | b2c | CD32 |
| TLR9 | ICOS | b2c | CD79a |
| TLR9 | ICOS | b2c | CD79b |
| TLR9 | ICOS | CD137/41BB | CD8 |
| TLR9 | ICOS | CD137/41BB | CD3ζ |
| TLR9 | ICOS | CD137/41BB | CD3δ |
| TLR9 | ICOS | CD137/41BB | CD3γ |
| TLR9 | ICOS | CD137/41BB | CD3ε |
| TLR9 | ICOS | CD137/41BB | FcγRI-γ |
| TLR9 | ICOS | CD137/41BB | FcγRIII-γ |
| TLR9 | ICOS | CD137/41BB | FcεRIβ |
| TLR9 | ICOS | CD137/41BB | FcεRIγ |
| TLR9 | ICOS | CD137/41BB | DAP10 |
| TLR9 | ICOS | CD137/41BB | DAP12 |
| TLR9 | ICOS | CD137/41BB | CD32 |
| TLR9 | ICOS | CD137/41BB | CD79a |
| TLR9 | ICOS | CD137/41BB | CD79b |
| TLR9 | ICOS | ICOS | CD8 |
| TLR9 | ICOS | ICOS | CD3ζ |
| TLR9 | ICOS | ICOS | CD3δ |
| TLR9 | ICOS | ICOS | CD3γ |
| TLR9 | ICOS | ICOS | CD3ε |
| TLR9 | ICOS | ICOS | FcγRI-γ |
| TLR9 | ICOS | ICOS | FcγRIII-γ |
| TLR9 | ICOS | ICOS | FcεRIβ |
| TLR9 | ICOS | ICOS | FcεRIγ |
| TLR9 | ICOS | ICOS | DAP10 |
| TLR9 | ICOS | ICOS | DAP12 |
| TLR9 | ICOS | ICOS | CD32 |
| TLR9 | ICOS | ICOS | CD79a |
| TLR9 | ICOS | ICOS | CD79b |
| TLR9 | ICOS | CD27 | CD8 |
| TLR9 | ICOS | CD27 | CD3ζ |
| TLR9 | ICOS | CD27 | CD3δ |
| TLR9 | ICOS | CD27 | CD3γ |
| TLR9 | ICOS | CD27 | CD3ε |
| TLR9 | ICOS | CD27 | FcγRI-γ |
| TLR9 | ICOS | CD27 | FcγRIII-γ |
| TLR9 | ICOS | CD27 | FcεRIβ |
| TLR9 | ICOS | CD27 | FcεRIγ |
| TLR9 | ICOS | CD27 | DAP10 |
| TLR9 | ICOS | CD27 | DAP12 |
| TLR9 | ICOS | CD27 | CD32 |
| TLR9 | ICOS | CD27 | CD79a |
| TLR9 | ICOS | CD27 | CD79b |
| TLR9 | ICOS | CD28δ | CD8 |
| TLR9 | ICOS | CD28δ | CD3ζ |
| TLR9 | ICOS | CD28δ | CD3δ |
| TLR9 | ICOS | CD28δ | CD3γ |
| TLR9 | ICOS | CD28δ | CD3ε |
| TLR9 | ICOS | CD28δ | FcγRI-γ |
| TLR9 | ICOS | CD28δ | FcγRIII-γ |
| TLR9 | ICOS | CD28δ | FcεRIβ |
| TLR9 | ICOS | CD28δ | FcεRIγ |
| TLR9 | ICOS | CD28δ | DAP10 |
| TLR9 | ICOS | CD28δ | DAP12 |
| TLR9 | ICOS | CD28δ | CD32 |
| TLR9 | ICOS | CD28δ | CD79a |
| TLR9 | ICOS | CD28δ | CD79b |
| TLR9 | ICOS | CD80 | CD8 |
| TLR9 | ICOS | CD80 | CD3ζ |
| TLR9 | ICOS | CD80 | CD3δ |
| TLR9 | ICOS | CD80 | CD3γ |
| TLR9 | ICOS | CD80 | CD3ε |
| TLR9 | ICOS | CD80 | FcγRI-γ |
| TLR9 | ICOS | CD80 | FcγRIII-γ |
| TLR9 | ICOS | CD80 | FcεRIβ |
| TLR9 | ICOS | CD80 | FcεRIγ |
| TLR9 | ICOS | CD80 | DAP10 |
| TLR9 | ICOS | CD80 | DAP12 |
| TLR9 | ICOS | CD80 | CD32 |
| TLR9 | ICOS | CD80 | CD79a |
| TLR9 | ICOS | CD80 | CD79b |
| TLR9 | ICOS | CD86 | CD8 |
| TLR9 | ICOS | CD86 | CD3ζ |
| TLR9 | ICOS | CD86 | CD3δ |
| TLR9 | ICOS | CD86 | CD3γ |
| TLR9 | ICOS | CD86 | CD3ε |
| TLR9 | ICOS | CD86 | FcγRI-γ |
| TLR9 | ICOS | CD86 | FcγRIII-γ |
| TLR9 | ICOS | CD86 | FcεRIβ |
| TLR9 | ICOS | CD86 | FcεRIγ |
| TLR9 | ICOS | CD86 | DAP10 |
| TLR9 | ICOS | CD86 | DAP12 |
| TLR9 | ICOS | CD86 | CD32 |
| TLR9 | ICOS | CD86 | CD79a |
| TLR9 | ICOS | CD86 | CD79b |
| TLR9 | ICOS | OX40 | CD8 |
| TLR9 | ICOS | OX40 | CD3ζ |
| TLR9 | ICOS | OX40 | CD3δ |
| TLR9 | ICOS | OX40 | CD3γ |
| TLR9 | ICOS | OX40 | CD3ε |
| TLR9 | ICOS | OX40 | FcγRI-γ |
| TLR9 | ICOS | OX40 | FcγRIII-γ |
| TLR9 | ICOS | OX40 | FcεRIβ |
| TLR9 | ICOS | OX40 | FcεRIγ |
| TLR9 | ICOS | OX40 | DAP10 |
| TLR9 | ICOS | OX40 | DAP12 |
| TLR9 | ICOS | OX40 | CD32 |
| TLR9 | ICOS | OX40 | CD79a |
| TLR9 | ICOS | OX40 | CD79b |
| TLR9 | ICOS | DAP10 | CD8 |
| TLR9 | ICOS | DAP10 | CD3ζ |
| TLR9 | ICOS | DAP10 | CD3δ |
| TLR9 | ICOS | DAP10 | CD3γ |
| TLR9 | ICOS | DAP10 | CD3ε |
| TLR9 | ICOS | DAP10 | FcγRI-γ |
| TLR9 | ICOS | DAP10 | FcγRIII-γ |
| TLR9 | ICOS | DAP10 | FcεRIβ |
| TLR9 | ICOS | DAP10 | FcεRIγ |
| TLR9 | ICOS | DAP10 | DAP10 |
| TLR9 | ICOS | DAP10 | DAP12 |

TABLE 3-continued

Third Generation CARs

| Binding Region | Co-stimulatory Signal | Co-stimulatory Signal | Signal Domain |
|---|---|---|---|
| TLR9 | ICOS | DAP10 | CD32 |
| TLR9 | ICOS | DAP10 | CD79a |
| TLR9 | ICOS | DAP10 | CD79b |
| TLR9 | ICOS | DAP12 | CD8 |
| TLR9 | ICOS | DAP12 | CD3ζ |
| TLR9 | ICOS | DAP12 | CD3δ |
| TLR9 | ICOS | DAP12 | CD3γ |
| TLR9 | ICOS | DAP12 | CD3ε |
| TLR9 | ICOS | DAP12 | FcγRI-γ |
| TLR9 | ICOS | DAP12 | FcγRIII-γ |
| TLR9 | ICOS | DAP12 | FcεRIβ |
| TLR9 | ICOS | DAP12 | FcεRIγ |
| TLR9 | ICOS | DAP12 | DAP10 |
| TLR9 | ICOS | DAP12 | DAP12 |
| TLR9 | ICOS | DAP12 | CD32 |
| TLR9 | ICOS | DAP12 | CD79a |
| TLR9 | ICOS | DAP12 | CD79b |
| TLR9 | ICOS | MyD88 | CD8 |
| TLR9 | ICOS | MyD88 | CD3ζ |
| TLR9 | ICOS | MyD88 | CD3δ |
| TLR9 | ICOS | MyD88 | CD3γ |
| TLR9 | ICOS | MyD88 | CD3ε |
| TLR9 | ICOS | MyD88 | FcγRI-γ |
| TLR9 | ICOS | MyD88 | FcγRIII-γ |
| TLR9 | ICOS | MyD88 | FcεRIβ |
| TLR9 | ICOS | MyD88 | FcεRIγ |
| TLR9 | ICOS | MyD88 | DAP10 |
| TLR9 | ICOS | MyD88 | DAP12 |
| TLR9 | ICOS | MyD88 | CD32 |
| TLR9 | ICOS | MyD88 | CD79a |
| TLR9 | ICOS | MyD88 | CD79b |
| TLR9 | ICOS | CD7 | CD8 |
| TLR9 | ICOS | CD7 | CD3ζ |
| TLR9 | ICOS | CD7 | CD3δ |
| TLR9 | ICOS | CD7 | CD3γ |
| TLR9 | ICOS | CD7 | CD3ε |
| TLR9 | ICOS | CD7 | FcγRI-γ |
| TLR9 | ICOS | CD7 | FcγRIII-γ |
| TLR9 | ICOS | CD7 | FcεRIβ |
| TLR9 | ICOS | CD7 | FcεRIγ |
| TLR9 | ICOS | CD7 | DAP10 |
| TLR9 | ICOS | CD7 | DAP12 |
| TLR9 | ICOS | CD7 | CD32 |
| TLR9 | ICOS | CD7 | CD79a |
| TLR9 | ICOS | CD7 | CD79b |
| TLR9 | ICOS | BTNL3 | CD8 |
| TLR9 | ICOS | BTNL3 | CD3ζ |
| TLR9 | ICOS | BTNL3 | CD3δ |
| TLR9 | ICOS | BTNL3 | CD3γ |
| TLR9 | ICOS | BTNL3 | CD3ε |
| TLR9 | ICOS | BTNL3 | FcγRI-γ |
| TLR9 | ICOS | BTNL3 | FcγRIII-γ |
| TLR9 | ICOS | BTNL3 | FcεRIβ |
| TLR9 | ICOS | BTNL3 | FcεRIγ |
| TLR9 | ICOS | BTNL3 | DAP10 |
| TLR9 | ICOS | BTNL3 | DAP12 |
| TLR9 | ICOS | BTNL3 | CD32 |
| TLR9 | ICOS | BTNL3 | CD79a |
| TLR9 | ICOS | BTNL3 | CD79b |
| TLR9 | ICOS | NKG2D | CD8 |
| TLR9 | ICOS | NKG2D | CD3ζ |
| TLR9 | ICOS | NKG2D | CD3δ |
| TLR9 | ICOS | NKG2D | CD3γ |
| TLR9 | ICOS | NKG2D | CD3ε |
| TLR9 | ICOS | NKG2D | FcγRI-γ |
| TLR9 | ICOS | NKG2D | FcγRIII-γ |
| TLR9 | ICOS | NKG2D | FcεRIβ |
| TLR9 | ICOS | NKG2D | FcεRIγ |
| TLR9 | ICOS | NKG2D | DAP10 |
| TLR9 | ICOS | NKG2D | DAP12 |
| TLR9 | ICOS | NKG2D | CD32 |
| TLR9 | ICOS | NKG2D | CD79a |
| TLR9 | ICOS | NKG2D | CD79b |
| TLR9 | CD27 | CD28 | CD8 |
| TLR9 | CD27 | CD28 | CD3ζ |
| TLR9 | CD27 | CD28 | CD3δ |
| TLR9 | CD27 | CD28 | CD3γ |
| TLR9 | CD27 | CD28 | CD3ε |
| TLR9 | CD27 | CD28 | FcγRI-γ |
| TLR9 | CD27 | CD28 | FcγRIII-γ |
| TLR9 | CD27 | CD28 | FcεRIβ |
| TLR9 | CD27 | CD28 | FcεRIγ |
| TLR9 | CD27 | CD28 | DAP10 |
| TLR9 | CD27 | CD28 | DAP12 |
| TLR9 | CD27 | CD28 | CD32 |
| TLR9 | CD27 | CD28 | CD79a |
| TLR9 | CD27 | CD28 | CD79b |
| TLR9 | CD27 | CD8 | CD8 |
| TLR9 | CD27 | CD8 | CD3ζ |
| TLR9 | CD27 | CD8 | CD3δ |
| TLR9 | CD27 | CD8 | CD3γ |
| TLR9 | CD27 | CD8 | CD3ε |
| TLR9 | CD27 | CD8 | FcγRI-γ |
| TLR9 | CD27 | CD8 | FcγRIII-γ |
| TLR9 | CD27 | CD8 | FcεRIβ |
| TLR9 | CD27 | CD8 | FcεRIγ |
| TLR9 | CD27 | CD8 | DAP10 |
| TLR9 | CD27 | CD8 | DAP12 |
| TLR9 | CD27 | CD8 | CD32 |
| TLR9 | CD27 | CD8 | CD79a |
| TLR9 | CD27 | CD8 | CD79b |
| TLR9 | CD27 | CD4 | CD8 |
| TLR9 | CD27 | CD4 | CD3ζ |
| TLR9 | CD27 | CD4 | CD3δ |
| TLR9 | CD27 | CD4 | CD3γ |
| TLR9 | CD27 | CD4 | CD3ε |
| TLR9 | CD27 | CD4 | FcγRI-γ |
| TLR9 | CD27 | CD4 | FcγRIII-γ |
| TLR9 | CD27 | CD4 | FcεRIβ |
| TLR9 | CD27 | CD4 | FcεRIγ |
| TLR9 | CD27 | CD4 | DAP10 |
| TLR9 | CD27 | CD4 | DAP12 |
| TLR9 | CD27 | CD4 | CD32 |
| TLR9 | CD27 | CD4 | CD79a |
| TLR9 | CD27 | CD4 | CD79b |
| TLR9 | CD27 | b2c | CD8 |
| TLR9 | CD27 | b2c | CD3ζ |
| TLR9 | CD27 | b2c | CD3δ |
| TLR9 | CD27 | b2c | CD3γ |
| TLR9 | CD27 | b2c | CD3ε |
| TLR9 | CD27 | b2c | FcγRI-γ |
| TLR9 | CD27 | b2c | FcγRIII-γ |
| TLR9 | CD27 | b2c | FcεRIβ |
| TLR9 | CD27 | b2c | FcεRIγ |
| TLR9 | CD27 | b2c | DAP10 |
| TLR9 | CD27 | b2c | DAP12 |
| TLR9 | CD27 | b2c | CD32 |
| TLR9 | CD27 | b2c | CD79a |
| TLR9 | CD27 | b2c | CD79b |
| TLR9 | CD27 | CD137/41BB | CD8 |
| TLR9 | CD27 | CD137/41BB | CD3ζ |
| TLR9 | CD27 | CD137/41BB | CD3δ |
| TLR9 | CD27 | CD137/41BB | CD3γ |
| TLR9 | CD27 | CD137/41BB | CD3ε |
| TLR9 | CD27 | CD137/41BB | FcγRI-γ |
| TLR9 | CD27 | CD137/41BB | FcγRIII-γ |
| TLR9 | CD27 | CD137/41BB | FcεRIβ |
| TLR9 | CD27 | CD137/41BB | FcεRIγ |
| TLR9 | CD27 | CD137/41BB | DAP10 |
| TLR9 | CD27 | CD137/41BB | DAP12 |
| TLR9 | CD27 | CD137/41BB | CD32 |
| TLR9 | CD27 | CD137/41BB | CD79a |
| TLR9 | CD27 | CD137/41BB | CD79b |
| TLR9 | CD27 | ICOS | CD8 |
| TLR9 | CD27 | ICOS | CD3ζ |
| TLR9 | CD27 | ICOS | CD3δ |
| TLR9 | CD27 | ICOS | CD3γ |
| TLR9 | CD27 | ICOS | CD3ε |

TABLE 3-continued

Third Generation CARs

| Binding Region | Co-stimulatory Signal | Co-stimulatory Signal | Signal Domain |
|---|---|---|---|
| TLR9 | CD27 | ICOS | FcγRI-γ |
| TLR9 | CD27 | ICOS | FcγRIII-γ |
| TLR9 | CD27 | ICOS | FcεRIβ |
| TLR9 | CD27 | ICOS | FcεRIγ |
| TLR9 | CD27 | ICOS | DAP10 |
| TLR9 | CD27 | ICOS | DAP12 |
| TLR9 | CD27 | ICOS | CD32 |
| TLR9 | CD27 | ICOS | CD79a |
| TLR9 | CD27 | ICOS | CD79b |
| TLR9 | CD27 | CD27 | CD8 |
| TLR9 | CD27 | CD27 | CD3ζ |
| TLR9 | CD27 | CD27 | CD3δ |
| TLR9 | CD27 | CD27 | CD3γ |
| TLR9 | CD27 | CD27 | CD3ε |
| TLR9 | CD27 | CD27 | FcγRI-γ |
| TLR9 | CD27 | CD27 | FcγRIII-γ |
| TLR9 | CD27 | CD27 | FcεRIβ |
| TLR9 | CD27 | CD27 | FcεRIγ |
| TLR9 | CD27 | CD27 | DAP10 |
| TLR9 | CD27 | CD27 | DAP12 |
| TLR9 | CD27 | CD27 | CD32 |
| TLR9 | CD27 | CD27 | CD79a |
| TLR9 | CD27 | CD27 | CD79b |
| TLR9 | CD27 | CD28δ | CD8 |
| TLR9 | CD27 | CD28δ | CD3ζ |
| TLR9 | CD27 | CD28δ | CD3δ |
| TLR9 | CD27 | CD28δ | CD3γ |
| TLR9 | CD27 | CD28δ | CD3ε |
| TLR9 | CD27 | CD28δ | FcγRI-γ |
| TLR9 | CD27 | CD28δ | FcγRIII-γ |
| TLR9 | CD27 | CD28δ | FcεRIβ |
| TLR9 | CD27 | CD28δ | FcεRIγ |
| TLR9 | CD27 | CD28δ | DAP10 |
| TLR9 | CD27 | CD28δ | DAP12 |
| TLR9 | CD27 | CD28δ | CD32 |
| TLR9 | CD27 | CD28δ | CD79a |
| TLR9 | CD27 | CD28δ | CD79b |
| TLR9 | CD27 | CD80 | CD8 |
| TLR9 | CD27 | CD80 | CD3ζ |
| TLR9 | CD27 | CD80 | CD3δ |
| TLR9 | CD27 | CD80 | CD3γ |
| TLR9 | CD27 | CD80 | CD3ε |
| TLR9 | CD27 | CD80 | FcγRI-γ |
| TLR9 | CD27 | CD80 | FcγRIII-γ |
| TLR9 | CD27 | CD80 | FcεRIβ |
| TLR9 | CD27 | CD80 | FcεRIγ |
| TLR9 | CD27 | CD80 | DAP10 |
| TLR9 | CD27 | CD80 | DAP12 |
| TLR9 | CD27 | CD80 | CD32 |
| TLR9 | CD27 | CD80 | CD79a |
| TLR9 | CD27 | CD80 | CD79b |
| TLR9 | CD27 | CD86 | CD8 |
| TLR9 | CD27 | CD86 | CD3ζ |
| TLR9 | CD27 | CD86 | CD3δ |
| TLR9 | CD27 | CD86 | CD3γ |
| TLR9 | CD27 | CD86 | CD3ε |
| TLR9 | CD27 | CD86 | FcγRI-γ |
| TLR9 | CD27 | CD86 | FcγRIII-γ |
| TLR9 | CD27 | CD86 | FcεRIβ |
| TLR9 | CD27 | CD86 | FcεRIγ |
| TLR9 | CD27 | CD86 | DAP10 |
| TLR9 | CD27 | CD86 | DAP12 |
| TLR9 | CD27 | CD86 | CD32 |
| TLR9 | CD27 | CD86 | CD79a |
| TLR9 | CD27 | CD86 | CD79b |
| TLR9 | CD27 | OX40 | CD8 |
| TLR9 | CD27 | OX40 | CD3ζ |
| TLR9 | CD27 | OX40 | CD3δ |
| TLR9 | CD27 | OX40 | CD3γ |
| TLR9 | CD27 | OX40 | CD3ε |
| TLR9 | CD27 | OX40 | FcγRI-γ |
| TLR9 | CD27 | OX40 | FcγRIII-γ |
| TLR9 | CD27 | OX40 | FcεRIβ |
| TLR9 | CD27 | OX40 | FcεRIγ |
| TLR9 | CD27 | OX40 | DAP10 |
| TLR9 | CD27 | OX40 | DAP12 |
| TLR9 | CD27 | OX40 | CD32 |
| TLR9 | CD27 | OX40 | CD79a |
| TLR9 | CD27 | OX40 | CD79b |
| TLR9 | CD27 | DAP10 | CD8 |
| TLR9 | CD27 | DAP10 | CD3ζ |
| TLR9 | CD27 | DAP10 | CD3δ |
| TLR9 | CD27 | DAP10 | CD3γ |
| TLR9 | CD27 | DAP10 | CD3ε |
| TLR9 | CD27 | DAP10 | FcγRI-γ |
| TLR9 | CD27 | DAP10 | FcγRIII-γ |
| TLR9 | CD27 | DAP10 | FcεRIβ |
| TLR9 | CD27 | DAP10 | FcεRIγ |
| TLR9 | CD27 | DAP10 | DAP10 |
| TLR9 | CD27 | DAP10 | DAP12 |
| TLR9 | CD27 | DAP10 | CD32 |
| TLR9 | CD27 | DAP10 | CD79a |
| TLR9 | CD27 | DAP10 | CD79b |
| TLR9 | CD27 | DAP12 | CD8 |
| TLR9 | CD27 | DAP12 | CD3ζ |
| TLR9 | CD27 | DAP12 | CD3δ |
| TLR9 | CD27 | DAP12 | CD3γ |
| TLR9 | CD27 | DAP12 | CD3ε |
| TLR9 | CD27 | DAP12 | FcγRI-γ |
| TLR9 | CD27 | DAP12 | FcγRIII-γ |
| TLR9 | CD27 | DAP12 | FcεRIβ |
| TLR9 | CD27 | DAP12 | FcεRIγ |
| TLR9 | CD27 | DAP12 | DAP10 |
| TLR9 | CD27 | DAP12 | DAP12 |
| TLR9 | CD27 | DAP12 | CD32 |
| TLR9 | CD27 | DAP12 | CD79a |
| TLR9 | CD27 | DAP12 | CD79b |
| TLR9 | CD27 | MyD88 | CD8 |
| TLR9 | CD27 | MyD88 | CD3ζ |
| TLR9 | CD27 | MyD88 | CD3δ |
| TLR9 | CD27 | MyD88 | CD3γ |
| TLR9 | CD27 | MyD88 | CD3ε |
| TLR9 | CD27 | MyD88 | FcγRI-γ |
| TLR9 | CD27 | MyD88 | FcγRIII-γ |
| TLR9 | CD27 | MyD88 | FcεRIβ |
| TLR9 | CD27 | MyD88 | FcεRIγ |
| TLR9 | CD27 | MyD88 | DAP10 |
| TLR9 | CD27 | MyD88 | DAP12 |
| TLR9 | CD27 | MyD88 | CD32 |
| TLR9 | CD27 | MyD88 | CD79a |
| TLR9 | CD27 | MyD88 | CD79b |
| TLR9 | CD27 | CD7 | CD8 |
| TLR9 | CD27 | CD7 | CD3ζ |
| TLR9 | CD27 | CD7 | CD3δ |
| TLR9 | CD27 | CD7 | CD3γ |
| TLR9 | CD27 | CD7 | CD3ε |
| TLR9 | CD27 | CD7 | FcγRI-γ |
| TLR9 | CD27 | CD7 | FcγRIII-γ |
| TLR9 | CD27 | CD7 | FcεRIβ |
| TLR9 | CD27 | CD7 | FcεRIγ |
| TLR9 | CD27 | CD7 | DAP10 |
| TLR9 | CD27 | CD7 | DAP12 |
| TLR9 | CD27 | CD7 | CD32 |
| TLR9 | CD27 | CD7 | CD79a |
| TLR9 | CD27 | CD7 | CD79b |
| TLR9 | CD27 | BTNL3 | CD8 |
| TLR9 | CD27 | BTNL3 | CD3ζ |
| TLR9 | CD27 | BTNL3 | CD3δ |
| TLR9 | CD27 | BTNL3 | CD3γ |
| TLR9 | CD27 | BTNL3 | CD3ε |
| TLR9 | CD27 | BTNL3 | FcγRI-γ |
| TLR9 | CD27 | BTNL3 | FcγRIII-γ |
| TLR9 | CD27 | BTNL3 | FcεRIβ |
| TLR9 | CD27 | BTNL3 | FcεRIγ |
| TLR9 | CD27 | BTNL3 | DAP10 |
| TLR9 | CD27 | BTNL3 | DAP12 |
| TLR9 | CD27 | BTNL3 | CD32 |
| TLR9 | CD27 | BTNL3 | CD79a |

TABLE 3-continued

Third Generation CARs

| Binding Region | Co-stimulatory Signal | Co-stimulatory Signal | Signal Domain |
|---|---|---|---|
| TLR9 | CD27 | BTNL3 | CD79b |
| TLR9 | CD27 | NKG2D | CD8 |
| TLR9 | CD27 | NKG2D | CD3ζ |
| TLR9 | CD27 | NKG2D | CD3δ |
| TLR9 | CD27 | NKG2D | CD3γ |
| TLR9 | CD27 | NKG2D | CD3ε |
| TLR9 | CD27 | NKG2D | FcγRI-γ |
| TLR9 | CD27 | NKG2D | FcγRIII-γ |
| TLR9 | CD27 | NKG2D | FcεRIβ |
| TLR9 | CD27 | NKG2D | FcεRIγ |
| TLR9 | CD27 | NKG2D | DAP10 |
| TLR9 | CD27 | NKG2D | DAP12 |
| TLR9 | CD27 | NKG2D | CD32 |
| TLR9 | CD27 | NKG2D | CD79a |
| TLR9 | CD27 | NKG2D | CD79b |
| TLR9 | CD28δ | CD28 | CD8 |
| TLR9 | CD28δ | CD28 | CD3ζ |
| TLR9 | CD28δ | CD28 | CD3δ |
| TLR9 | CD28δ | CD28 | CD3γ |
| TLR9 | CD28δ | CD28 | CD3ε |
| TLR9 | CD28δ | CD28 | FcγRI-γ |
| TLR9 | CD28δ | CD28 | FcγRIII-γ |
| TLR9 | CD28δ | CD28 | FcεRIβ |
| TLR9 | CD28δ | CD28 | FcεRIγ |
| TLR9 | CD28δ | CD28 | DAP10 |
| TLR9 | CD28δ | CD28 | DAP12 |
| TLR9 | CD28δ | CD28 | CD32 |
| TLR9 | CD28δ | CD28 | CD79a |
| TLR9 | CD28δ | CD28 | CD79b |
| TLR9 | CD28δ | CD8 | CD8 |
| TLR9 | CD28δ | CD8 | CD3ζ |
| TLR9 | CD28δ | CD8 | CD3δ |
| TLR9 | CD28δ | CD8 | CD3γ |
| TLR9 | CD28δ | CD8 | CD3ε |
| TLR9 | CD28δ | CD8 | FcγRI-γ |
| TLR9 | CD28δ | CD8 | FcγRIII-γ |
| TLR9 | CD28δ | CD8 | FcεRIβ |
| TLR9 | CD28δ | CD8 | FcεRIγ |
| TLR9 | CD28δ | CD8 | DAP10 |
| TLR9 | CD28δ | CD8 | DAP12 |
| TLR9 | CD28δ | CD8 | CD32 |
| TLR9 | CD28δ | CD8 | CD79a |
| TLR9 | CD28δ | CD8 | CD79b |
| TLR9 | CD28δ | CD4 | CD8 |
| TLR9 | CD28δ | CD4 | CD3ζ |
| TLR9 | CD28δ | CD4 | CD3δ |
| TLR9 | CD28δ | CD4 | CD3γ |
| TLR9 | CD28δ | CD4 | CD3ε |
| TLR9 | CD28δ | CD4 | FcγRI-γ |
| TLR9 | CD28δ | CD4 | FcγRIII-γ |
| TLR9 | CD28δ | CD4 | FcεRIβ |
| TLR9 | CD28δ | CD4 | FcεRIγ |
| TLR9 | CD28δ | CD4 | DAP10 |
| TLR9 | CD28δ | CD4 | DAP12 |
| TLR9 | CD28δ | CD4 | CD32 |
| TLR9 | CD28δ | CD4 | CD79a |
| TLR9 | CD28δ | CD4 | CD79b |
| TLR9 | CD28δ | b2c | CD8 |
| TLR9 | CD28δ | b2c | CD3ζ |
| TLR9 | CD28δ | b2c | CD3δ |
| TLR9 | CD28δ | b2c | CD3γ |
| TLR9 | CD28δ | b2c | CD3ε |
| TLR9 | CD28δ | b2c | FcγRI-γ |
| TLR9 | CD28δ | b2c | FcγRIII-γ |
| TLR9 | CD28δ | b2c | FcεRIβ |
| TLR9 | CD28δ | b2c | FcεRIγ |
| TLR9 | CD28δ | b2c | DAP10 |
| TLR9 | CD28δ | b2c | DAP12 |
| TLR9 | CD28δ | b2c | CD32 |
| TLR9 | CD28δ | b2c | CD79a |
| TLR9 | CD28δ | b2c | CD79b |
| TLR9 | CD28δ | CD137/41BB | CD8 |
| TLR9 | CD28δ | CD137/41BB | CD3ζ |
| TLR9 | CD28δ | CD137/41BB | CD3δ |
| TLR9 | CD28δ | CD137/41BB | CD3γ |
| TLR9 | CD28δ | CD137/41BB | CD3ε |
| TLR9 | CD28δ | CD137/41BB | FcγRI-γ |
| TLR9 | CD28δ | CD137/41BB | FcγRIII-γ |
| TLR9 | CD28δ | CD137/41BB | FcεRIβ |
| TLR9 | CD28δ | CD137/41BB | FcεRIγ |
| TLR9 | CD28δ | CD137/41BB | DAP10 |
| TLR9 | CD28δ | CD137/41BB | DAP12 |
| TLR9 | CD28δ | CD137/41BB | CD32 |
| TLR9 | CD28δ | CD137/41BB | CD79a |
| TLR9 | CD28δ | CD137/41BB | CD79b |
| TLR9 | CD28δ | ICOS | CD8 |
| TLR9 | CD28δ | ICOS | CD3ζ |
| TLR9 | CD28δ | ICOS | CD3δ |
| TLR9 | CD28δ | ICOS | CD3γ |
| TLR9 | CD28δ | ICOS | CD3ε |
| TLR9 | CD28δ | ICOS | FcγRI-γ |
| TLR9 | CD28δ | ICOS | FcγRIII-γ |
| TLR9 | CD28δ | ICOS | FcεRIβ |
| TLR9 | CD28δ | ICOS | FcεRIγ |
| TLR9 | CD28δ | ICOS | DAP10 |
| TLR9 | CD28δ | ICOS | DAP12 |
| TLR9 | CD28δ | ICOS | CD32 |
| TLR9 | CD28δ | ICOS | CD79a |
| TLR9 | CD28δ | ICOS | CD79b |
| TLR9 | CD28δ | CD27 | CD8 |
| TLR9 | CD28δ | CD27 | CD3ζ |
| TLR9 | CD28δ | CD27 | CD3δ |
| TLR9 | CD28δ | CD27 | CD3γ |
| TLR9 | CD28δ | CD27 | CD3ε |
| TLR9 | CD28δ | CD27 | FcγRI-γ |
| TLR9 | CD28δ | CD27 | FcγRIII-γ |
| TLR9 | CD28δ | CD27 | FcεRIβ |
| TLR9 | CD28δ | CD27 | FcεRIγ |
| TLR9 | CD28δ | CD27 | DAP10 |
| TLR9 | CD28δ | CD27 | DAP12 |
| TLR9 | CD28δ | CD27 | CD32 |
| TLR9 | CD28δ | CD27 | CD79a |
| TLR9 | CD28δ | CD27 | CD79b |
| TLR9 | CD28δ | CD28δ | CD8 |
| TLR9 | CD28δ | CD28δ | CD3ζ |
| TLR9 | CD28δ | CD28δ | CD3δ |
| TLR9 | CD28δ | CD28δ | CD3γ |
| TLR9 | CD28δ | CD28δ | CD3ε |
| TLR9 | CD28δ | CD28δ | FcγRI-γ |
| TLR9 | CD28δ | CD28δ | FcγRIII-γ |
| TLR9 | CD28δ | CD28δ | FcεRIβ |
| TLR9 | CD28δ | CD28δ | FcεRIγ |
| TLR9 | CD28δ | CD28δ | DAP10 |
| TLR9 | CD28δ | CD28δ | DAP12 |
| TLR9 | CD28δ | CD28δ | CD32 |
| TLR9 | CD28δ | CD28δ | CD79a |
| TLR9 | CD28δ | CD28δ | CD79b |
| TLR9 | CD28δ | CD80 | CD8 |
| TLR9 | CD28δ | CD80 | CD3ζ |
| TLR9 | CD28δ | CD80 | CD3δ |
| TLR9 | CD28δ | CD80 | CD3γ |
| TLR9 | CD28δ | CD80 | CD3ε |
| TLR9 | CD28δ | CD80 | FcγRI-γ |
| TLR9 | CD28δ | CD80 | FcγRIII-γ |
| TLR9 | CD28δ | CD80 | FcεRIβ |
| TLR9 | CD28δ | CD80 | FcεRIγ |
| TLR9 | CD28δ | CD80 | DAP10 |
| TLR9 | CD28δ | CD80 | DAP12 |
| TLR9 | CD28δ | CD80 | CD32 |
| TLR9 | CD28δ | CD80 | CD79a |
| TLR9 | CD28δ | CD80 | CD79b |
| TLR9 | CD28δ | CD86 | CD8 |
| TLR9 | CD28δ | CD86 | CD3ζ |
| TLR9 | CD28δ | CD86 | CD3δ |
| TLR9 | CD28δ | CD86 | CD3γ |
| TLR9 | CD28δ | CD86 | CD3ε |
| TLR9 | CD28δ | CD86 | FcγRI-γ |
| TLR9 | CD28δ | CD86 | FcγRIII-γ |

TABLE 3-continued

Third Generation CARs

| Binding Region | Co-stimulatory Signal | Co-stimulatory Signal | Signal Domain |
|---|---|---|---|
| TLR9 | CD28δ | CD86 | FcεRIβ |
| TLR9 | CD28δ | CD86 | FcεRIγ |
| TLR9 | CD28δ | CD86 | DAP10 |
| TLR9 | CD28δ | CD86 | DAP12 |
| TLR9 | CD28δ | CD86 | CD32 |
| TLR9 | CD28δ | CD86 | CD79a |
| TLR9 | CD28δ | CD86 | CD79b |
| TLR9 | CD28δ | OX40 | CD8 |
| TLR9 | CD28δ | OX40 | CD3ζ |
| TLR9 | CD28δ | OX40 | CD3δ |
| TLR9 | CD28δ | OX40 | CD3γ |
| TLR9 | CD28δ | OX40 | CD3ε |
| TLR9 | CD28δ | OX40 | FcγRI-γ |
| TLR9 | CD28δ | OX40 | FcγRIII-γ |
| TLR9 | CD28δ | OX40 | FcεRIβ |
| TLR9 | CD28δ | OX40 | FcεRIγ |
| TLR9 | CD28δ | OX40 | DAP10 |
| TLR9 | CD28δ | OX40 | DAP12 |
| TLR9 | CD28δ | OX40 | CD32 |
| TLR9 | CD28δ | OX40 | CD79a |
| TLR9 | CD28δ | OX40 | CD79b |
| TLR9 | CD28δ | DAP10 | CD8 |
| TLR9 | CD28δ | DAP10 | CD3ζ |
| TLR9 | CD28δ | DAP10 | CD3δ |
| TLR9 | CD28δ | DAP10 | CD3γ |
| TLR9 | CD28δ | DAP10 | CD3ε |
| TLR9 | CD28δ | DAP10 | FcγRI-γ |
| TLR9 | CD28δ | DAP10 | FcγRIII-γ |
| TLR9 | CD28δ | DAP10 | FcεRIβ |
| TLR9 | CD28δ | DAP10 | FcεRIγ |
| TLR9 | CD28δ | DAP10 | DAP10 |
| TLR9 | CD28δ | DAP10 | DAP12 |
| TLR9 | CD28δ | DAP10 | CD32 |
| TLR9 | CD28δ | DAP10 | CD79a |
| TLR9 | CD28δ | DAP10 | CD79b |
| TLR9 | CD28δ | DAP12 | CD8 |
| TLR9 | CD28δ | DAP12 | CD3ζ |
| TLR9 | CD28δ | DAP12 | CD3δ |
| TLR9 | CD28δ | DAP12 | CD3γ |
| TLR9 | CD28δ | DAP12 | CD3ε |
| TLR9 | CD28δ | DAP12 | FcγRI-γ |
| TLR9 | CD28δ | DAP12 | FcγRIII-γ |
| TLR9 | CD28δ | DAP12 | FcεRIβ |
| TLR9 | CD28δ | DAP12 | FcεRIγ |
| TLR9 | CD28δ | DAP12 | DAP10 |
| TLR9 | CD28δ | DAP12 | DAP12 |
| TLR9 | CD28δ | DAP12 | CD32 |
| TLR9 | CD28δ | DAP12 | CD79a |
| TLR9 | CD28δ | DAP12 | CD79b |
| TLR9 | CD28δ | MyD88 | CD8 |
| TLR9 | CD28δ | MyD88 | CD3ζ |
| TLR9 | CD28δ | MyD88 | CD3δ |
| TLR9 | CD28δ | MyD88 | CD3γ |
| TLR9 | CD28δ | MyD88 | CD3ε |
| TLR9 | CD28δ | MyD88 | FcγRI-γ |
| TLR9 | CD28δ | MyD88 | FcγRIII-γ |
| TLR9 | CD28δ | MyD88 | FcεRIβ |
| TLR9 | CD28δ | MyD88 | FcεRIγ |
| TLR9 | CD28δ | MyD88 | DAP10 |
| TLR9 | CD28δ | MyD88 | DAP12 |
| TLR9 | CD28δ | MyD88 | CD32 |
| TLR9 | CD28δ | MyD88 | CD79a |
| TLR9 | CD28δ | MyD88 | CD79b |
| TLR9 | CD28δ | CD7 | CD8 |
| TLR9 | CD28δ | CD7 | CD3ζ |
| TLR9 | CD28δ | CD7 | CD3δ |
| TLR9 | CD28δ | CD7 | CD3γ |
| TLR9 | CD28δ | CD7 | CD3ε |
| TLR9 | CD28δ | CD7 | FcγRI-γ |
| TLR9 | CD28δ | CD7 | FcγRIII-γ |
| TLR9 | CD28δ | CD7 | FcεRIβ |
| TLR9 | CD28δ | CD7 | FcεRIγ |
| TLR9 | CD28δ | CD7 | DAP10 |
| TLR9 | CD28δ | CD7 | DAP12 |
| TLR9 | CD28δ | CD7 | CD32 |
| TLR9 | CD28δ | CD7 | CD79a |
| TLR9 | CD28δ | CD7 | CD79b |
| TLR9 | CD28δ | BTNL3 | CD8 |
| TLR9 | CD28δ | BTNL3 | CD3ζ |
| TLR9 | CD28δ | BTNL3 | CD3δ |
| TLR9 | CD28δ | BTNL3 | CD3γ |
| TLR9 | CD28δ | BTNL3 | CD3ε |
| TLR9 | CD28δ | BTNL3 | FcγRI-γ |
| TLR9 | CD28δ | BTNL3 | FcγRIII-γ |
| TLR9 | CD28δ | BTNL3 | FcεRIβ |
| TLR9 | CD28δ | BTNL3 | FcεRIγ |
| TLR9 | CD28δ | BTNL3 | DAP10 |
| TLR9 | CD28δ | BTNL3 | DAP12 |
| TLR9 | CD28δ | BTNL3 | CD32 |
| TLR9 | CD28δ | BTNL3 | CD79a |
| TLR9 | CD28δ | BTNL3 | CD79b |
| TLR9 | CD28δ | NKG2D | CD8 |
| TLR9 | CD28δ | NKG2D | CD3ζ |
| TLR9 | CD28δ | NKG2D | CD3δ |
| TLR9 | CD28δ | NKG2D | CD3γ |
| TLR9 | CD28δ | NKG2D | CD3ε |
| TLR9 | CD28δ | NKG2D | FcγRI-γ |
| TLR9 | CD28δ | NKG2D | FcγRIII-γ |
| TLR9 | CD28δ | NKG2D | FcεRIβ |
| TLR9 | CD28δ | NKG2D | FcεRIγ |
| TLR9 | CD28δ | NKG2D | DAP10 |
| TLR9 | CD28δ | NKG2D | DAP12 |
| TLR9 | CD28δ | NKG2D | CD32 |
| TLR9 | CD28δ | NKG2D | CD79a |
| TLR9 | CD28δ | NKG2D | CD79b |
| TLR9 | CD80 | CD28 | CD8 |
| TLR9 | CD80 | CD28 | CD3ζ |
| TLR9 | CD80 | CD28 | CD3δ |
| TLR9 | CD80 | CD28 | CD3γ |
| TLR9 | CD80 | CD28 | CD3ε |
| TLR9 | CD80 | CD28 | FcγRI-γ |
| TLR9 | CD80 | CD28 | FcγRIII-γ |
| TLR9 | CD80 | CD28 | FcεRIβ |
| TLR9 | CD80 | CD28 | FcεRIγ |
| TLR9 | CD80 | CD28 | DAP10 |
| TLR9 | CD80 | CD28 | DAP12 |
| TLR9 | CD80 | CD28 | CD32 |
| TLR9 | CD80 | CD28 | CD79a |
| TLR9 | CD80 | CD28 | CD79b |
| TLR9 | CD80 | CD8 | CD8 |
| TLR9 | CD80 | CD8 | CD3ζ |
| TLR9 | CD80 | CD8 | CD3δ |
| TLR9 | CD80 | CD8 | CD3γ |
| TLR9 | CD80 | CD8 | CD3ε |
| TLR9 | CD80 | CD8 | FcγRI-γ |
| TLR9 | CD80 | CD8 | FcγRIII-γ |
| TLR9 | CD80 | CD8 | FcεRIβ |
| TLR9 | CD80 | CD8 | FcεRIγ |
| TLR9 | CD80 | CD8 | DAP10 |
| TLR9 | CD80 | CD8 | DAP12 |
| TLR9 | CD80 | CD8 | CD32 |
| TLR9 | CD80 | CD8 | CD79a |
| TLR9 | CD80 | CD8 | CD79b |
| TLR9 | CD80 | CD4 | CD8 |
| TLR9 | CD80 | CD4 | CD3ζ |
| TLR9 | CD80 | CD4 | CD3δ |
| TLR9 | CD80 | CD4 | CD3γ |
| TLR9 | CD80 | CD4 | CD3ε |
| TLR9 | CD80 | CD4 | FcγRI-γ |
| TLR9 | CD80 | CD4 | FcγRIII-γ |
| TLR9 | CD80 | CD4 | FcεRIβ |
| TLR9 | CD80 | CD4 | FcεRIγ |
| TLR9 | CD80 | CD4 | DAP10 |
| TLR9 | CD80 | CD4 | DAP12 |
| TLR9 | CD80 | CD4 | CD32 |
| TLR9 | CD80 | CD4 | CD79a |
| TLR9 | CD80 | CD4 | CD79b |
| TLR9 | CD80 | b2c | CD8 |

TABLE 3-continued

Third Generation CARs

| Binding Region | Co-stimulatory Signal | Co-stimulatory Signal | Signal Domain |
|---|---|---|---|
| TLR9 | CD80 | b2c | CD3ζ |
| TLR9 | CD80 | b2c | CD3δ |
| TLR9 | CD80 | b2c | CD3γ |
| TLR9 | CD80 | b2c | CD3ε |
| TLR9 | CD80 | b2c | FcγRI-γ |
| TLR9 | CD80 | b2c | FcγRIII-γ |
| TLR9 | CD80 | b2c | FcεRIβ |
| TLR9 | CD80 | b2c | FcεRIγ |
| TLR9 | CD80 | b2c | DAP10 |
| TLR9 | CD80 | b2c | DAP12 |
| TLR9 | CD80 | b2c | CD32 |
| TLR9 | CD80 | b2c | CD79a |
| TLR9 | CD80 | b2c | CD79b |
| TLR9 | CD80 | CD137/41BB | CD8 |
| TLR9 | CD80 | CD137/41BB | CD3ζ |
| TLR9 | CD80 | CD137/41BB | CD3δ |
| TLR9 | CD80 | CD137/41BB | CD3γ |
| TLR9 | CD80 | CD137/41BB | CD3ε |
| TLR9 | CD80 | CD137/41BB | FcγRI-γ |
| TLR9 | CD80 | CD137/41BB | FcγRIII-γ |
| TLR9 | CD80 | CD137/41BB | FcεRIβ |
| TLR9 | CD80 | CD137/41BB | FcεRIγ |
| TLR9 | CD80 | CD137/41BB | DAP10 |
| TLR9 | CD80 | CD137/41BB | DAP12 |
| TLR9 | CD80 | CD137/41BB | CD32 |
| TLR9 | CD80 | CD137/41BB | CD79a |
| TLR9 | CD80 | CD137/41BB | CD79b |
| TLR9 | CD80 | ICOS | CD8 |
| TLR9 | CD80 | ICOS | CD3ζ |
| TLR9 | CD80 | ICOS | CD3δ |
| TLR9 | CD80 | ICOS | CD3γ |
| TLR9 | CD80 | ICOS | CD3ε |
| TLR9 | CD80 | ICOS | FcγRI-γ |
| TLR9 | CD80 | ICOS | FcγRIII-γ |
| TLR9 | CD80 | ICOS | FcεRIβ |
| TLR9 | CD80 | ICOS | FcεRIγ |
| TLR9 | CD80 | ICOS | DAP10 |
| TLR9 | CD80 | ICOS | DAP12 |
| TLR9 | CD80 | ICOS | CD32 |
| TLR9 | CD80 | ICOS | CD79a |
| TLR9 | CD80 | ICOS | CD79b |
| TLR9 | CD80 | CD27 | CD8 |
| TLR9 | CD80 | CD27 | CD3ζ |
| TLR9 | CD80 | CD27 | CD3δ |
| TLR9 | CD80 | CD27 | CD3γ |
| TLR9 | CD80 | CD27 | CD3ε |
| TLR9 | CD80 | CD27 | FcγRI-γ |
| TLR9 | CD80 | CD27 | FcγRIII-γ |
| TLR9 | CD80 | CD27 | FcεRIβ |
| TLR9 | CD80 | CD27 | FcεRIγ |
| TLR9 | CD80 | CD27 | DAP10 |
| TLR9 | CD80 | CD27 | DAP12 |
| TLR9 | CD80 | CD27 | CD32 |
| TLR9 | CD80 | CD27 | CD79a |
| TLR9 | CD80 | CD27 | CD79b |
| TLR9 | CD80 | CD28δ | CD8 |
| TLR9 | CD80 | CD28δ | CD3ζ |
| TLR9 | CD80 | CD28δ | CD3δ |
| TLR9 | CD80 | CD28δ | CD3γ |
| TLR9 | CD80 | CD28δ | CD3ε |
| TLR9 | CD80 | CD28δ | FcγRI-γ |
| TLR9 | CD80 | CD28δ | FcγRIII-γ |
| TLR9 | CD80 | CD28δ | FcεRIβ |
| TLR9 | CD80 | CD28δ | FcεRIγ |
| TLR9 | CD80 | CD28δ | DAP10 |
| TLR9 | CD80 | CD28δ | DAP12 |
| TLR9 | CD80 | CD28δ | CD32 |
| TLR9 | CD80 | CD28δ | CD79a |
| TLR9 | CD80 | CD28δ | CD79b |
| TLR9 | CD80 | CD80 | CD8 |
| TLR9 | CD80 | CD80 | CD3ζ |
| TLR9 | CD80 | CD80 | CD3δ |
| TLR9 | CD80 | CD80 | CD3γ |
| TLR9 | CD80 | CD80 | CD3ε |
| TLR9 | CD80 | CD80 | FcγRI-γ |
| TLR9 | CD80 | CD80 | FcγRIII-γ |
| TLR9 | CD80 | CD80 | FcεRIβ |
| TLR9 | CD80 | CD80 | FcεRIγ |
| TLR9 | CD80 | CD80 | DAP10 |
| TLR9 | CD80 | CD80 | DAP12 |
| TLR9 | CD80 | CD80 | CD32 |
| TLR9 | CD80 | CD80 | CD79a |
| TLR9 | CD80 | CD80 | CD79b |
| TLR9 | CD80 | CD86 | CD8 |
| TLR9 | CD80 | CD86 | CD3ζ |
| TLR9 | CD80 | CD86 | CD3δ |
| TLR9 | CD80 | CD86 | CD3γ |
| TLR9 | CD80 | CD86 | CD3ε |
| TLR9 | CD80 | CD86 | FcγRI-γ |
| TLR9 | CD80 | CD86 | FcγRIII-γ |
| TLR9 | CD80 | CD86 | FcεRIβ |
| TLR9 | CD80 | CD86 | FcεRIγ |
| TLR9 | CD80 | CD86 | DAP10 |
| TLR9 | CD80 | CD86 | DAP12 |
| TLR9 | CD80 | CD86 | CD32 |
| TLR9 | CD80 | CD86 | CD79a |
| TLR9 | CD80 | CD86 | CD79b |
| TLR9 | CD80 | OX40 | CD8 |
| TLR9 | CD80 | OX40 | CD3ζ |
| TLR9 | CD80 | OX40 | CD3δ |
| TLR9 | CD80 | OX40 | CD3γ |
| TLR9 | CD80 | OX40 | CD3ε |
| TLR9 | CD80 | OX40 | FcγRI-γ |
| TLR9 | CD80 | OX40 | FcγRIII-γ |
| TLR9 | CD80 | OX40 | FcεRIβ |
| TLR9 | CD80 | OX40 | FcεRIγ |
| TLR9 | CD80 | OX40 | DAP10 |
| TLR9 | CD80 | OX40 | DAP12 |
| TLR9 | CD80 | OX40 | CD32 |
| TLR9 | CD80 | OX40 | CD79a |
| TLR9 | CD80 | OX40 | CD79b |
| TLR9 | CD80 | DAP10 | CD8 |
| TLR9 | CD80 | DAP10 | CD3ζ |
| TLR9 | CD80 | DAP10 | CD3δ |
| TLR9 | CD80 | DAP10 | CD3γ |
| TLR9 | CD80 | DAP10 | CD3ε |
| TLR9 | CD80 | DAP10 | FcγRI-γ |
| TLR9 | CD80 | DAP10 | FcγRIII-γ |
| TLR9 | CD80 | DAP10 | FcεRIβ |
| TLR9 | CD80 | DAP10 | FcεRIγ |
| TLR9 | CD80 | DAP10 | DAP10 |
| TLR9 | CD80 | DAP10 | DAP12 |
| TLR9 | CD80 | DAP10 | CD32 |
| TLR9 | CD80 | DAP10 | CD79a |
| TLR9 | CD80 | DAP10 | CD79b |
| TLR9 | CD80 | DAP12 | CD8 |
| TLR9 | CD80 | DAP12 | CD3ζ |
| TLR9 | CD80 | DAP12 | CD3δ |
| TLR9 | CD80 | DAP12 | CD3γ |
| TLR9 | CD80 | DAP12 | CD3ε |
| TLR9 | CD80 | DAP12 | FcγRI-γ |
| TLR9 | CD80 | DAP12 | FcγRIII-γ |
| TLR9 | CD80 | DAP12 | FcεRIβ |
| TLR9 | CD80 | DAP12 | FcεRIγ |
| TLR9 | CD80 | DAP12 | DAP10 |
| TLR9 | CD80 | DAP12 | DAP12 |
| TLR9 | CD80 | DAP12 | CD32 |
| TLR9 | CD80 | DAP12 | CD79a |
| TLR9 | CD80 | DAP12 | CD79b |
| TLR9 | CD80 | MyD88 | CD8 |
| TLR9 | CD80 | MyD88 | CD3ζ |
| TLR9 | CD80 | MyD88 | CD3δ |
| TLR9 | CD80 | MyD88 | CD3γ |
| TLR9 | CD80 | MyD88 | CD3ε |
| TLR9 | CD80 | MyD88 | FcγRI-γ |
| TLR9 | CD80 | MyD88 | FcγRIII-γ |
| TLR9 | CD80 | MyD88 | FcεRIβ |
| TLR9 | CD80 | MyD88 | FcεRIγ |

TABLE 3-continued

Third Generation CARs

| Binding Region | Co-stimulatory Signal | Co-stimulatory Signal | Signal Domain |
| --- | --- | --- | --- |
| TLR9 | CD80 | MyD88 | DAP10 |
| TLR9 | CD80 | MyD88 | DAP12 |
| TLR9 | CD80 | MyD88 | CD32 |
| TLR9 | CD80 | MyD88 | CD79a |
| TLR9 | CD80 | MyD88 | CD79b |
| TLR9 | CD80 | CD7 | CD8 |
| TLR9 | CD80 | CD7 | CD3ζ |
| TLR9 | CD80 | CD7 | CD3δ |
| TLR9 | CD80 | CD7 | CD3γ |
| TLR9 | CD80 | CD7 | CD3ε |
| TLR9 | CD80 | CD7 | FcγRI-γ |
| TLR9 | CD80 | CD7 | FcγRIII-γ |
| TLR9 | CD80 | CD7 | FcεRIβ |
| TLR9 | CD80 | CD7 | FcεRIγ |
| TLR9 | CD80 | CD7 | DAP10 |
| TLR9 | CD80 | CD7 | DAP12 |
| TLR9 | CD80 | CD7 | CD32 |
| TLR9 | CD80 | CD7 | CD79a |
| TLR9 | CD80 | CD7 | CD79b |
| TLR9 | CD80 | BTNL3 | CD8 |
| TLR9 | CD80 | BTNL3 | CD3ζ |
| TLR9 | CD80 | BTNL3 | CD3δ |
| TLR9 | CD80 | BTNL3 | CD3γ |
| TLR9 | CD80 | BTNL3 | CD3ε |
| TLR9 | CD80 | BTNL3 | FcγRI-γ |
| TLR9 | CD80 | BTNL3 | FcγRIII-γ |
| TLR9 | CD80 | BTNL3 | FcεRIβ |
| TLR9 | CD80 | BTNL3 | FcεRIγ |
| TLR9 | CD80 | BTNL3 | DAP10 |
| TLR9 | CD80 | BTNL3 | DAP12 |
| TLR9 | CD80 | BTNL3 | CD32 |
| TLR9 | CD80 | BTNL3 | CD79a |
| TLR9 | CD80 | BTNL3 | CD79b |
| TLR9 | CD80 | NKG2D | CD8 |
| TLR9 | CD80 | NKG2D | CD3ζ |
| TLR9 | CD80 | NKG2D | CD3δ |
| TLR9 | CD80 | NKG2D | CD3γ |
| TLR9 | CD80 | NKG2D | CD3ε |
| TLR9 | CD80 | NKG2D | FcγRI-γ |
| TLR9 | CD80 | NKG2D | FcγRIII-γ |
| TLR9 | CD80 | NKG2D | FcεRIβ |
| TLR9 | CD80 | NKG2D | FcεRIγ |
| TLR9 | CD80 | NKG2D | DAP10 |
| TLR9 | CD80 | NKG2D | DAP12 |
| TLR9 | CD80 | NKG2D | CD32 |
| TLR9 | CD80 | NKG2D | CD79a |
| TLR9 | CD80 | NKG2D | CD79b |
| TLR9 | CD86 | CD28 | CD8 |
| TLR9 | CD86 | CD28 | CD3ζ |
| TLR9 | CD86 | CD28 | CD3δ |
| TLR9 | CD86 | CD28 | CD3γ |
| TLR9 | CD86 | CD28 | CD3ε |
| TLR9 | CD86 | CD28 | FcγRI-γ |
| TLR9 | CD86 | CD28 | FcγRIII-γ |
| TLR9 | CD86 | CD28 | FcεRIβ |
| TLR9 | CD86 | CD28 | FcεRIγ |
| TLR9 | CD86 | CD28 | DAP10 |
| TLR9 | CD86 | CD28 | DAP12 |
| TLR9 | CD86 | CD28 | CD32 |
| TLR9 | CD86 | CD28 | CD79a |
| TLR9 | CD86 | CD28 | CD79b |
| TLR9 | CD86 | CD8 | CD8 |
| TLR9 | CD86 | CD8 | CD3ζ |
| TLR9 | CD86 | CD8 | CD3δ |
| TLR9 | CD86 | CD8 | CD3γ |
| TLR9 | CD86 | CD8 | CD3ε |
| TLR9 | CD86 | CD8 | FcγRI-γ |
| TLR9 | CD86 | CD8 | FcγRIII-γ |
| TLR9 | CD86 | CD8 | FcεRIβ |
| TLR9 | CD86 | CD8 | FcεRIγ |
| TLR9 | CD86 | CD8 | DAP10 |
| TLR9 | CD86 | CD8 | DAP12 |
| TLR9 | CD86 | CD8 | CD32 |
| TLR9 | CD86 | CD8 | CD79a |
| TLR9 | CD86 | CD8 | CD79b |
| TLR9 | CD86 | CD8 | CD8 |
| TLR9 | CD86 | CD4 | CD3ζ |
| TLR9 | CD86 | CD4 | CD3δ |
| TLR9 | CD86 | CD4 | CD3γ |
| TLR9 | CD86 | CD4 | CD3ε |
| TLR9 | CD86 | CD4 | FcγRI-γ |
| TLR9 | CD86 | CD4 | FcγRIII-γ |
| TLR9 | CD86 | CD4 | FcεRIβ |
| TLR9 | CD86 | CD4 | FcεRIγ |
| TLR9 | CD86 | CD4 | DAP10 |
| TLR9 | CD86 | CD4 | DAP12 |
| TLR9 | CD86 | CD4 | CD32 |
| TLR9 | CD86 | CD4 | CD79a |
| TLR9 | CD86 | CD4 | CD79b |
| TLR9 | CD86 | b2c | CD8 |
| TLR9 | CD86 | b2c | CD3ζ |
| TLR9 | CD86 | b2c | CD3δ |
| TLR9 | CD86 | b2c | CD3γ |
| TLR9 | CD86 | b2c | CD3ε |
| TLR9 | CD86 | b2c | FcγRI-γ |
| TLR9 | CD86 | b2c | FcγRIII-γ |
| TLR9 | CD86 | b2c | FcεRIβ |
| TLR9 | CD86 | b2c | FcεRIγ |
| TLR9 | CD86 | b2c | DAP10 |
| TLR9 | CD86 | b2c | DAP12 |
| TLR9 | CD86 | b2c | CD32 |
| TLR9 | CD86 | b2c | CD79a |
| TLR9 | CD86 | b2c | CD79b |
| TLR9 | CD86 | CD137/41BB | CD8 |
| TLR9 | CD86 | CD137/41BB | CD3ζ |
| TLR9 | CD86 | CD137/41BB | CD3δ |
| TLR9 | CD86 | CD137/41BB | CD3γ |
| TLR9 | CD86 | CD137/41BB | CD3ε |
| TLR9 | CD86 | CD137/41BB | FcγRI-γ |
| TLR9 | CD86 | CD137/41BB | FcγRIII-γ |
| TLR9 | CD86 | CD137/41BB | FcεRIβ |
| TLR9 | CD86 | CD137/41BB | FcεRIγ |
| TLR9 | CD86 | CD137/41BB | DAP10 |
| TLR9 | CD86 | CD137/41BB | DAP12 |
| TLR9 | CD86 | CD137/41BB | CD32 |
| TLR9 | CD86 | CD137/41BB | CD79a |
| TLR9 | CD86 | CD137/41BB | CD79b |
| TLR9 | CD86 | ICOS | CD8 |
| TLR9 | CD86 | ICOS | CD3ζ |
| TLR9 | CD86 | ICOS | CD3δ |
| TLR9 | CD86 | ICOS | CD3γ |
| TLR9 | CD86 | ICOS | CD3ε |
| TLR9 | CD86 | ICOS | FcγRI-γ |
| TLR9 | CD86 | ICOS | FcγRIII-γ |
| TLR9 | CD86 | ICOS | FcεRIβ |
| TLR9 | CD86 | ICOS | FcεRIγ |
| TLR9 | CD86 | ICOS | DAP10 |
| TLR9 | CD86 | ICOS | DAP12 |
| TLR9 | CD86 | ICOS | CD32 |
| TLR9 | CD86 | ICOS | CD79a |
| TLR9 | CD86 | ICOS | CD79b |
| TLR9 | CD86 | CD27 | CD8 |
| TLR9 | CD86 | CD27 | CD3ζ |
| TLR9 | CD86 | CD27 | CD3δ |
| TLR9 | CD86 | CD27 | CD3γ |
| TLR9 | CD86 | CD27 | CD3ε |
| TLR9 | CD86 | CD27 | FcγRI-γ |
| TLR9 | CD86 | CD27 | FcγRIII-γ |
| TLR9 | CD86 | CD27 | FcεRIβ |
| TLR9 | CD86 | CD27 | FcεRIγ |
| TLR9 | CD86 | CD27 | DAP10 |
| TLR9 | CD86 | CD27 | DAP12 |
| TLR9 | CD86 | CD27 | CD32 |
| TLR9 | CD86 | CD27 | CD79a |
| TLR9 | CD86 | CD27 | CD79b |
| TLR9 | CD86 | CD28δ | CD8 |
| TLR9 | CD86 | CD28δ | CD3ζ |
| TLR9 | CD86 | CD28δ | CD3δ |

TABLE 3-continued

Third Generation CARs

| Binding Region | Co-stimulatory Signal | Co-stimulatory Signal | Signal Domain |
|---|---|---|---|
| TLR9 | CD86 | CD28δ | CD3γ |
| TLR9 | CD86 | CD28δ | CD3ε |
| TLR9 | CD86 | CD28δ | FcγRI-γ |
| TLR9 | CD86 | CD28δ | FcγRIII-γ |
| TLR9 | CD86 | CD28δ | FcεRIβ |
| TLR9 | CD86 | CD28δ | FcεRIγ |
| TLR9 | CD86 | CD28δ | DAP10 |
| TLR9 | CD86 | CD28δ | DAP12 |
| TLR9 | CD86 | CD28δ | CD32 |
| TLR9 | CD86 | CD28δ | CD79a |
| TLR9 | CD86 | CD28δ | CD79b |
| TLR9 | CD86 | CD80 | CD8 |
| TLR9 | CD86 | CD80 | CD3ζ |
| TLR9 | CD86 | CD80 | CD3δ |
| TLR9 | CD86 | CD80 | CD3γ |
| TLR9 | CD86 | CD80 | CD3ε |
| TLR9 | CD86 | CD80 | FcγRI-γ |
| TLR9 | CD86 | CD80 | FcγRIII-γ |
| TLR9 | CD86 | CD80 | FcεRIβ |
| TLR9 | CD86 | CD80 | FcεRIγ |
| TLR9 | CD86 | CD80 | DAP10 |
| TLR9 | CD86 | CD80 | DAP12 |
| TLR9 | CD86 | CD80 | CD32 |
| TLR9 | CD86 | CD80 | CD79a |
| TLR9 | CD86 | CD80 | CD79b |
| TLR9 | CD86 | CD86 | CD8 |
| TLR9 | CD86 | CD86 | CD3ζ |
| TLR9 | CD86 | CD86 | CD3δ |
| TLR9 | CD86 | CD86 | CD3γ |
| TLR9 | CD86 | CD86 | CD3ε |
| TLR9 | CD86 | CD86 | FcγRI-γ |
| TLR9 | CD86 | CD86 | FcγRIII-γ |
| TLR9 | CD86 | CD86 | FcεRIβ |
| TLR9 | CD86 | CD86 | FcεRIγ |
| TLR9 | CD86 | CD86 | DAP10 |
| TLR9 | CD86 | CD86 | DAP12 |
| TLR9 | CD86 | CD86 | CD32 |
| TLR9 | CD86 | CD86 | CD79a |
| TLR9 | CD86 | CD86 | CD79b |
| TLR9 | CD86 | OX40 | CD8 |
| TLR9 | CD86 | OX40 | CD3ζ |
| TLR9 | CD86 | OX40 | CD3δ |
| TLR9 | CD86 | OX40 | CD3γ |
| TLR9 | CD86 | OX40 | CD3ε |
| TLR9 | CD86 | OX40 | FcγRI-γ |
| TLR9 | CD86 | OX40 | FcγRIII-γ |
| TLR9 | CD86 | OX40 | FcεRIβ |
| TLR9 | CD86 | OX40 | FcεRIγ |
| TLR9 | CD86 | OX40 | DAP10 |
| TLR9 | CD86 | OX40 | DAP12 |
| TLR9 | CD86 | OX40 | CD32 |
| TLR9 | CD86 | OX40 | CD79a |
| TLR9 | CD86 | OX40 | CD79b |
| TLR9 | CD86 | DAP10 | CD8 |
| TLR9 | CD86 | DAP10 | CD3ζ |
| TLR9 | CD86 | DAP10 | CD3δ |
| TLR9 | CD86 | DAP10 | CD3γ |
| TLR9 | CD86 | DAP10 | CD3ε |
| TLR9 | CD86 | DAP10 | FcγRI-γ |
| TLR9 | CD86 | DAP10 | FcγRIII-γ |
| TLR9 | CD86 | DAP10 | FcεRIβ |
| TLR9 | CD86 | DAP10 | FcεRIγ |
| TLR9 | CD86 | DAP10 | DAP10 |
| TLR9 | CD86 | DAP10 | DAP12 |
| TLR9 | CD86 | DAP10 | CD32 |
| TLR9 | CD86 | DAP10 | CD79a |
| TLR9 | CD86 | DAP10 | CD79b |
| TLR9 | CD86 | DAP12 | CD8 |
| TLR9 | CD86 | DAP12 | CD3ζ |
| TLR9 | CD86 | DAP12 | CD3δ |
| TLR9 | CD86 | DAP12 | CD3γ |
| TLR9 | CD86 | DAP12 | CD3ε |
| TLR9 | CD86 | DAP12 | FcγRI-γ |
| TLR9 | CD86 | DAP12 | FcγRIII-γ |
| TLR9 | CD86 | DAP12 | FcεRIβ |
| TLR9 | CD86 | DAP12 | FcεRIγ |
| TLR9 | CD86 | DAP12 | DAP10 |
| TLR9 | CD86 | DAP12 | DAP12 |
| TLR9 | CD86 | DAP12 | CD32 |
| TLR9 | CD86 | DAP12 | CD79a |
| TLR9 | CD86 | DAP12 | CD79b |
| TLR9 | CD86 | MyD88 | CD8 |
| TLR9 | CD86 | MyD88 | CD3ζ |
| TLR9 | CD86 | MyD88 | CD3δ |
| TLR9 | CD86 | MyD88 | CD3γ |
| TLR9 | CD86 | MyD88 | CD3ε |
| TLR9 | CD86 | MyD88 | FcγRI-γ |
| TLR9 | CD86 | MyD88 | FcγRIII-γ |
| TLR9 | CD86 | MyD88 | FcεRIβ |
| TLR9 | CD86 | MyD88 | FcεRIγ |
| TLR9 | CD86 | MyD88 | DAP10 |
| TLR9 | CD86 | MyD88 | DAP12 |
| TLR9 | CD86 | MyD88 | CD32 |
| TLR9 | CD86 | MyD88 | CD79a |
| TLR9 | CD86 | MyD88 | CD79b |
| TLR9 | CD86 | CD7 | CD8 |
| TLR9 | CD86 | CD7 | CD3ζ |
| TLR9 | CD86 | CD7 | CD3δ |
| TLR9 | CD86 | CD7 | CD3γ |
| TLR9 | CD86 | CD7 | CD3ε |
| TLR9 | CD86 | CD7 | FcγRI-γ |
| TLR9 | CD86 | CD7 | FcγRIII-γ |
| TLR9 | CD86 | CD7 | FcεRIβ |
| TLR9 | CD86 | CD7 | FcεRIγ |
| TLR9 | CD86 | CD7 | DAP10 |
| TLR9 | CD86 | CD7 | DAP12 |
| TLR9 | CD86 | CD7 | CD32 |
| TLR9 | CD86 | CD7 | CD79a |
| TLR9 | CD86 | CD7 | CD79b |
| TLR9 | CD86 | BTNL3 | CD8 |
| TLR9 | CD86 | BTNL3 | CD3ζ |
| TLR9 | CD86 | BTNL3 | CD3δ |
| TLR9 | CD86 | BTNL3 | CD3γ |
| TLR9 | CD86 | BTNL3 | CD3ε |
| TLR9 | CD86 | BTNL3 | FcγRI-γ |
| TLR9 | CD86 | BTNL3 | FcγRIII-γ |
| TLR9 | CD86 | BTNL3 | FcεRIβ |
| TLR9 | CD86 | BTNL3 | FcεRIγ |
| TLR9 | CD86 | BTNL3 | DAP10 |
| TLR9 | CD86 | BTNL3 | DAP12 |
| TLR9 | CD86 | BTNL3 | CD32 |
| TLR9 | CD86 | BTNL3 | CD79a |
| TLR9 | CD86 | BTNL3 | CD79b |
| TLR9 | CD86 | NKG2D | CD8 |
| TLR9 | CD86 | NKG2D | CD3ζ |
| TLR9 | CD86 | NKG2D | CD3δ |
| TLR9 | CD86 | NKG2D | CD3γ |
| TLR9 | CD86 | NKG2D | CD3ε |
| TLR9 | CD86 | NKG2D | FcγRI-γ |
| TLR9 | CD86 | NKG2D | FcγRIII-γ |
| TLR9 | CD86 | NKG2D | FcεRIβ |
| TLR9 | CD86 | NKG2D | FcεRIγ |
| TLR9 | CD86 | NKG2D | DAP10 |
| TLR9 | CD86 | NKG2D | DAP12 |
| TLR9 | CD86 | NKG2D | CD32 |
| TLR9 | CD86 | NKG2D | CD79a |
| TLR9 | CD86 | NKG2D | CD79b |
| TLR9 | OX40 | CD28 | CD8 |
| TLR9 | OX40 | CD28 | CD3ζ |
| TLR9 | OX40 | CD28 | CD3δ |
| TLR9 | OX40 | CD28 | CD3γ |
| TLR9 | OX40 | CD28 | CD3ε |
| TLR9 | OX40 | CD28 | FcγRI-γ |
| TLR9 | OX40 | CD28 | FcγRIII-γ |
| TLR9 | OX40 | CD28 | FcεRIβ |
| TLR9 | OX40 | CD28 | FcεRIγ |
| TLR9 | OX40 | CD28 | DAP10 |
| TLR9 | OX40 | CD28 | DAP12 |

TABLE 3-continued

Third Generation CARs

| Binding Region | Co-stimulatory Signal | Co-stimulatory Signal | Signal Domain |
|---|---|---|---|
| TLR9 | OX40 | CD28 | CD32 |
| TLR9 | OX40 | CD28 | CD79a |
| TLR9 | OX40 | CD28 | CD79b |
| TLR9 | OX40 | CD8 | CD8 |
| TLR9 | OX40 | CD8 | CD3ζ |
| TLR9 | OX40 | CD8 | CD3δ |
| TLR9 | OX40 | CD8 | CD3γ |
| TLR9 | OX40 | CD8 | CD3ε |
| TLR9 | OX40 | CD8 | FcγRI-γ |
| TLR9 | OX40 | CD8 | FcγRIII-γ |
| TLR9 | OX40 | CD8 | FcεRIβ |
| TLR9 | OX40 | CD8 | FcεRIγ |
| TLR9 | OX40 | CD8 | DAP10 |
| TLR9 | OX40 | CD8 | DAP12 |
| TLR9 | OX40 | CD8 | CD32 |
| TLR9 | OX40 | CD8 | CD79a |
| TLR9 | OX40 | CD8 | CD79b |
| TLR9 | OX40 | CD4 | CD8 |
| TLR9 | OX40 | CD4 | CD3ζ |
| TLR9 | OX40 | CD4 | CD3δ |
| TLR9 | OX40 | CD4 | CD3γ |
| TLR9 | OX40 | CD4 | CD3ε |
| TLR9 | OX40 | CD4 | FcγRI-γ |
| TLR9 | OX40 | CD4 | FcγRIII-γ |
| TLR9 | OX40 | CD4 | FcεRIβ |
| TLR9 | OX40 | CD4 | FcεRIγ |
| TLR9 | OX40 | CD4 | DAP10 |
| TLR9 | OX40 | CD4 | DAP12 |
| TLR9 | OX40 | CD4 | CD32 |
| TLR9 | OX40 | CD4 | CD79a |
| TLR9 | OX40 | CD4 | CD79b |
| TLR9 | OX40 | b2c | CD8 |
| TLR9 | OX40 | b2c | CD3ζ |
| TLR9 | OX40 | b2c | CD3δ |
| TLR9 | OX40 | b2c | CD3γ |
| TLR9 | OX40 | b2c | CD3ε |
| TLR9 | OX40 | b2c | FcγRI-γ |
| TLR9 | OX40 | b2c | FcγRIII-γ |
| TLR9 | OX40 | b2c | FcεRIβ |
| TLR9 | OX40 | b2c | FcεRIγ |
| TLR9 | OX40 | b2c | DAP10 |
| TLR9 | OX40 | b2c | DAP12 |
| TLR9 | OX40 | b2c | CD32 |
| TLR9 | OX40 | b2c | CD79a |
| TLR9 | OX40 | b2c | CD79b |
| TLR9 | OX40 | CD137/41BB | CD8 |
| TLR9 | OX40 | CD137/41BB | CD3ζ |
| TLR9 | OX40 | CD137/41BB | CD3δ |
| TLR9 | OX40 | CD137/41BB | CD3γ |
| TLR9 | OX40 | CD137/41BB | CD3ε |
| TLR9 | OX40 | CD137/41BB | FcγRI-γ |
| TLR9 | OX40 | CD137/41BB | FcγRIII-γ |
| TLR9 | OX40 | CD137/41BB | FcεRIβ |
| TLR9 | OX40 | CD137/41BB | FcεRIγ |
| TLR9 | OX40 | CD137/41BB | DAP10 |
| TLR9 | OX40 | CD137/41BB | DAP12 |
| TLR9 | OX40 | CD137/41BB | CD32 |
| TLR9 | OX40 | CD137/41BB | CD79a |
| TLR9 | OX40 | CD137/41BB | CD79b |
| TLR9 | OX40 | ICOS | CD8 |
| TLR9 | OX40 | ICOS | CD3ζ |
| TLR9 | OX40 | ICOS | CD3δ |
| TLR9 | OX40 | ICOS | CD3γ |
| TLR9 | OX40 | ICOS | CD3ε |
| TLR9 | OX40 | ICOS | FcγRI-γ |
| TLR9 | OX40 | ICOS | FcγRIII-γ |
| TLR9 | OX40 | ICOS | FcεRIβ |
| TLR9 | OX40 | ICOS | FcεRIγ |
| TLR9 | OX40 | ICOS | DAP10 |
| TLR9 | OX40 | ICOS | DAP12 |
| TLR9 | OX40 | ICOS | CD32 |
| TLR9 | OX40 | ICOS | CD79a |
| TLR9 | OX40 | ICOS | CD79b |
| TLR9 | OX40 | CD27 | CD8 |
| TLR9 | OX40 | CD27 | CD3ζ |
| TLR9 | OX40 | CD27 | CD3δ |
| TLR9 | OX40 | CD27 | CD3γ |
| TLR9 | OX40 | CD27 | CD3ε |
| TLR9 | OX40 | CD27 | FcγRI-γ |
| TLR9 | OX40 | CD27 | FcγRIII-γ |
| TLR9 | OX40 | CD27 | FcεRIβ |
| TLR9 | OX40 | CD27 | FcεRIγ |
| TLR9 | OX40 | CD27 | DAP10 |
| TLR9 | OX40 | CD27 | DAP12 |
| TLR9 | OX40 | CD27 | CD32 |
| TLR9 | OX40 | CD27 | CD79a |
| TLR9 | OX40 | CD27 | CD79b |
| TLR9 | OX40 | CD28δ | CD8 |
| TLR9 | OX40 | CD28δ | CD3ζ |
| TLR9 | OX40 | CD28δ | CD3δ |
| TLR9 | OX40 | CD28δ | CD3γ |
| TLR9 | OX40 | CD28δ | CD3ε |
| TLR9 | OX40 | CD28δ | FcγRI-γ |
| TLR9 | OX40 | CD28δ | FcγRIII-γ |
| TLR9 | OX40 | CD28δ | FcεRIβ |
| TLR9 | OX40 | CD28δ | FcεRIγ |
| TLR9 | OX40 | CD28δ | DAP10 |
| TLR9 | OX40 | CD28δ | DAP12 |
| TLR9 | OX40 | CD28δ | CD32 |
| TLR9 | OX40 | CD28δ | CD79a |
| TLR9 | OX40 | CD28δ | CD79b |
| TLR9 | OX40 | CD80 | CD8 |
| TLR9 | OX40 | CD80 | CD3ζ |
| TLR9 | OX40 | CD80 | CD3δ |
| TLR9 | OX40 | CD80 | CD3γ |
| TLR9 | OX40 | CD80 | CD3ε |
| TLR9 | OX40 | CD80 | FcγRI-γ |
| TLR9 | OX40 | CD80 | FcγRIII-γ |
| TLR9 | OX40 | CD80 | FcεRIβ |
| TLR9 | OX40 | CD80 | FcεRIγ |
| TLR9 | OX40 | CD80 | DAP10 |
| TLR9 | OX40 | CD80 | DAP12 |
| TLR9 | OX40 | CD80 | CD32 |
| TLR9 | OX40 | CD80 | CD79a |
| TLR9 | OX40 | CD80 | CD79b |
| TLR9 | OX40 | CD86 | CD8 |
| TLR9 | OX40 | CD86 | CD3ζ |
| TLR9 | OX40 | CD86 | CD3δ |
| TLR9 | OX40 | CD86 | CD3γ |
| TLR9 | OX40 | CD86 | CD3ε |
| TLR9 | OX40 | CD86 | FcγRI-γ |
| TLR9 | OX40 | CD86 | FcγRIII-γ |
| TLR9 | OX40 | CD86 | FcεRIβ |
| TLR9 | OX40 | CD86 | FcεRIγ |
| TLR9 | OX40 | CD86 | DAP10 |
| TLR9 | OX40 | CD86 | DAP12 |
| TLR9 | OX40 | CD86 | CD32 |
| TLR9 | OX40 | CD86 | CD79a |
| TLR9 | OX40 | CD86 | CD79b |
| TLR9 | OX40 | OX40 | CD8 |
| TLR9 | OX40 | OX40 | CD3ζ |
| TLR9 | OX40 | OX40 | CD3δ |
| TLR9 | OX40 | OX40 | CD3γ |
| TLR9 | OX40 | OX40 | CD3ε |
| TLR9 | OX40 | OX40 | FcγRI-γ |
| TLR9 | OX40 | OX40 | FcγRIII-γ |
| TLR9 | OX40 | OX40 | FcεRIβ |
| TLR9 | OX40 | OX40 | FcεRIγ |
| TLR9 | OX40 | OX40 | DAP10 |
| TLR9 | OX40 | OX40 | DAP12 |
| TLR9 | OX40 | OX40 | CD32 |
| TLR9 | OX40 | OX40 | CD79a |
| TLR9 | OX40 | OX40 | CD79b |
| TLR9 | OX40 | DAP10 | CD8 |
| TLR9 | OX40 | DAP10 | CD3ζ |
| TLR9 | OX40 | DAP10 | CD3δ |
| TLR9 | OX40 | DAP10 | CD3γ |
| TLR9 | OX40 | DAP10 | CD3ε |

TABLE 3-continued

Third Generation CARs

| Binding Region | Co-stimulatory Signal | Co-stimulatory Signal | Signal Domain |
| --- | --- | --- | --- |
| TLR9 | OX40 | DAP10 | FcγRI-γ |
| TLR9 | OX40 | DAP10 | FcγRIII-γ |
| TLR9 | OX40 | DAP10 | FcεRIβ |
| TLR9 | OX40 | DAP10 | FcεRIγ |
| TLR9 | OX40 | DAP10 | DAP10 |
| TLR9 | OX40 | DAP10 | DAP12 |
| TLR9 | OX40 | DAP10 | CD32 |
| TLR9 | OX40 | DAP10 | CD79a |
| TLR9 | OX40 | DAP10 | CD79b |
| TLR9 | OX40 | DAP12 | CD8 |
| TLR9 | OX40 | DAP12 | CD3ζ |
| TLR9 | OX40 | DAP12 | CD3δ |
| TLR9 | OX40 | DAP12 | CD3γ |
| TLR9 | OX40 | DAP12 | CD3ε |
| TLR9 | OX40 | DAP12 | FcγRI-γ |
| TLR9 | OX40 | DAP12 | FcγRIII-γ |
| TLR9 | OX40 | DAP12 | FcεRIβ |
| TLR9 | OX40 | DAP12 | FcεRIγ |
| TLR9 | OX40 | DAP12 | DAP10 |
| TLR9 | OX40 | DAP12 | DAP12 |
| TLR9 | OX40 | DAP12 | CD32 |
| TLR9 | OX40 | DAP12 | CD79a |
| TLR9 | OX40 | DAP12 | CD79b |
| TLR9 | OX40 | MyD88 | CD8 |
| TLR9 | OX40 | MyD88 | CD3ζ |
| TLR9 | OX40 | MyD88 | CD3δ |
| TLR9 | OX40 | MyD88 | CD3γ |
| TLR9 | OX40 | MyD88 | CD3ε |
| TLR9 | OX40 | MyD88 | FcγRI-γ |
| TLR9 | OX40 | MyD88 | FcγRIII-γ |
| TLR9 | OX40 | MyD88 | FcεRIβ |
| TLR9 | OX40 | MyD88 | FcεRIγ |
| TLR9 | OX40 | MyD88 | DAP10 |
| TLR9 | OX40 | MyD88 | DAP12 |
| TLR9 | OX40 | MyD88 | CD32 |
| TLR9 | OX40 | MyD88 | CD79a |
| TLR9 | OX40 | MyD88 | CD79b |
| TLR9 | OX40 | CD7 | CD8 |
| TLR9 | OX40 | CD7 | CD3ζ |
| TLR9 | OX40 | CD7 | CD3δ |
| TLR9 | OX40 | CD7 | CD3γ |
| TLR9 | OX40 | CD7 | CD3ε |
| TLR9 | OX40 | CD7 | FcγRI-γ |
| TLR9 | OX40 | CD7 | FcγRIII-γ |
| TLR9 | OX40 | CD7 | FcεRIβ |
| TLR9 | OX40 | CD7 | FcεRIγ |
| TLR9 | OX40 | CD7 | DAP10 |
| TLR9 | OX40 | CD7 | DAP12 |
| TLR9 | OX40 | CD7 | CD32 |
| TLR9 | OX40 | CD7 | CD79a |
| TLR9 | OX40 | CD7 | CD79b |
| TLR9 | OX40 | BTNL3 | CD8 |
| TLR9 | OX40 | BTNL3 | CD3ζ |
| TLR9 | OX40 | BTNL3 | CD3δ |
| TLR9 | OX40 | BTNL3 | CD3γ |
| TLR9 | OX40 | BTNL3 | CD3ε |
| TLR9 | OX40 | BTNL3 | FcγRI-γ |
| TLR9 | OX40 | BTNL3 | FcγRIII-γ |
| TLR9 | OX40 | BTNL3 | FcεRIβ |
| TLR9 | OX40 | BTNL3 | FcεRIγ |
| TLR9 | OX40 | BTNL3 | DAP10 |
| TLR9 | OX40 | BTNL3 | DAP12 |
| TLR9 | OX40 | BTNL3 | CD32 |
| TLR9 | OX40 | BTNL3 | CD79a |
| TLR9 | OX40 | BTNL3 | CD79b |
| TLR9 | OX40 | NKG2D | CD8 |
| TLR9 | OX40 | NKG2D | CD3ζ |
| TLR9 | OX40 | NKG2D | CD3δ |
| TLR9 | OX40 | NKG2D | CD3γ |
| TLR9 | OX40 | NKG2D | CD3ε |
| TLR9 | OX40 | NKG2D | FcγRI-γ |
| TLR9 | OX40 | NKG2D | FcγRIII-γ |
| TLR9 | OX40 | NKG2D | FcεRIβ |
| TLR9 | OX40 | NKG2D | FcεRIγ |
| TLR9 | OX40 | NKG2D | DAP10 |
| TLR9 | OX40 | NKG2D | DAP12 |
| TLR9 | OX40 | NKG2D | CD32 |
| TLR9 | OX40 | NKG2D | CD79a |
| TLR9 | OX40 | NKG2D | CD79b |
| TLR9 | DAP10 | CD28 | CD8 |
| TLR9 | DAP10 | CD28 | CD3ζ |
| TLR9 | DAP10 | CD28 | CD3δ |
| TLR9 | DAP10 | CD28 | CD3γ |
| TLR9 | DAP10 | CD28 | CD3ε |
| TLR9 | DAP10 | CD28 | FcγRI-γ |
| TLR9 | DAP10 | CD28 | FcγRIII-γ |
| TLR9 | DAP10 | CD28 | FcεRIβ |
| TLR9 | DAP10 | CD28 | FcεRIγ |
| TLR9 | DAP10 | CD28 | DAP10 |
| TLR9 | DAP10 | CD28 | DAP12 |
| TLR9 | DAP10 | CD28 | CD32 |
| TLR9 | DAP10 | CD28 | CD79a |
| TLR9 | DAP10 | CD28 | CD79b |
| TLR9 | DAP10 | CD8 | CD8 |
| TLR9 | DAP10 | CD8 | CD3ζ |
| TLR9 | DAP10 | CD8 | CD3δ |
| TLR9 | DAP10 | CD8 | CD3γ |
| TLR9 | DAP10 | CD8 | CD3ε |
| TLR9 | DAP10 | CD8 | FcγRI-γ |
| TLR9 | DAP10 | CD8 | FcγRIII-γ |
| TLR9 | DAP10 | CD8 | FcεRIβ |
| TLR9 | DAP10 | CD8 | FcεRIγ |
| TLR9 | DAP10 | CD8 | DAP10 |
| TLR9 | DAP10 | CD8 | DAP12 |
| TLR9 | DAP10 | CD8 | CD32 |
| TLR9 | DAP10 | CD8 | CD79a |
| TLR9 | DAP10 | CD8 | CD79b |
| TLR9 | DAP10 | CD4 | CD8 |
| TLR9 | DAP10 | CD4 | CD3ζ |
| TLR9 | DAP10 | CD4 | CD3δ |
| TLR9 | DAP10 | CD4 | CD3γ |
| TLR9 | DAP10 | CD4 | CD3ε |
| TLR9 | DAP10 | CD4 | FcγRI-γ |
| TLR9 | DAP10 | CD4 | FcγRIII-γ |
| TLR9 | DAP10 | CD4 | FcεRIβ |
| TLR9 | DAP10 | CD4 | FcεRIγ |
| TLR9 | DAP10 | CD4 | DAP10 |
| TLR9 | DAP10 | CD4 | DAP12 |
| TLR9 | DAP10 | CD4 | CD32 |
| TLR9 | DAP10 | CD4 | CD79a |
| TLR9 | DAP10 | CD4 | CD79b |
| TLR9 | DAP10 | b2c | CD8 |
| TLR9 | DAP10 | b2c | CD3ζ |
| TLR9 | DAP10 | b2c | CD3δ |
| TLR9 | DAP10 | b2c | CD3γ |
| TLR9 | DAP10 | b2c | CD3ε |
| TLR9 | DAP10 | b2c | FcγRI-γ |
| TLR9 | DAP10 | b2c | FcγRIII-γ |
| TLR9 | DAP10 | b2c | FcεRIβ |
| TLR9 | DAP10 | b2c | FcεRIγ |
| TLR9 | DAP10 | b2c | DAP10 |
| TLR9 | DAP10 | b2c | DAP12 |
| TLR9 | DAP10 | b2c | CD32 |
| TLR9 | DAP10 | b2c | CD79a |
| TLR9 | DAP10 | b2c | CD79b |
| TLR9 | DAP10 | CD137/41BB | CD8 |
| TLR9 | DAP10 | CD137/41BB | CD3ζ |
| TLR9 | DAP10 | CD137/41BB | CD3δ |
| TLR9 | DAP10 | CD137/41BB | CD3γ |
| TLR9 | DAP10 | CD137/41BB | CD3ε |
| TLR9 | DAP10 | CD137/41BB | FcγRI-γ |
| TLR9 | DAP10 | CD137/41BB | FcγRIII-γ |
| TLR9 | DAP10 | CD137/41BB | FcεRIβ |
| TLR9 | DAP10 | CD137/41BB | FcεRIγ |
| TLR9 | DAP10 | CD137/41BB | DAP10 |
| TLR9 | DAP10 | CD137/41BB | DAP12 |
| TLR9 | DAP10 | CD137/41BB | CD32 |
| TLR9 | DAP10 | CD137/41BB | CD79a |

TABLE 3-continued

Third Generation CARs

| Binding Region | Co-stimulatory Signal | Co-stimulatory Signal | Signal Domain |
|---|---|---|---|
| TLR9 | DAP10 | CD137/41BB | CD79b |
| TLR9 | DAP10 | ICOS | CD8 |
| TLR9 | DAP10 | ICOS | CD3ζ |
| TLR9 | DAP10 | ICOS | CD3δ |
| TLR9 | DAP10 | ICOS | CD3γ |
| TLR9 | DAP10 | ICOS | CD3ε |
| TLR9 | DAP10 | ICOS | FcγRI-γ |
| TLR9 | DAP10 | ICOS | FcγRIII-γ |
| TLR9 | DAP10 | ICOS | FcεRIβ |
| TLR9 | DAP10 | ICOS | FcεRIγ |
| TLR9 | DAP10 | ICOS | DAP10 |
| TLR9 | DAP10 | ICOS | DAP12 |
| TLR9 | DAP10 | ICOS | CD32 |
| TLR9 | DAP10 | ICOS | CD79a |
| TLR9 | DAP10 | ICOS | CD79b |
| TLR9 | DAP10 | CD27 | CD8 |
| TLR9 | DAP10 | CD27 | CD3ζ |
| TLR9 | DAP10 | CD27 | CD3δ |
| TLR9 | DAP10 | CD27 | CD3γ |
| TLR9 | DAP10 | CD27 | CD3ε |
| TLR9 | DAP10 | CD27 | FcγRI-γ |
| TLR9 | DAP10 | CD27 | FcγRIII-γ |
| TLR9 | DAP10 | CD27 | FcεRIβ |
| TLR9 | DAP10 | CD27 | FcεRIγ |
| TLR9 | DAP10 | CD27 | DAP10 |
| TLR9 | DAP10 | CD27 | DAP12 |
| TLR9 | DAP10 | CD27 | CD32 |
| TLR9 | DAP10 | CD27 | CD79a |
| TLR9 | DAP10 | CD27 | CD79b |
| TLR9 | DAP10 | CD28δ | CD8 |
| TLR9 | DAP10 | CD28δ | CD3ζ |
| TLR9 | DAP10 | CD28δ | CD3δ |
| TLR9 | DAP10 | CD28δ | CD3γ |
| TLR9 | DAP10 | CD28δ | CD3ε |
| TLR9 | DAP10 | CD28δ | FcγRI-γ |
| TLR9 | DAP10 | CD28δ | FcγRIII-γ |
| TLR9 | DAP10 | CD28δ | FcεRIβ |
| TLR9 | DAP10 | CD28δ | FcεRIγ |
| TLR9 | DAP10 | CD28δ | DAP10 |
| TLR9 | DAP10 | CD28δ | DAP12 |
| TLR9 | DAP10 | CD28δ | CD32 |
| TLR9 | DAP10 | CD28δ | CD79a |
| TLR9 | DAP10 | CD28δ | CD79b |
| TLR9 | DAP10 | CD80 | CD8 |
| TLR9 | DAP10 | CD80 | CD3ζ |
| TLR9 | DAP10 | CD80 | CD3δ |
| TLR9 | DAP10 | CD80 | CD3γ |
| TLR9 | DAP10 | CD80 | CD3ε |
| TLR9 | DAP10 | CD80 | FcγRI-γ |
| TLR9 | DAP10 | CD80 | FcγRIII-γ |
| TLR9 | DAP10 | CD80 | FcεRIβ |
| TLR9 | DAP10 | CD80 | FcεRIγ |
| TLR9 | DAP10 | CD80 | DAP10 |
| TLR9 | DAP10 | CD80 | DAP12 |
| TLR9 | DAP10 | CD80 | CD32 |
| TLR9 | DAP10 | CD80 | CD79a |
| TLR9 | DAP10 | CD80 | CD79b |
| TLR9 | DAP10 | CD86 | CD8 |
| TLR9 | DAP10 | CD86 | CD3ζ |
| TLR9 | DAP10 | CD86 | CD3δ |
| TLR9 | DAP10 | CD86 | CD3γ |
| TLR9 | DAP10 | CD86 | CD3ε |
| TLR9 | DAP10 | CD86 | FcγRI-γ |
| TLR9 | DAP10 | CD86 | FcγRIII-γ |
| TLR9 | DAP10 | CD86 | FcεRIβ |
| TLR9 | DAP10 | CD86 | FcεRIγ |
| TLR9 | DAP10 | CD86 | DAP10 |
| TLR9 | DAP10 | CD86 | DAP12 |
| TLR9 | DAP10 | CD86 | CD32 |
| TLR9 | DAP10 | CD86 | CD79a |
| TLR9 | DAP10 | CD86 | CD79b |
| TLR9 | DAP10 | OX40 | CD8 |
| TLR9 | DAP10 | OX40 | CD3ζ |
| TLR9 | DAP10 | OX40 | CD3δ |
| TLR9 | DAP10 | OX40 | CD3γ |
| TLR9 | DAP10 | OX40 | CD3ε |
| TLR9 | DAP10 | OX40 | FcγRI-γ |
| TLR9 | DAP10 | OX40 | FcγRIII-γ |
| TLR9 | DAP10 | OX40 | FcεRIβ |
| TLR9 | DAP10 | OX40 | FcεRIγ |
| TLR9 | DAP10 | OX40 | DAP10 |
| TLR9 | DAP10 | OX40 | DAP12 |
| TLR9 | DAP10 | OX40 | CD32 |
| TLR9 | DAP10 | OX40 | CD79a |
| TLR9 | DAP10 | OX40 | CD79b |
| TLR9 | DAP10 | DAP10 | CD8 |
| TLR9 | DAP10 | DAP10 | CD3ζ |
| TLR9 | DAP10 | DAP10 | CD3δ |
| TLR9 | DAP10 | DAP10 | CD3γ |
| TLR9 | DAP10 | DAP10 | CD3ε |
| TLR9 | DAP10 | DAP10 | FcγRI-γ |
| TLR9 | DAP10 | DAP10 | FcγRIII-γ |
| TLR9 | DAP10 | DAP10 | FcεRIβ |
| TLR9 | DAP10 | DAP10 | FcεRIγ |
| TLR9 | DAP10 | DAP10 | DAP10 |
| TLR9 | DAP10 | DAP10 | DAP12 |
| TLR9 | DAP10 | DAP10 | CD32 |
| TLR9 | DAP10 | DAP10 | CD79a |
| TLR9 | DAP10 | DAP10 | CD79b |
| TLR9 | DAP10 | DAP12 | CD8 |
| TLR9 | DAP10 | DAP12 | CD3ζ |
| TLR9 | DAP10 | DAP12 | CD3δ |
| TLR9 | DAP10 | DAP12 | CD3γ |
| TLR9 | DAP10 | DAP12 | CD3ε |
| TLR9 | DAP10 | DAP12 | FcγRI-γ |
| TLR9 | DAP10 | DAP12 | FcγRIII-γ |
| TLR9 | DAP10 | DAP12 | FcεRIβ |
| TLR9 | DAP10 | DAP12 | FcεRIγ |
| TLR9 | DAP10 | DAP12 | DAP10 |
| TLR9 | DAP10 | DAP12 | DAP12 |
| TLR9 | DAP10 | DAP12 | CD32 |
| TLR9 | DAP10 | DAP12 | CD79a |
| TLR9 | DAP10 | DAP12 | CD79b |
| TLR9 | DAP10 | MyD88 | CD8 |
| TLR9 | DAP10 | MyD88 | CD3ζ |
| TLR9 | DAP10 | MyD88 | CD3δ |
| TLR9 | DAP10 | MyD88 | CD3γ |
| TLR9 | DAP10 | MyD88 | CD3ε |
| TLR9 | DAP10 | MyD88 | FcγRI-γ |
| TLR9 | DAP10 | MyD88 | FcγRIII-γ |
| TLR9 | DAP10 | MyD88 | FcεRIβ |
| TLR9 | DAP10 | MyD88 | FcεRIγ |
| TLR9 | DAP10 | MyD88 | DAP10 |
| TLR9 | DAP10 | MyD88 | DAP12 |
| TLR9 | DAP10 | MyD88 | CD32 |
| TLR9 | DAP10 | MyD88 | CD79a |
| TLR9 | DAP10 | MyD88 | CD79b |
| TLR9 | DAP10 | CD7 | CD8 |
| TLR9 | DAP10 | CD7 | CD3ζ |
| TLR9 | DAP10 | CD7 | CD3δ |
| TLR9 | DAP10 | CD7 | CD3γ |
| TLR9 | DAP10 | CD7 | CD3ε |
| TLR9 | DAP10 | CD7 | FcγRI-γ |
| TLR9 | DAP10 | CD7 | FcγRIII-γ |
| TLR9 | DAP10 | CD7 | FcεRIβ |
| TLR9 | DAP10 | CD7 | FcεRIγ |
| TLR9 | DAP10 | CD7 | DAP10 |
| TLR9 | DAP10 | CD7 | DAP12 |
| TLR9 | DAP10 | CD7 | CD32 |
| TLR9 | DAP10 | CD7 | CD79a |
| TLR9 | DAP10 | CD7 | CD79b |
| TLR9 | DAP10 | BTNL3 | CD8 |
| TLR9 | DAP10 | BTNL3 | CD3ζ |
| TLR9 | DAP10 | BTNL3 | CD3δ |
| TLR9 | DAP10 | BTNL3 | CD3γ |
| TLR9 | DAP10 | BTNL3 | CD3ε |
| TLR9 | DAP10 | BTNL3 | FcγRI-γ |
| TLR9 | DAP10 | BTNL3 | FcγRIII-γ |

TABLE 3-continued

Third Generation CARs

| Binding Region | Co-stimulatory Signal | Co-stimulatory Signal | Signal Domain |
|---|---|---|---|
| TLR9 | DAP10 | BTNL3 | FcεRIβ |
| TLR9 | DAP10 | BTNL3 | FcεRIγ |
| TLR9 | DAP10 | BTNL3 | DAP10 |
| TLR9 | DAP10 | BTNL3 | DAP12 |
| TLR9 | DAP10 | BTNL3 | CD32 |
| TLR9 | DAP10 | BTNL3 | CD79a |
| TLR9 | DAP10 | BTNL3 | CD79b |
| TLR9 | DAP10 | NKG2D | CD8 |
| TLR9 | DAP10 | NKG2D | CD3ζ |
| TLR9 | DAP10 | NKG2D | CD3δ |
| TLR9 | DAP10 | NKG2D | CD3γ |
| TLR9 | DAP10 | NKG2D | CD3ε |
| TLR9 | DAP10 | NKG2D | FcγRI-γ |
| TLR9 | DAP10 | NKG2D | FcγRIII-γ |
| TLR9 | DAP10 | NKG2D | FcεRIβ |
| TLR9 | DAP10 | NKG2D | FcεRIγ |
| TLR9 | DAP10 | NKG2D | DAP10 |
| TLR9 | DAP10 | NKG2D | DAP12 |
| TLR9 | DAP10 | NKG2D | CD32 |
| TLR9 | DAP10 | NKG2D | CD79a |
| TLR9 | DAP10 | NKG2D | CD79b |
| TLR9 | DAP12 | CD28 | CD8 |
| TLR9 | DAP12 | CD28 | CD3ζ |
| TLR9 | DAP12 | CD28 | CD3δ |
| TLR9 | DAP12 | CD28 | CD3γ |
| TLR9 | DAP12 | CD28 | CD3ε |
| TLR9 | DAP12 | CD28 | FcγRI-γ |
| TLR9 | DAP12 | CD28 | FcγRIII-γ |
| TLR9 | DAP12 | CD28 | FcεRIβ |
| TLR9 | DAP12 | CD28 | FcεRIγ |
| TLR9 | DAP12 | CD28 | DAP10 |
| TLR9 | DAP12 | CD28 | DAP12 |
| TLR9 | DAP12 | CD28 | CD32 |
| TLR9 | DAP12 | CD28 | CD79a |
| TLR9 | DAP12 | CD28 | CD79b |
| TLR9 | DAP12 | CD8 | CD8 |
| TLR9 | DAP12 | CD8 | CD3ζ |
| TLR9 | DAP12 | CD8 | CD3δ |
| TLR9 | DAP12 | CD8 | CD3γ |
| TLR9 | DAP12 | CD8 | CD3ε |
| TLR9 | DAP12 | CD8 | FcγRI-γ |
| TLR9 | DAP12 | CD8 | FcγRIII-γ |
| TLR9 | DAP12 | CD8 | FcεRIβ |
| TLR9 | DAP12 | CD8 | FcεRIγ |
| TLR9 | DAP12 | CD8 | DAP10 |
| TLR9 | DAP12 | CD8 | DAP12 |
| TLR9 | DAP12 | CD8 | CD32 |
| TLR9 | DAP12 | CD8 | CD79a |
| TLR9 | DAP12 | CD8 | CD79b |
| TLR9 | DAP12 | CD4 | CD8 |
| TLR9 | DAP12 | CD4 | CD3ζ |
| TLR9 | DAP12 | CD4 | CD3δ |
| TLR9 | DAP12 | CD4 | CD3γ |
| TLR9 | DAP12 | CD4 | CD3ε |
| TLR9 | DAP12 | CD4 | FcγRI-γ |
| TLR9 | DAP12 | CD4 | FcγRIII-γ |
| TLR9 | DAP12 | CD4 | FcεRIβ |
| TLR9 | DAP12 | CD4 | FcεRIγ |
| TLR9 | DAP12 | CD4 | DAP10 |
| TLR9 | DAP12 | CD4 | DAP12 |
| TLR9 | DAP12 | CD4 | CD32 |
| TLR9 | DAP12 | CD4 | CD79a |
| TLR9 | DAP12 | CD4 | CD79b |
| TLR9 | DAP12 | b2c | CD8 |
| TLR9 | DAP12 | b2c | CD3ζ |
| TLR9 | DAP12 | b2c | CD3δ |
| TLR9 | DAP12 | b2c | CD3γ |
| TLR9 | DAP12 | b2c | CD3ε |
| TLR9 | DAP12 | b2c | FcγRI-γ |
| TLR9 | DAP12 | b2c | FcγRIII-γ |
| TLR9 | DAP12 | b2c | FcεRIβ |
| TLR9 | DAP12 | b2c | FcεRIγ |
| TLR9 | DAP12 | b2c | DAP10 |
| TLR9 | DAP12 | b2c | DAP12 |
| TLR9 | DAP12 | b2c | CD32 |
| TLR9 | DAP12 | b2c | CD79a |
| TLR9 | DAP12 | b2c | CD79b |
| TLR9 | DAP12 | CD137/41BB | CD8 |
| TLR9 | DAP12 | CD137/41BB | CD3ζ |
| TLR9 | DAP12 | CD137/41BB | CD3δ |
| TLR9 | DAP12 | CD137/41BB | CD3γ |
| TLR9 | DAP12 | CD137/41BB | CD3ε |
| TLR9 | DAP12 | CD137/41BB | FcγRI-γ |
| TLR9 | DAP12 | CD137/41BB | FcγRIII-γ |
| TLR9 | DAP12 | CD137/41BB | FcεRIβ |
| TLR9 | DAP12 | CD137/41BB | FcεRIγ |
| TLR9 | DAP12 | CD137/41BB | DAP10 |
| TLR9 | DAP12 | CD137/41BB | DAP12 |
| TLR9 | DAP12 | CD137/41BB | CD32 |
| TLR9 | DAP12 | CD137/41BB | CD79a |
| TLR9 | DAP12 | CD137/41BB | CD79b |
| TLR9 | DAP12 | ICOS | CD8 |
| TLR9 | DAP12 | ICOS | CD3ζ |
| TLR9 | DAP12 | ICOS | CD3δ |
| TLR9 | DAP12 | ICOS | CD3γ |
| TLR9 | DAP12 | ICOS | CD3ε |
| TLR9 | DAP12 | ICOS | FcγRI-γ |
| TLR9 | DAP12 | ICOS | FcγRIII-γ |
| TLR9 | DAP12 | ICOS | FcεRIβ |
| TLR9 | DAP12 | ICOS | FcεRIγ |
| TLR9 | DAP12 | ICOS | DAP10 |
| TLR9 | DAP12 | ICOS | DAP12 |
| TLR9 | DAP12 | ICOS | CD32 |
| TLR9 | DAP12 | ICOS | CD79a |
| TLR9 | DAP12 | ICOS | CD79b |
| TLR9 | DAP12 | CD27 | CD8 |
| TLR9 | DAP12 | CD27 | CD3ζ |
| TLR9 | DAP12 | CD27 | CD3δ |
| TLR9 | DAP12 | CD27 | CD3γ |
| TLR9 | DAP12 | CD27 | CD3ε |
| TLR9 | DAP12 | CD27 | FcγRI-γ |
| TLR9 | DAP12 | CD27 | FcγRIII-γ |
| TLR9 | DAP12 | CD27 | FcεRIβ |
| TLR9 | DAP12 | CD27 | FcεRIγ |
| TLR9 | DAP12 | CD27 | DAP10 |
| TLR9 | DAP12 | CD27 | DAP12 |
| TLR9 | DAP12 | CD27 | CD32 |
| TLR9 | DAP12 | CD27 | CD79a |
| TLR9 | DAP12 | CD27 | CD79b |
| TLR9 | DAP12 | CD28δ | CD8 |
| TLR9 | DAP12 | CD28δ | CD3ζ |
| TLR9 | DAP12 | CD28δ | CD3δ |
| TLR9 | DAP12 | CD28δ | CD3γ |
| TLR9 | DAP12 | CD28δ | CD3ε |
| TLR9 | DAP12 | CD28δ | FcγRI-γ |
| TLR9 | DAP12 | CD28δ | FcγRIII-γ |
| TLR9 | DAP12 | CD28δ | FcεRIβ |
| TLR9 | DAP12 | CD28δ | FcεRIγ |
| TLR9 | DAP12 | CD28δ | DAP10 |
| TLR9 | DAP12 | CD28δ | DAP12 |
| TLR9 | DAP12 | CD28δ | CD32 |
| TLR9 | DAP12 | CD28δ | CD79a |
| TLR9 | DAP12 | CD28δ | CD79b |
| TLR9 | DAP12 | CD80 | CD8 |
| TLR9 | DAP12 | CD80 | CD3ζ |
| TLR9 | DAP12 | CD80 | CD3δ |
| TLR9 | DAP12 | CD80 | CD3γ |
| TLR9 | DAP12 | CD80 | CD3ε |
| TLR9 | DAP12 | CD80 | FcγRI-γ |
| TLR9 | DAP12 | CD80 | FcγRIII-γ |
| TLR9 | DAP12 | CD80 | FcεRIβ |
| TLR9 | DAP12 | CD80 | FcεRIγ |
| TLR9 | DAP12 | CD80 | DAP10 |
| TLR9 | DAP12 | CD80 | DAP12 |
| TLR9 | DAP12 | CD80 | CD32 |
| TLR9 | DAP12 | CD80 | CD79a |
| TLR9 | DAP12 | CD80 | CD79b |
| TLR9 | DAP12 | CD86 | CD8 |

TABLE 3-continued

Third Generation CARs

| Binding Region | Co-stimulatory Signal | Co-stimulatory Signal | Signal Domain |
|---|---|---|---|
| TLR9 | DAP12 | CD86 | CD3ζ |
| TLR9 | DAP12 | CD86 | CD3δ |
| TLR9 | DAP12 | CD86 | CD3γ |
| TLR9 | DAP12 | CD86 | CD3ε |
| TLR9 | DAP12 | CD86 | FcγRI-γ |
| TLR9 | DAP12 | CD86 | FcγRIII-γ |
| TLR9 | DAP12 | CD86 | FcεRIβ |
| TLR9 | DAP12 | CD86 | FcεRIγ |
| TLR9 | DAP12 | CD86 | DAP10 |
| TLR9 | DAP12 | CD86 | DAP12 |
| TLR9 | DAP12 | CD86 | CD32 |
| TLR9 | DAP12 | CD86 | CD79a |
| TLR9 | DAP12 | CD86 | CD79b |
| TLR9 | DAP12 | OX40 | CD8 |
| TLR9 | DAP12 | OX40 | CD3ζ |
| TLR9 | DAP12 | OX40 | CD3δ |
| TLR9 | DAP12 | OX40 | CD3γ |
| TLR9 | DAP12 | OX40 | CD3ε |
| TLR9 | DAP12 | OX40 | FcγRI-γ |
| TLR9 | DAP12 | OX40 | FcγRIII-γ |
| TLR9 | DAP12 | OX40 | FcεRIβ |
| TLR9 | DAP12 | OX40 | FcεRIγ |
| TLR9 | DAP12 | OX40 | DAP10 |
| TLR9 | DAP12 | OX40 | DAP12 |
| TLR9 | DAP12 | OX40 | CD32 |
| TLR9 | DAP12 | OX40 | CD79a |
| TLR9 | DAP12 | OX40 | CD79b |
| TLR9 | DAP12 | DAP10 | CD8 |
| TLR9 | DAP12 | DAP10 | CD3ζ |
| TLR9 | DAP12 | DAP10 | CD3δ |
| TLR9 | DAP12 | DAP10 | CD3γ |
| TLR9 | DAP12 | DAP10 | CD3ε |
| TLR9 | DAP12 | DAP10 | FcγRI-γ |
| TLR9 | DAP12 | DAP10 | FcγRIII-γ |
| TLR9 | DAP12 | DAP10 | FcεRIβ |
| TLR9 | DAP12 | DAP10 | FcεRIγ |
| TLR9 | DAP12 | DAP10 | DAP10 |
| TLR9 | DAP12 | DAP10 | DAP12 |
| TLR9 | DAP12 | DAP10 | CD32 |
| TLR9 | DAP12 | DAP10 | CD79a |
| TLR9 | DAP12 | DAP10 | CD79b |
| TLR9 | DAP12 | DAP12 | CD8 |
| TLR9 | DAP12 | DAP12 | CD3ζ |
| TLR9 | DAP12 | DAP12 | CD3δ |
| TLR9 | DAP12 | DAP12 | CD3γ |
| TLR9 | DAP12 | DAP12 | CD3ε |
| TLR9 | DAP12 | DAP12 | FcγRI-γ |
| TLR9 | DAP12 | DAP12 | FcγRIII-γ |
| TLR9 | DAP12 | DAP12 | FcεRIβ |
| TLR9 | DAP12 | DAP12 | FcεRIγ |
| TLR9 | DAP12 | DAP12 | DAP10 |
| TLR9 | DAP12 | DAP12 | DAP12 |
| TLR9 | DAP12 | DAP12 | CD32 |
| TLR9 | DAP12 | DAP12 | CD79a |
| TLR9 | DAP12 | DAP12 | CD79b |
| TLR9 | DAP12 | MyD88 | CD8 |
| TLR9 | DAP12 | MyD88 | CD3ζ |
| TLR9 | DAP12 | MyD88 | CD3δ |
| TLR9 | DAP12 | MyD88 | CD3γ |
| TLR9 | DAP12 | MyD88 | CD3ε |
| TLR9 | DAP12 | MyD88 | FcγRI-γ |
| TLR9 | DAP12 | MyD88 | FcγRIII-γ |
| TLR9 | DAP12 | MyD88 | FcεRIβ |
| TLR9 | DAP12 | MyD88 | FcεRIγ |
| TLR9 | DAP12 | MyD88 | DAP10 |
| TLR9 | DAP12 | MyD88 | DAP12 |
| TLR9 | DAP12 | MyD88 | CD32 |
| TLR9 | DAP12 | MyD88 | CD79a |
| TLR9 | DAP12 | MyD88 | CD79b |
| TLR9 | DAP12 | CD7 | CD8 |
| TLR9 | DAP12 | CD7 | CD3ζ |
| TLR9 | DAP12 | CD7 | CD3δ |
| TLR9 | DAP12 | CD7 | CD3γ |
| TLR9 | DAP12 | CD7 | CD3ε |
| TLR9 | DAP12 | CD7 | FcγRI-γ |
| TLR9 | DAP12 | CD7 | FcγRIII-γ |
| TLR9 | DAP12 | CD7 | FcεRIβ |
| TLR9 | DAP12 | CD7 | FcεRIγ |
| TLR9 | DAP12 | CD7 | DAP10 |
| TLR9 | DAP12 | CD7 | DAP12 |
| TLR9 | DAP12 | CD7 | CD32 |
| TLR9 | DAP12 | CD7 | CD79a |
| TLR9 | DAP12 | CD7 | CD79b |
| TLR9 | DAP12 | BTNL3 | CD8 |
| TLR9 | DAP12 | BTNL3 | CD3ζ |
| TLR9 | DAP12 | BTNL3 | CD3δ |
| TLR9 | DAP12 | BTNL3 | CD3γ |
| TLR9 | DAP12 | BTNL3 | CD3ε |
| TLR9 | DAP12 | BTNL3 | FcγRI-γ |
| TLR9 | DAP12 | BTNL3 | FcγRIII-γ |
| TLR9 | DAP12 | BTNL3 | FcεRIβ |
| TLR9 | DAP12 | BTNL3 | FcεRIγ |
| TLR9 | DAP12 | BTNL3 | DAP10 |
| TLR9 | DAP12 | BTNL3 | DAP12 |
| TLR9 | DAP12 | BTNL3 | CD32 |
| TLR9 | DAP12 | BTNL3 | CD79a |
| TLR9 | DAP12 | BTNL3 | CD79b |
| TLR9 | DAP12 | NKG2D | CD8 |
| TLR9 | DAP12 | NKG2D | CD3ζ |
| TLR9 | DAP12 | NKG2D | CD3δ |
| TLR9 | DAP12 | NKG2D | CD3γ |
| TLR9 | DAP12 | NKG2D | CD3ε |
| TLR9 | DAP12 | NKG2D | FcγRI-γ |
| TLR9 | DAP12 | NKG2D | FcγRIII-γ |
| TLR9 | DAP12 | NKG2D | FcεRIβ |
| TLR9 | DAP12 | NKG2D | FcεRIγ |
| TLR9 | DAP12 | NKG2D | DAP10 |
| TLR9 | DAP12 | NKG2D | DAP12 |
| TLR9 | DAP12 | NKG2D | CD32 |
| TLR9 | DAP12 | NKG2D | CD79a |
| TLR9 | DAP12 | NKG2D | CD79b |
| TLR9 | MyD88 | CD28 | CD8 |
| TLR9 | MyD88 | CD28 | CD3ζ |
| TLR9 | MyD88 | CD28 | CD3δ |
| TLR9 | MyD88 | CD28 | CD3γ |
| TLR9 | MyD88 | CD28 | CD3ε |
| TLR9 | MyD88 | CD28 | FcγRI-γ |
| TLR9 | MyD88 | CD28 | FcγRIII-γ |
| TLR9 | MyD88 | CD28 | FcεRIβ |
| TLR9 | MyD88 | CD28 | FcεRIγ |
| TLR9 | MyD88 | CD28 | DAP10 |
| TLR9 | MyD88 | CD28 | DAP12 |
| TLR9 | MyD88 | CD28 | CD32 |
| TLR9 | MyD88 | CD28 | CD79a |
| TLR9 | MyD88 | CD28 | CD79b |
| TLR9 | MyD88 | CD8 | CD8 |
| TLR9 | MyD88 | CD8 | CD3ζ |
| TLR9 | MyD88 | CD8 | CD3δ |
| TLR9 | MyD88 | CD8 | CD3γ |
| TLR9 | MyD88 | CD8 | CD3ε |
| TLR9 | MyD88 | CD8 | FcγRI-γ |
| TLR9 | MyD88 | CD8 | FcγRIII-γ |
| TLR9 | MyD88 | CD8 | FcεRIβ |
| TLR9 | MyD88 | CD8 | FcεRIγ |
| TLR9 | MyD88 | CD8 | DAP10 |
| TLR9 | MyD88 | CD8 | DAP12 |
| TLR9 | MyD88 | CD8 | CD32 |
| TLR9 | MyD88 | CD8 | CD79a |
| TLR9 | MyD88 | CD8 | CD79b |
| TLR9 | MyD88 | CD4 | CD8 |
| TLR9 | MyD88 | CD4 | CD3ζ |
| TLR9 | MyD88 | CD4 | CD3δ |
| TLR9 | MyD88 | CD4 | CD3γ |
| TLR9 | MyD88 | CD4 | CD3ε |
| TLR9 | MyD88 | CD4 | FcγRI-γ |
| TLR9 | MyD88 | CD4 | FcγRIII-γ |
| TLR9 | MyD88 | CD4 | FcεRIβ |
| TLR9 | MyD88 | CD4 | FcεRIγ |

TABLE 3-continued

Third Generation CARs

| Binding Region | Co-stimulatory Signal | Co-stimulatory Signal | Signal Domain |
|---|---|---|---|
| TLR9 | MyD88 | CD4 | DAP10 |
| TLR9 | MyD88 | CD4 | DAP12 |
| TLR9 | MyD88 | CD4 | CD32 |
| TLR9 | MyD88 | CD4 | CD79a |
| TLR9 | MyD88 | CD4 | CD79b |
| TLR9 | MyD88 | b2c | CD8 |
| TLR9 | MyD88 | b2c | CD3ζ |
| TLR9 | MyD88 | b2c | CD3δ |
| TLR9 | MyD88 | b2c | CD3γ |
| TLR9 | MyD88 | b2c | CD3ε |
| TLR9 | MyD88 | b2c | FcγRI-γ |
| TLR9 | MyD88 | b2c | FcγRIII-γ |
| TLR9 | MyD88 | b2c | FcεRIβ |
| TLR9 | MyD88 | b2c | FcεRIγ |
| TLR9 | MyD88 | b2c | DAP10 |
| TLR9 | MyD88 | b2c | DAP12 |
| TLR9 | MyD88 | b2c | CD32 |
| TLR9 | MyD88 | b2c | CD79a |
| TLR9 | MyD88 | b2c | CD79b |
| TLR9 | MyD88 | CD137/41BB | CD8 |
| TLR9 | MyD88 | CD137/41BB | CD3ζ |
| TLR9 | MyD88 | CD137/41BB | CD3δ |
| TLR9 | MyD88 | CD137/41BB | CD3γ |
| TLR9 | MyD88 | CD137/41BB | CD3ε |
| TLR9 | MyD88 | CD137/41BB | FcγRI-γ |
| TLR9 | MyD88 | CD137/41BB | FcγRIII-γ |
| TLR9 | MyD88 | CD137/41BB | FcεRIβ |
| TLR9 | MyD88 | CD137/41BB | FcεRIγ |
| TLR9 | MyD88 | CD137/41BB | DAP10 |
| TLR9 | MyD88 | CD137/41BB | DAP12 |
| TLR9 | MyD88 | CD137/41BB | CD32 |
| TLR9 | MyD88 | CD137/41BB | CD79a |
| TLR9 | MyD88 | CD137/41BB | CD79b |
| TLR9 | MyD88 | ICOS | CD8 |
| TLR9 | MyD88 | ICOS | CD3ζ |
| TLR9 | MyD88 | ICOS | CD3δ |
| TLR9 | MyD88 | ICOS | CD3γ |
| TLR9 | MyD88 | ICOS | CD3ε |
| TLR9 | MyD88 | ICOS | FcγRI-γ |
| TLR9 | MyD88 | ICOS | FcγRIII-γ |
| TLR9 | MyD88 | ICOS | FcεRIβ |
| TLR9 | MyD88 | ICOS | FcεRIγ |
| TLR9 | MyD88 | ICOS | DAP10 |
| TLR9 | MyD88 | ICOS | DAP12 |
| TLR9 | MyD88 | ICOS | CD32 |
| TLR9 | MyD88 | ICOS | CD79a |
| TLR9 | MyD88 | ICOS | CD79b |
| TLR9 | MyD88 | CD27 | CD8 |
| TLR9 | MyD88 | CD27 | CD3ζ |
| TLR9 | MyD88 | CD27 | CD3δ |
| TLR9 | MyD88 | CD27 | CD3γ |
| TLR9 | MyD88 | CD27 | CD3ε |
| TLR9 | MyD88 | CD27 | FcγRI-γ |
| TLR9 | MyD88 | CD27 | FcγRIII-γ |
| TLR9 | MyD88 | CD27 | FcεRIβ |
| TLR9 | MyD88 | CD27 | FcεRIγ |
| TLR9 | MyD88 | CD27 | DAP10 |
| TLR9 | MyD88 | CD27 | DAP12 |
| TLR9 | MyD88 | CD27 | CD32 |
| TLR9 | MyD88 | CD27 | CD79a |
| TLR9 | MyD88 | CD27 | CD79b |
| TLR9 | MyD88 | CD28δ | CD8 |
| TLR9 | MyD88 | CD28δ | CD3ζ |
| TLR9 | MyD88 | CD28δ | CD3δ |
| TLR9 | MyD88 | CD28δ | CD3γ |
| TLR9 | MyD88 | CD28δ | CD3ε |
| TLR9 | MyD88 | CD28δ | FcγRI-γ |
| TLR9 | MyD88 | CD28δ | FcγRIII-γ |
| TLR9 | MyD88 | CD28δ | FcεRIβ |
| TLR9 | MyD88 | CD28δ | FcεRIγ |
| TLR9 | MyD88 | CD28δ | DAP10 |
| TLR9 | MyD88 | CD28δ | DAP12 |
| TLR9 | MyD88 | CD28δ | CD32 |
| TLR9 | MyD88 | CD28δ | CD79a |
| TLR9 | MyD88 | CD28δ | CD79b |
| TLR9 | MyD88 | CD80 | CD8 |
| TLR9 | MyD88 | CD80 | CD3ζ |
| TLR9 | MyD88 | CD80 | CD3δ |
| TLR9 | MyD88 | CD80 | CD3γ |
| TLR9 | MyD88 | CD80 | CD3ε |
| TLR9 | MyD88 | CD80 | FcγRI-γ |
| TLR9 | MyD88 | CD80 | FcγRIII-γ |
| TLR9 | MyD88 | CD80 | FcεRIβ |
| TLR9 | MyD88 | CD80 | FcεRIγ |
| TLR9 | MyD88 | CD80 | DAP10 |
| TLR9 | MyD88 | CD80 | DAP12 |
| TLR9 | MyD88 | CD80 | CD32 |
| TLR9 | MyD88 | CD80 | CD79a |
| TLR9 | MyD88 | CD80 | CD79b |
| TLR9 | MyD88 | CD86 | CD8 |
| TLR9 | MyD88 | CD86 | CD3ζ |
| TLR9 | MyD88 | CD86 | CD3δ |
| TLR9 | MyD88 | CD86 | CD3γ |
| TLR9 | MyD88 | CD86 | CD3ε |
| TLR9 | MyD88 | CD86 | FcγRI-γ |
| TLR9 | MyD88 | CD86 | FcγRIII-γ |
| TLR9 | MyD88 | CD86 | FcεRIβ |
| TLR9 | MyD88 | CD86 | FcεRIγ |
| TLR9 | MyD88 | CD86 | DAP10 |
| TLR9 | MyD88 | CD86 | DAP12 |
| TLR9 | MyD88 | CD86 | CD32 |
| TLR9 | MyD88 | CD86 | CD79a |
| TLR9 | MyD88 | CD86 | CD79b |
| TLR9 | MyD88 | OX40 | CD8 |
| TLR9 | MyD88 | OX40 | CD3ζ |
| TLR9 | MyD88 | OX40 | CD3δ |
| TLR9 | MyD88 | OX40 | CD3γ |
| TLR9 | MyD88 | OX40 | CD3ε |
| TLR9 | MyD88 | OX40 | FcγRI-γ |
| TLR9 | MyD88 | OX40 | FcγRIII-γ |
| TLR9 | MyD88 | OX40 | FcεRIβ |
| TLR9 | MyD88 | OX40 | FcεRIγ |
| TLR9 | MyD88 | OX40 | DAP10 |
| TLR9 | MyD88 | OX40 | DAP12 |
| TLR9 | MyD88 | OX40 | CD32 |
| TLR9 | MyD88 | OX40 | CD79a |
| TLR9 | MyD88 | OX40 | CD79b |
| TLR9 | MyD88 | DAP10 | CD8 |
| TLR9 | MyD88 | DAP10 | CD3ζ |
| TLR9 | MyD88 | DAP10 | CD3δ |
| TLR9 | MyD88 | DAP10 | CD3γ |
| TLR9 | MyD88 | DAP10 | CD3ε |
| TLR9 | MyD88 | DAP10 | FcγRI-γ |
| TLR9 | MyD88 | DAP10 | FcγRIII-γ |
| TLR9 | MyD88 | DAP10 | FcεRIβ |
| TLR9 | MyD88 | DAP10 | FcεRIγ |
| TLR9 | MyD88 | DAP10 | DAP10 |
| TLR9 | MyD88 | DAP10 | DAP12 |
| TLR9 | MyD88 | DAP10 | CD32 |
| TLR9 | MyD88 | DAP10 | CD79a |
| TLR9 | MyD88 | DAP10 | CD79b |
| TLR9 | MyD88 | DAP12 | CD8 |
| TLR9 | MyD88 | DAP12 | CD3ζ |
| TLR9 | MyD88 | DAP12 | CD3δ |
| TLR9 | MyD88 | DAP12 | CD3γ |
| TLR9 | MyD88 | DAP12 | CD3ε |
| TLR9 | MyD88 | DAP12 | FcγRI-γ |
| TLR9 | MyD88 | DAP12 | FcγRIII-γ |
| TLR9 | MyD88 | DAP12 | FcεRIβ |
| TLR9 | MyD88 | DAP12 | FcεRIγ |
| TLR9 | MyD88 | DAP12 | DAP10 |
| TLR9 | MyD88 | DAP12 | DAP12 |
| TLR9 | MyD88 | DAP12 | CD32 |
| TLR9 | MyD88 | DAP12 | CD79a |
| TLR9 | MyD88 | DAP12 | CD79b |
| TLR9 | MyD88 | MyD88 | CD8 |
| TLR9 | MyD88 | MyD88 | CD3ζ |
| TLR9 | MyD88 | MyD88 | CD3δ |

TABLE 3-continued

Third Generation CARs

| Binding Region | Co-stimulatory Signal | Co-stimulatory Signal | Signal Domain |
|---|---|---|---|
| TLR9 | MyD88 | MyD88 | CD3γ |
| TLR9 | MyD88 | MyD88 | CD3ε |
| TLR9 | MyD88 | MyD88 | FcγRI-γ |
| TLR9 | MyD88 | MyD88 | FcγRIII-γ |
| TLR9 | MyD88 | MyD88 | FcεRIβ |
| TLR9 | MyD88 | MyD88 | FcεRIγ |
| TLR9 | MyD88 | MyD88 | DAP10 |
| TLR9 | MyD88 | MyD88 | DAP12 |
| TLR9 | MyD88 | MyD88 | CD32 |
| TLR9 | MyD88 | MyD88 | CD79a |
| TLR9 | MyD88 | MyD88 | CD79b |
| TLR9 | MyD88 | CD7 | CD8 |
| TLR9 | MyD88 | CD7 | CD3ζ |
| TLR9 | MyD88 | CD7 | CD3δ |
| TLR9 | MyD88 | CD7 | CD3γ |
| TLR9 | MyD88 | CD7 | CD3ε |
| TLR9 | MyD88 | CD7 | FcγRI-γ |
| TLR9 | MyD88 | CD7 | FcγRIII-γ |
| TLR9 | MyD88 | CD7 | FcεRIβ |
| TLR9 | MyD88 | CD7 | FcεRIγ |
| TLR9 | MyD88 | CD7 | DAP10 |
| TLR9 | MyD88 | CD7 | DAP12 |
| TLR9 | MyD88 | CD7 | CD32 |
| TLR9 | MyD88 | CD7 | CD79a |
| TLR9 | MyD88 | CD7 | CD79b |
| TLR9 | MyD88 | BTNL3 | CD8 |
| TLR9 | MyD88 | BTNL3 | CD3ζ |
| TLR9 | MyD88 | BTNL3 | CD3δ |
| TLR9 | MyD88 | BTNL3 | CD3γ |
| TLR9 | MyD88 | BTNL3 | CD3ε |
| TLR9 | MyD88 | BTNL3 | FcγRI-γ |
| TLR9 | MyD88 | BTNL3 | FcγRIII-γ |
| TLR9 | MyD88 | BTNL3 | FcεRIβ |
| TLR9 | MyD88 | BTNL3 | FcεRIγ |
| TLR9 | MyD88 | BTNL3 | DAP10 |
| TLR9 | MyD88 | BTNL3 | DAP12 |
| TLR9 | MyD88 | BTNL3 | CD32 |
| TLR9 | MyD88 | BTNL3 | CD79a |
| TLR9 | MyD88 | BTNL3 | CD79b |
| TLR9 | MyD88 | NKG2D | CD8 |
| TLR9 | MyD88 | NKG2D | CD3ζ |
| TLR9 | MyD88 | NKG2D | CD3δ |
| TLR9 | MyD88 | NKG2D | CD3γ |
| TLR9 | MyD88 | NKG2D | CD3ε |
| TLR9 | MyD88 | NKG2D | FcγRI-γ |
| TLR9 | MyD88 | NKG2D | FcγRIII-γ |
| TLR9 | MyD88 | NKG2D | FcεRIβ |
| TLR9 | MyD88 | NKG2D | FcεRIγ |
| TLR9 | MyD88 | NKG2D | DAP10 |
| TLR9 | MyD88 | NKG2D | DAP12 |
| TLR9 | MyD88 | NKG2D | CD32 |
| TLR9 | MyD88 | NKG2D | CD79a |
| TLR9 | MyD88 | NKG2D | CD79b |
| TLR9 | CD7 | CD28 | CD8 |
| TLR9 | CD7 | CD28 | CD3ζ |
| TLR9 | CD7 | CD28 | CD3δ |
| TLR9 | CD7 | CD28 | CD3γ |
| TLR9 | CD7 | CD28 | CD3ε |
| TLR9 | CD7 | CD28 | FcγRI-γ |
| TLR9 | CD7 | CD28 | FcγRIII-γ |
| TLR9 | CD7 | CD28 | FcεRIβ |
| TLR9 | CD7 | CD28 | FcεRIγ |
| TLR9 | CD7 | CD28 | DAP10 |
| TLR9 | CD7 | CD28 | DAP12 |
| TLR9 | CD7 | CD28 | CD32 |
| TLR9 | CD7 | CD28 | CD79a |
| TLR9 | CD7 | CD28 | CD79b |
| TLR9 | CD7 | CD8 | CD8 |
| TLR9 | CD7 | CD8 | CD3ζ |
| TLR9 | CD7 | CD8 | CD3δ |
| TLR9 | CD7 | CD8 | CD3γ |
| TLR9 | CD7 | CD8 | CD3ε |
| TLR9 | CD7 | CD8 | FcγRI-γ |
| TLR9 | CD7 | CD8 | FcγRIII-γ |
| TLR9 | CD7 | CD8 | FcεRIβ |
| TLR9 | CD7 | CD8 | FcεRIγ |
| TLR9 | CD7 | CD8 | DAP10 |
| TLR9 | CD7 | CD8 | DAP12 |
| TLR9 | CD7 | CD8 | CD32 |
| TLR9 | CD7 | CD8 | CD79a |
| TLR9 | CD7 | CD8 | CD79b |
| TLR9 | CD7 | CD4 | CD8 |
| TLR9 | CD7 | CD4 | CD3ζ |
| TLR9 | CD7 | CD4 | CD3δ |
| TLR9 | CD7 | CD4 | CD3γ |
| TLR9 | CD7 | CD4 | CD3ε |
| TLR9 | CD7 | CD4 | FcγRI-γ |
| TLR9 | CD7 | CD4 | FcγRIII-γ |
| TLR9 | CD7 | CD4 | FcεRIβ |
| TLR9 | CD7 | CD4 | FcεRIγ |
| TLR9 | CD7 | CD4 | DAP10 |
| TLR9 | CD7 | CD4 | DAP12 |
| TLR9 | CD7 | CD4 | CD32 |
| TLR9 | CD7 | CD4 | CD79a |
| TLR9 | CD7 | CD4 | CD79b |
| TLR9 | CD7 | b2c | CD8 |
| TLR9 | CD7 | b2c | CD3ζ |
| TLR9 | CD7 | b2c | CD3δ |
| TLR9 | CD7 | b2c | CD3γ |
| TLR9 | CD7 | b2c | CD3ε |
| TLR9 | CD7 | b2c | FcγRI-γ |
| TLR9 | CD7 | b2c | FcγRIII-γ |
| TLR9 | CD7 | b2c | FcεRIβ |
| TLR9 | CD7 | b2c | FcεRIγ |
| TLR9 | CD7 | b2c | DAP10 |
| TLR9 | CD7 | b2c | DAP12 |
| TLR9 | CD7 | b2c | CD32 |
| TLR9 | CD7 | b2c | CD79a |
| TLR9 | CD7 | b2c | CD79b |
| TLR9 | CD7 | CD137/41BB | CD8 |
| TLR9 | CD7 | CD137/41BB | CD3ζ |
| TLR9 | CD7 | CD137/41BB | CD3δ |
| TLR9 | CD7 | CD137/41BB | CD3γ |
| TLR9 | CD7 | CD137/41BB | CD3ε |
| TLR9 | CD7 | CD137/41BB | FcγRI-γ |
| TLR9 | CD7 | CD137/41BB | FcγRIII-γ |
| TLR9 | CD7 | CD137/41BB | FcεRIβ |
| TLR9 | CD7 | CD137/41BB | FcεRIγ |
| TLR9 | CD7 | CD137/41BB | DAP10 |
| TLR9 | CD7 | CD137/41BB | DAP12 |
| TLR9 | CD7 | CD137/41BB | CD32 |
| TLR9 | CD7 | CD137/41BB | CD79a |
| TLR9 | CD7 | CD137/41BB | CD79b |
| TLR9 | CD7 | ICOS | CD8 |
| TLR9 | CD7 | ICOS | CD3ζ |
| TLR9 | CD7 | ICOS | CD3δ |
| TLR9 | CD7 | ICOS | CD3γ |
| TLR9 | CD7 | ICOS | CD3ε |
| TLR9 | CD7 | ICOS | FcγRI-γ |
| TLR9 | CD7 | ICOS | FcγRIII-γ |
| TLR9 | CD7 | ICOS | FcεRIβ |
| TLR9 | CD7 | ICOS | FcεRIγ |
| TLR9 | CD7 | ICOS | DAP10 |
| TLR9 | CD7 | ICOS | DAP12 |
| TLR9 | CD7 | ICOS | CD32 |
| TLR9 | CD7 | ICOS | CD79a |
| TLR9 | CD7 | ICOS | CD79b |
| TLR9 | CD7 | CD27 | CD8 |
| TLR9 | CD7 | CD27 | CD3ζ |
| TLR9 | CD7 | CD27 | CD3δ |
| TLR9 | CD7 | CD27 | CD3γ |
| TLR9 | CD7 | CD27 | CD3ε |
| TLR9 | CD7 | CD27 | FcγRI-γ |
| TLR9 | CD7 | CD27 | FcγRIII-γ |
| TLR9 | CD7 | CD27 | FcεRIβ |
| TLR9 | CD7 | CD27 | FcεRIγ |
| TLR9 | CD7 | CD27 | DAP10 |
| TLR9 | CD7 | CD27 | DAP12 |

TABLE 3-continued

Third Generation CARs

| Binding Region | Co-stimulatory Signal | Co-stimulatory Signal | Signal Domain |
|---|---|---|---|
| TLR9 | CD7 | CD27 | CD32 |
| TLR9 | CD7 | CD27 | CD79a |
| TLR9 | CD7 | CD27 | CD79b |
| TLR9 | CD7 | CD28δ | CD8 |
| TLR9 | CD7 | CD28δ | CD3ζ |
| TLR9 | CD7 | CD28δ | CD3δ |
| TLR9 | CD7 | CD28δ | CD3γ |
| TLR9 | CD7 | CD28δ | CD3ε |
| TLR9 | CD7 | CD28δ | FcγRI-γ |
| TLR9 | CD7 | CD28δ | FcγRIII-γ |
| TLR9 | CD7 | CD28δ | FcεRIβ |
| TLR9 | CD7 | CD28δ | FcεRIγ |
| TLR9 | CD7 | CD28δ | DAP10 |
| TLR9 | CD7 | CD28δ | DAP12 |
| TLR9 | CD7 | CD28δ | CD32 |
| TLR9 | CD7 | CD28δ | CD79a |
| TLR9 | CD7 | CD28δ | CD79b |
| TLR9 | CD7 | CD80 | CD8 |
| TLR9 | CD7 | CD80 | CD3ζ |
| TLR9 | CD7 | CD80 | CD3δ |
| TLR9 | CD7 | CD80 | CD3γ |
| TLR9 | CD7 | CD80 | CD3ε |
| TLR9 | CD7 | CD80 | FcγRI-γ |
| TLR9 | CD7 | CD80 | FcγRIII-γ |
| TLR9 | CD7 | CD80 | FcεRIβ |
| TLR9 | CD7 | CD80 | FcεRIγ |
| TLR9 | CD7 | CD80 | DAP10 |
| TLR9 | CD7 | CD80 | DAP12 |
| TLR9 | CD7 | CD80 | CD32 |
| TLR9 | CD7 | CD80 | CD79a |
| TLR9 | CD7 | CD80 | CD79b |
| TLR9 | CD7 | CD86 | CD8 |
| TLR9 | CD7 | CD86 | CD3ζ |
| TLR9 | CD7 | CD86 | CD3δ |
| TLR9 | CD7 | CD86 | CD3γ |
| TLR9 | CD7 | CD86 | CD3ε |
| TLR9 | CD7 | CD86 | FcγRI-γ |
| TLR9 | CD7 | CD86 | FcγRIII-γ |
| TLR9 | CD7 | CD86 | FcεRIβ |
| TLR9 | CD7 | CD86 | FcεRIγ |
| TLR9 | CD7 | CD86 | DAP10 |
| TLR9 | CD7 | CD86 | DAP12 |
| TLR9 | CD7 | CD86 | CD32 |
| TLR9 | CD7 | CD86 | CD79a |
| TLR9 | CD7 | CD86 | CD79b |
| TLR9 | CD7 | OX40 | CD8 |
| TLR9 | CD7 | OX40 | CD3ζ |
| TLR9 | CD7 | OX40 | CD3δ |
| TLR9 | CD7 | OX40 | CD3γ |
| TLR9 | CD7 | OX40 | CD3ε |
| TLR9 | CD7 | OX40 | FcγRI-γ |
| TLR9 | CD7 | OX40 | FcγRIII-γ |
| TLR9 | CD7 | OX40 | FcεRIβ |
| TLR9 | CD7 | OX40 | FcεRIγ |
| TLR9 | CD7 | OX40 | DAP10 |
| TLR9 | CD7 | OX40 | DAP12 |
| TLR9 | CD7 | OX40 | CD32 |
| TLR9 | CD7 | OX40 | CD79a |
| TLR9 | CD7 | OX40 | CD79b |
| TLR9 | CD7 | DAP10 | CD8 |
| TLR9 | CD7 | DAP10 | CD3ζ |
| TLR9 | CD7 | DAP10 | CD3δ |
| TLR9 | CD7 | DAP10 | CD3γ |
| TLR9 | CD7 | DAP10 | CD3ε |
| TLR9 | CD7 | DAP10 | FcγRI-γ |
| TLR9 | CD7 | DAP10 | FcγRIII-γ |
| TLR9 | CD7 | DAP10 | FcεRIβ |
| TLR9 | CD7 | DAP10 | FcεRIγ |
| TLR9 | CD7 | DAP10 | DAP10 |
| TLR9 | CD7 | DAP10 | DAP12 |
| TLR9 | CD7 | DAP10 | CD32 |
| TLR9 | CD7 | DAP10 | CD79a |
| TLR9 | CD7 | DAP10 | CD79b |
| TLR9 | CD7 | DAP12 | CD8 |
| TLR9 | CD7 | DAP12 | CD3ζ |
| TLR9 | CD7 | DAP12 | CD3δ |
| TLR9 | CD7 | DAP12 | CD3γ |
| TLR9 | CD7 | DAP12 | CD3ε |
| TLR9 | CD7 | DAP12 | FcγRI-γ |
| TLR9 | CD7 | DAP12 | FcγRIII-γ |
| TLR9 | CD7 | DAP12 | FcεRIβ |
| TLR9 | CD7 | DAP12 | FcεRIγ |
| TLR9 | CD7 | DAP12 | DAP10 |
| TLR9 | CD7 | DAP12 | DAP12 |
| TLR9 | CD7 | DAP12 | CD32 |
| TLR9 | CD7 | DAP12 | CD79a |
| TLR9 | CD7 | DAP12 | CD79b |
| TLR9 | CD7 | MyD88 | CD8 |
| TLR9 | CD7 | MyD88 | CD3ζ |
| TLR9 | CD7 | MyD88 | CD3δ |
| TLR9 | CD7 | MyD88 | CD3γ |
| TLR9 | CD7 | MyD88 | CD3ε |
| TLR9 | CD7 | MyD88 | FcγRI-γ |
| TLR9 | CD7 | MyD88 | FcγRIII-γ |
| TLR9 | CD7 | MyD88 | FcεRIβ |
| TLR9 | CD7 | MyD88 | FcεRIγ |
| TLR9 | CD7 | MyD88 | DAP10 |
| TLR9 | CD7 | MyD88 | DAP12 |
| TLR9 | CD7 | MyD88 | CD32 |
| TLR9 | CD7 | MyD88 | CD79a |
| TLR9 | CD7 | MyD88 | CD79b |
| TLR9 | CD7 | CD7 | CD8 |
| TLR9 | CD7 | CD7 | CD3ζ |
| TLR9 | CD7 | CD7 | CD3δ |
| TLR9 | CD7 | CD7 | CD3γ |
| TLR9 | CD7 | CD7 | CD3ε |
| TLR9 | CD7 | CD7 | FcγRI-γ |
| TLR9 | CD7 | CD7 | FcγRIII-γ |
| TLR9 | CD7 | CD7 | FcεRIβ |
| TLR9 | CD7 | CD7 | FcεRIγ |
| TLR9 | CD7 | CD7 | DAP10 |
| TLR9 | CD7 | CD7 | DAP12 |
| TLR9 | CD7 | CD7 | CD32 |
| TLR9 | CD7 | CD7 | CD79a |
| TLR9 | CD7 | CD7 | CD79b |
| TLR9 | CD7 | BTNL3 | CD8 |
| TLR9 | CD7 | BTNL3 | CD3ζ |
| TLR9 | CD7 | BTNL3 | CD3δ |
| TLR9 | CD7 | BTNL3 | CD3γ |
| TLR9 | CD7 | BTNL3 | CD3ε |
| TLR9 | CD7 | BTNL3 | FcγRI-γ |
| TLR9 | CD7 | BTNL3 | FcγRIII-γ |
| TLR9 | CD7 | BTNL3 | FcεRIβ |
| TLR9 | CD7 | BTNL3 | FcεRIγ |
| TLR9 | CD7 | BTNL3 | DAP10 |
| TLR9 | CD7 | BTNL3 | DAP12 |
| TLR9 | CD7 | BTNL3 | CD32 |
| TLR9 | CD7 | BTNL3 | CD79a |
| TLR9 | CD7 | BTNL3 | CD79b |
| TLR9 | CD7 | NKG2D | CD8 |
| TLR9 | CD7 | NKG2D | CD3ζ |
| TLR9 | CD7 | NKG2D | CD3δ |
| TLR9 | CD7 | NKG2D | CD3γ |
| TLR9 | CD7 | NKG2D | CD3ε |
| TLR9 | CD7 | NKG2D | FcγRI-γ |
| TLR9 | CD7 | NKG2D | FcγRIII-γ |
| TLR9 | CD7 | NKG2D | FcεRIβ |
| TLR9 | CD7 | NKG2D | FcεRIγ |
| TLR9 | CD7 | NKG2D | DAP10 |
| TLR9 | CD7 | NKG2D | DAP12 |
| TLR9 | CD7 | NKG2D | CD32 |
| TLR9 | CD7 | NKG2D | CD79a |
| TLR9 | CD7 | NKG2D | CD79b |
| TLR9 | BTNL3 | CD28 | CD8 |
| TLR9 | BTNL3 | CD28 | CD3ζ |
| TLR9 | BTNL3 | CD28 | CD3δ |
| TLR9 | BTNL3 | CD28 | CD3γ |
| TLR9 | BTNL3 | CD28 | CD3ε |

TABLE 3-continued

Third Generation CARs

| Binding Region | Co-stimulatory Signal | Co-stimulatory Signal | Signal Domain |
|---|---|---|---|
| TLR9 | BTNL3 | CD28 | FcγRI-γ |
| TLR9 | BTNL3 | CD28 | FcγRIII-γ |
| TLR9 | BTNL3 | CD28 | FcεRIβ |
| TLR9 | BTNL3 | CD28 | FcεRIγ |
| TLR9 | BTNL3 | CD28 | DAP10 |
| TLR9 | BTNL3 | CD28 | DAP12 |
| TLR9 | BTNL3 | CD28 | CD32 |
| TLR9 | BTNL3 | CD28 | CD79a |
| TLR9 | BTNL3 | CD28 | CD79b |
| TLR9 | BTNL3 | CD8 | CD8 |
| TLR9 | BTNL3 | CD8 | CD3ζ |
| TLR9 | BTNL3 | CD8 | CD3δ |
| TLR9 | BTNL3 | CD8 | CD3γ |
| TLR9 | BTNL3 | CD8 | CD3ε |
| TLR9 | BTNL3 | CD8 | FcγRI-γ |
| TLR9 | BTNL3 | CD8 | FcγRIII-γ |
| TLR9 | BTNL3 | CD8 | FcεRIβ |
| TLR9 | BTNL3 | CD8 | FcεRIγ |
| TLR9 | BTNL3 | CD8 | DAP10 |
| TLR9 | BTNL3 | CD8 | DAP12 |
| TLR9 | BTNL3 | CD8 | CD32 |
| TLR9 | BTNL3 | CD8 | CD79a |
| TLR9 | BTNL3 | CD8 | CD79b |
| TLR9 | BTNL3 | CD4 | CD8 |
| TLR9 | BTNL3 | CD4 | CD3ζ |
| TLR9 | BTNL3 | CD4 | CD3δ |
| TLR9 | BTNL3 | CD4 | CD3γ |
| TLR9 | BTNL3 | CD4 | CD3ε |
| TLR9 | BTNL3 | CD4 | FcγRI-γ |
| TLR9 | BTNL3 | CD4 | FcγRIII-γ |
| TLR9 | BTNL3 | CD4 | FcεRIβ |
| TLR9 | BTNL3 | CD4 | FcεRIγ |
| TLR9 | BTNL3 | CD4 | DAP10 |
| TLR9 | BTNL3 | CD4 | DAP12 |
| TLR9 | BTNL3 | CD4 | CD32 |
| TLR9 | BTNL3 | CD4 | CD79a |
| TLR9 | BTNL3 | CD4 | CD79b |
| TLR9 | BTNL3 | b2c | CD8 |
| TLR9 | BTNL3 | b2c | CD3ζ |
| TLR9 | BTNL3 | b2c | CD3δ |
| TLR9 | BTNL3 | b2c | CD3γ |
| TLR9 | BTNL3 | b2c | CD3ε |
| TLR9 | BTNL3 | b2c | FcγRI-γ |
| TLR9 | BTNL3 | b2c | FcγRIII-γ |
| TLR9 | BTNL3 | b2c | FcεRIβ |
| TLR9 | BTNL3 | b2c | FcεRIγ |
| TLR9 | BTNL3 | b2c | DAP10 |
| TLR9 | BTNL3 | b2c | DAP12 |
| TLR9 | BTNL3 | b2c | CD32 |
| TLR9 | BTNL3 | b2c | CD79a |
| TLR9 | BTNL3 | b2c | CD79b |
| TLR9 | BTNL3 | CD137/41BB | CD8 |
| TLR9 | BTNL3 | CD137/41BB | CD3ζ |
| TLR9 | BTNL3 | CD137/41BB | CD3δ |
| TLR9 | BTNL3 | CD137/41BB | CD3γ |
| TLR9 | BTNL3 | CD137/41BB | CD3ε |
| TLR9 | BTNL3 | CD137/41BB | FcγRI-γ |
| TLR9 | BTNL3 | CD137/41BB | FcγRIII-γ |
| TLR9 | BTNL3 | CD137/41BB | FcεRIβ |
| TLR9 | BTNL3 | CD137/41BB | FcεRIγ |
| TLR9 | BTNL3 | CD137/41BB | DAP10 |
| TLR9 | BTNL3 | CD137/41BB | DAP12 |
| TLR9 | BTNL3 | CD137/41BB | CD32 |
| TLR9 | BTNL3 | CD137/41BB | CD79a |
| TLR9 | BTNL3 | CD137/41BB | CD79b |
| TLR9 | BTNL3 | ICOS | CD8 |
| TLR9 | BTNL3 | ICOS | CD3ζ |
| TLR9 | BTNL3 | ICOS | CD3δ |
| TLR9 | BTNL3 | ICOS | CD3γ |
| TLR9 | BTNL3 | ICOS | CD3ε |
| TLR9 | BTNL3 | ICOS | FcγRI-γ |
| TLR9 | BTNL3 | ICOS | FcγRIII-γ |
| TLR9 | BTNL3 | ICOS | FcεRIβ |
| TLR9 | BTNL3 | ICOS | FcεRIγ |
| TLR9 | BTNL3 | ICOS | DAP10 |
| TLR9 | BTNL3 | ICOS | DAP12 |
| TLR9 | BTNL3 | ICOS | CD32 |
| TLR9 | BTNL3 | ICOS | CD79a |
| TLR9 | BTNL3 | ICOS | CD79b |
| TLR9 | BTNL3 | CD27 | CD8 |
| TLR9 | BTNL3 | CD27 | CD3ζ |
| TLR9 | BTNL3 | CD27 | CD3δ |
| TLR9 | BTNL3 | CD27 | CD3γ |
| TLR9 | BTNL3 | CD27 | CD3ε |
| TLR9 | BTNL3 | CD27 | FcγRI-γ |
| TLR9 | BTNL3 | CD27 | FcγRIII-γ |
| TLR9 | BTNL3 | CD27 | FcεRIβ |
| TLR9 | BTNL3 | CD27 | FcεRIγ |
| TLR9 | BTNL3 | CD27 | DAP10 |
| TLR9 | BTNL3 | CD27 | DAP12 |
| TLR9 | BTNL3 | CD27 | CD32 |
| TLR9 | BTNL3 | CD27 | CD79a |
| TLR9 | BTNL3 | CD27 | CD79b |
| TLR9 | BTNL3 | CD28δ | CD8 |
| TLR9 | BTNL3 | CD28δ | CD3ζ |
| TLR9 | BTNL3 | CD28δ | CD3δ |
| TLR9 | BTNL3 | CD28δ | CD3γ |
| TLR9 | BTNL3 | CD28δ | CD3ε |
| TLR9 | BTNL3 | CD28δ | FcγRI-γ |
| TLR9 | BTNL3 | CD28δ | FcγRIII-γ |
| TLR9 | BTNL3 | CD28δ | FcεRIβ |
| TLR9 | BTNL3 | CD28δ | FcεRIγ |
| TLR9 | BTNL3 | CD28δ | DAP10 |
| TLR9 | BTNL3 | CD28δ | DAP12 |
| TLR9 | BTNL3 | CD28δ | CD32 |
| TLR9 | BTNL3 | CD28δ | CD79a |
| TLR9 | BTNL3 | CD28δ | CD79b |
| TLR9 | BTNL3 | CD80 | CD8 |
| TLR9 | BTNL3 | CD80 | CD3ζ |
| TLR9 | BTNL3 | CD80 | CD3δ |
| TLR9 | BTNL3 | CD80 | CD3γ |
| TLR9 | BTNL3 | CD80 | CD3ε |
| TLR9 | BTNL3 | CD80 | FcγRI-γ |
| TLR9 | BTNL3 | CD80 | FcγRIII-γ |
| TLR9 | BTNL3 | CD80 | FcεRIβ |
| TLR9 | BTNL3 | CD80 | FcεRIγ |
| TLR9 | BTNL3 | CD80 | DAP10 |
| TLR9 | BTNL3 | CD80 | DAP12 |
| TLR9 | BTNL3 | CD80 | CD32 |
| TLR9 | BTNL3 | CD80 | CD79a |
| TLR9 | BTNL3 | CD80 | CD79b |
| TLR9 | BTNL3 | CD86 | CD8 |
| TLR9 | BTNL3 | CD86 | CD3ζ |
| TLR9 | BTNL3 | CD86 | CD3δ |
| TLR9 | BTNL3 | CD86 | CD3γ |
| TLR9 | BTNL3 | CD86 | CD3ε |
| TLR9 | BTNL3 | CD86 | FcγRI-γ |
| TLR9 | BTNL3 | CD86 | FcγRIII-γ |
| TLR9 | BTNL3 | CD86 | FcεRIβ |
| TLR9 | BTNL3 | CD86 | FcεRIγ |
| TLR9 | BTNL3 | CD86 | DAP10 |
| TLR9 | BTNL3 | CD86 | DAP12 |
| TLR9 | BTNL3 | CD86 | CD32 |
| TLR9 | BTNL3 | CD86 | CD79a |
| TLR9 | BTNL3 | CD86 | CD79b |
| TLR9 | BTNL3 | OX40 | CD8 |
| TLR9 | BTNL3 | OX40 | CD3ζ |
| TLR9 | BTNL3 | OX40 | CD3δ |
| TLR9 | BTNL3 | OX40 | CD3γ |
| TLR9 | BTNL3 | OX40 | CD3ε |
| TLR9 | BTNL3 | OX40 | FcγRI-γ |
| TLR9 | BTNL3 | OX40 | FcγRIII-γ |
| TLR9 | BTNL3 | OX40 | FcεRIβ |
| TLR9 | BTNL3 | OX40 | FcεRIγ |
| TLR9 | BTNL3 | OX40 | DAP10 |
| TLR9 | BTNL3 | OX40 | DAP12 |
| TLR9 | BTNL3 | OX40 | CD32 |
| TLR9 | BTNL3 | OX40 | CD79a |

TABLE 3-continued

Third Generation CARs

| Binding Region | Co-stimulatory Signal | Co-stimulatory Signal | Signal Domain |
|---|---|---|---|
| TLR9 | BTNL3 | OX40 | CD79b |
| TLR9 | BTNL3 | DAP10 | CD8 |
| TLR9 | BTNL3 | DAP10 | CD3ζ |
| TLR9 | BTNL3 | DAP10 | CD3δ |
| TLR9 | BTNL3 | DAP10 | CD3γ |
| TLR9 | BTNL3 | DAP10 | CD3ε |
| TLR9 | BTNL3 | DAP10 | FcγRI-γ |
| TLR9 | BTNL3 | DAP10 | FcγRIII-γ |
| TLR9 | BTNL3 | DAP10 | FcεRIβ |
| TLR9 | BTNL3 | DAP10 | FcεRIγ |
| TLR9 | BTNL3 | DAP10 | DAP10 |
| TLR9 | BTNL3 | DAP10 | DAP12 |
| TLR9 | BTNL3 | DAP10 | CD32 |
| TLR9 | BTNL3 | DAP10 | CD79a |
| TLR9 | BTNL3 | DAP10 | CD79b |
| TLR9 | BTNL3 | DAP12 | CD8 |
| TLR9 | BTNL3 | DAP12 | CD3ζ |
| TLR9 | BTNL3 | DAP12 | CD3δ |
| TLR9 | BTNL3 | DAP12 | CD3γ |
| TLR9 | BTNL3 | DAP12 | CD3ε |
| TLR9 | BTNL3 | DAP12 | FcγRI-γ |
| TLR9 | BTNL3 | DAP12 | FcγRIII-γ |
| TLR9 | BTNL3 | DAP12 | FcεRIβ |
| TLR9 | BTNL3 | DAP12 | FcεRIγ |
| TLR9 | BTNL3 | DAP12 | DAP10 |
| TLR9 | BTNL3 | DAP12 | DAP12 |
| TLR9 | BTNL3 | DAP12 | CD32 |
| TLR9 | BTNL3 | DAP12 | CD79a |
| TLR9 | BTNL3 | DAP12 | CD79b |
| TLR9 | BTNL3 | MyD88 | CD8 |
| TLR9 | BTNL3 | MyD88 | CD3ζ |
| TLR9 | BTNL3 | MyD88 | CD3δ |
| TLR9 | BTNL3 | MyD88 | CD3γ |
| TLR9 | BTNL3 | MyD88 | CD3ε |
| TLR9 | BTNL3 | MyD88 | FcγRI-γ |
| TLR9 | BTNL3 | MyD88 | FcγRIII-γ |
| TLR9 | BTNL3 | MyD88 | FcεRIβ |
| TLR9 | BTNL3 | MyD88 | FcεRIγ |
| TLR9 | BTNL3 | MyD88 | DAP10 |
| TLR9 | BTNL3 | MyD88 | DAP12 |
| TLR9 | BTNL3 | MyD88 | CD32 |
| TLR9 | BTNL3 | MyD88 | CD79a |
| TLR9 | BTNL3 | MyD88 | CD79b |
| TLR9 | BTNL3 | CD7 | CD8 |
| TLR9 | BTNL3 | CD7 | CD3ζ |
| TLR9 | BTNL3 | CD7 | CD3δ |
| TLR9 | BTNL3 | CD7 | CD3γ |
| TLR9 | BTNL3 | CD7 | CD3ε |
| TLR9 | BTNL3 | CD7 | FcγRI-γ |
| TLR9 | BTNL3 | CD7 | FcγRIII-γ |
| TLR9 | BTNL3 | CD7 | FcεRIβ |
| TLR9 | BTNL3 | CD7 | FcεRIγ |
| TLR9 | BTNL3 | CD7 | DAP10 |
| TLR9 | BTNL3 | CD7 | DAP12 |
| TLR9 | BTNL3 | CD7 | CD32 |
| TLR9 | BTNL3 | CD7 | CD79a |
| TLR9 | BTNL3 | CD7 | CD79b |
| TLR9 | BTNL3 | BTNL3 | CD8 |
| TLR9 | BTNL3 | BTNL3 | CD3ζ |
| TLR9 | BTNL3 | BTNL3 | CD3δ |
| TLR9 | BTNL3 | BTNL3 | CD3γ |
| TLR9 | BTNL3 | BTNL3 | CD3ε |
| TLR9 | BTNL3 | BTNL3 | FcγRI-γ |
| TLR9 | BTNL3 | BTNL3 | FcγRIII-γ |
| TLR9 | BTNL3 | BTNL3 | FcεRIβ |
| TLR9 | BTNL3 | BTNL3 | FcεRIγ |
| TLR9 | BTNL3 | BTNL3 | DAP10 |
| TLR9 | BTNL3 | BTNL3 | DAP12 |
| TLR9 | BTNL3 | BTNL3 | CD32 |
| TLR9 | BTNL3 | BTNL3 | CD79a |
| TLR9 | BTNL3 | BTNL3 | CD79b |
| TLR9 | BTNL3 | NKG2D | CD8 |
| TLR9 | BTNL3 | NKG2D | CD3ζ |
| TLR9 | BTNL3 | NKG2D | CD3δ |
| TLR9 | BTNL3 | NKG2D | CD3γ |
| TLR9 | BTNL3 | NKG2D | CD3ε |
| TLR9 | BTNL3 | NKG2D | FcγRI-γ |
| TLR9 | BTNL3 | NKG2D | FcγRIII-γ |
| TLR9 | BTNL3 | NKG2D | FcεRIβ |
| TLR9 | BTNL3 | NKG2D | FcεRIγ |
| TLR9 | BTNL3 | NKG2D | DAP10 |
| TLR9 | BTNL3 | NKG2D | DAP12 |
| TLR9 | BTNL3 | NKG2D | CD32 |
| TLR9 | BTNL3 | NKG2D | CD79a |
| TLR9 | BTNL3 | NKG2D | CD79b |
| TLR9 | NKG2D | CD28 | CD8 |
| TLR9 | NKG2D | CD28 | CD3ζ |
| TLR9 | NKG2D | CD28 | CD3δ |
| TLR9 | NKG2D | CD28 | CD3γ |
| TLR9 | NKG2D | CD28 | CD3ε |
| TLR9 | NKG2D | CD28 | FcγRI-γ |
| TLR9 | NKG2D | CD28 | FcγRIII-γ |
| TLR9 | NKG2D | CD28 | FcεRIβ |
| TLR9 | NKG2D | CD28 | FcεRIγ |
| TLR9 | NKG2D | CD28 | DAP10 |
| TLR9 | NKG2D | CD28 | DAP12 |
| TLR9 | NKG2D | CD28 | CD32 |
| TLR9 | NKG2D | CD28 | CD79a |
| TLR9 | NKG2D | CD28 | CD79b |
| TLR9 | NKG2D | CD8 | CD8 |
| TLR9 | NKG2D | CD8 | CD3ζ |
| TLR9 | NKG2D | CD8 | CD3δ |
| TLR9 | NKG2D | CD8 | CD3γ |
| TLR9 | NKG2D | CD8 | CD3ε |
| TLR9 | NKG2D | CD8 | FcγRI-γ |
| TLR9 | NKG2D | CD8 | FcγRIII-γ |
| TLR9 | NKG2D | CD8 | FcεRIβ |
| TLR9 | NKG2D | CD8 | FcεRIγ |
| TLR9 | NKG2D | CD8 | DAP10 |
| TLR9 | NKG2D | CD8 | DAP12 |
| TLR9 | NKG2D | CD8 | CD32 |
| TLR9 | NKG2D | CD8 | CD79a |
| TLR9 | NKG2D | CD8 | CD79b |
| TLR9 | NKG2D | CD4 | CD8 |
| TLR9 | NKG2D | CD4 | CD3ζ |
| TLR9 | NKG2D | CD4 | CD3δ |
| TLR9 | NKG2D | CD4 | CD3γ |
| TLR9 | NKG2D | CD4 | CD3ε |
| TLR9 | NKG2D | CD4 | FcγRI-γ |
| TLR9 | NKG2D | CD4 | FcγRIII-γ |
| TLR9 | NKG2D | CD4 | FcεRIβ |
| TLR9 | NKG2D | CD4 | FcεRIγ |
| TLR9 | NKG2D | CD4 | DAP10 |
| TLR9 | NKG2D | CD4 | DAP12 |
| TLR9 | NKG2D | CD4 | CD32 |
| TLR9 | NKG2D | CD4 | CD79a |
| TLR9 | NKG2D | CD4 | CD79b |
| TLR9 | NKG2D | b2c | CD8 |
| TLR9 | NKG2D | b2c | CD3ζ |
| TLR9 | NKG2D | b2c | CD3δ |
| TLR9 | NKG2D | b2c | CD3γ |
| TLR9 | NKG2D | b2c | CD3ε |
| TLR9 | NKG2D | b2c | FcγRI-γ |
| TLR9 | NKG2D | b2c | FcγRIII-γ |
| TLR9 | NKG2D | b2c | FcεRIβ |
| TLR9 | NKG2D | b2c | FcεRIγ |
| TLR9 | NKG2D | b2c | DAP10 |
| TLR9 | NKG2D | b2c | DAP12 |
| TLR9 | NKG2D | b2c | CD32 |
| TLR9 | NKG2D | b2c | CD79a |
| TLR9 | NKG2D | b2c | CD79b |
| TLR9 | NKG2D | CD137/41BB | CD8 |
| TLR9 | NKG2D | CD137/41BB | CD3ζ |
| TLR9 | NKG2D | CD137/41BB | CD3δ |
| TLR9 | NKG2D | CD137/41BB | CD3γ |
| TLR9 | NKG2D | CD137/41BB | CD3ε |
| TLR9 | NKG2D | CD137/41BB | FcγRI-γ |
| TLR9 | NKG2D | CD137/41BB | FcγRIII-γ |

TABLE 3-continued

Third Generation CARs

| Binding Region | Co-stimulatory Signal | Co-stimulatory Signal | Signal Domain |
|---|---|---|---|
| TLR9 | NKG2D | CD137/41BB | FcεRIβ |
| TLR9 | NKG2D | CD137/41BB | FcεRIγ |
| TLR9 | NKG2D | CD137/41BB | DAP10 |
| TLR9 | NKG2D | CD137/41BB | DAP12 |
| TLR9 | NKG2D | CD137/41BB | CD32 |
| TLR9 | NKG2D | CD137/41BB | CD79a |
| TLR9 | NKG2D | CD137/41BB | CD79b |
| TLR9 | NKG2D | ICOS | CD8 |
| TLR9 | NKG2D | ICOS | CD3ζ |
| TLR9 | NKG2D | ICOS | CD3δ |
| TLR9 | NKG2D | ICOS | CD3γ |
| TLR9 | NKG2D | ICOS | CD3ε |
| TLR9 | NKG2D | ICOS | FcγRI-γ |
| TLR9 | NKG2D | ICOS | FcγRIII-γ |
| TLR9 | NKG2D | ICOS | FcεRIβ |
| TLR9 | NKG2D | ICOS | FcεRIγ |
| TLR9 | NKG2D | ICOS | DAP10 |
| TLR9 | NKG2D | ICOS | DAP12 |
| TLR9 | NKG2D | ICOS | CD32 |
| TLR9 | NKG2D | ICOS | CD79a |
| TLR9 | NKG2D | ICOS | CD79b |
| TLR9 | NKG2D | CD27 | CD8 |
| TLR9 | NKG2D | CD27 | CD3ζ |
| TLR9 | NKG2D | CD27 | CD3δ |
| TLR9 | NKG2D | CD27 | CD3γ |
| TLR9 | NKG2D | CD27 | CD3ε |
| TLR9 | NKG2D | CD27 | FcγRI-γ |
| TLR9 | NKG2D | CD27 | FcγRIII-γ |
| TLR9 | NKG2D | CD27 | FcεRIβ |
| TLR9 | NKG2D | CD27 | FcεRIγ |
| TLR9 | NKG2D | CD27 | DAP10 |
| TLR9 | NKG2D | CD27 | DAP12 |
| TLR9 | NKG2D | CD27 | CD32 |
| TLR9 | NKG2D | CD27 | CD79a |
| TLR9 | NKG2D | CD27 | CD79b |
| TLR9 | NKG2D | CD28δ | CD8 |
| TLR9 | NKG2D | CD28δ | CD3ζ |
| TLR9 | NKG2D | CD28δ | CD3δ |
| TLR9 | NKG2D | CD28δ | CD3γ |
| TLR9 | NKG2D | CD28δ | CD3ε |
| TLR9 | NKG2D | CD28δ | FcγRI-γ |
| TLR9 | NKG2D | CD28δ | FcγRIII-γ |
| TLR9 | NKG2D | CD28δ | FcεRIβ |
| TLR9 | NKG2D | CD28δ | FcεRIγ |
| TLR9 | NKG2D | CD28δ | DAP10 |
| TLR9 | NKG2D | CD28δ | DAP12 |
| TLR9 | NKG2D | CD28δ | CD32 |
| TLR9 | NKG2D | CD28δ | CD79a |
| TLR9 | NKG2D | CD28δ | CD79b |
| TLR9 | NKG2D | CD80 | CD8 |
| TLR9 | NKG2D | CD80 | CD3ζ |
| TLR9 | NKG2D | CD80 | CD3δ |
| TLR9 | NKG2D | CD80 | CD3γ |
| TLR9 | NKG2D | CD80 | CD3ε |
| TLR9 | NKG2D | CD80 | FcγRI-γ |
| TLR9 | NKG2D | CD80 | FcγRIII-γ |
| TLR9 | NKG2D | CD80 | FcεRIβ |
| TLR9 | NKG2D | CD80 | FcεRIγ |
| TLR9 | NKG2D | CD80 | DAP10 |
| TLR9 | NKG2D | CD80 | DAP12 |
| TLR9 | NKG2D | CD80 | CD32 |
| TLR9 | NKG2D | CD80 | CD79a |
| TLR9 | NKG2D | CD80 | CD79b |
| TLR9 | NKG2D | CD86 | CD8 |
| TLR9 | NKG2D | CD86 | CD3ζ |
| TLR9 | NKG2D | CD86 | CD3δ |
| TLR9 | NKG2D | CD86 | CD3γ |
| TLR9 | NKG2D | CD86 | CD3ε |
| TLR9 | NKG2D | CD86 | FcγRI-γ |
| TLR9 | NKG2D | CD86 | FcγRIII-γ |
| TLR9 | NKG2D | CD86 | FcεRIβ |
| TLR9 | NKG2D | CD86 | FcεRIγ |
| TLR9 | NKG2D | CD86 | DAP10 |
| TLR9 | NKG2D | CD86 | DAP12 |
| TLR9 | NKG2D | CD86 | CD32 |
| TLR9 | NKG2D | CD86 | CD79a |
| TLR9 | NKG2D | CD86 | CD79b |
| TLR9 | NKG2D | OX40 | CD8 |
| TLR9 | NKG2D | OX40 | CD3ζ |
| TLR9 | NKG2D | OX40 | CD3δ |
| TLR9 | NKG2D | OX40 | CD3γ |
| TLR9 | NKG2D | OX40 | CD3ε |
| TLR9 | NKG2D | OX40 | FcγRI-γ |
| TLR9 | NKG2D | OX40 | FcγRIII-γ |
| TLR9 | NKG2D | OX40 | FcεRIβ |
| TLR9 | NKG2D | OX40 | FcεRIγ |
| TLR9 | NKG2D | OX40 | DAP10 |
| TLR9 | NKG2D | OX40 | DAP12 |
| TLR9 | NKG2D | OX40 | CD32 |
| TLR9 | NKG2D | OX40 | CD79a |
| TLR9 | NKG2D | OX40 | CD79b |
| TLR9 | NKG2D | DAP10 | CD8 |
| TLR9 | NKG2D | DAP10 | CD3ζ |
| TLR9 | NKG2D | DAP10 | CD3δ |
| TLR9 | NKG2D | DAP10 | CD3γ |
| TLR9 | NKG2D | DAP10 | CD3ε |
| TLR9 | NKG2D | DAP10 | FcγRI-γ |
| TLR9 | NKG2D | DAP10 | FcγRIII-γ |
| TLR9 | NKG2D | DAP10 | FcεRIβ |
| TLR9 | NKG2D | DAP10 | FcεRIγ |
| TLR9 | NKG2D | DAP10 | DAP10 |
| TLR9 | NKG2D | DAP10 | DAP12 |
| TLR9 | NKG2D | DAP10 | CD32 |
| TLR9 | NKG2D | DAP10 | CD79a |
| TLR9 | NKG2D | DAP10 | CD79b |
| TLR9 | NKG2D | DAP12 | CD8 |
| TLR9 | NKG2D | DAP12 | CD3ζ |
| TLR9 | NKG2D | DAP12 | CD3δ |
| TLR9 | NKG2D | DAP12 | CD3γ |
| TLR9 | NKG2D | DAP12 | CD3ε |
| TLR9 | NKG2D | DAP12 | FcγRI-γ |
| TLR9 | NKG2D | DAP12 | FcγRIII-γ |
| TLR9 | NKG2D | DAP12 | FcεRIβ |
| TLR9 | NKG2D | DAP12 | FcεRIγ |
| TLR9 | NKG2D | DAP12 | DAP10 |
| TLR9 | NKG2D | DAP12 | DAP12 |
| TLR9 | NKG2D | DAP12 | CD32 |
| TLR9 | NKG2D | DAP12 | CD79a |
| TLR9 | NKG2D | DAP12 | CD79b |
| TLR9 | NKG2D | MyD88 | CD8 |
| TLR9 | NKG2D | MyD88 | CD3ζ |
| TLR9 | NKG2D | MyD88 | CD3δ |
| TLR9 | NKG2D | MyD88 | CD3γ |
| TLR9 | NKG2D | MyD88 | CD3ε |
| TLR9 | NKG2D | MyD88 | FcγRI-γ |
| TLR9 | NKG2D | MyD88 | FcγRIII-γ |
| TLR9 | NKG2D | MyD88 | FcεRIβ |
| TLR9 | NKG2D | MyD88 | FcεRIγ |
| TLR9 | NKG2D | MyD88 | DAP10 |
| TLR9 | NKG2D | MyD88 | DAP12 |
| TLR9 | NKG2D | MyD88 | CD32 |
| TLR9 | NKG2D | MyD88 | CD79a |
| TLR9 | NKG2D | MyD88 | CD79b |
| TLR9 | NKG2D | CD7 | CD8 |
| TLR9 | NKG2D | CD7 | CD3ζ |
| TLR9 | NKG2D | CD7 | CD3δ |
| TLR9 | NKG2D | CD7 | CD3γ |
| TLR9 | NKG2D | CD7 | CD3ε |
| TLR9 | NKG2D | CD7 | FcγRI-γ |
| TLR9 | NKG2D | CD7 | FcγRIII-γ |
| TLR9 | NKG2D | CD7 | FcεRIβ |
| TLR9 | NKG2D | CD7 | FcεRIγ |
| TLR9 | NKG2D | CD7 | DAP10 |
| TLR9 | NKG2D | CD7 | DAP12 |
| TLR9 | NKG2D | CD7 | CD32 |
| TLR9 | NKG2D | CD7 | CD79a |
| TLR9 | NKG2D | CD7 | CD79b |
| TLR9 | NKG2D | BTNL3 | CD8 |

TABLE 3-continued

Third Generation CARs

| Binding Region | Co-stimulatory Signal | Co-stimulatory Signal | Signal Domain |
|---|---|---|---|
| TLR9 | NKG2D | BTNL3 | CD3ζ |
| TLR9 | NKG2D | BTNL3 | CD3δ |
| TLR9 | NKG2D | BTNL3 | CD3γ |
| TLR9 | NKG2D | BTNL3 | CD3ε |
| TLR9 | NKG2D | BTNL3 | FcγRI-γ |
| TLR9 | NKG2D | BTNL3 | FcγRIII-γ |
| TLR9 | NKG2D | BTNL3 | FcεRIβ |
| TLR9 | NKG2D | BTNL3 | FcεRIγ |
| TLR9 | NKG2D | BTNL3 | DAP10 |
| TLR9 | NKG2D | BTNL3 | DAP12 |
| TLR9 | NKG2D | BTNL3 | CD32 |
| TLR9 | NKG2D | BTNL3 | CD79a |
| TLR9 | NKG2D | BTNL3 | CD79b |
| TLR9 | NKG2D | NKG2D | CD8 |
| TLR9 | NKG2D | NKG2D | CD3ζ |
| TLR9 | NKG2D | NKG2D | CD3δ |
| TLR9 | NKG2D | NKG2D | CD3γ |
| TLR9 | NKG2D | NKG2D | CD3ε |
| TLR9 | NKG2D | NKG2D | FcγRI-γ |
| TLR9 | NKG2D | NKG2D | FcγRIII-γ |
| TLR9 | NKG2D | NKG2D | FcεRIβ |
| TLR9 | NKG2D | NKG2D | FcεRIγ |
| TLR9 | NKG2D | NKG2D | DAP10 |
| TLR9 | NKG2D | NKG2D | DAP12 |
| TLR9 | NKG2D | NKG2D | CD32 |
| TLR9 | NKG2D | NKG2D | CD79a |
| TLR9 | NKG2D | NKG2D | CD79b |

TABLE 4

CARs lacking Co-Simulatory Signal (for dual CAR approach)

| ScFv | Co-stimulatory Signal | Signal Domain |
|---|---|---|
| TLR9 | none | CD8 |
| TLR9 | none | CD3ζ |
| TLR9 | none | CD3δ |
| TLR9 | none | CD3γ |
| TLR9 | none | CD3ε |
| TLR9 | none | FcγRI-γ |
| TLR9 | none | FcγRIII-γ |
| TLR9 | none | FcεRIβ |
| TLR9 | none | FcεRIγ |
| TLR9 | none | DAP10 |
| TLR9 | none | DAP12 |
| TLR9 | none | CD32 |
| TLR9 | none | CD79a |
| TLR9 | none | CD8 |
| TLR9 | none | CD3ζ |
| TLR9 | none | CD3δ |
| TLR9 | none | CD3γ |
| TLR9 | none | CD3ε |
| TLR9 | none | FcγRI-γ |

TABLE 5

CARs lacking Signal Domain (for dual CAR approach)

| ScFv | Co-stimulatory Signal | Signal Domain |
|---|---|---|
| TLR9 | CD28 | none |
| TLR9 | CD8 | none |
| TLR9 | CD4 | none |
| TLR9 | b2c | none |
| TLR9 | CD137/41BB | none |

TABLE 5-continued

CARs lacking Signal Domain (for dual CAR approach)

| ScFv | Co-stimulatory Signal | Signal Domain |
|---|---|---|
| TLR9 | ICOS | none |
| TLR9 | CD27 | none |
| TLR9 | CD28δ | none |
| TLR9 | CD80 | none |
| TLR9 | CD86 | none |
| TLR9 | OX40 | none |
| TLR9 | DAP10 | none |
| TLR9 | MyD88 | none |
| TLR9 | CD7 | none |
| TLR9 | DAP12 | none |
| TLR9 | MyD88 | none |
| TLR9 | CD7 | none |
| TLR9 | BTNL3 | none |
| TLR9 | NKG2D | none |

TABLE 6

Third Generation CARs lacking Signal Domain (for dual CAR approach)

| ScFv | Co-stimulatory Signal | Co-stimulatory Signal | Signal Domain |
|---|---|---|---|
| TLR9 | CD28 | CD28 | none |
| TLR9 | CD28 | CD8 | none |
| TLR9 | CD28 | CD4 | none |
| TLR9 | CD28 | b2c | none |
| TLR9 | CD28 | CD137/41BB | none |
| TLR9 | CD28 | ICOS | none |
| TLR9 | CD28 | CD27 | none |
| TLR9 | CD28 | CD28δ | none |
| TLR9 | CD28 | CD80 | none |
| TLR9 | CD28 | CD86 | none |
| TLR9 | CD28 | OX40 | none |
| TLR9 | CD28 | DAP10 | none |
| TLR9 | CD28 | MyD88 | none |
| TLR9 | CD28 | CD7 | none |
| TLR9 | CD28 | DAP12 | none |
| TLR9 | CD28 | MyD88 | none |
| TLR9 | CD28 | CD7 | none |
| TLR9 | CD8 | CD28 | none |
| TLR9 | CD8 | CD8 | none |
| TLR9 | CD8 | CD4 | none |
| TLR9 | CD8 | b2c | none |
| TLR9 | CD8 | CD137/41BB | none |
| TLR9 | CD8 | ICOS | none |
| TLR9 | CD8 | CD27 | none |
| TLR9 | CD8 | CD28δ | none |
| TLR9 | CD8 | CD80 | none |
| TLR9 | CD8 | CD86 | none |
| TLR9 | CD8 | OX40 | none |
| TLR9 | CD8 | DAP10 | none |
| TLR9 | CD8 | MyD88 | none |
| TLR9 | CD8 | CD7 | none |
| TLR9 | CD8 | DAP12 | none |
| TLR9 | CD8 | MyD88 | none |
| TLR9 | CD8 | CD7 | none |
| TLR9 | CD4 | CD28 | none |
| TLR9 | CD4 | CD8 | none |
| TLR9 | CD4 | CD4 | none |
| TLR9 | CD4 | b2c | none |
| TLR9 | CD4 | CD137/41BB | none |
| TLR9 | CD4 | ICOS | none |
| TLR9 | CD4 | CD27 | none |
| TLR9 | CD4 | CD28δ | none |
| TLR9 | CD4 | CD80 | none |
| TLR9 | CD4 | CD86 | none |
| TLR9 | CD4 | OX40 | none |
| TLR9 | CD4 | DAP10 | none |
| TLR9 | CD4 | MyD88 | none |
| TLR9 | CD4 | CD7 | none |

TABLE 6-continued

Third Generation CARs lacking Signal Domain
(for dual CAR approach)

| ScFv | Co-stimulatory Signal | Co-stimulatory Signal | Signal Domain |
|---|---|---|---|
| TLR9 | CD4 | DAP12 | none |
| TLR9 | CD4 | MyD88 | none |
| TLR9 | CD4 | CD7 | none |
| TLR9 | b2c | CD28 | none |
| TLR9 | b2c | CD8 | none |
| TLR9 | b2c | CD4 | none |
| TLR9 | b2c | b2c | none |
| TLR9 | b2c | CD137/41BB | none |
| TLR9 | b2c | ICOS | none |
| TLR9 | b2c | CD27 | none |
| TLR9 | b2c | CD28δ | none |
| TLR9 | b2c | CD80 | none |
| TLR9 | b2c | CD86 | none |
| TLR9 | b2c | OX40 | none |
| TLR9 | b2c | DAP10 | none |
| TLR9 | b2c | MyD88 | none |
| TLR9 | b2c | CD7 | none |
| TLR9 | b2c | DAP12 | none |
| TLR9 | b2c | MyD88 | none |
| TLR9 | b2c | CD7 | none |
| TLR9 | CD137/41BB | CD28 | none |
| TLR9 | CD137/41BB | CD8 | none |
| TLR9 | CD137/41BB | CD4 | none |
| TLR9 | CD137/41BB | b2c | none |
| TLR9 | CD137/41BB | CD137/41BB | none |
| TLR9 | CD137/41BB | ICOS | none |
| TLR9 | CD137/41BB | CD27 | none |
| TLR9 | CD137/41BB | CD28δ | none |
| TLR9 | CD137/41BB | CD80 | none |
| TLR9 | CD137/41BB | CD86 | none |
| TLR9 | CD137/41BB | OX40 | none |
| TLR9 | CD137/41BB | DAP10 | none |
| TLR9 | CD137/41BB | MyD88 | none |
| TLR9 | CD137/41BB | CD7 | none |
| TLR9 | CD137/41BB | DAP12 | none |
| TLR9 | CD137/41BB | MyD88 | none |
| TLR9 | CD137/41BB | CD7 | none |
| TLR9 | ICOS | CD28 | none |
| TLR9 | ICOS | CD8 | none |
| TLR9 | ICOS | CD4 | none |
| TLR9 | ICOS | b2c | none |
| TLR9 | ICOS | CD137/41BB | none |
| TLR9 | ICOS | ICOS | none |
| TLR9 | ICOS | CD27 | none |
| TLR9 | ICOS | CD28δ | none |
| TLR9 | ICOS | CD80 | none |
| TLR9 | ICOS | CD86 | none |
| TLR9 | ICOS | OX40 | none |
| TLR9 | ICOS | DAP10 | none |
| TLR9 | ICOS | MyD88 | none |
| TLR9 | ICOS | CD7 | none |
| TLR9 | ICOS | DAP12 | none |
| TLR9 | ICOS | MyD88 | none |
| TLR9 | ICOS | CD7 | none |
| TLR9 | ICOS | CD28 | none |
| TLR9 | ICOS | CD8 | none |
| TLR9 | ICOS | CD4 | none |
| TLR9 | ICOS | b2c | none |
| TLR9 | ICOS | CD137/41BB | none |
| TLR9 | ICOS | ICOS | none |
| TLR9 | ICOS | CD27 | none |
| TLR9 | ICOS | CD28δ | none |
| TLR9 | ICOS | CD80 | none |
| TLR9 | ICOS | CD86 | none |
| TLR9 | ICOS | OX40 | none |
| TLR9 | ICOS | DAP10 | none |
| TLR9 | ICOS | MyD88 | none |
| TLR9 | ICOS | CD7 | none |
| TLR9 | ICOS | DAP12 | none |
| TLR9 | ICOS | MyD88 | none |
| TLR9 | ICOS | CD7 | none |
| TLR9 | CD27 | CD28 | none |
| TLR9 | CD27 | CD8 | none |
| TLR9 | CD27 | CD4 | none |
| TLR9 | CD27 | b2c | none |
| TLR9 | CD27 | CD137/41BB | none |
| TLR9 | CD27 | ICOS | none |
| TLR9 | CD27 | CD27 | none |
| TLR9 | CD27 | CD28δ | none |
| TLR9 | CD27 | CD80 | none |
| TLR9 | CD27 | CD86 | none |
| TLR9 | CD27 | OX40 | none |
| TLR9 | CD27 | DAP10 | none |
| TLR9 | CD27 | MyD88 | none |
| TLR9 | CD27 | CD7 | none |
| TLR9 | CD27 | DAP12 | none |
| TLR9 | CD27 | MyD88 | none |
| TLR9 | CD27 | CD7 | none |
| TLR9 | CD28δ | CD28 | none |
| TLR9 | CD28δ | CD8 | none |
| TLR9 | CD28δ | CD4 | none |
| TLR9 | CD28δ | b2c | none |
| TLR9 | CD28δ | CD137/41BB | none |
| TLR9 | CD28δ | ICOS | none |
| TLR9 | CD28δ | CD27 | none |
| TLR9 | CD28δ | CD28δ | none |
| TLR9 | CD28δ | CD80 | none |
| TLR9 | CD28δ | CD86 | none |
| TLR9 | CD28δ | OX40 | none |
| TLR9 | CD28δ | DAP10 | none |
| TLR9 | CD28δ | MyD88 | none |
| TLR9 | CD28δ | CD7 | none |
| TLR9 | CD28δ | DAP12 | none |
| TLR9 | CD28δ | MyD88 | none |
| TLR9 | CD28δ | CD7 | none |
| TLR9 | CD80 | CD28 | none |
| TLR9 | CD80 | CD8 | none |
| TLR9 | CD80 | CD4 | none |
| TLR9 | CD80 | b2c | none |
| TLR9 | CD80 | CD137/41BB | none |
| TLR9 | CD80 | ICOS | none |
| TLR9 | CD80 | CD27 | none |
| TLR9 | CD80 | CD28δ | none |
| TLR9 | CD80 | CD80 | none |
| TLR9 | CD80 | CD86 | none |
| TLR9 | CD80 | OX40 | none |
| TLR9 | CD80 | DAP10 | none |
| TLR9 | CD80 | MyD88 | none |
| TLR9 | CD80 | CD7 | none |
| TLR9 | CD80 | DAP12 | none |
| TLR9 | CD80 | MyD88 | none |
| TLR9 | CD80 | CD7 | none |
| TLR9 | CD86 | CD28 | none |
| TLR9 | CD86 | CD8 | none |
| TLR9 | CD86 | CD4 | none |
| TLR9 | CD86 | b2c | none |
| TLR9 | CD86 | CD137/41BB | none |
| TLR9 | CD86 | ICOS | none |
| TLR9 | CD86 | CD27 | none |
| TLR9 | CD86 | CD28δ | none |
| TLR9 | CD86 | CD80 | none |
| TLR9 | CD86 | CD86 | none |
| TLR9 | CD86 | OX40 | none |
| TLR9 | CD86 | DAP10 | none |
| TLR9 | CD86 | MyD88 | none |
| TLR9 | CD86 | CD7 | none |
| TLR9 | CD86 | DAP12 | none |
| TLR9 | CD86 | MyD88 | none |
| TLR9 | CD86 | CD7 | none |
| TLR9 | OX40 | CD28 | none |
| TLR9 | OX40 | CD8 | none |
| TLR9 | OX40 | CD4 | none |
| TLR9 | OX40 | b2c | none |
| TLR9 | OX40 | CD137/41BB | none |
| TLR9 | OX40 | ICOS | none |
| TLR9 | OX40 | CD27 | none |
| TLR9 | OX40 | CD28δ | none |
| TLR9 | OX40 | CD80 | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| TLR9 | OX40 | CD86 | none |
| TLR9 | OX40 | OX40 | none |
| TLR9 | OX40 | DAP10 | none |
| TLR9 | OX40 | MyD88 | none |
| TLR9 | OX40 | CD7 | none |
| TLR9 | OX40 | DAP12 | none |
| TLR9 | OX40 | MyD88 | none |
| TLR9 | OX40 | CD7 | none |
| TLR9 | DAP10 | CD28 | none |
| TLR9 | DAP10 | CD8 | none |
| TLR9 | DAP10 | CD4 | none |
| TLR9 | DAP10 | b2c | none |
| TLR9 | DAP10 | CD137/41BB | none |
| TLR9 | DAP10 | ICOS | none |
| TLR9 | DAP10 | CD27 | none |
| TLR9 | DAP10 | CD28δ | none |
| TLR9 | DAP10 | CD80 | none |
| TLR9 | DAP10 | CD86 | none |
| TLR9 | DAP10 | OX40 | none |
| TLR9 | DAP10 | DAP10 | none |
| TLR9 | DAP10 | MyD88 | none |
| TLR9 | DAP10 | CD7 | none |
| TLR9 | DAP10 | DAP12 | none |
| TLR9 | DAP10 | MyD88 | none |
| TLR9 | DAP10 | CD7 | none |
| TLR9 | DAP12 | CD28 | none |
| TLR9 | DAP12 | CD8 | none |
| TLR9 | DAP12 | CD4 | none |
| TLR9 | DAP12 | b2c | none |
| TLR9 | DAP12 | CD137/41BB | none |
| TLR9 | DAP12 | ICOS | none |
| TLR9 | DAP12 | CD27 | none |
| TLR9 | DAP12 | CD28δ | none |
| TLR9 | DAP12 | CD80 | none |
| TLR9 | DAP12 | CD86 | none |
| TLR9 | DAP12 | OX40 | none |
| TLR9 | DAP12 | DAP10 | none |
| TLR9 | DAP12 | MyD88 | none |
| TLR9 | DAP12 | CD7 | none |
| TLR9 | DAP12 | DAP12 | none |
| TLR9 | DAP12 | MyD88 | none |
| TLR9 | DAP12 | CD7 | none |
| TLR9 | MyD88 | CD28 | none |
| TLR9 | MyD88 | CD8 | none |
| TLR9 | MyD88 | CD4 | none |
| TLR9 | MyD88 | b2c | none |
| TLR9 | MyD88 | CD137/41BB | none |
| TLR9 | MyD88 | ICOS | none |
| TLR9 | MyD88 | CD27 | none |
| TLR9 | MyD88 | CD28δ | none |
| TLR9 | MyD88 | CD80 | none |
| TLR9 | MyD88 | CD86 | none |
| TLR9 | MyD88 | OX40 | none |
| TLR9 | MyD88 | DAP10 | none |
| TLR9 | MyD88 | MyD88 | none |
| TLR9 | MyD88 | CD7 | none |
| TLR9 | MyD88 | DAP12 | none |
| TLR9 | MyD88 | MyD88 | none |
| TLR9 | MyD88 | CD7 | none |
| TLR9 | CD7 | CD28 | none |
| TLR9 | CD7 | CD8 | none |
| TLR9 | CD7 | CD4 | none |
| TLR9 | CD7 | b2c | none |
| TLR9 | CD7 | CD137/41BB | none |
| TLR9 | CD7 | ICOS | none |
| TLR9 | CD7 | CD27 | none |
| TLR9 | CD7 | CD28δ | none |
| TLR9 | CD7 | CD80 | none |
| TLR9 | CD7 | CD86 | none |
| TLR9 | CD7 | OX40 | none |
| TLR9 | CD7 | DAP10 | none |
| TLR9 | CD7 | MyD88 | none |
| TLR9 | CD7 | CD7 | none |
| TLR9 | CD7 | DAP12 | none |
| TLR9 | CD7 | MyD88 | none |
| TLR9 | CD7 | CD7 | none |
| TLR9 | BTNL3 | CD28 | none |
| TLR9 | BTNL3 | CD8 | none |
| TLR9 | BTNL3 | CD4 | none |
| TLR9 | BTNL3 | b2c | none |
| TLR9 | BTNL3 | CD137/41BB | none |
| TLR9 | BTNL3 | ICOS | none |
| TLR9 | BTNL3 | CD27 | none |
| TLR9 | BTNL3 | CD28δ | none |
| TLR9 | BTNL3 | CD80 | none |
| TLR9 | BTNL3 | CD86 | none |
| TLR9 | BTNL3 | OX40 | none |
| TLR9 | BTNL3 | DAP10 | none |
| TLR9 | BTNL3 | MyD88 | none |
| TLR9 | BTNL3 | CD7 | none |
| TLR9 | BTNL3 | DAP12 | none |
| TLR9 | BTNL3 | MyD88 | none |
| TLR9 | BTNL3 | CD7 | none |
| TLR9 | NKG2D | CD28 | none |
| TLR9 | NKG2D | CD8 | none |
| TLR9 | NKG2D | CD4 | none |
| TLR9 | NKG2D | b2c | none |
| TLR9 | NKG2D | CD137/41BB | none |
| TLR9 | NKG2D | ICOS | none |
| TLR9 | NKG2D | CD27 | none |
| TLR9 | NKG2D | CD28δ | none |
| TLR9 | NKG2D | CD80 | none |
| TLR9 | NKG2D | CD86 | none |
| TLR9 | NKG2D | OX40 | none |
| TLR9 | NKG2D | DAP10 | none |
| TLR9 | NKG2D | MyD88 | none |
| TLR9 | NKG2D | CD7 | none |
| TLR9 | NKG2D | DAP12 | none |
| TLR9 | NKG2D | MyD88 | none |
| TLR9 | NKG2D | CD7 | none |

In some embodiments, the anti-TLR9 binding agent is single chain variable fragment (scFv) antibody. The affinity/specificity of an anti-TLR9 scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3). In some cases, the anti-TLR9 has a dissociation constant ($K_D$) for TLR9 that is less than 100 nM, 50 nM, 40 nM, 30 nM, 25 nM, 20 nM, 15 nM, or 10 nM.

In some embodiments, the anti-TLR9 binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs that target TLR9 and at least one additional tumor antigen. Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CALX, CS-1, MUC1, BCMA, bcr-abl, HER2, β-human chorionic gonadotropin, alphafetoprotein (AFP), ALK, CD19, CD123, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LACE-Ia, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, CD33, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, CD33, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; over-expressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85erbB2, pl80erbB-3, c-met, nm-23H1, PSA, TLR9, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Nucleic Acids and Vectors

Also disclosed are polynucleotides and polynucleotide vectors encoding the disclosed TLR9-specific CARs that allow expression of the TLR9-specific CARs in the disclosed immune effector cells.

In some embodiments, the TLR9-binding region is encoded by the nucleic acid sequence

```
                           (A23, SEQ ID NO: 33)
ATGGTCCTCCTGGTTACCTCTCTGCTTCTGTGCGAACTGCCTCATCCTGC

CTTCCTTCTTATACCGCCCCGCGAGCCACAGGTGTATACTCTTCCTCCCT
```

```
-continued
CAAGGGACGAACTCGGCATCGCCCAAGTCAGCCTGACGTGTCTTGTGAAA

GGGTTTTACCCCAGCGATATCGCCGTGGAGTGGGAAAGCAACGGCCAGCC

TGAGAACAATTATAAGACTACCCCTCCCGTACTGGACTCTGACGGCAGTT

TCTTTCTCTATTCTAAACTGACCGTGCTCGGAAGGCGCTGGACGCTCGGC

AACGTATTTTCTTGCAGTGTGATGCATGAAGCACTGCACAATCATTATAC

TCAGAAGAGCTTGTCACTGTCCCCGGGAAAGGGCAGCACATCCGGCAGCG

GGAAACCGGGTAGCGGCGAAGGGAGCACTAAGGGG.
```

In some embodiments, the TLR9-binding region is encoded by the nucleic acid sequence

```
                          (D2, SEQ ID NO: 34)
ATGGTGCTGCTCGTTACAAGTCTGCTTCTCTGTGAACTGCCGCATCCGGC

CTTTCTTTTGATCCCGCCAAGGGAACCCCAGGTTTACACACTGCCCCCAT

CCCGGGACGAGTTGCTGCCTTGTCAGGTGAGTCTTACATGCTTGGTGAAG

GGCTTTTACCCGTCTGACATAGCAGTGGAATGGGAGTCCAACGGACAGCC

AGAAAATAACTACAAGACCACCCCTCCCGTCCTTGACAGCGATGGAAGCT

TTTTTCTGTATAGCAAGCTGACTGTGTTCTGTCCTAGATGGCTGGGGGGC

AATGTTTTTTCTTGCAGCGTCATGCACGAAGCCCTCCACAACCACTACAC

CCAGAAAAGCCTGTCCTTGTCTCCTGGCAAGGGTAGCACATCAGGTAGCG

GCAAGCCCGGGAGTGGCGAGGGCAGTACCAAGGGC.
```

In some embodiments, the TLR9-binding region is encoded by the nucleic acid sequence

```
                         (D68, SEQ ID NO: 35)
ATGGTTCTGCTCGTTACATCTCTTCTGCTCTGCGAACTGCCACATCCGGC

GTTCCTCCTTATTCCACCGCGAGAACCTCAGGTTTACACCCTCCCCCCTA

GCAGGGACGAGCTGACTAAAAATCAAGTATCATTGACCTGTCTGGTTAAG

GGCTTTTATCCGTCCGATATTGCTGTTGAGTGGGAATCTAACGGCCAACC

TGAGAACAATTATAAAACTACGCCGCCGGTACTCGACTCTGACGGCAGCT

TCTTCCTCTACTCTAAACTCACTGTACCTTGCATGAGATGGTGGGGGGGT

AATGTTTTTAGCTGCTCCGTGATGCATGAGGCCCTCCACAACCATTACAC

GCAGAAGTCTCTCAGCCTCAGTCCCGGCAAGGGCTCTACGTCAGGCTCAG

GCAAACCGGGAAGTGGGGAAGGATCAACTAAGGGA.
```

In some embodiments, the TLR9-binding region is encoded by the nucleic acid sequence

```
                      (A23-D2, SEQ ID NO: 36)
ATGGTTCTGTTGGTGACTTCTCTTCTTTTGTGCGAGCTCCCACATCCTGC

GTTCCTTTTGATTCCGCCGAGGGAGCCCCAAGTTTATACCCTGCCTCCTA

GTCGGGATGAGTTGGGTATCGCACAAGTGAGCCTGACTTGTCTCGTAAAG

GGATTCTATCCGTCCGATATAGCAGTCGAGTGGGAAAGTAATGGGCAGCC

GGAGAACAACTACAAGACAACTCCCCCAGTTCTTGACTCCGACGGATCAT

TTTTTTTTGTACTCTAAATTGACGGTCCTGGGTAGGCGCTGGACCCTCGGC
```

AATGTCTTCAGTTGTAGCGTAATGCATGAAGCCCTTCACAACCATTATAC

CCAGAAGAGTTTGTCCCTTTCTCCCGGTAAGGGGGAGGAGGTTCTGGAG

GTGGAGGTAGCGGTGGTGGGGGTTCCCCACGAGAGCCCCAAGTGTACACT

CTCCCACCGTCTCGGGATGAATTGCTTCCGTGCCAGGTATCCCTTACTTG

CCTCGTTAAAGGGTTCTACCCAAGCGACATTGCGGTGGAATGGGAATCAA

ATGGTCAGCCAGAAAACAATTACAAGACGACCCCTCCAGTCCTCGACTCA

GATGGATCTTTCTTTCTGTATTCCAAGCTGACGGTTTTTTGTCCGAGGTG

GCTTGGAGGGAACGTCTTCTCATGCTCCGTCATGCACGAGGCGCTGCATA

ACCACTACACACAGAAAAGTTTGTCCTTGAGCCCGGGTAAAGGCAGCACC

AGCGGGAGCGGAAAACCTGGAAGTGGGGAAGGGTCTACCAAGGGC.

In some embodiments, the TLR9-binding region is encoded by the nucleic acid sequence (A23-D68, SEQ ID NO: 37)
ATGGTTCTGCTGGTAACCTCCCTCCTTCTGTGCGAGCTCCCCCACCCCGC

ATTCCTCCTGATTCCGCCCAGAGAACCCCAGGTGTATACCCTTCCCCCTA

GCAGAGATGAGCTGGGCATAGCTCAGGTATCCCTCACATGCCTCGTGAAA

GGATTCTACCCAAGTGACATCGCCGTGGAGTGGGAAAGCAACGGGCAGCC

GGAAAACAATTATAAGACGACCCCACCCGTGCTCGACAGTGACGGCTCTT

TCTTCCTGTACTCCAAACTGACCGTCCTTGGACGGCGATGGACACTGGGC

AATGTTTTTAGCTGTTCCGTGATGCATGAGGCCCTGCACAACCACTATAC

CCAGAAGTCACTCTCTCTGTCTCCTGGGAAAGGAGGGGGTGGCAGCGGCG

GTGGCGGATCTGGCGGAGGAGGTTCTCCCAGGGAGCCTCAGGTATATACC

CTGCCCCCTTCTCGCGACGAGTTGACGAAGAACCAAGTGTCTCTGACCTG

CCTGGTCAAAGGATTCTACCCTTCTGATATTGCAGTGGAATGGGAATCCA

ACGGGCAGCCTGAGAATAATTACAAGACCACCCCACCTGTTCTTGATAGT

GACGGTTCATTCTTCCTCTACAGCAAGCTGACCGTGCCCTGTATGAGGTG

GTGGGGCGGCAACGTCTTTTCTTGTTCCGTCATGCACGAAGCACTGCATA

ACCACTACACCCAGAAAAGCCTGTCTCTTAGCCCTGGGAAGGGATCTACC

TCAGGATCTGGGAAACCTGGTAGCGGCGAGGGTAGCACCAAAGGA.

In some embodiments, the hinge and transmembrane domain derived from CD8 is encoded by the nucleic acid sequence (SEQ ID NO: 38)
TTCGTGCCGGTCTTCCTGCCAGCGAAGCCCACCACGACGCCAGCGCCGCG

ACCACCAACACCGGCGCCCACCATCGCGTCGCAGCCCCTGTCCCTGCGCC

CAGAGGCGTGCCGGCCAGCGGCGGGGGCGCAGTGCACACGAGGGGCTG

GACTTCGCCTGTGATATCTACATCTGGGCGCCCTTGGCCGGGACTTGTGG

GGTCCTTCTCCTGTCACTGGTTATCACCCTTTACTGCAACCACAGGAACA

GGAGTAAGAGG.

In some embodiments, the hinge and transmembrane domain derived from CD28 is encoded by the nucleic acid sequence (SEQ ID NO: 39)
AAGTTATGTATCCTCCTCCTTACCTAGACAATGAGAAGAGCAATGGAACC

ATTATCCATGTGAAAGGGAAACACCTTTGTCCAAGTCCCCTATTTCCCGG

ACCTTCTAAGCCCTTTTGGGTGCTGGTGGTGGTTGGGGGAGTCCTGGCTT

GCTATAGCTTGCTAGTAACAGTGGCCTTTATTATTTTCTGGGTG.

In some embodiments, the 4-1BB costimulatory molecule is encoded by the nucleic acid sequence (SEQ ID NO: 40)
CGTTTCTCTGTTGTTAAACGGGGCAGAAAGAAACTCCTGTATATATTCAA

ACAACCATTTATGAGACCAGTACAAACTACTCAAGAGGAAGATGGCTGTA

GCTGCCGATTTCCAGAAGAAGAAGAAGGAGGATGTGAACTG.

In some embodiments, the CD3ζ domain is encoded by the nucleic acid sequence (SEQ ID NO: 41)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAA.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific sub-population of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells ($T_C$ cells, or CTLs) destroy virally infected cells and tumor cells, and are also implicated in transplant rejection. These cells are also known as CD8+ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4+ or CD8+. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4+ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic CD8+ T lymphocytes. In some embodiments, the T cells comprise γδ T cells, which possess a distinct T-cell receptor (TCR) having one γ chain and one δ chain instead of a and β chains.

Natural-killer (NK) cells are CD56+CD3− large granular lymphocytes that can kill virally infected and transformed cells, and constitute a critical cellular subset of the innate immune system (Godfrey J, et al. Leuk Lymphoma 2012 53:1666-1676). Unlike cytotoxic CD8+ T lymphocytes, NK cells launch cytotoxicity against tumor cells without the requirement for prior sensitization, and can also eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Therapeutic Methods

Immune effector cells expressing the disclosed CARs can elicit an anti-tumor immune response against TLR9-expressing cancer cells. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to TLR9.

Adoptive transfer of immune effector cells expressing chimeric antigen receptors is a promising anti-cancer therapeutic. Following the collection of a patient's immune effector cells, the cells may be genetically engineered to express the disclosed TLR9-specific CARs, then infused back into the patient.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any cancer cell that expresses TLR9 on its plasma membrane undergoing unregulated growth, invasion, or metastasis. Cancers that express TLR9 on the plasma membrane include MDS, AML, and hepatocellular carcinoma.

In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MED14736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and *vinca* alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed CARs is administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC tag, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional-CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using α-β T cells, however γ-δ T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein domain" refers to a portion of a protein, portions of a protein, or an entire protein showing structural integrity; this determination may be based on amino acid composition of a portion of a protein, portions of a protein, or the entire protein.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1: TLR9-Targeted Car-T Cell Immunotherapy for Myelodysplastic Syndrome

Expression of a number of candidate genes implicated in the pathogenesis of the del(5q) phenotype is reduced, commensurate with mono-allelic deletion of those genes residing within the distal commonly deleted region (CDR) at 5q32 (Boultwood, J. et al. Blood 99:4638-4641 (2002); Ebert, B. L. et al. Nature 451:335-U7 (2008); Ebert, B. L. Leukemia 23:1252-1256 (2009)). Haploinsufficiency of the ribosomal protein (RP)-S14 gene, which encodes a component of the 40S ribosomal subunit, is a key determinant of the hypoplastic anemia characteristic of del5q MDS (Ebert, B. L. et al. Nature 451:335-U7 (2008)). The ensuing disruption of ribosome assembly leads to release of free RPs that bind to MDM2, triggering its degradation with consequent p53 activation in affected erythroid precursors (Zhou, X., et al. Oncogene 32:388-396 (2013); Dutt, S. et al. Blood 117:2567-2576 (2011); Danilova, N., et al. Blood 112:5228-5237 (2008)). A murine model of the human 5q-syndrome generated by allelic deletion of the syntenic genes within the human 5q32-33 CDR replicates the pathological features of human del5q MDS, whereas inactivation of p53 rescued the hematologic phenotype, confirming the critical role of p53 in the del5q MDS phenotype (Barlow, J. L. et al. Nature Medicine 16, 59-U93 (2010)). Moreover, suppression of TP53 expression using an antisense oligonucleotide restores erythroid colony forming capacity in primary del5q MDS specimens (Caceres, G. et al. Proc Nat Acad Sci USA 110:16127-16132 (2013)). Recent analysis of primary del5q MDS specimens confirmed that p53 is over-expressed in a lineage restricted manner (Wei, S. et al. Oncogene 32:1110-1120 (2013)). Treatment with LEN restores MDM2 stability to promote p53 degradation in both cell lines and primary del5q MDS specimens, an effect that is accompanied by suppression of downstream p53 effector genes (Wei, S. et al. Oncogene 32:1110-1120 (2013)). P53 degradation thereby restores cell cycle transition from G0/G1 with subsequent arrest in G2/M. Whether members of the RP-MDM2-p53 pathway are direct binding targets of LEN remains unknown. Independently of its effects on MDS cells, LEN has been shown to stimulate T cells 22.

Figure 2A:
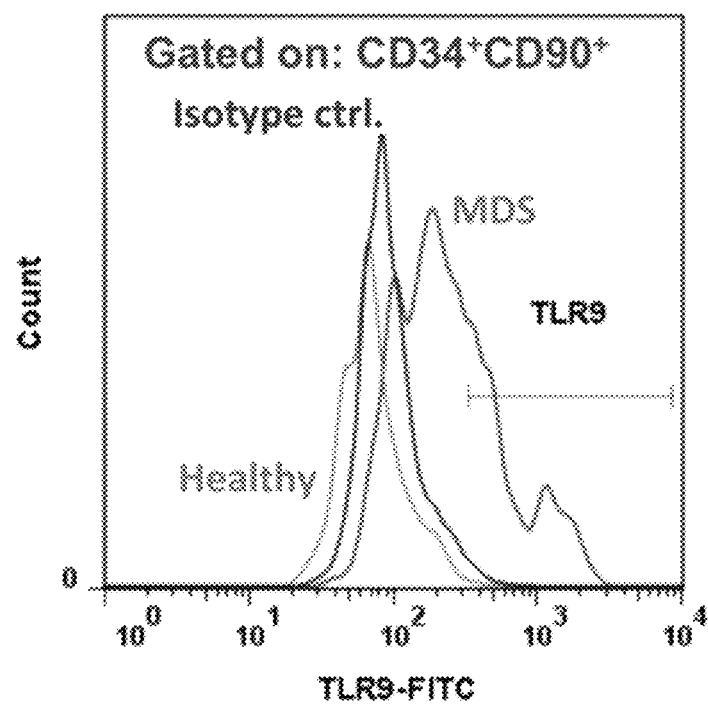
FIG. 2A is a histogram from a representative experiment showing TLR9 expression on fresh hematopoietic stem pluripotent cells (HSPC, defined as CD34+ CD90+) from the bone marrow of a healthy donor, MDS patient, or isotype control.
Figure 2B:
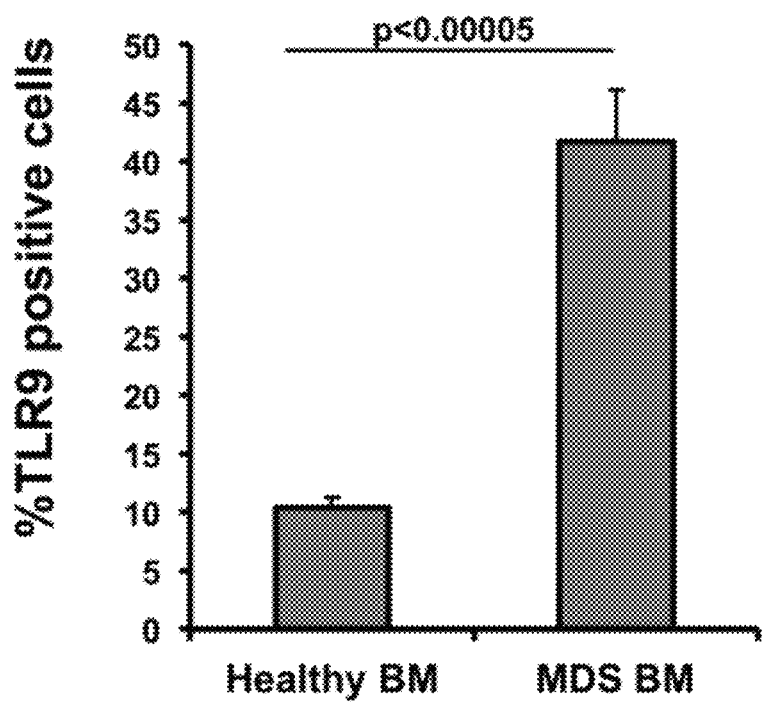
FIG. 2B is a bar graph showing the percentage of cells expressing TLR9 on the surface in healthy or MDS bone marrows (n=10 per group).

Toll-like receptor 9 (TLR9) is an endosomal sensor of foreign nucleic acids that activates the innate immunity through TRAF6, IRAK4 or MyD88-mediated pathways, depending on the cell type where it is expressed (Blasius, A. L. & Beutler, B. Immunity 32:305-315 (2010)). The observation that TLR9 is aberrantly expressed on the plasma membrane of MDS cells (FIG. 1 and FIG. 2), offered the possibility of designing TLR9-targeted chimeric antigen receptors (CARs) to detect and destroy MDS cells. CARs are synthetic immune receptors that can be expressed in autologous peripheral blood T cells and reinfused into patients for the treatment of various malignancies. CAR-T cell therapies have achieved outstanding clinical responses in refractory B cell leukemias (Kochenderfer, J. N. et al. Blood 122:4129-39 (2013); Abate-Daga, D., et al. Molecular Therapy Oncolytics 3(2016)), leading to the expected approval, by the US Food and Drug Administration (FDA), of the first CAR-T cell product, directed against CD19, within the next year or two.

Results

Figure 3A:
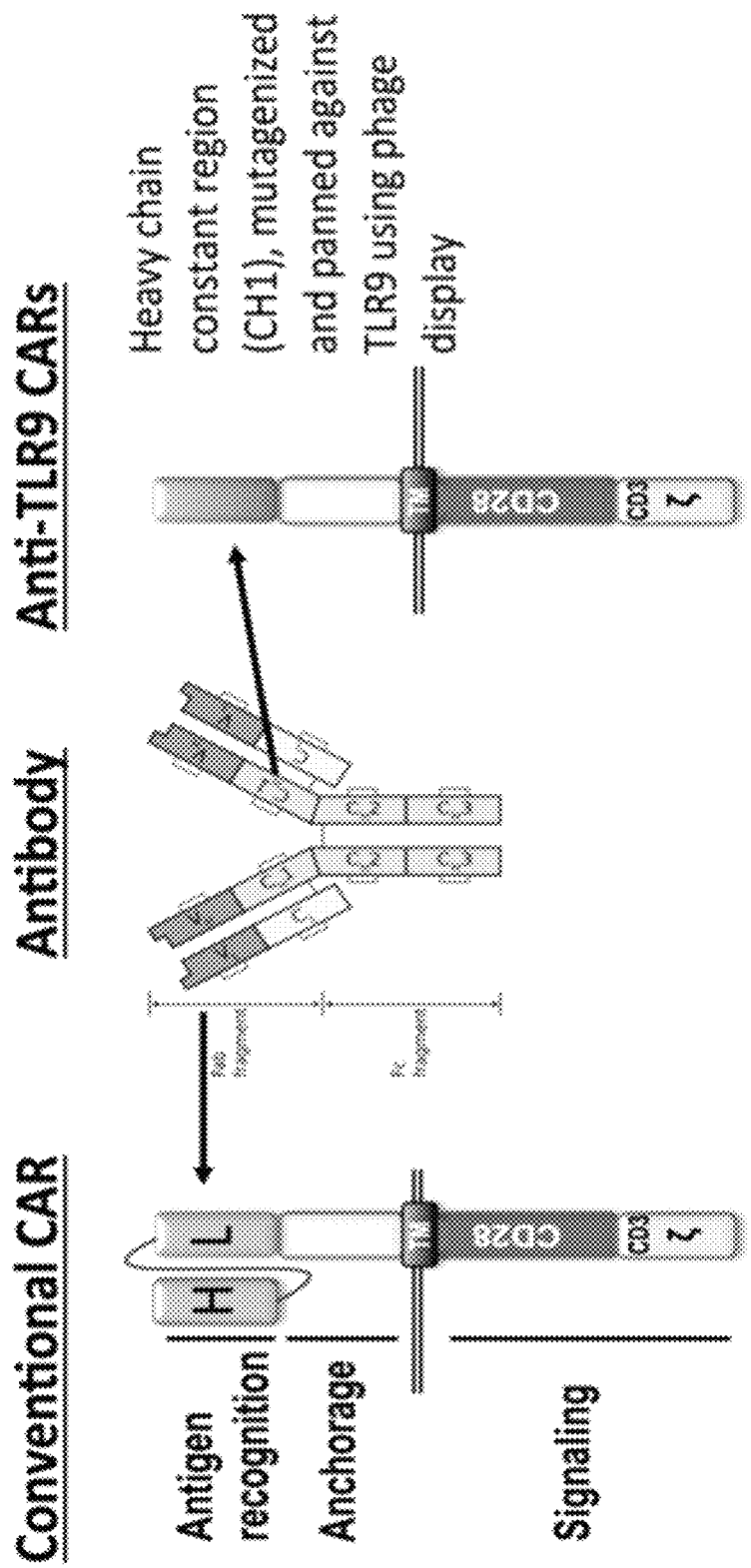
FIG. 3A illustrates that conventional CARs combine single chain antibodies (scFv) containing heavy and light variable regions linked to an intracellular signaling tail. An embodiment CAR uses a synthetic antibody constant region-derived TLR9-binding molecule.
Figure 3B:
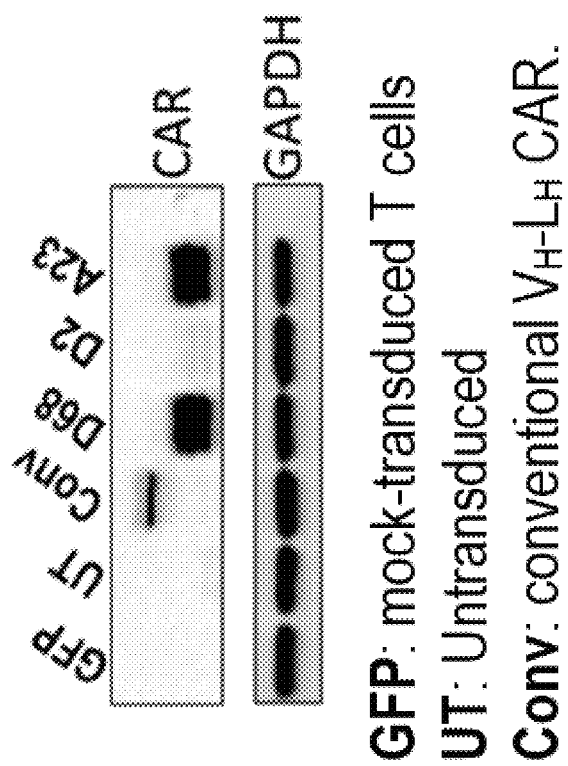
FIG. 3B is a blot showing 3 CARs containing CD28-costimulation, differing in their antibody domains (D68, D2, A23), and their expression by retrovirally-transduced human T cells tested by WB using an anti-CD3zeta antibody. Robust expression was confirmed for D68 and A23 CARs. GAPDH was used as loading control.
Figure 3C:
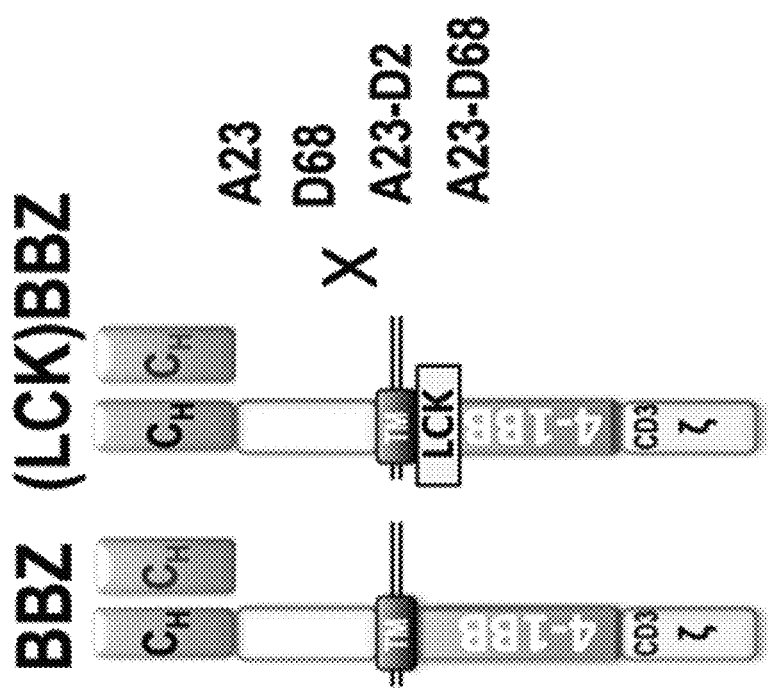
FIG. 3C is a schematic representation of 4-1BB and LCK-4-1BB CARs containing more than one TLR9-targeting molecule.

A series of CARs were designed and cloned into the MSGV-1 retroviral vector. TLR9-binding antibody sequences were identified in literature (Wozniak-Knopp G, R. F., et al. in EP 1 699 826 B1) and used to synthesize the cDNA for 3 second generation CARs (D68, D2, A23), containing CD28 co-stimulation and a CD3zeta activation domain (FIG. 3A). Western blot (WB) was used against the CD3zeta portion of the CARs to verify their expression after transduction of primary human T cells, finding that while the D68 and A23 sequences yielded robust expression, the D2 sequence was not efficiently expressed by the T cells (FIG. 3B). The combination of TLR9-binding sequences and co-stimulatory domains was then expanded by creating all possible combinations between A23, D68 and 2 new tandem sequences A23-D2 and A23-D68, with a second generation signaling tail comprised of 4-1BB co-stimulation linked to CD3zeta or its derivative containing an extra LCK binding site (FIG. 3C). LCK is an immediate downstream signaling effector of the T-cell activation pathway, and experiments were conducted to test if an additional binding site might increase CAR potency.

Figure 4A:
FIG. 4A is a schematic representation of experimental design where primary human peripheral blood mononuclear cells (PBMC) from healthy donors were stimulated with anti-CD3 antibody (OKT3), and transduced twice (day 2 and 3) with retroviral vectors encoding anti-TLR9 CARs. Seven days post-transduction, CAR-T cells were co-cultured with SKM-1 cells.
Figure 4B:
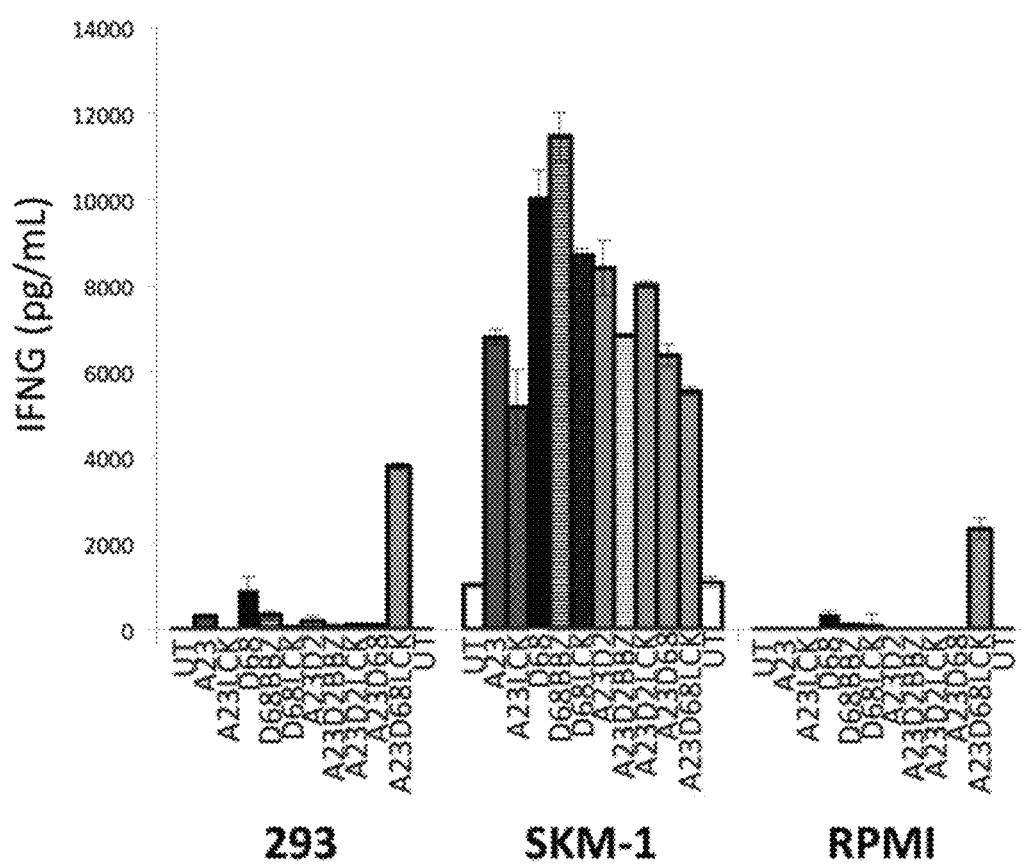
FIG. 4B is a bar graph showing interferon-gamma (IFNG) in co-culture supernatants, measured by ELISA. The 10 most highly expressed CARs were screened for specific recognition of TLR9-positive SKM-1 cells. HEK293 cells or media alone were used as negative controls.
Figure 6:
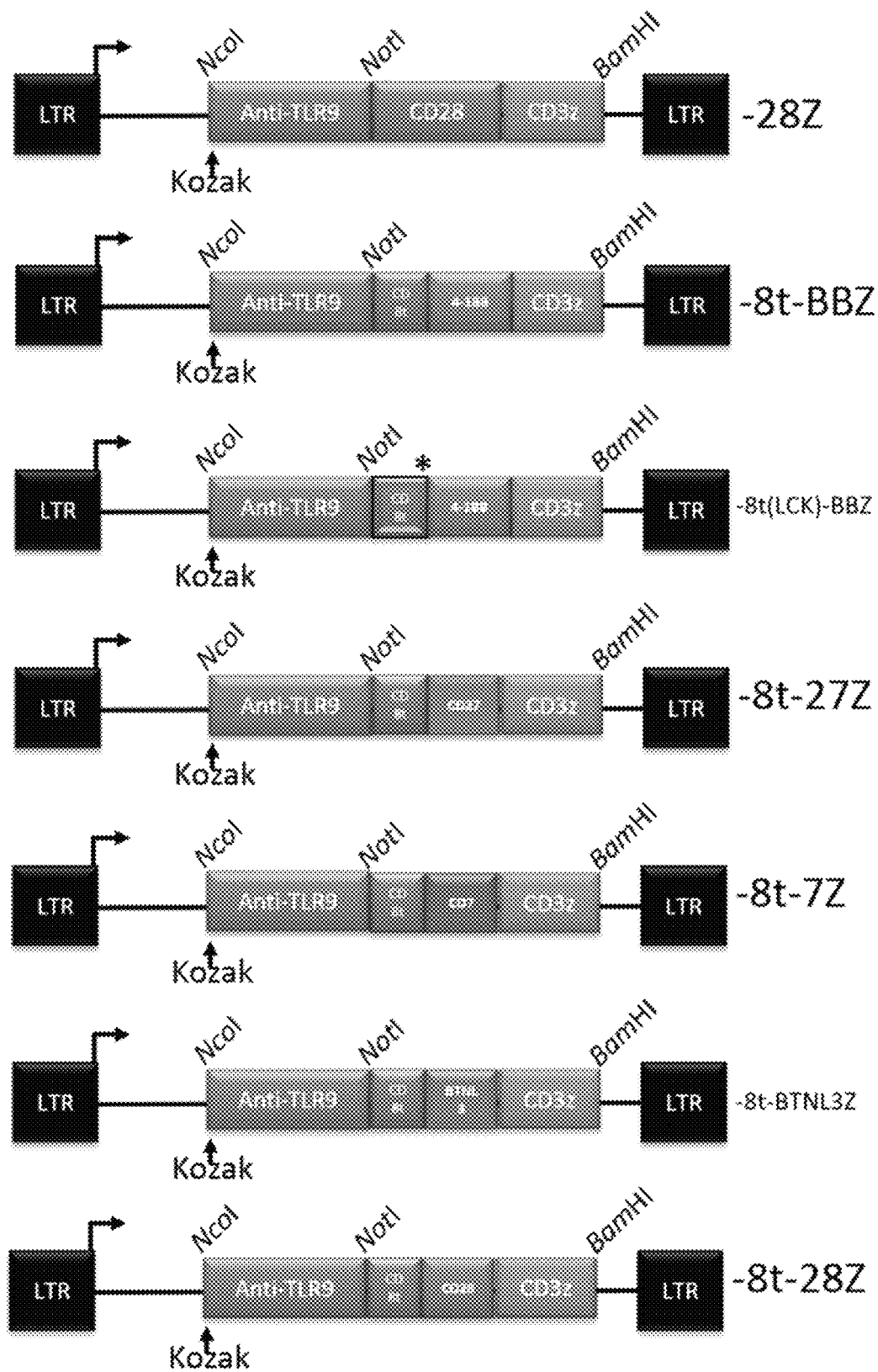
FIG. 6 is a schematic representation of retroviral vector design for various anti-TLR9 CAR expression. The anti-TLR9 boxes represent any TLR9-targeting molecule (such as A23, D2, D68, A23D2, A23D68, etc.). LTR boxes represent the retroviral long terminal repeats. Broken arrows represent the promoter activity of LTRs, and site initiation of translation. NcoI and NotI represent restriction sites for the corresponding enzymes, used for cloning of signaling and antigen binding modules. TLR9-28Z CARs have a hinge, transmembrane, and costimulatory domains derived from CD28, in addition to the CD3zeta T cell activation domain present in all constructs. The rest of the CARs have a CD8-derived hinge and transmembrane domain (8t). The TLR9-8t(LCK)BBZ CAR contains a longer CD8-derived intracellular domain (CD8t*) that includes an LCK-binding domain.
Figure 7:
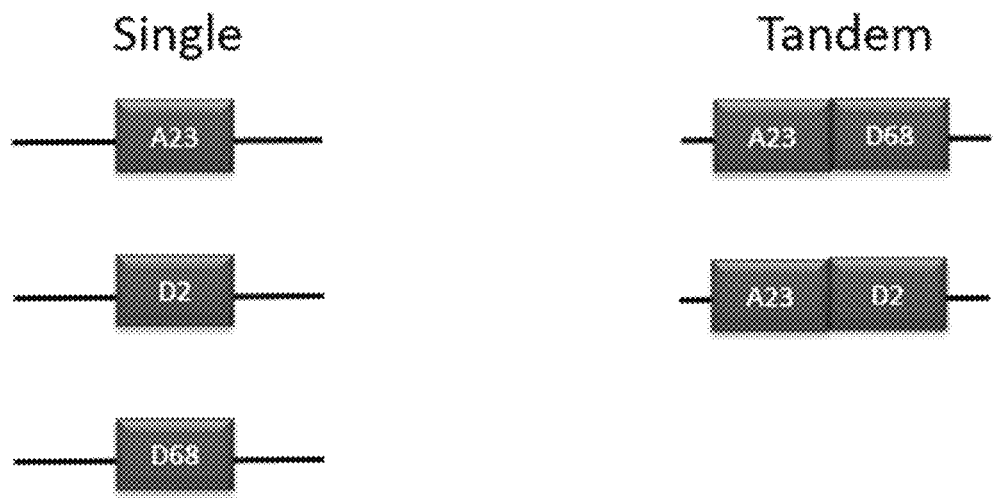
FIG. 7 illustrates variations of the TLR9-binding domain of CH-based CARs.
Figure 8A:
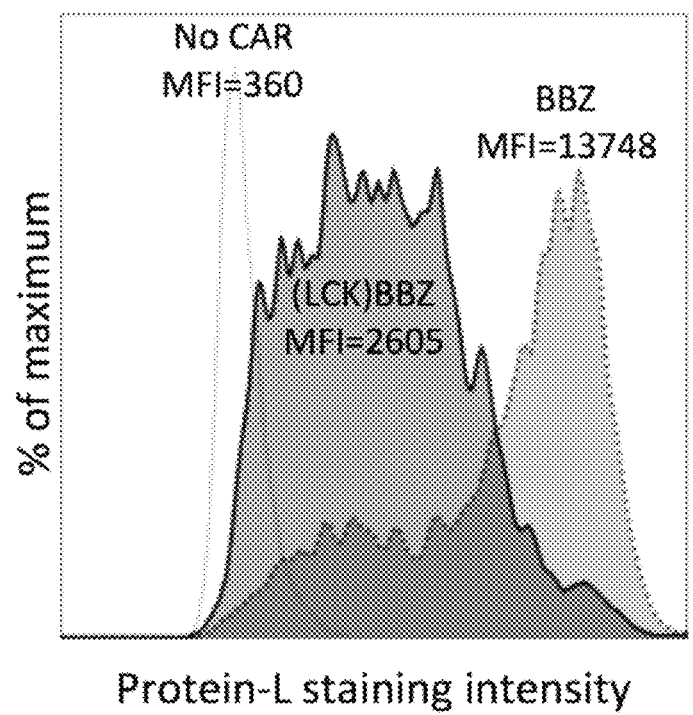
FIG. 8A shows flow cytometry analysis of CAR expression for anti-PSCA CARs containing a BBZ or (LCK)BBZ endodomain (spacer). Results show that CARs containing the spacer express lower levels of CAR on the surface. MFI: mean fluorescence intensity. T cells that do not express any CAR were used as negative control. CAR staining was performed using protein-L.
Figure 8B:
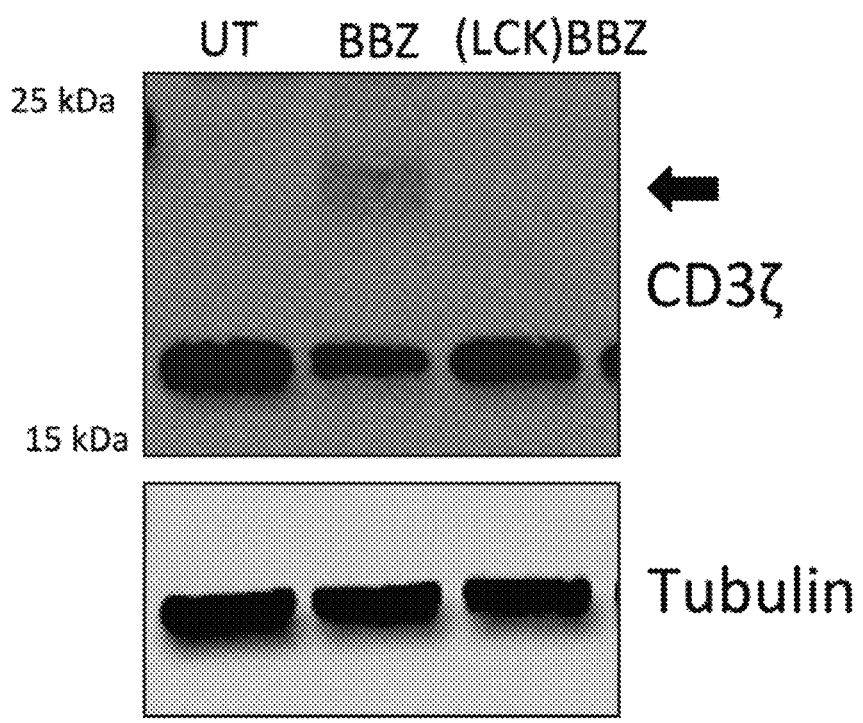
FIG. 8B shows Western blot analysis of the endogenous CD3ζ in untransduced T cells, or T cells expressing BBZ or (LCK)BBZ CARs. Whole-cell extracts were prepared from $3 \times 10^6$ human primary lymphocytes, resolved by SDS-PAGE, and immunobloted using specific antibodies. The arrow indicates the presence of a higher molecular weight species of CD3ζ (21 kDa approximately), which correspond to phosphorylated CD3ζ. This species is not present in (LCK)BBZ CAR-transduced lymphocytes.
Figure 8C:
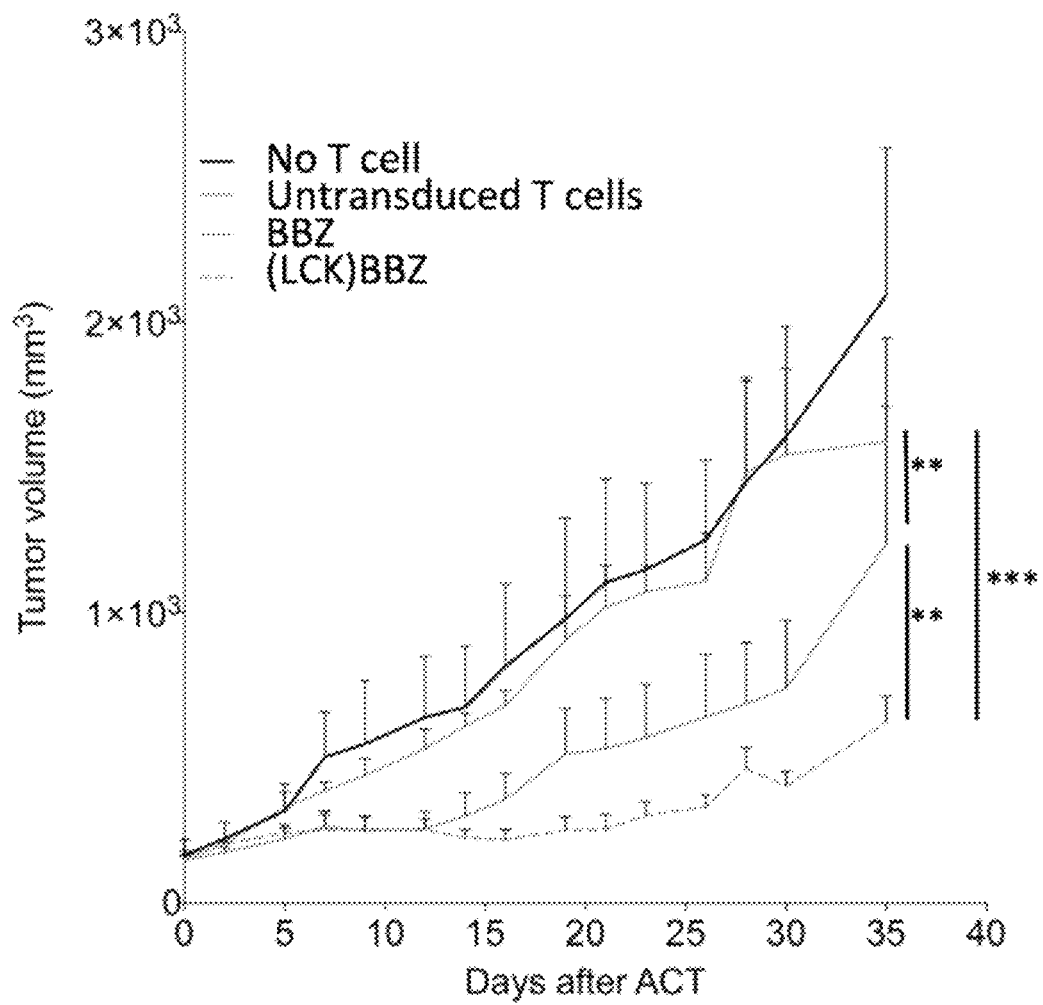
FIG. 8C is a bar graph showing tumor volume in an in vivo tumor growth study performed on a xenograft model of pancreatic cancer, following treatment with adoptive transfer of human lymphocytes expressing CARs. Tumors treated with the BBZ CAR (n=5) experienced a significant delay of growth, compared tumors treated with lymphocytes expressing no CAR (n=5). However, the (LCK)BBZ CAR T cells were more efficient in delaying tumor growth than the BBZ CARs. These results suggest that CARs containing a linker that prevents the spontaneous phosphorylation of the endogenous CD3ζ display a more potent antitumor effect in vivo.

From the pool of CARs, 10 were consistently expressed to high levels by transduced T cells. As shown in FIG. 4A, their ability to specifically recognize TLR9-expressing SKM1 cells was tested by quantifying the release of IFNG in the supernatant of overnight co-cultures. Specific recognition of SKM1 was observed in all CARs except for A23-D68-(LCK)-BBZ, which reacted against SKM1 cells but also against HEK293 and media alone. D68-based CARs appeared to have a slightly higher activity than the rest, and no major differences were associated with use of different intracellular domains, except for A23-D68-(LCK)-BBZ. FIG. 4B.

A thorough analysis of the anti-MDS activity and in vivo persistence of CAR-T cells expressing each of these constructs is conducted to determine the optimal design for anti-TLR9 CAR therapy. These constructs are used to evaluate the changes in TLR9 externalization and antigenicity upon treatment of SKM1 cells, and clinical samples, with protease inhibitors.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising a TLR9-binding region, a transmembrane domain, a signaling domain, and a co-stimulatory signaling region,
   wherein the TLR9-binding region is a single-chain variable fragment (scFv) of an antibody that specifically binds TLR9,
   wherein the anti-TLR9 scFv comprises a variable heavy ($V_H$) domain having CDR1, CDR2 and CDR3 sequences and a variable light ($V_L$) domain having CDR1, CDR2 and CDR3 sequences,
   wherein the CDR1 sequence of the $V_H$ domain comprises the amino acid sequence TAGMQ (SEQ ID NO:1),
   wherein the CDR2 sequence of the $V_H$ domain comprises the amino acid sequence WINTHSGEPKYAEDFKG (SEQ ID NO:2),
   wherein the CDR3 sequence of the $V_H$ domain comprises the amino acid sequence GDSSGYGAWFAY (SEQ ID NO:3),
   wherein the CDR1 sequence of the $V_L$ domain comprises the amino acid sequence RSSTGAVTTSNYAN (SEQ ID NO:4)
   wherein the CDR2 sequence of the $V_L$ domain comprises the amino acid sequence DTNNRAP (SEQ ID NO:5), and
   wherein the CDR3 sequence of the $V_L$ domain comprises the amino acid sequence ALWCSNHWV (SEQ ID NO:6).

2. The CAR polypeptide of claim 1, wherein the costimulatory signaling region comprises the cytoplasmic domain of a costimulatory molecule selected from the group consisting of CD27, CD28, CD7, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

3. The CAR polypeptide of claim 1, wherein the CAR polypeptide is defined by the formula:

SP-TLR9-HG-TM-CSR-SD; or

SP-TLR9-HG-TM-SD-CSR wherein "SP" represents a signal peptide,
wherein "TLR9" represents the TLR9-binding region,
wherein "HG" represents an optional hinge domain,
wherein "TM" represents a transmembrane domain,
wherein "CSR" represents a co-stimulatory signaling region,
wherein "SD" represents the signaling domain, and
wherein "-" represents a peptide bond, linker, or spacer.

4. The CAR polypeptide of claim 3, wherein the spacer linking the TLR9-binding domain to the hinge domain comprises the amino acid sequence SEQ ID NO:11 or SEQ ID NO:12.

5. The CAR polypeptide of claim 3, wherein the spacer linking the transmembrane domain to the signal signaling domain comprises an LCK-binding region of CD8alpha.

6. The CAR polypeptide of claim 5, wherein the LCK-binding region has the amino acid sequence SEQ ID NO:31.

7. The CAR polypeptide of claim 1, wherein the signaling domain comprises a CD3 zeta (CD3ζ) signaling domain.

8. The CAR polypeptide of claim 1, wherein the anti-TLR9 scFv $V_H$ domain comprises the amino acid sequence SEQ ID NO:7 or SEQ ID NO:8.

9. The CAR polypeptide of claim 1, wherein the anti-TLR9 scFv $V_L$ domain comprises the amino acid sequence SEQ ID NO:9 or SEQ ID NO:10.

10. An isolated nucleic acid sequence encoding the CAR polypeptide of claim 1.

11. A vector comprising the isolated nucleic acid sequence of claim 10.

12. A cell comprising the vector of claim 11.

13. The cell of claim 12, wherein the cell is selected from the group consisting of an αβT cell, γδT cell, a Natural Killer (NK) cell, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, a regulatory T cell, or any combination thereof.

14. A method of providing an anti-tumor immunity in a subject with a TLR9-expressing cancer, the method comprising administering to the subject an effective amount of an immune effector cell genetically modified to express the CAR polypeptide of claim 1, thereby providing an anti-tumor immunity in the mammal.

15. The method of claim 14, wherein the immune effector cell is selected from the group consisting of a T cell, a Natural Killer (NK) cell, a cytotoxic T lymphocyte (CTL), and a regulatory T cell.

16. The method of claim 14 further comprising administering to the subject a checkpoint inhibitor.

17. The method of claim 16, wherein the checkpoint inhibitor comprises an anti-PD-1 antibody, anti-PD-L1 antibody, anti-CTLA-4 antibody, or a combination thereof.

* * * * *

```
                         SEQUENCE LISTING

<160> NUMBER OF SEQ ID NOS: 41

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Thr Ala Gly Met Gln
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Asn Thr His Ser Gly Glu Pro Lys Tyr Ala Glu Asp Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Gly Asp Ser Ser Gly Tyr Gly Ala Trp Phe Ala Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic Construct

<400> SEQUENCE: 4

Arg Ser Ser Thr Gly Ala Val Thr Thr Ser Asn Tyr Ala Asn
1               5                   10

<210> SEQ ID NO 5
<211> LENGTH: 7
<212> TYPE: PRT
<213> ORGANISM: Artificial Sequence
<220> FEATURE:
```

<223> OTHER INFORMATION: Synthetic Construct

<400> SEQUENCE: 5

Asp Thr Asn Asn Arg Ala Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Ala Leu Trp Cys Ser Asn His Trp Val
1               5

<210> SEQ ID NO 7
<211> LENGTH: 122
<212> TYPE: PRT
<213> ORGANISM: Artificial Sequence
<220> FEATURE:
<223> OTHER INFORMATION: Synthetic Construct

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Ala
                20                  25                  30

Gly Met Gln Trp Tyr Gln Lys Met Pro Gly Lys Gly Phe Lys Trp Ile
        35                  40                  45

Gly Trp Ile Asn Thr His Ser Gly Glu Pro Lys Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Ala Arg Gly Asp Ser Ser Gly Tyr Gly Ala Trp Phe Ala Tyr Trp Gly
            100                 105                 110

Gln Gly Thr Leu Val Thr Val Ser Ala Ala
        115                 120

<210> SEQ ID NO 8
<211> LENGTH: 109
<212> TYPE: PRT
<213> ORGANISM: Artificial Sequence
<220> FEATURE:
<223> OTHER INFORMATION: Synthetic Construct

<400> SEQUENCE: 8

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Asp Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

```
Gln Thr Glu Asp Glu Ala Ile Tyr Phe Cys Ala Leu Trp Cys Ser Asn
                85                  90                  95

His Trp Val Phe Gly Gly Gly Thr Lys Leu Thr Val Leu
            100                 105
```

<210> SEQ ID NO 9
<211> LENGTH: 109
<212> TYPE: PRT
<213> ORGANISM: Artificial Sequence
<220> FEATURE:
<223> OTHER INFORMATION: Synthetic Construct

<400> SEQUENCE: 9

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Asp Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Cys Ser Asn
                85                  90                  95

His Trp Val Phe Gly Gly Gly Thr Lys Leu Thr Val Leu
            100                 105
```

<210> SEQ ID NO 10
<211> LENGTH: 109
<212> TYPE: PRT
<213> ORGANISM: Artificial Sequence
<220> FEATURE:
<223> OTHER INFORMATION: Synthetic Construct

<400> SEQUENCE: 10

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Asp Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Cys Ser Asn
                85                  90                  95

His Trp Val Phe Gly Gly Gly Thr Lys Leu Thr Val Leu
            100                 105
```

<210> SEQ ID NO 11
<211> LENGTH: 18
<212> TYPE: PRT
<213> ORGANISM: Artificial Sequence
<220> FEATURE:
<223> OTHER INFORMATION: Synthetic Construct

<400> SEQUENCE: 11

```
Gly Ser Thr Ser Gly Ser Gly Lys Pro Gly Ser Gly Glu Gly Ser Thr
```

Lys Gly

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Gly Gly Gly Gly Ser Gly Gly Gly Gly Ser Gly Gly Gly Gly Ser
1               5                   10                  15

<210> SEQ ID NO 13
<211> LENGTH: 22
<212> TYPE: PRT
<213> ORGANISM: Artificial Sequence
<220> FEATURE:
<223> OTHER INFORMATION: Synthetic Construct

<400> SEQUENCE: 13

Met Val Leu Leu Val Thr Ser Leu Leu Cys Glu Leu Pro His Pro
1               5                   10                  15

Ala Phe Leu Leu Ile Pro
            20

<210> SEQ ID NO 14
<211> LENGTH: 271
<212> TYPE: PRT
<213> ORGANISM: Artificial Sequence
<220> FEATURE:
<223> OTHER INFORMATION: Synthetic Construct

<400> SEQUENCE: 14

Met Val Leu Leu Val Thr Ser Leu Leu Cys Glu Leu Pro His Pro
1               5                   10                  15

Ala Phe Leu Leu Ile Pro Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Thr Ala Gly Met Gln Trp Tyr Gln Lys Met Pro Gly
    50                  55                  60

Lys Gly Phe Lys Trp Ile Gly Trp Ile Asn Thr His Ser Gly Glu Pro
65                  70                  75                  80

Lys Tyr Ala Glu Asp Phe Lys Gly Arg Phe Ala Phe Ser Leu Glu Thr
                85                  90                  95

Ser Ala Ser Thr Ala Tyr Leu Gln Ile Ser Asn Leu Lys Asn Glu Asp
            100                 105                 110

Thr Ala Thr Tyr Phe Cys Ala Arg Gly Asp Ser Ser Gly Tyr Gly Ala
        115                 120                 125

Trp Phe Ala Tyr Trp Gly Gln Gly Thr Leu Val Thr Val Ser Ala Ala
    130                 135                 140

Gly Ser Thr Ser Gly Ser Gly Lys Pro Gly Ser Gly Glu Gly Ser Thr
145                 150                 155                 160

Lys Gly Gln Ala Val Val Thr Gln Glu Ser Ala Leu Thr Thr Ser Pro
                165                 170                 175

Gly Glu Thr Val Thr Leu Thr Cys Arg Ser Ser Thr Gly Ala Val Thr
            180                 185                 190

```
Thr Ser Asn Tyr Ala Asn Trp Val Gln Glu Lys Pro Asp His Leu Phe
        195                 200                 205

Thr Gly Leu Ile Gly Asp Thr Asn Asn Arg Ala Pro Gly Val Pro Ala
    210                 215                 220

Arg Phe Ser Gly Ser Leu Ile Gly Asp Lys Ala Ala Leu Thr Ile Thr
225                 230                 235                 240

Gly Ala Gln Thr Glu Asp Glu Ala Ile Tyr Phe Cys Ala Leu Trp Cys
                245                 250                 255

Ser Asn His Trp Val Phe Gly Gly Thr Lys Leu Thr Val Leu
        260                 265                 270

<210> SEQ ID NO 15
<211> LENGTH: 258
<212> TYPE: PRT
<213> ORGANISM: Artificial Sequence
<220> FEATURE:
<223> OTHER INFORMATION: Synthetic Construct

<400> SEQUENCE: 15

Met Val Leu Leu Val Thr Ser Leu Leu Leu Cys Glu Leu Pro His Pro
1               5                   10                  15

Ala Phe Leu Leu Ile Pro Gln Ala Val Val Thr Gln Glu Ser Ala Leu
            20                  25                  30

Thr Thr Ser Pro Gly Glu Thr Val Thr Leu Thr Cys Arg Ser Ser Thr
        35                  40                  45

Gly Ala Val Thr Thr Ser Asn Tyr Ala Asn Trp Val Gln Glu Lys Pro
    50                  55                  60

Asp His Leu Phe Thr Gly Leu Ile Gly Asp Thr Asn Asn Arg Ala Pro
65                  70                  75                  80

Gly Val Pro Ala Arg Phe Ser Gly Ser Leu Ile Gly Asp Lys Ala Ala
                85                  90                  95

Leu Thr Ile Thr Gly Ala Gln Thr Glu Asp Glu Ala Ile Tyr Phe Cys
            100                 105                 110

Ala Leu Trp Cys Ser Asn His Trp Val Phe Gly Gly Gly Thr Lys Leu
        115                 120                 125

Thr Val Leu Gly Ser Thr Ser Gly Ser Gly Lys Pro Gly Ser Gly Glu
    130                 135                 140

Gly Ser Thr Lys Gly Gln Ala Val Val Thr Gln Glu Ser Ala Leu Thr
145                 150                 155                 160

Thr Ser Pro Gly Glu Thr Val Thr Leu Thr Cys Arg Ser Ser Thr Gly
                165                 170                 175

Ala Val Thr Thr Ser Asn Tyr Ala Asn Trp Val Gln Glu Lys Pro Asp
            180                 185                 190

His Leu Phe Thr Gly Leu Ile Gly Asp Thr Asn Asn Arg Ala Pro Gly
        195                 200                 205

Val Pro Ala Arg Phe Ser Gly Ser Leu Ile Gly Asp Lys Ala Ala Leu
    210                 215                 220

Thr Ile Thr Gly Ala Gln Thr Glu Asp Glu Ala Ile Tyr Phe Cys Ala
225                 230                 235                 240

Leu Trp Cys Ser Asn His Trp Val Phe Gly Gly Gly Thr Lys Leu Thr
                245                 250                 255

Val Leu

<210> SEQ ID NO 16
<211> LENGTH: 268
<212> TYPE: PRT
```

<213> ORGANISM: Artificial Sequence
<220> FEATURE:
<223> OTHER INFORMATION: Synthetic Construct

<400> SEQUENCE: 16

```
Met Val Leu Leu Val Thr Ser Leu Leu Leu Cys Glu Leu Pro His Pro
1               5                   10                  15

Ala Phe Leu Leu Ile Pro Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Thr Ala Gly Met Gln Trp Tyr Gln Lys Met Pro Gly
    50                  55                  60

Lys Gly Phe Lys Trp Ile Gly Trp Ile Asn Thr His Ser Gly Glu Pro
65                  70                  75                  80

Lys Tyr Ala Glu Asp Phe Lys Gly Arg Phe Ala Phe Ser Leu Glu Thr
                85                  90                  95

Ser Ala Ser Thr Ala Tyr Leu Gln Ile Ser Asn Leu Lys Asn Glu Asp
            100                 105                 110

Thr Ala Thr Tyr Phe Cys Ala Arg Gly Asp Ser Gly Tyr Gly Ala
        115                 120                 125

Trp Phe Ala Tyr Trp Gly Gln Gly Thr Leu Val Thr Val Ser Ala Ala
    130                 135                 140

Gly Gly Gly Gly Ser Gly Gly Gly Ser Gly Gly Gly Ser Gln
145                 150                 155                 160

Ala Val Val Thr Gln Glu Ser Ala Leu Thr Thr Ser Pro Gly Glu Thr
                165                 170                 175

Val Thr Leu Thr Cys Arg Ser Ser Thr Gly Ala Val Thr Thr Ser Asn
            180                 185                 190

Tyr Ala Asn Trp Val Gln Glu Lys Pro Asp His Leu Phe Thr Gly Leu
        195                 200                 205

Ile Gly Asp Thr Asn Asn Arg Ala Pro Gly Val Pro Ala Arg Phe Ser
    210                 215                 220

Gly Ser Leu Ile Gly Asp Lys Ala Ala Leu Thr Ile Thr Gly Ala Gln
225                 230                 235                 240

Thr Glu Asp Glu Ala Ile Tyr Phe Cys Ala Leu Trp Cys Ser Asn His
                245                 250                 255

Trp Val Phe Gly Gly Thr Lys Leu Thr Val Leu
            260                 265
```

<210> SEQ ID NO 17
<211> LENGTH: 255
<212> TYPE: PRT
<213> ORGANISM: Artificial Sequence
<220> FEATURE:
<223> OTHER INFORMATION: Synthetic Construct

<400> SEQUENCE: 17

```
Met Val Leu Leu Val Thr Ser Leu Leu Leu Cys Glu Leu Pro His Pro
1               5                   10                  15

Ala Phe Leu Leu Ile Pro Gln Ala Val Val Thr Gln Glu Ser Ala Leu
            20                  25                  30

Thr Thr Ser Pro Gly Glu Thr Val Thr Leu Thr Cys Arg Ser Ser Thr
        35                  40                  45

Gly Ala Val Thr Thr Ser Asn Tyr Ala Asn Trp Val Gln Glu Lys Pro
    50                  55                  60
```

```
Asp His Leu Phe Thr Gly Leu Ile Gly Asp Thr Asn Asn Arg Ala Pro
 65                  70                  75                  80

Gly Val Pro Ala Arg Phe Ser Gly Ser Leu Ile Gly Asp Lys Ala Ala
                 85                  90                  95

Leu Thr Ile Thr Gly Ala Gln Thr Glu Asp Glu Ala Ile Tyr Phe Cys
            100                 105                 110

Ala Leu Trp Cys Ser Asn His Trp Val Phe Gly Gly Gly Thr Lys Leu
        115                 120                 125

Thr Val Leu Gly Gly Gly Ser Gly Gly Gly Ser Gly Gly
    130                 135                 140

Gly Ser Gln Ala Val Val Thr Gln Glu Ser Ala Leu Thr Thr Ser Pro
145                 150                 155                 160

Gly Glu Thr Val Thr Leu Thr Cys Arg Ser Ser Thr Gly Ala Val Thr
                165                 170                 175

Thr Ser Asn Tyr Ala Asn Trp Val Gln Glu Lys Pro Asp His Leu Phe
            180                 185                 190

Thr Gly Leu Ile Gly Asp Thr Asn Asn Arg Ala Pro Gly Val Pro Ala
        195                 200                 205

Arg Phe Ser Gly Ser Leu Ile Gly Asp Lys Ala Ala Leu Thr Ile Thr
    210                 215                 220

Gly Ala Gln Thr Glu Asp Glu Ala Ile Tyr Phe Cys Ala Leu Trp Cys
225                 230                 235                 240

Ser Asn His Trp Val Phe Gly Gly Gly Thr Lys Leu Thr Val Leu
                245                 250                 255

<210> SEQ ID NO 18
<211> LENGTH: 105
<212> TYPE: PRT
<213> ORGANISM: Artificial Sequence
<220> FEATURE:
<223> OTHER INFORMATION: Synthetic Construct

<400> SEQUENCE: 18

Pro Arg Glu Pro Gln Val Tyr Thr Leu Pro Pro Ser Arg Asp Glu Leu
1               5                   10                  15

Gly Ile Ala Gln Val Ser Leu Thr Cys Leu Val Lys Gly Phe Tyr Pro
                20                  25                  30

Ser Asp Ile Ala Val Glu Trp Glu Ser Asn Gly Gln Pro Glu Asn Asn
            35                  40                  45

Tyr Lys Thr Thr Pro Pro Val Leu Asp Ser Asp Gly Ser Phe Phe Leu
        50                  55                  60

Tyr Ser Lys Leu Thr Val Leu Gly Arg Arg Trp Thr Leu Gly Asn Val
 65                  70                  75                  80

Phe Ser Cys Ser Val Met His Glu Ala Leu His Asn His Tyr Thr Gln
                 85                  90                  95

Lys Ser Leu Ser Leu Ser Pro Gly Lys
            100                 105

<210> SEQ ID NO 19
<211> LENGTH: 104
<212> TYPE: PRT
<213> ORGANISM: Artificial Sequence
<220> FEATURE:
<223> OTHER INFORMATION: Synthetic Construct

<400> SEQUENCE: 19

Pro Arg Glu Pro Gln Val Tyr Thr Leu Pro Pro Ser Arg Asp Glu Leu
1               5                   10                  15
```

Leu Pro Cys Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
            35                  40                  45

Tyr Lys Thr Thr Pro Pro Val Leu Asp Ser Asp Gly Ser Phe Phe Tyr
    50                  55                  60

Ser Lys Leu Thr Val Phe Cys Pro Arg Trp Leu Gly Gly Asn Val Phe
65                  70                  75                  80

Ser Cys Ser Val Met His Glu Ala Leu His Asn His Tyr Thr Gln Lys
                85                  90                  95

Ser Leu Ser Leu Ser Pro Gly Lys
            100

<210> SEQ ID NO 20
<211> LENGTH: 105
<212> TYPE: PRT
<213> ORGANISM: Artificial Sequence
<220> FEATURE:
<223> OTHER INFORMATION: Synthetic Construct

<400> SEQUENCE: 20

Pro Arg Glu Pro Gln Val Tyr Thr Leu Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
            35                  40                  45

Tyr Lys Thr Thr Pro Pro Val Leu Asp Ser Asp Gly Ser Phe Phe Leu
    50                  55                  60

Tyr Ser Lys Leu Thr Val Pro Cys Met Arg Trp Trp Gly Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
            100                 105

<210> SEQ ID NO 21
<211> LENGTH: 225
<212> TYPE: PRT
<213> ORGANISM: Artificial Sequence
<220> FEATURE:
<223> OTHER INFORMATION: Synthetic Construct

<400> SEQUENCE: 21

Pro Arg Glu Pro Gln Val Tyr Thr Leu Pro Pro Ser Arg Asp Glu Leu
1               5                   10                  15

Gly Ile Ala Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
            35                  40                  45

Tyr Lys Thr Thr Pro Pro Val Leu Asp Ser Asp Gly Ser Phe Phe Leu
    50                  55                  60

Tyr Ser Lys Leu Thr Val Leu Gly Arg Arg Trp Thr Leu Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys Gly Gly Gly Gly Ser Gly Gly

```
            100                 105                 110
Gly Gly Ser Gly Gly Gly Ser Pro Arg Glu Pro Gln Val Tyr Thr
            115                 120                 125

Leu Pro Pro Ser Arg Asp Glu Leu Leu Pro Cys Gln Val Ser Leu Thr
            130                 135             140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Phe Cys
            180                 185                 190

Pro Arg Trp Leu Gly Gly Asn Val Phe Ser Cys Ser Val Met His Glu
            195                 200                 205

Ala Leu His Asn His Tyr Thr Gln Lys Ser Leu Ser Leu Ser Pro Gly
            210                 215                 220

Lys
225

<210> SEQ ID NO 22
<211> LENGTH: 225
<212> TYPE: PRT
<213> ORGANISM: Artificial Sequence
<220> FEATURE:
<223> OTHER INFORMATION: Synthetic Construct

<400> SEQUENCE: 22

Pro Arg Glu Pro Gln Val Tyr Thr Leu Pro Pro Ser Arg Asp Glu Leu
1               5                   10                  15

Gly Ile Ala Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
            35                  40                  45

Tyr Lys Thr Thr Pro Pro Val Leu Asp Ser Asp Gly Ser Phe Phe Leu
        50                  55                  60

Tyr Ser Lys Leu Thr Val Leu Gly Arg Arg Trp Thr Leu Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys Gly Gly Gly Gly Ser Gly Gly
            100                 105                 110

Gly Gly Ser Gly Gly Gly Ser Pro Arg Glu Pro Gln Val Tyr Thr
            115                 120                 125

Leu Pro Pro Ser Arg Asp Glu Leu Thr Lys Asn Gln Val Ser Leu Thr
            130                 135             140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Pro Cys
            180                 185                 190

Met Arg Trp Trp Gly Gly Asn Val Phe Ser Cys Ser Val Met His Glu
            195                 200                 205

Ala Leu His Asn His Tyr Thr Gln Lys Ser Leu Ser Leu Ser Pro Gly
            210                 215                 220

Lys
```

```
<210> SEQ ID NO 23
<211> LENGTH: 247
<212> TYPE: PRT
<213> ORGANISM: Artificial Sequence
<220> FEATURE:
<223> OTHER INFORMATION: Synthetic Construct

<400> SEQUENCE: 23

Met Val Leu Leu Val Thr Ser Leu Leu Leu Cys Glu Leu Pro His Pro
1               5                   10                  15

Ala Phe Leu Leu Ile Pro Pro Arg Glu Pro Gln Val Tyr Thr Leu Pro
                20                  25                  30

Pro Ser Arg Asp Glu Leu Gly Ile Ala Gln Val Ser Leu Thr Cys Leu
            35                  40                  45

Val Lys Gly Phe Tyr Pro Ser Asp Ile Ala Val Glu Trp Glu Ser Asn
        50                  55                  60

Gly Gln Pro Glu Asn Asn Tyr Lys Thr Pro Pro Val Leu Asp Ser
65                  70                  75                  80

Asp Gly Ser Phe Phe Leu Tyr Ser Lys Leu Thr Val Leu Gly Arg Arg
                85                  90                  95

Trp Thr Leu Gly Asn Val Phe Ser Cys Ser Val Met His Glu Ala Leu
                100                 105                 110

His Asn His Tyr Thr Gln Lys Ser Leu Ser Leu Ser Pro Gly Lys Gly
                115                 120                 125

Gly Gly Gly Ser Gly Gly Gly Ser Gly Gly Gly Ser Pro Arg
            130                 135                 140

Glu Pro Gln Val Tyr Thr Leu Pro Pro Ser Arg Asp Glu Leu Leu Pro
145                 150                 155                 160

Cys Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
                180                 185                 190

Thr Thr Pro Pro Val Leu Asp Ser Asp Gly Ser Phe Phe Leu Tyr Ser
                195                 200                 205

Lys Leu Thr Val Phe Cys Pro Arg Trp Leu Gly Gly Asn Val Phe Ser
            210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 24
<211> LENGTH: 247
<212> TYPE: PRT
<213> ORGANISM: Artificial Sequence
<220> FEATURE:
<223> OTHER INFORMATION: Synthetic Construct

<400> SEQUENCE: 24

Met Val Leu Leu Val Thr Ser Leu Leu Leu Cys Glu Leu Pro His Pro
1               5                   10                  15

Ala Phe Leu Leu Ile Pro Pro Arg Glu Pro Gln Val Tyr Thr Leu Pro
                20                  25                  30

Pro Ser Arg Asp Glu Leu Gly Ile Ala Gln Val Ser Leu Thr Cys Leu
            35                  40                  45
```

```
Val Lys Gly Phe Tyr Pro Ser Asp Ile Ala Val Glu Trp Glu Ser Asn
    50                  55                  60

Gly Gln Pro Glu Asn Asn Tyr Lys Thr Thr Pro Pro Val Leu Asp Ser
65                  70                  75                  80

Asp Gly Ser Phe Phe Leu Tyr Ser Lys Leu Thr Val Leu Gly Arg Arg
                85                  90                  95

Trp Thr Leu Gly Asn Val Phe Ser Cys Ser Val Met His Glu Ala Leu
            100                 105                 110

His Asn His Tyr Thr Gln Lys Ser Leu Ser Leu Ser Pro Gly Lys Gly
                115                 120                 125

Gly Gly Gly Ser Gly Gly Gly Ser Gly Gly Gly Ser Pro Arg
130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
                195                 200                 205

Lys Leu Thr Val Pro Cys Met Arg Trp Trp Gly Gly Asn Val Phe Ser
210                 215                 220

Cys Ser Val Met His Glu Ala Leu His Asn His Tyr Thr Gln Lys Ser
225                 230                 235                 240

Leu Ser Leu Ser Pro Gly Lys
                245
```

<210> SEQ ID NO 25
<211> LENGTH: 265
<212> TYPE: PRT
<213> ORGANISM: Artificial Sequence
<220> FEATURE:
<223> OTHER INFORMATION: Synthetic Construct

<400> SEQUENCE: 25

```
Met Val Leu Leu Val Thr Ser Leu Leu Cys Glu Leu Pro His Pro
1               5                   10                  15

Ala Phe Leu Leu Ile Pro Pro Arg Glu Pro Gln Val Tyr Thr Leu Pro
                20                  25                  30

Pro Ser Arg Asp Glu Leu Gly Ile Ala Gln Val Ser Leu Thr Cys Leu
            35                  40                  45

Val Lys Gly Phe Tyr Pro Ser Asp Ile Ala Val Glu Trp Glu Ser Asn
    50                  55                  60

Gly Gln Pro Glu Asn Asn Tyr Lys Thr Thr Pro Pro Val Leu Asp Ser
65                  70                  75                  80

Asp Gly Ser Phe Phe Leu Tyr Ser Lys Leu Thr Val Leu Gly Arg Arg
                85                  90                  95

Trp Thr Leu Gly Asn Val Phe Ser Cys Ser Val Met His Glu Ala Leu
            100                 105                 110

His Asn His Tyr Thr Gln Lys Ser Leu Ser Leu Ser Pro Gly Lys Gly
                115                 120                 125

Gly Gly Gly Ser Gly Gly Gly Ser Gly Gly Gly Ser Pro Arg
130                 135                 140

Glu Pro Gln Val Tyr Thr Leu Pro Pro Ser Arg Asp Glu Leu Leu Pro
145                 150                 155                 160
```

```
Cys Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Phe Cys Pro Arg Trp Leu Gly Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys Gly Ser Thr Ser Gly Ser Gly Lys Pro
                245                 250                 255

Gly Ser Gly Glu Gly Ser Thr Lys Gly
                260                 265

<210> SEQ ID NO 26
<211> LENGTH: 265
<212> TYPE: PRT
<213> ORGANISM: Artificial Sequence
<220> FEATURE:
<223> OTHER INFORMATION: Synthetic Construct

<400> SEQUENCE: 26

Met Val Leu Leu Val Thr Ser Leu Leu Leu Cys Glu Leu Pro His Pro
1               5                   10                  15

Ala Phe Leu Leu Ile Pro Pro Arg Glu Pro Gln Val Tyr Thr Leu Pro
            20                  25                  30

Pro Ser Arg Asp Glu Leu Gly Ile Ala Gln Val Ser Leu Thr Cys Leu
        35                  40                  45

Val Lys Gly Phe Tyr Pro Ser Asp Ile Ala Val Glu Trp Glu Ser Asn
    50                  55                  60

Gly Gln Pro Glu Asn Asn Tyr Lys Thr Thr Pro Pro Val Leu Asp Ser
65                  70                  75                  80

Asp Gly Ser Phe Phe Leu Tyr Ser Lys Leu Thr Val Leu Gly Arg Arg
                85                  90                  95

Trp Thr Leu Gly Asn Val Phe Ser Cys Ser Val Met His Glu Ala Leu
                100                 105                 110

His Asn His Tyr Thr Gln Lys Ser Leu Ser Leu Ser Pro Gly Lys Gly
            115                 120                 125

Gly Gly Gly Ser Gly Gly Gly Gly Ser Gly Gly Gly Gly Ser Pro Arg
        130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Pro Cys Met Arg Trp Trp Gly Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys Gly Ser Thr Ser Gly Ser Gly Lys Pro
                245                 250                 255
```

Gly Ser Gly Glu Gly Ser Thr Lys Gly
        260                 265

<210> SEQ ID NO 27
<211> LENGTH: 84
<212> TYPE: PRT
<213> ORGANISM: Artificial Sequence
<220> FEATURE:
<223> OTHER INFORMATION: Synthetic Construct

<400> SEQUENCE: 27

Phe Val Pro Val Phe Leu Pro Ala Lys Pro Thr Thr Thr Pro Ala Pro
1             5                 10               15

Arg Pro Pro Thr Pro Ala Pro Thr Ile Ala Ser Gln Pro Leu Ser Leu
          20               25               30

Arg Pro Glu Ala Cys Arg Pro Ala Ala Gly Gly Ala Val His Thr Arg
        35                 40               45

Gly Leu Asp Phe Ala Cys Asp Ile Tyr Ile Trp Ala Pro Leu Ala Gly
    50                 55               60

Thr Cys Gly Val Leu Leu Leu Ser Leu Val Ile Thr Leu Tyr Cys Asn
65             70               75               80

His Arg Asn Arg

<210> SEQ ID NO 28
<211> LENGTH: 41
<212> TYPE: PRT
<213> ORGANISM: Artificial Sequence
<220> FEATURE:
<223> OTHER INFORMATION: Synthetic Construct

<400> SEQUENCE: 28

Arg Ser Lys Arg Ser Arg Leu Leu His Ser Asp Tyr Met Asn Met Thr
1             5                 10               15

Pro Arg Arg Pro Gly Pro Thr Arg Lys His Tyr Gln Pro Tyr Ala Pro
          20               25               30

Pro Arg Asp Phe Ala Ala Tyr Arg Ser
        35                 40

<210> SEQ ID NO 29
<211> LENGTH: 47
<212> TYPE: PRT
<213> ORGANISM: Artificial Sequence
<220> FEATURE:
<223> OTHER INFORMATION: Synthetic Construct

<400> SEQUENCE: 29

Arg Phe Ser Val Val Lys Arg Gly Arg Lys Lys Leu Leu Tyr Ile Phe
1             5                 10               15

Lys Gln Pro Phe Met Arg Pro Val Gln Thr Thr Gln Glu Glu Asp Gly
          20               25               30

Cys Ser Cys Arg Phe Pro Glu Glu Glu Glu Gly Gly Cys Glu Leu
        35                 40               45

<210> SEQ ID NO 30
<211> LENGTH: 112
<212> TYPE: PRT
<213> ORGANISM: Artificial Sequence
<220> FEATURE:
<223> OTHER INFORMATION: Synthetic Construct

<400> SEQUENCE: 30

Arg Val Lys Phe Ser Arg Ser Ala Asp Ala Pro Ala Tyr Gln Gln Gly

```
                1               5                   10                  15
            Gln Asn Gln Leu Tyr Asn Glu Leu Asn Leu Gly Arg Arg Glu Glu Tyr
                            20                  25                  30

Asp Val Leu Asp Lys Arg Arg Gly Arg Asp Pro Glu Met Gly Gly Lys
                        35                  40                  45

Pro Arg Arg Lys Asn Pro Gln Glu Gly Leu Tyr Asn Glu Leu Gln Lys
                    50                  55                  60

Asp Lys Met Ala Glu Ala Tyr Ser Glu Ile Gly Met Lys Gly Glu Arg
            65                  70                  75                  80

Arg Arg Gly Lys Gly His Asp Gly Leu Tyr Gln Gly Leu Ser Thr Ala
                            85                  90                  95

Thr Lys Asp Thr Tyr Asp Ala Leu His Met Gln Ala Leu Pro Pro Arg
                        100                 105                 110

<210> SEQ ID NO 31
<211> LENGTH: 24
<212> TYPE: PRT
<213> ORGANISM: Artificial Sequence
<220> FEATURE:
<223> OTHER INFORMATION: Synthetic Construct

<400> SEQUENCE: 31

Arg Arg Val Cys Lys Cys Pro Arg Pro Val Val Lys Ser Gly Asp Lys
1               5                   10                  15

Pro Ser Leu Ser Ala Arg Tyr Val
            20

<210> SEQ ID NO 32
<211> LENGTH: 108
<212> TYPE: PRT
<213> ORGANISM: Artificial Sequence
<220> FEATURE:
<223> OTHER INFORMATION: Synthetic Construct

<400> SEQUENCE: 32

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg Arg Arg Val Cys Lys Cys Pro Arg Pro Val Val Lys
                85                  90                  95

Ser Gly Asp Lys Pro Ser Leu Ser Ala Arg Tyr Val
            100                 105

<210> SEQ ID NO 33
<211> LENGTH: 435
<212> TYPE: DNA
<213> ORGANISM: Artificial Sequence
<220> FEATURE:
<223> OTHER INFORMATION: Synthetic Construct

<400> SEQUENCE: 33
atggtcctcc tggttaccct tctgcttctg tgcgaactgc ctcatcctgc cttccttctt      60
```

| | |
|---|---|
| ataccgcccc gcgagccaca ggtgtatact cttcctccct caagggacga actcggcatc | 120 |
| gcccaagtca gcctgacgtg tcttgtgaaa gggttttacc ccagcgatat cgccgtggag | 180 |
| tgggaaagca acggccagcc tgagaacaat tataagacta cccctcccgt actggactct | 240 |
| gacggcagtt tctttctcta ttctaaactg accgtgctcg gaaggcgctg acgctcggc | 300 |
| aacgtatttt cttgcagtgt gatgcatgaa gcactgcaca atcattatac tcagaagagc | 360 |
| ttgtcactgt ccccgggaaa gggcagcaca tccggcagcg ggaaaccggg tagcggcgaa | 420 |
| gggagcacta agggg | 435 |

<210> SEQ ID NO 34
<211> LENGTH: 435
<212> TYPE: DNA
<213> ORGANISM: Artificial Sequence
<220> FEATURE:
<223> OTHER INFORMATION: Synthetic Construct

<400> SEQUENCE: 34

| | |
|---|---|
| atggtgctgc tcgttacaag tctgcttctc tgtgaactgc cgcatccggc ctttcttttg | 60 |
| atcccgccaa gggaaccccca ggtttacaca ctgcccccat cccgggacga gttgctgcct | 120 |
| tgtcaggtga gtcttacatg cttggtgaag ggcttttacc cgtctgacat agcagtggaa | 180 |
| tgggagtcca acggacagcc agaaaataac tacaagacca cccctcccgt ccttgacagc | 240 |
| gatggaagct tttttctgta tagcaagctg actgtgttct gtcctagatg gctgggggc | 300 |
| aatgtttttt cttgcagcgt catgcacgaa gccctccaca accactacac ccagaaaagc | 360 |
| ctgtccttgt ctcctggcaa gggtagcaca tcaggtagcg gcaagcccgg gagtggcgag | 420 |
| ggcagtacca agggc | 435 |

<210> SEQ ID NO 35
<211> LENGTH: 435
<212> TYPE: DNA
<213> ORGANISM: Artificial Sequence
<220> FEATURE:
<223> OTHER INFORMATION: Synthetic Construct

<400> SEQUENCE: 35

| | |
|---|---|
| atggttctgc tcgttacatc tcttctgctc tgcgaactgc cacatccggc gttcctcctt | 60 |
| attccaccgc gagaacctca ggtttacacc ctccccccta gcagggacga gctgactaaa | 120 |
| aatcaagtat cattgacctg tctggttaag ggcttttatc cgtccgatat tgctgttgag | 180 |
| tgggaatcta acggccaacc tgagaacaat tataaaacta cgccgccggt actcgactct | 240 |
| gacggcagct tcttcctcta ctctaaactc actgtaccct tgcatgagatg gtgggggggt | 300 |
| aatgttttta gctgctccgt gatgcatgag gccctccaca accattacac gcagaagtct | 360 |
| ctcagcctca gtcccggcaa gggctctacg tcaggctcag gcaaaccggg aagtggggaa | 420 |
| ggatcaacta aggga | 435 |

<210> SEQ ID NO 36
<211> LENGTH: 795
<212> TYPE: DNA
<213> ORGANISM: Artificial Sequence
<220> FEATURE:
<223> OTHER INFORMATION: Synthetic Construct

<400> SEQUENCE: 36

| | |
|---|---|
| atggttctgt tggtgacttc tcttcttttg tgcgagctcc cacatcctgc gttccttttg | 60 |
| attccgccga gggagcccca agtttatacc ctgcctccta gtcgggatga gttgggtatc | 120 |

```
gcacaagtga gcctgacttg tctcgtaaag ggattctatc cgtccgatat agcagtcgag      180
tgggaaagta atgggcagcc ggagaacaac tacaagacaa ctcccccagt tcttgactcc      240
gacggatcat ttttttgta ctctaaattg acggtcctgg gtaggcgctg gaccctcggc      300
aatgtcttca gttgtagcgt aatgcatgaa gcccttcaca accattatac ccagaagagt      360
ttgtcccttt ctcccggtaa ggggggagga ggttctggag gtggaggtag cggtggtggg      420
ggttccccac gagagcccca agtgtacact ctcccaccgt ctcggatga attgcttccg       480 tgccaggtat cccttacttg cctcgttaaa gggttctacc caagcgacat tgcggtggaa      540
tgggaatcaa atggtcagcc agaaaacaat tacaagacga cccctccagt cctcgactca      600
gatggatctt tctttctgta ttccaagctg acggttttt gtccgaggtg gcttggaggg       660
aacgtcttct catgctccgt catgcacgag gcgctgcata accactacac acagaaaagt      720
ttgtccttga gcccgggtaa aggcagcacc agcgggagcg gaaaacctgg aagtggggaa      780
gggtctacca agggc                                                      795

<210> SEQ ID NO 37
<211> LENGTH: 795
<212> TYPE: DNA
<213> ORGANISM: Artificial Sequence
<220> FEATURE:
<223> OTHER INFORMATION: Synthetic Construct

<400> SEQUENCE: 37
atggttctgc tggtaacctc cctccttctg tgcgagctcc cccacccgc attcctcctg        60 attccgccca gagaacccca ggtgtatacc cttcccccta gcagagatga gctgggcata      120
gctcaggtat ccctcacatg cctcgtgaaa ggattctacc caagtgacat cgccgtggag      180
tgggaaagca acgggcagcc ggaaaacaat tataagacga ccccacccgt gctcgacagt      240
gacggctctt tcttcctgta ctccaaactg accgtccttg acggcgatg gacactgggc       300 aatgtttta gctgttccgt gatgcatgag gccctgcaca accactatac ccagaagtca       360
ctctctctgt ctcctgggaa aggagggggt ggcagcggcg gtggcggatc tggcggagga      420
ggttctccca gggagcctca ggtatatacc ctgccccctt ctcgcgacga gttgacgaag      480
aaccaagtgt ctctgacctg cctggtcaaa ggattctacc cttctgatat tgcagtggaa      540
tgggaatcca acgggcagcc tgagaataat tacaagacca ccccacctgt tcttgatagt      600
gacggttcat tcttcctcta cagcaagctg accgtgccct gtatgaggtg gtgggcggc      660 aacgtctttt cttgttccgt catgcacgaa gcactgcata accactacac ccagaaaagc      720
ctgtctctta gccctgggaa gggatctacc tcaggatctg ggaaacctgg tagcggcgag      780
ggtagcacca aagga                                                      795

<210> SEQ ID NO 38
<211> LENGTH: 261
<212> TYPE: DNA
<213> ORGANISM: Artificial Sequence
<220> FEATURE:
<223> OTHER INFORMATION: Synthetic Construct

<400> SEQUENCE: 38
ttcgtgccgg tcttcctgcc agcgaagccc accacgacgc cagcgccgcg accaccaaca       60
ccggcgccca ccatcgcgtc gcagcccctg tccctgcgcc cagaggcgtg ccggccagcg      120
gcggggggcg cagtgcacac gagggggctg gacttcgcct gtgatatcta catctgggcg      180
```

```
ccccttggccg ggacttgtgg ggtccttctc ctgtcactgg ttatcaccct ttactgcaac      240
cacaggaaca ggagtaagag g                                                 261

<210> SEQ ID NO 39
<211> LENGTH: 194
<212> TYPE: DNA
<213> ORGANISM: Artificial Sequence
<220> FEATURE:
<223> OTHER INFORMATION: Synthetic Construct

<400> SEQUENCE: 39
aagttatgta tcctcctcct tacctagaca atgagaagag caatggaacc attatccatg       60
tgaaagggaa acacctttgt ccaagtcccc tatttcccgg accttctaag cccttttggg      120
tgctggtggt ggttggggga gtcctggctt gctatagctt gctagtaaca gtggccttta      180
ttattttctg ggtg                                                        194

<210> SEQ ID NO 40
<211> LENGTH: 141
<212> TYPE: DNA
<213> ORGANISM: Artificial Sequence
<220> FEATURE:
<223> OTHER INFORMATION: Synthetic Construct

<400> SEQUENCE: 40
cgtttctctg ttgttaaacg gggcagaaag aaactcctgt atatattcaa acaaccattt       60
atgagaccag tacaaactac tcaagaggaa gatggctgta gctgccgatt tccagaagaa      120
gaagaaggag gatgtgaact g                                                141

<210> SEQ ID NO 41
<211> LENGTH: 339
<212> TYPE: DNA
<213> ORGANISM: Artificial Sequence
<220> FEATURE:
<223> OTHER INFORMATION: Synthetic Construct

<400> SEQUENCE: 41
agagtgaagt tcagcaggag cgcagacgcc cccgcgtacc agcagggcca gaaccagctc       60
tataacgagc tcaatctagg acgaagagag gagtacgatg tttggacaa gagacgtggc      120 cgggaccctg agatgggggg aaagccgaga aggaagaacc ctcaggaagg cctgtacaat      180
gaactgcaga aagataagat ggcggaggcc tacagtgaga ttgggatgaa aggcgagcgc      240 cggagggca aggggcacga tggcctttac cagggtctca gtacagccac caaggacacc      300
tacgacgccc ttcacatgca ggccctgccc cctcgctaa                             339
```